(12) United States Patent
Cheng et al.

(10) Patent No.: US 8,110,179 B2
(45) Date of Patent: *Feb. 7, 2012

(54) CYCLODEXTRIN-BASED POLYMERS FOR THERAPEUTICS DELIVERY

(75) Inventors: Jianjun Cheng, Arcadia, CA (US); Mark E. Davis, Pasadena, CA (US); Kay T. Khin, San Gabriel, CA (US)

(73) Assignee: Cerulean Pharma Inc., Cambridge, MA (US)

( * ) Notice: Subject to any disclaimer, the term of this patent is extended or adjusted under 35 U.S.C. 154(b) by 584 days.

This patent is subject to a terminal disclaimer.

(21) Appl. No.: 11/881,325

(22) Filed: Jul. 25, 2007

(65) Prior Publication Data

US 2008/0058427 A1    Mar. 6, 2008

Related U.S. Application Data

(63) Continuation of application No. 10/656,838, filed on Sep. 5, 2003, now Pat. No. 7,270,808.

(60) Provisional application No. 60/408,855, filed on Sep. 6, 2002, provisional application No. 60/422,830, filed on Oct. 31, 2002, provisional application No. 60/451,998, filed on Mar. 4, 2003.

(51) Int. Cl.
*A61K 9/48* (2006.01)
*A61K 47/40* (2006.01)

(52) U.S. Cl. ........ 424/78.3; 424/486; 424/488; 514/778

(58) Field of Classification Search .................. None
See application file for complete search history.

(56) References Cited

U.S. PATENT DOCUMENTS

| | | |
|---|---|---|
| 3,426,011 A | 2/1969 | Parmerter et al. |
| 3,453,257 A | 7/1969 | Parmerter et al. |
| 3,472,835 A | 10/1969 | Buckler et al. |
| 3,502,601 A | 3/1970 | Case et al. |
| 3,654,261 A | 4/1972 | Johnson |
| 4,291,013 A | 9/1981 | Wahlig et al. |
| 4,347,234 A | 8/1982 | Wahlig et al. |
| 4,367,072 A | 1/1983 | Vogtle et al. |
| 4,438,253 A | 3/1984 | Casey et al. |
| 4,525,495 A | 6/1985 | Dorman et al. |
| 4,526,938 A | 7/1985 | Churchill et al. |
| 4,535,152 A * | 8/1985 | Szejtli et al. ............. 536/103 |
| 4,570,629 A | 2/1986 | Widra |
| 4,572,832 A | 2/1986 | Kigasawa et al. |
| 4,582,865 A | 4/1986 | Balazs et al. |
| 4,587,268 A | 5/1986 | Pfirrmann |
| RE32,268 E | 10/1986 | Gordon |
| 4,625,014 A | 11/1986 | Senter et al. |
| 4,638,045 A | 1/1987 | Kohn et al. |
| 4,652,441 A | 3/1987 | Okada et al. |
| 4,675,381 A | 6/1987 | Bichon |
| 4,727,064 A | 2/1988 | Pitha |
| 4,745,160 A | 5/1988 | Churchill et al. |
| 4,746,734 A | 5/1988 | Tsuchiyama et al. |
| 4,764,604 A | 8/1988 | Muller |
| 4,774,329 A | 9/1988 | Friedman |
| 4,818,542 A | 4/1989 | DeLuca et al. |
| 4,841,081 A | 6/1989 | Toda et al. |
| 4,877,778 A | 10/1989 | Carpenter et al. |
| 4,898,654 A | 2/1990 | Toda et al. |
| 4,902,788 A | 2/1990 | Zemel et al. |
| 4,941,996 A | 7/1990 | Trend et al. |
| 5,098,793 A | 3/1992 | Rohrbach et al. |
| 5,100,669 A | 3/1992 | Hyon et al. |
| 5,143,854 A | 9/1992 | Pirrung et al. |
| 5,148,854 A | 9/1992 | Nakamoto |
| 5,183,883 A | 2/1993 | Tanaka et al. |
| 5,208,316 A * | 5/1993 | Yoshinaga ............. 528/68 |
| 5,219,980 A | 6/1993 | Swidler |
| 5,275,824 A | 1/1994 | Carli et al. |
| 5,276,088 A | 1/1994 | Yoshinaga |
| 5,278,804 A | 1/1994 | Halvorsen |
| 5,330,768 A | 7/1994 | Park et al. |
| 5,357,012 A | 10/1994 | Nussstein et al. |
| 5,405,783 A | 4/1995 | Pirrung et al. |
| 5,424,186 A | 6/1995 | Fodor et al. |
| 5,482,719 A | 1/1996 | Guillet et al. |
| 5,488,102 A | 1/1996 | Vetter |
| 5,510,240 A | 4/1996 | Lam et al. |

(Continued)

FOREIGN PATENT DOCUMENTS

EP    0 258 780 A1    3/1988
(Continued)

OTHER PUBLICATIONS

Danysz et al., "Aminoadamantanes as NMDA receptor agonists and antiparkinsonian agents-preclinical studies," Neurosci. Biobehav. Rev., vol. 21(4), pp. 455-468 (1997). David et al., "Synthesis of hydrophobically end-capped poly(ethyleneglycol)s with UV absorbing properties," Macromol. Rapid Commun., vol. 21(14), pp. 990-993 (2000).

Du et al., "Steric Considerations in Supramoleular Incision of Modified β-Cyclodextrins with Triton X-100 and α-Bromonaphthalene," Supramolecular Chem., vol. 7, pp. 209-214 (2005).

Epa et al., "Downregulation of the p75 Neurotrophin Receptor in Tissue Culture and in Vivo, Using β-Cyclodextrin-Adamantane-Oligonucleotide Conjugates," Antisense & Nucleic Acid Drug Development, vol. 10, pp. 469-478 (2000).

Finsinger et al., "Protective Copolymers for Nonviral Gene Vectors: Synthesis, Vector Characterization and Application in Gene Delivery," Gene Delivery, 7:1183-1192 (2000).

(Continued)

*Primary Examiner* — Leigh Maier
(74) *Attorney, Agent, or Firm* — Lando & Anastasi, LLP

(57) ABSTRACT

The present invention relates to novel compositions of therapeutic cyclodextrin containing polymeric compounds designed as a carrier for small molecule therapeutics delivery and pharmaceutical compositions thereof. These cyclodextrin-containing polymers improve drug stability and solubility, and reduce toxicity of the small molecule therapeutic when used in vivo. Furthermore, by selecting from a variety of linker groups and targeting ligands the polymers present methods for controlled delivery of the therapeutic agents. The invention also relates to methods of treating subjects with the therapeutic compositions described herein. The invention further relates to methods for conducting pharmaceutical business comprising manufacturing, licensing, or distributing kits containing or relating to the polymeric compounds described herein.

165 Claims, 8 Drawing Sheets

U.S. PATENT DOCUMENTS

| | | |
|---|---|---|
| 5,529,915 A | 6/1996 | Phillips et al. |
| 5,547,932 A | 8/1996 | Curiel et al. |
| 5,549,974 A | 8/1996 | Holmes |
| 5,571,882 A | 11/1996 | Vetter |
| 5,608,015 A | 3/1997 | Yoshinaga |
| 5,612,389 A | 3/1997 | Chabrecek et al. |
| 5,635,383 A | 6/1997 | Wu et al. |
| 5,652,347 A | 7/1997 | Pouyani et al. |
| 5,656,611 A | 8/1997 | Kabanov et al. |
| 5,679,773 A | 10/1997 | Holmes |
| 5,688,488 A | 11/1997 | Low et al. |
| 5,691,316 A | 11/1997 | Agrawal et al. |
| 5,693,768 A | 12/1997 | Bachmann et al. |
| 5,698,535 A | 12/1997 | Geczy et al. |
| 5,700,848 A | 12/1997 | Soon-Shiong et al. |
| 5,716,594 A | 2/1998 | Elmalh et al. |
| 5,728,804 A | 3/1998 | Sharma et al. |
| 5,820,847 A | 10/1998 | Low et al. |
| 5,840,485 A | 11/1998 | Lebl et al. |
| 5,855,900 A | 1/1999 | Nobuhiko |
| 5,880,154 A | 3/1999 | Boukrinskaia et al. |
| 5,917,016 A | 6/1999 | Holmes |
| 5,985,916 A | 11/1999 | Duncan et al. |
| 6,033,486 A | 3/2000 | Andros |
| 6,048,736 A | 4/2000 | Kosak |
| 6,060,597 A | 5/2000 | Tobe et al. |
| 6,132,734 A | 10/2000 | Thomas et al. |
| 6,207,195 B1 | 3/2001 | Walsh et al. |
| 6,353,055 B1 | 3/2002 | Kabanov et al. |
| 6,410,342 B1 | 6/2002 | Affleck et al. |
| 6,420,176 B1 | 7/2002 | Lisziewicz et al. |
| 6,426,184 B1 | 7/2002 | Gao et al. |
| 6,509,323 B1 | 1/2003 | Davis et al. |
| 6,515,017 B1 | 2/2003 | Li et al. |
| 6,527,887 B1 | 3/2003 | Ruebner et al. |
| 6,589,736 B1 | 7/2003 | Rothschild et al. |
| 6,602,707 B2 | 8/2003 | Hefeneider et al. |
| 6,660,804 B1 * | 12/2003 | Weltrowski et al. ....... 525/54.23 |
| 6,667,293 B1 | 12/2003 | Zhao et al. |
| 6,730,699 B2 | 5/2004 | Li et al. |
| 6,740,643 B2 | 5/2004 | Wolff et al. |
| 6,828,392 B2 | 12/2004 | Meldal et al. |
| 6,849,462 B1 | 2/2005 | Winkler et al. |
| 6,884,789 B2 | 4/2005 | Davis et al. |
| 7,018,609 B2 | 3/2006 | Hwang Pun et al. |
| 7,091,192 B1 | 8/2006 | Davis et al. |
| 7,132,399 B2 | 11/2006 | Hefeneider et al. |
| 7,141,540 B2 | 11/2006 | Wang et al. |
| 7,166,302 B2 | 1/2007 | Hwang Pun et al. |
| 7,270,808 B2 | 9/2007 | Cheng et al. |
| 7,375,096 B1 | 5/2008 | Davis et al. |
| 7,427,605 B2 | 9/2008 | Davis et al. |
| 7,807,198 B2 | 10/2010 | Pun et al. |
| 2001/0034333 A1 | 10/2001 | Kosak |
| 2001/0044412 A1 | 11/2001 | Wolff et al. |
| 2002/0032161 A1 | 3/2002 | Ringshaw et al. |
| 2002/0151523 A1 | 10/2002 | Davis et al. |
| 2003/0008818 A1 | 1/2003 | Pun et al. |
| 2003/0017972 A1 | 1/2003 | Pun et al. |
| 2003/0049203 A1 | 3/2003 | Elmaleh et al. |
| 2003/0157030 A1 | 8/2003 | Davis et al. |
| 2004/0063654 A1 | 4/2004 | Davis et al. |
| 2004/0077595 A1 | 4/2004 | Cheng et al. |
| 2004/0087024 A1 | 5/2004 | Bellocq et al. |
| 2004/0109888 A1 | 6/2004 | Pun et al. |
| 2004/0248842 A1 | 12/2004 | Wagner et al. |
| 2006/0182795 A1 | 8/2006 | Pun et al. |
| 2006/0210527 A1 | 9/2006 | Davis et al. |
| 2006/0263435 A1 | 11/2006 | Davis et al. |
| 2007/0025952 A1 | 2/2007 | Davis et al. |
| 2007/0128167 A1 | 6/2007 | Pun et al. |
| 2008/0058427 A1 | 3/2008 | Cheng et al. |
| 2008/0176958 A1 | 7/2008 | Davis et al. |
| 2008/0279954 A1 | 11/2008 | Davis et al. |
| 2009/0169638 A1 | 7/2009 | Davis et al. |
| 2009/0304798 A1 | 12/2009 | Davis et al. |
| 2010/0010071 A1 | 1/2010 | Davis |

FOREIGN PATENT DOCUMENTS

| | | |
|---|---|---|
| EP | 0502194 A1 | 9/1992 |
| EP | 0587106 A | 3/1994 |
| EP | 0 730 869 A1 | 9/1996 |
| EP | 1243276 | 9/2002 |
| EP | 1525890 | 4/2005 |
| FR | 2 665 169 A1 | 1/1992 |
| GB | 1390479 | 4/1975 |
| GB | 2197720 | 5/1988 |
| JP | 58-113198 | 7/1983 |
| JP | 58167613 | 10/1983 |
| JP | 02149513 | 6/1990 |
| JP | 4106101 | 4/1992 |
| JP | 3221505 | 12/1993 |
| JP | 05331074 | 12/1993 |
| JP | 7048451 | 2/1995 |
| JP | 07316205 | 12/1995 |
| JP | 9263535 | 10/1997 |
| JP | 10158195 | 6/1998 |
| RU | 2094059 | 8/1993 |
| WO | 90/02141 | 3/1990 |
| WO | 90/15070 | 12/1990 |
| WO | WO-91/13100 | 9/1991 |
| WO | 91/17300 | 11/1991 |
| WO | 92/10092 | 6/1992 |
| WO | 93/05084 | 3/1993 |
| WO | WO 93/24150 A1 | 12/1993 |
| WO | 94/02518 | 2/1994 |
| WO | 94/09826 | 5/1994 |
| WO | 94/28031 | 12/1994 |
| WO | 95/24221 | 9/1995 |
| WO | 95/32739 | 12/1995 |
| WO | 96/09073 | 3/1996 |
| WO | WO-96/31220 | 10/1996 |
| WO | 97/33044 | 9/1997 |
| WO | 97/36948 | 10/1997 |
| WO | WO-98/05689 | 2/1998 |
| WO | 98/20967 | 5/1998 |
| WO | 98/42382 | 10/1998 |
| WO | 98/47536 | 10/1998 |
| WO | WO-98/47496 | 10/1998 |
| WO | 98/49350 | 11/1998 |
| WO | 99/30727 | 6/1999 |
| WO | 99/47172 | 9/1999 |
| WO | WO 99/61062 A1 | 12/1999 |
| WO | WO-00/01734 | 1/2000 |
| WO | 00/06117 | 2/2000 |
| WO | 00/09073 | 2/2000 |
| WO | WO 0033885 | 6/2000 |
| WO | 00/40962 | 7/2000 |
| WO | WO-00/66635 | 11/2000 |
| WO | 00/75162 | 12/2000 |
| WO | 00/75164 | 12/2000 |
| WO | 01/37665 | 5/2001 |
| WO | 01/66601 | 9/2001 |
| WO | 02/49676 | 6/2002 |
| WO | 02/057424 | 7/2002 |
| WO | 03/052060 | 6/2003 |
| WO | WO-03/047518 | 6/2003 |
| WO | 03/079073 | 10/2003 |
| WO | 2004/019993 | 3/2004 |
| WO | 2004/022099 | 3/2004 |
| WO | 2004/032862 | 4/2004 |
| WO | 2004/033620 | 4/2004 |
| WO | WO 2004/039869 A1 | 5/2004 |
| WO | 2006/089007 | 8/2006 |
| WO | 2006/105361 | 10/2006 |
| WO | 2008/076333 | 6/2008 |
| WO | 2009/123764 | 10/2009 |

OTHER PUBLICATIONS

Fisher, "A Versatile System for Receptor-Mediated Gene Delivery Permits Increased Entry of DNA into Target Cells, Enhanced Delivery to the Nucleus and Elevated Rates of Transgene Expression," Gene Therapy, 7: 1337-1343 (2000).

Gonzalez et al., "New Class of Polymers for the Delivery of Macromolecular Therapeutics," Bioconjugate Chem., vol. 10, No. 6. pp. 1068-1074 (1999).

Gosselet et al., "Association of hydrophobically modified poly (N,N-dimethylacrylamide hydroxyethylmethacrylate) with water soluble β-cyclodextrin polymers," Colloids and Surfaces: A: Physicochemical and Engineering Aspects, vol. 155, pp. 177-188 (1999).

Hwang et al., "Effects of Structure of β-Cyclodextrin-Containing Polymers on Gene Delivery," Bioconjugate Chem., 12 (2):280-290 (2001).

Iser et al., "Chenodeoxycholic acid treatment of gallstones: A follow-up report and analysis of factors influencing response to therapy," N. Engl. J. Med., vol. 293(8), pp. 378-383 (1975) (abstract only).

Ooya et al., "Synthesis and Characterization of an Oligopeptide-terminated Polyrotaxane as a Drug Carrier," Polym. Adv. Technol., 11:642-651 (2000).

Smith et al., "Spectral Characterization of β-Cyclodextrin: Triton X-100 Complexes," J. Include. Phen. and Mol. Rec. Chem., vol. 10, pp. 471-484 (1991).

Szente et al., "Highly soluble cyclodextrin derivatives: chemistry, properties, and trends in development," Adv. Drug. Deily. Rev., pp. 3617-3628 (1999).

Tabushi et al., "Artificial Receptor Recognizing Hydrophobic Carbonyl Compounds," Journal of Organic Chemistry, 51 (10):1918-1921 (1986).

Tojima et al., "Preparation of an α-Cyclodextrin-Linked Chitosan Derivative via Reductive Amination Strategy," J. Polym. Sci., Part A: Polym. Chem., 36:1965-1968 (1998).

Torchilin et al., "TAT Peptide on the Surface of Liposomes Affords Their Efficient Intracellular Delivery Even at Low Temperature and in the Presence of ametabolic Inhibitors," PNAS, 98(15)8786-8791 (2001).

Uekama et al., "Cyclodextrin Drug Carrier Systems," Chem. Rev., 98:2045-2076 (1998).

Weickenmeier et al., "Cyclodextrin sidechain polyesters—synthesis and inclusion of adamantan derivatives," Macromol. Rapid Commun., vol. 17, pp. 731-736 (1996).

Zanta et al., "In Vitro Gene Delivery to Hepatocytes with Galactosylated Polyethylenimine," Bioconjugate Chem., 8:839-844 (1997).

Zhang et al., "Enthalpic Domination of the Chelate Effect in Cyclodextrin Dimers," J. Am. Chem. Soc., 115:9353-9354 (1993).

Shabat et al., "Chemical adaptor systems," Chemistry—A European Journal., vol. 10, pp. 2626-2634, 2004.

De Groot et al. "Elongated multiple electronic cascade and cyclization spacer systems in activatible anticancer prodrugs for enhanced drug release," Journal of Organic Chemistry, vol. 66, pp. 8815-8830, (2001).

Gopin et al., "New Chemical Adaptor Unit Designed to Release a Drug From a Tumor Targeting Device by Enzymatic Triggering," Bioorganic & Medicinal Chemistry, Elsevier Science, vol. 12, pp. 1853-1858 (2004).

Shabat et al., "In vivo activity in a catalytic antibody-prodrug system: Antibody catalyzed etoposide prodrug activation for selective chemotherapy," PNAS, vol. 98, No. 13, 7528-7533 (Jun. 19, 2001).

Tijerina Monical et al., "Mechanisms of cytotoxcity in human ovarian carcinoma cells exposed to free Mce6 or HPMA copolymer-Mce6 conjugates," Photochemistry and Photobiology, vol. 77, No. 6, pp. 645-652 (2003).

Vrueh De R L A et al., "Synthesis of a Lipophilic Prodrug of 9-(2-Phosphonylmethoxyethyl ) Ade Nine (PMEA) and its Incorporation into a Hepatocyte-Specific Lipidic Carrier," Pharmaceutical Research, vol. 16, No. 8, pp. 1179-1185 (1999).

Ebright et al., "Incorporation of an EDTA-Metal Complex at a Rationally Selected Site within a Protein: Application to EDTA-Iron DNA Affinity Cleaving with Catabolite Gene Activator Protein (CAP) and CRO," Biochemistry, 1992, 31, 10664-10670.

Jeong et al., "Novel Intracellular Delivery System of Antisense Oligonucleotide by Self-Assembled Hybrid Micelles Composed of DNA/PEG Conjugate and Cationic Fusogenic Peptide," Bioconjugate Chem., 2003, 14, 473-479.

Jones et al., "Releasable Luciferin-Transporter Conjugates: Tools for the Real-Time Analysis of Cellular Uptake and Release," J. Am. Chem. Soc., 2006, 128, 6526-6527.

Karathanasis et al.,"Preparation of in vivo cleavable agglomerated liposomes suitable for modulated pulmonary drug delivery," Journal of Controlled Release 103 (2005) 159-175.

Rejmanova et al., "Polymers Containing Enzymatically Degradeable Bonds," Macromol. Chem., 184, 2009-2020 (1983).

Middleton et al., "Synthetic biodegradable polymers as orthopedic devices," Biomaterials, 21 (2000) 2335-2346.

Amit et al., "Photosensitive Protecting Groups of Amino Sugars and Their Use in Glycoside Synthesis. 2-Nitrobenzyloxycarbonylamino and 6-Nitroveratryloxycarbonylamino Derivatives," J. Org. Chem., 39:192-196 (1974).

Baldwin et al., "New Photolabile Phosphate Protecting Groups," Tetrahedron, 46:6879-6884 (1990).

Baramy et al., "A Three-Dimensional Orthogonal Protection Scheme for Solid-Phase Peptide Synthesis Under Mild Conditions," J. Am. Chem. Soc., 107:4936-4942 (1985).

Bellof et al., "A New Phenacyl-Type Handle for Polymer Supported Peptide Synthesis," Chimia, 39317-320 (1985).

Fodor et al., "Light-Directed, Spatially Addressable Parallel Chemical Synthesis," Science, 251:767-773 (1991).

Hammer et al., "Practical Approach to Solid-Phase Synthesis of C-Terminal Peptide Amides Under Mild Conditions Based on a Photolysable Anchoring Linkage," Int. J. Peptide Protein Res., 36:31-45 (1990).

Hazum et al., "A Photocleavable Protecting Group for the Thiol Function of Cysteine," Proc. 16th Sup. European Peptide Sym., 105-110 (1980).

Holmes et al., "Reagents for Combinatorial Organic Synthesis: Development of a New O-Nitrobenzyl Photolabile Linker for Solid Phase Synthesis," J. Org. Chem., 60:2318-2319 (1995).

Kneib-Cordonier et al., "Orthogonal Solid-Phase Synthesis of Human Gastrin-I Under Mild Conditions," Chem. Struc. and Biol., Rivier and Marshall, eds. pp. 895-897 (1990).

Lam et al., "The One-Bead-One Compound Combinatorial Library Method," Chem. Rev., 97:411-448 (1997).

McCray et al., "Properties and Uses of Photoreactive Caged Compounds," Annu. Rev. Biophys. Chem., 18:239-270 (1989).

McGall et al., "Light-Directed Synthesis of High-Density Oligonucleotide Arrays Using Semiconductor Photoresists," Proc. Natl. Acad. Sci., 93:13555-13560 (1996).

McGall et al., "The Efficiency of Light-Directed Synthesis of DNA Arrays on Glass Substrates," J. Am. Chem. Soc., 119:5081-5090 (1997).

Patchornik et al., "Photosensitive Protecting Groups," J. Am. Chem. Soc., 92:6333-6335 (1970).

Pillai et al., "Photoremovable Protecting Froups in Organic Synthesis," Synthesis, 1-26 (1980).

Pirrung et al., "Comparison of Methods for Photochemical Phosphoramidite-Based DNA Synthesis," J. Org. Chem., 60:6270-6276 (1995).

Deratani et al., Linear cyclodextrin-containing polyelectrolytes, 1 Synthesis of poly(1-vinylimidazole)-supported β-cyclodextrin. Effect of pH and ionic strength on the solution behavior. Macrolmol. Chem. Phys. 196, pp. 343-352 (1995).

Tanka et al., Synthesis of Doxorubicin-Cyclodextrin Conjugates. The Journal of Antibiotics. vol. 47, No. 9 pp. 1025-1029, (1994).

Yano et al. Prednisolone-Appended α-Cyclodextrin: Alleviation of Systemic Adverse Effect of Prednisolone After Intracolonic Administration in 2, 4, 6-Trinitrobenzenesulfonic Acid-Induced Colitis Rats. Journal of Pharmaceutical Sciences. vol. 90., No. 12 pp. 2103-2112, (2001).

"Arrowhead announces issuance of patent on subsidiary's key technology," Aug. 16, 2006, Press release.

"Arrowhead Subsidiary, Insert Therapeutics, signs collaboration and option agreement for potent anticancer compound, tubulysin," Jan. 17, 2007, Press release.

Insert Therapeutics signs new partnership with R&D Biopharmaceuticals for epothilones, Mar. 1, 2007, Press Release.

"Mark Davis to moderate 'novel approaches to drug delivery in cancer,'" Apr. 12, 2007, Press Release.

"Arrowhead Subsidiaries, Insert and Calando, present data on Cyclosert(TM) drug delivery system at AACR meeting," Apr. 16, 2007, Press Release.

"Arrowhead announces issuance of patent on subsidiary's key technology," May 8, 2007, Press Release.

"Arrowhead Subsidiary, Insert, publishes interim phase I data from human clinical trials for new cancer drug," Jun. 1, 2007, Press Release.

"Insert Therapeutics to initiate a multinational phase II clinical trial of lead drug candidate IT-101 in ovarian cancer," Apr. 17, 2008, Press Release.

"Arrowhead Subsidiary Calando Pharmaceuticals enters into license agreement with Cerulean Pharma Inc.," Jun. 23, 2009, Press Release.

Jeremy Heidel, "Linear Cyclodextrin-containing polymers and their use as delivery agents," 2006, Expert Opinion on Drug Delivery, 3(5), 641-646.

"Calando Pharmaceuticals phase II clinical study opens to patient enrollment," Sep. 11, 2008, Press Release.

"Calando Pharmaceuticals announces completion of IT-101 Phase I clinical study," Oct. 23, 2008, Press Release.

Alizadeh et al., "Tumor-associated macrophages are predominant carriers of cyclodextrin-based nanoparticles in gliomas," Nanomedicine: Nanotechnology, Biology, and Medicine, (2010) 6:382-390 (pubished online Oct. 15, 2009).

J.C. Oliver et al., "A dose finding pharmacokinetic study of IT-101, the first de novo designed nanoparticle therapeutic, in refractory solid tumors," American Society of Clinical Oncology, 2008 Annual Meeting (May 30-Jun. 3, 2008) Chicago, IL.

Davis et al., "Nanoparticle Therapeutics: An emerging treatment modality for cancer," Sep. 2008, Nature Reviews, Drug Discovery, 7(9), 771-782.

Heath et al., "Nanomedicine—revolutionizing the fight against cancer," Jan. 19, 2009, Scientific American.

Davis et al., "Design and Development of IT-101, a cyclodextrin-containing polymer conjugate camptothecin," May 2009, Advanced Drug Delivery Reviews, 61:1189-1192.

Heidel et al., "Clinical Developments in Nanotechnolgoy for Cancer Therapy," Jun. 12, 2010, Pharm Res (online).

Davis et al., "Cyclodextrin-containing Polymers for Drug Delivery," 2001, PharmTech, 2-5, p. 185-188.

Y. Yen et al., "First-in-human phase I trial of a cyclodextrin-containing polymer-camptothecin nanoparticle in patients with solid tumors", American Society of Clinical Oncology, 2007 annual meeting (Jun. 1-5, 2007) Chicago, IL.

"Mark Davis Q&A—making it personal: finding a new way to treat cancer," Oct. 2007, Press release WNET (New York).

Heath et al., "Nanotechnology and Cancer," Annual Review of Medicine 2008 (published online Oct. 15, 2007) vol. 59. p. 251-265.

Davis et al., "Cyclodextrin-based Pharmaceutics: past, present and future," Dec. 1, 2004, Nature Reviews Drug Discovery 3(12); 1023-1035.

Zeidan et al., "A solvent-free method for isotopically or radioactively labeling cyclodextrins and cyclodextrin-containing polymers," Bioconjugage Chemistry, vol. 17, p. 1624-1626 (available online Oct. 31, 2006).

Yen et al., "Toxicokinetic and pharmacokinatic study of IT-101 in humans with refractory solid tumors," Apr. 21, 2009, AACR Annual Meeting (Apr. 18-22, 2009), Denver, CO.

Schleup et al.,"Pharmacokinetics and tumor dynamics of the nanoparticle IT-101 from PET imaging and tumor histological measurements," PNAS, vol. 106, No. 27, 11394-11399 (available online Jun. 29, 2009).

Totanai Numbenjapon MD et al., "Preclinical results of the camptothecin-polymer conjugate IT-101 in multiple human lymphoma xenografts," Dec. 2007, Blood (Ash Annual Meeting Abstracts), 2007 110:Abstract 1376.

Schluep et al., "Pharmacokinetics and biodistributaion of the camptothecin-polymer conjugate IT-101 in rats and tumor bearing mice," Cancer Chemotherapy and Pharmacology (2006) vol. 57, p. 654-662 (available online Aug. 26, 2005).

Totanai Numbenjapon MD, et al., "Preclinical results of camptothecin-polymer conjugate (IT-101) in multiple human lymphoma xenograft models," Clinical Cancer Research (2009) vol. 15, p. 4365-4373 (available online Jun. 23, 2009).

Svenson et al., "Polymeric Nanoparticles of Camptothecin—Early Clinical Development of IT-101," May 22, 2010, Particles 2010, (May 22-25, 2010) Lake Buena Vista, FL.

Eliasof et al., "Rationale for Design and Early Clinical Development of IT-101," May 26, 2010, 8th International Symposium on Polymer Therapeutics: From Laboratory to Clinical Practice (May 24-26, 2010) Valencia, Spain.

Case et al., "IT-101 Nanoparticle Characterization," Jul. 2010, 2010 ACS National Meeting (Aug. 22-26, 2010) Boston, MA.

Wolfgang et al., "Rationale for Design and Early Clinical Development of IT-101, a Cyclodextrin-Polyethylene-glycol copolymer Nanoparticle Delivery of Camptothecin," Jul. 2010, 2010 ACS National Meeting (Aug. 22-26, 2010) Boston, MA.

"Cerulean Pharma Inc. to Convene Nanomedicine Pioneers at 2010 American Chemical Society (ACS) National Meeting & Exposition in Boston," Aug. 19, 2010.

"Cerulean Pharma Inc. Presents Data on Nanopharmaceutical Development Candidates and Platform Technologies at American Chemical Society Nationa Meeting & Espoition," Aug. 25, 2010, Press Release.

Young et al., "CRLX101 (formerly IT-101)—A Novel Nanopharmaceutical in Phase 1b/2a Clinical Development," Current Bioactive Compounds, vol. 7(1), pp. 8-14 (2011).

Svenson et al., "Preclinical to Clinical Development of the Novel Camptothecin Nanopharmaceutical CRLX101 (formerly IT-101)," Oct. 3, 2010, 8th International Nanomedicine and Drug Delivery Symposium (Oct. 3-5, 2010) Omaha, NE.

Yen et al., "Phase 1 dose escalation, safety and pharmacokinetic study of IT-101 (CRLX101), a novel nanopharmaceutical containing camptothecin, in advanced solid tumor cancer patients," Nov. 16, 2010, EORTC-NCI-AACR International Symposium on Molecular Targets and Cancer Therapeutics (Nov. 16-19, 2010) Berlin, Germany.

Numbenjapon, MD et al., "Preclinical efficacy of camptothecin polymer conjugate (IT-101) in human burkitt lymphoma bearing mice," Dec. 2006, 2006 ASH Annual meeting (Dec. 9-12, 2006) Washington, DC.

"Insert Therapeutics, Inc. receives first patent on its Cyclosert(TM) polymer Technology," Feb. 4, 2003, Insert Therapeutics News Release.

Cheng et al., "Antitumor Activity of Linear-Cyclodextrin Polymer Conjugates of Camptothecin," Nov. 1, 2003, AlChE Annual Meeting, (Nov. 16-21, 2003) San Francisco, CA.

"Insert Therapeutics describes in vivo performance and versatility of lead anticancer compound," Apr. 17, 2005, News Release.

"Insert Therapeutics files investigational new drug application for lead anti-cancer compound IT-101," Feb. 9, 2006, Press release.

"Arrowhead research subsidiary, Insert Therapeutics, receivees FDA Approval for IT-101 Phase I Clinical," Mar. 14, 2006, Press release.

Nande et al., "In vitro and in vivo toxicity testing for the prolonged local delivery of a cyclosert-camptothecin polymer conjugate in a model of intracranial glioma," 74th Annual American Association of Neurological Surgeons (Apr. 22-27, 2006) San Francisco, CA.

Cheng et al., Abstract, 11th International Symposium on Recent Advances in Drug Delivery Systems, Salt Lake City, UT, Mar. 3, 2003.

Cheng et al., Poster Presentation, 11th International Symposium on Recent Advances in Drug Delivery Systems, Salt Lake City, UT, Mar. 3-6, 2003.

Cheng et al., Mini-Abstract, 226th American Chemical Society National Meeting, New York, NY, Sep. 7, 2003.

Cheng et al., Abstract, American Chemical Society National Meeting, New York, NY, Sep. 7, 2003.

Cheng et al., Presentation, 226th American Chemical Society National Meeting, New York, NY, Sep. 7-11, 2003.

Cheng et al., Bioconjugate Chem, 14:1007-1017, 2003 (Published online Aug. 27, 2003).

Davis et al., Abstract, 30th Annual Meeting of the Controlled Release Society, Glasgow, Scotland, Jul. 19, 2003.

Davis et al., Poster Presentation, 30th Annual Meeting of the Controlled Release Society, Glasgow, Scotland, Jul. 19-23, 2003.

Henry, C&EN—Chemical & Engineering News, vol. 79, No. 14, Apr. 2, 2001.

"Insert Therapeutics, Inc. Describes in Vivo performance and Versatility of Drug Delivery Platform." Press Release. Jul. 22, 2003.
"Insert Therapeutics, Inc. Presents Capabilities and Versatility of Drug Delivery Platform." Press Release. Sep. 9, 2003.
"Insert Therapeutics, Inc. Reports in Vivo performance of CyclosertTM-Camptothecin Anti-Cancer Formulation." Press Release. Apr. 1, 2003.
Bellocq et al., "Synthetic Biocompatible Cyclodextrin-Based Constructs for Local Gene Delivery to Improve Cutaneous Would Healing," Bioconjugate Chem. (2004) vol. 15, p. 1201-1211 (available online Oct. 26, 2004).
Bellocq et al. "Transferrin-containing, cyclodextrin polymer-based particles for tumor-targeted gene delivery," Bioconjugate Chem. (2003) vol. 14, p. 1122-1132 (available online Nov. 4, 2003).
Bellocq et al. "Transferrin-targeted, cyclodextrin polycation-based gene vector for systemic delivery," Molecular Therapy, vol. 7, p. S290, May 2003.
Kang et al., "Cyclodextrin complexation: influence on the solubility, stability, and cytotoxicity of camptothecin, an antineoplastic agent," European Journal of Pharmaceutical Sciences vol. 15, pp. 163-170 (2002).
Rich et al., "Preparation of a New O-Nitrobenzyl Resin for Solid-Phase Synthesis of Tert-Butyloxycarbonyl-Protected Peptide Acids," J. Am. Chem. Soc., 97:1575-1579 (1975).
Teague, S.J., "Facile Synthesis of a O-Nitrobenzyl Photolabile Linker for Combinatorial Chemistry," Tetrahedron Lett., 37:5751-5754 (1996).
Yoo et al., "Synthesis of Oligonucleotides Containing 3'-Alkyl Carboxylic Acids Using Universal, Photolabile Solid Phase Synthesis Supports," J. Org. Chem., 60:3358-3364 (1995).
Husain et al., "Complexation of Doxorubicin with β- and γ-Cyclodextrins," Applied Spectroscopy, 46:652-658, 1992.
Jicsinszky et al., "Comprehensive Supramolecular Chemistry," vol. 3, Chap. 4, pp. 138-185, Szeitli et al., Eds., Pergamon 1996.
Breslow et al., "Biomimetic reactions catalyzed by cyclodextrins and their derivatives," Chemical Reviews, 98(5): 1997-2001 (1998).
Breslow et al., "Molecular Recognition by Cyclodextrin Dimers," Tetrahedron, 51(2): 377-388 (1995).
Breslow, "Biomimetic Chemistry and Artificial Enzymes: Catalysts by Design," Accounts of Chemical Research, 28(3): 146-1534 (1995).
Breslow, "Studies in Biomimetic Chemistry," Pure & Applied Chemistry, 70(2): 267-270 (1988).
Crini et al., "Linear Cyclodectrin-Poly (Vinylamine): Synthesis and NMR Characterization," Euro. Polm. J., 33(7): 1143-1151 (1997).
Forgacs et al., "Interactions of some Steroid drugs with b-cyclodextrin polymers," Journal of Chromatography A, 845 (1 & 2): 447-453 (1999).
Gao et al., "Potentiation of cationic liposome-mediated gene delivery by polycations," Biochemistry, 35: 1027-1036 (1996).
Habus et al., "Synthesis, Hybridization properties, Nuclease Stability, and Cellular Uptake of the Oligonucleotide-Amino-b-cyclodextrins and Adamantane Conjugates," Bioconjugate Chem., 6(4): 327-331 (1995).
Karunaratne et al., "Synthesis of bulky b-lactams for inhibition of cell surface b-lactamase activity," Bioconjugate Chem., 4:434-439 (1993).
Reineke et al., "Structural effects of Carbohydrate containing polycations on gene delivery. 1. Carbohydrate size and its distance from charge centers," Bioconjugate Chemistry, 14(1): 247-254 (2003).
Reineke et al., "Structural effects of carbohydrate-containing polycations on gene delivery. 2. Charge center type," Bioconjugate Chemistry, 14(1): 255-261(2003).
Pulfer S. et al., "Incorporation of nitric oxide-releasing crosslinked polyethyleneimine microspheres into vascular grafts," J. Biomed. Mat. Res., 37(2): 182-189 (1997).
Trubetskoy, V. S., et al., "Self Assembly of DNA-Polymer Complexes using template polymerization," Nucleic Acids Research, 26(18):4178-4185 (1998).
Pun et al., "Development of a nonviral gene delivery vehicle for systemic application," Bioconjugate Chemistry, 13: 630-639, (2002).

Harada et al. "The Molecular Necklace: A Rotaxane Containing Many Threaded alpha-Cyclodextrins," Nature, vol. 356, p. 325-327 (1992).
Harada et al. "Synthesis of a Tubular Polymer from Threaded Cyclodextrins," Nature, vol. 364, p. 516-518 (1993).
Harada et al. "Macromolecular Recognition by Cyclodextrins (I) Inclusion of Water-Soluble Polymers by Cyclodextrins," Polymer Preprints, Japan (English Edition), 40(5-11), Abstract 4L 10 at p. E 1172 (1991).
Hoffman, "Chromatography of Nucleic Acids on Cross-Linked Cyclodextrin Gels Having Inclusion Forming Capacity," J. Macromol. Sci.-Chem., A7(5), p. 1147-1157 (1973).
Li et al., "The Complex Formation Between Alpha-Cyclodextrin and Poly(ethyleneglycol) and Its Stoichiometic Discussion," Polymer Preprints, Japan (English Edition), 40(1-4), Abstract 11-12-26 at p. E 400 (1991).
Li et al., "Molecular Recognition by Cyclodextrins (II) Inclusion of Poly(ethyleneglycol) by alpha-Cyclodextrin," Polymer Preprints, Japan (English Edition), 40(5-11), Abstract 4L 11 at p. E 1173 (1991).
Seanger, "Structural Aspects of Cyclodextrins and Their Inclusion Complexes," Chapter 8 in Inclusion Compounds, vol. 2, J. L Atwood (ed.), Academic Press, New York, NY, pp. 231-259 (1984).
Uekama et al., "Improvement of Dissolution and Absorption Characteristics on Phenytoin by a Water-Soluble beta-Cyclodextrin-Epichlorohydrin Polymer," Int. J. Pharm., vol. 23, p. 35-42 (1985).
Wenz et al., "Threading Cyclodextrin Rings on Polymer Chains," Angewandte Chemie, International Edition, 31(2), p. 197-199 (1992).
Schluep et al., "Polymeric Tubulysin-Peptide Nanoparticles with Potent Antitumor Activity," Clin. Cancer Res., (2009) vol. 15, p. 181-189 (available online Dec. 31, 2008).
Hwang et al., "Alpha-methylprednisolone conjugated cyclodextrin polymer-based nanoparticles for rheumatoid arthritis therapy," International Journal of Nanomedicine, (2008) vol. 3, p. 359-372 (available online Sep. 2008).
Schluep et al. "Preclinical efficacy of the camptothecin-polymer conjugate IT-101 in multiple cancer models," Clin. Cancer Res., (2006) vol. 12, p. 1606-1614 (available online Mar. 6, 2006).
Pun et al., "Cyclodextrin-modified polyethylenimine polymers for gene delivery," Bioconjugate Chem., (2004) vol. 15, p. 831-840 (available online Jun. 29, 2004).
Ashton et al., "Amino Acid Derivatives of β-Cyclodextrin," J. Org. Chem. 61:903-908 (1996).
Atwood et al., eds., Comprehensive Supramolecular Chemistry, vol. 3, Pergamon Press (1996), TOC only.
Cserhati, Analytical Biochemistry, 225:328-332 (1995).
D. F. Williams, J. Mater. Sci. 1233 (1982).
Hisamatsu et al., Starch 44:188-191 (1992).
Hristova-Kazmierski M K et al: Bioorangic and Medicinal Chemistry Letters, vol. 3 No. 5 (1993) pp. 831-834.
Huh, K.M. et al: Macromolecular Rapid Communications, vol. 23, No. 3, (2002).
Husain et al., Applied Spectroscopy, 46:652-658 (1992).
Melton, L.D. and Slessor, K.N., Carbohydrate Research, 18, p. 29 (1971).
Minani et al, "Colon-specific drug delivery based on a cyclodextrin pro-drug . . . " J. Pharm. Sci 87(6):715-720 (1998).
Mungall et al., J. Org. Chem. 1659-1662, (1975).
Ortega-Caballero F et al: Journal of Organic Chemistry vol. 66 No. 23, pp. 7786-7795 (2001).
Putnam, et al., Nature Med. 824-826 (1996).
Song et al., "Catalyzed Hydrolysis of RNA by Metallic Complexes of β-Cyclodextrin Derivative," Journal of Molecular Catalysis (China) 15(2):139-142 (2001), abs only.
Suh, J. and Noh, Y., Bioorg. Med. Chem. Lett. (1998), 8, 1327-1330.
Tabushi et al., J. Am. Chem. 106, 4580-4584 (1984).
Tabushi et al., J. Am. Chem. 106, 5267-5270 (1984).
Tabushi et al., Tetrahedron Lett. 18:1527-1530 (1977).
U.S. App. No. 09/339,818, filed Jun. 25, 1999, Davis, et al.
U.S. App. No. 09/453,707, filed Dec. 3, 1999, Davis, et al.
U.S. App. No. 10/372,723, filed Feb. 24, 2003, Bellocq, et al.
U.S. App. No. 60/417,373 filed Oct. 9, 2002, Bellocq, et al.

Yano H et al, "Colon-specific delivery of prednisolone-appended alpha-cyclodextrin conjugate; alleviation of systemic side effect after oral administration" Journal of Controlled Release, Elsevier Science Publishers B.V. Amsterda, NL, 79(1-3):103-112 (2002).

Yano et al., "Preparation of prednisolone-appended alpha-, beta-, and gamma-cyclodextrins . . . " J. Pharm. Sci. 4:493-503 (2001).

Zhang et al., J. Am. Chem. Soc. (1997), 119, 1676-1681.

"Arrowhead Research Subsidiary, Insert Therapeutics, Treats first patient with nano-engineered anti-cancer therapeutic," Jul. 19, 2006, Business Wire.

Schluep,"Nanoparticulate chemotherapy with linear, cyclodextrin-containing polymers," May 15, 2006, XIII International Cyclodextrin Symposium, (May 14-17, 2006) Torino, Italy.

Schluep, "Insert Therapeutics—product development update NSTI nanotech," May 21, 2007, Nanotech for Investors, (May 21, 2007) Santa Clara, CA.

Jensen, "Antitumor activity of IT-101, a cyclodextrin-containing polymer camptothecin nanoparticle, in combination with various anticancer agents in human ovarian cancer xenografts," Apr. 17, 2008, AACR Annual Meeting—Abstracts Online.

Cheng et al., "Antitumor Activity of β-Cyclodextrin Polymer-Camtothecin Conjugates," Molecular Pharmaceutics, vol. 1, p. 183-193 (available online Apr. 3, 2004).

Schluep, et al., "Camptothecin-polymer conjugate shows improved biodistribution and preclinical efficacy in vivo," 2005 AACR Annual Meeting, (Apr. 16-20, 2005) Anaheim, CA.

Smith, "Sweet Revenge," Mar. 2007, Engineering & Science Caltech monthly newsletter, LXX, 1.

Boussif et al., "A Versatile Vector for Gene and Oligonucleotide Transfer into Cells in Culture and in vivo: Polyethyleninmine," Proceedings of the National Academy of Sciences 92(16):7297-7301 (1995).

Breslow et al., "Cholesterol Recognition and Binding by Cyclodextrin Dimers," J. Am. Chem. Soc. 118:8495-8496 (1996).

Pierce 1989 Handbook and General Catalog, Rockford, Illinois, 1989, pp. 288-293.

May et al., "Development of Toxin-binding agent as a treatment for tunicaminyluracil toxicity: protection against tunicamycin poisoning of sheep," Australian Veterinary Journal 76(11): 752-756 (1998); chemical abstracts 131(3) pp. 193. Abstract No. 28805p (1999).

Fujita K. et al., "Selective recognition of alkanoates by a b-cyclodextrin flexibly capped with a chromophore," Bioorganic Chemistry, 11:108-114 (1982).

Fujita K. et al., "Guest-induced conformational change of b-cyclodextrin capped with an environmentally sensitive chromophore," Bioorganic Chemistry, 11:72-84 (1982).

Liu et al., "Sugar containing polyamines prepared using galactose oxidase coupled with chemical reduction," J. Am. Chem. Soc., 121:466-467 (1999).

Lowry O.H. et al., "Protein Measurement with the Folin Phenol Reagent," The Journal of Biological Chemistry, 193:265-275 (1951).

Lewis R.J., Hawley's Condensed Chemical Dictionary, John Wiley & Sons, Inc. New York NY, 1987, only pp. 311-312 supplied.

Fieser M. et al., "Reagents for Organic Synthesis," Wiley New York, 3:265-266 (1967).

Ferrari S. et al., "ExGen 500 is an efficient vector for gene delivery to lung epithelial cells in vitro and in vivo," Gene Therapy, 4;1100-1106 (1997).

Suh et al., "A new backbone of artificial enzymes obtained by cross-linkage of Poly(ethylenimine)," Bioorg. Med. Chem. Lett., (1998), 8, 1327-1330.

Alexakis et al., "Microencapsulation of DNA within Alginate Microspheres and Crosslinked Chitosan Membranes for in Vivo Application," Appl. Biochem. Biotechnol., 50:93-106 (1995).

Albers et al., "Cyclodextrin Derivatives in Pharmaceutics," Crit. Rev. Ther. Drug Carrier Syst., 1995, 12, 311-337.

Cram, D.J., "Cavitands: Organic Hosts with Enforced Cavities," Science, 1983, 219, 1177-1183.

Cram, D.J., "The Design of Molecular Hosts, Guests, and Their Complexes," Science, 1988, 240, 760-767.

Lee et al., "Cucurbituril Homologues and Derivatives: New Opportunities in Supramolecular Chemistry," Acc. Chem. Res., 2003, 36, 621-630.

Tenjarla, S. et al., "Preparation, Characterization, and Evaluation of Miconazole-Cyclodextrin Complexes for Improved Oral and Topical Delivery," Journal of Pharmaceutical Sciences, 1998, 87, 425-429.

Warmuth, R. et al., "Recent Highlights in Hemicarcerand Chemistry," Acc. Chem. Res., 2001, 34, 95-105.

Zughul, M.B. et al., "Thermodynamics of Propylparaben/β-Cyclodextrin Inclusion Complexes," Pharm. Dev. Technol., 1998, 3, 43-53.

"Adamantane," in The Merck Index, 11th ed., Merck Research Laboratories, p. 24: No. 140 (1989).

"Amantadine," in The Merck Index, 11th ed., Merck Research Laboratories, p. 60: No. 380 (1989).

Amiel et al., "Association Between Amphiphilic Poly(ethylene oxide) and β-Cyclodextrin Polymers: Aggregation and Phase Separation," Advances in Colloid and Interface Science, 79:105-122 (1999).

Amiel et al., "New Associating Polymer Systems Involving Water Soluble β-Cyclodextrin Polymers," Journal of Inclusion Phemomena and Molecular Recognition in Chemistry, 25:61-67 (1996).

Ceccato et al., "Molecular Dynamics of Novel alpha-Cyclodextrin Adducts Studied by 13C-NMR Relaxation," J. Phys. Chem., 101 (26) p. 5094-5099 (1997).

* cited by examiner

The tumor growth curve as a function of time for the D5W, CPT, irinotecan, LGGG10 at its highest non-toxic dose tested (18 mg CPT/kg), and the other three conjugates with high MW polymer (HGGG6, HG6, HGGG10) at their MTDs

CYCLODEXTRIN-BASED POLYMERS FOR THERAPEUTICS DELIVERY

RELATED APPLICATIONS

This patent application is a continuation application of U.S. patent application Ser. No. 10/656,838, filed on Sep. 5, 2003, which claims the benefit of U.S. Provisional Application Nos. 60/408,855 filed on Sep. 6, 2002, 60/422,830 filed on Oct. 31, 2002, and 60/451,998 filed on Mar. 4, 2003. The specifications of all the above applications are incorporated herein by reference in their entirety.

BACKGROUND OF THE INVENTION

Drug delivery of some small molecule therapeutic agents, such as camptothecin, has been problematic due to their poor pharmacological profiles. These therapeutic agents often have low aqueous solubility, their bioactive forms exist in equilibrium with an inactive form, or high systemic concentrations of the agents lead to toxic side-effects. Some approaches to circumvent the problem of their delivery have been to conjugate the agent directly to a water-soluble polymer such as hydroxypropyl methacrylate (HPMA), polyethyleneglycol, and poly-L-glutamic acid. In some cases, such conjugates have been successful in solubilizing or stabilizing the bioactive form of the therapeutic agent, or achieving a sustained release formulation which circumvents complications associated with high systemic concentrations of the agent.

Another approach to the drug delivery problem has been to form host/guest inclusion complexes between the therapeutic agent and cyclodextrins or derivatives thereof. Cyclodextrins ($\alpha, \beta, \gamma$) and their oxidized forms have unique physico-chemical properties such as good water solubility, low toxicity and low immune response. To date, most of the drug delivery studies with cyclodextrins have focused on their ability to form supra-molecular complexes, wherein cyclodextrins form host/guest inclusion complexes with therapeutic molecules and thus alter the physical, chemical, and/or biological properties of these guest molecules.

U.S. Pat. No. 5,276,088 describes a method for synthesizing cyclodextrin-containing polymers by either reacting polyvinyl alcohol or cellulose or derivatives thereof with cyclodextrin derivatives, or by copolymerization of a cyclodextrin derivative with vinyl acetate or methyl methacrylate.

U.S. Pat. No. 5,855,900 describes a biodegradable cyclodextrin-containing polymer. The patent discloses a supramolecular-structured biodegradable polymeric assembly comprising a plurality of drug-modified $\alpha, \beta, \gamma$-cyclodextrins and a linear polymeric chain threading through the structural cavity of the cyclodextrins.

There is an ongoing need for new approaches to the delivery of small therapeutic agents that have poor pharmacological profiles such as camptothecin, paclitaxel, doxorubicin, and cyclosporine A.

SUMMARY OF THE INVENTION

The present invention relates to novel compositions of polymer conjugates, defined as polymeric materials covalently coupled to therapeutic/bioactive agents, as carriers for therapeutics delivery. In one aspect, the present invention provides water-soluble, biocompatible polymer conjugates comprising a water-soluble, biocompatible polymer covalently attached to bioactive moieties through attachments that are cleaved under biological conditions to release the bioactive moieties. In certain such embodiments, the polymer comprises cyclic moieties alternating with linker moieties that connect the cyclic structures, e.g., into linear or branched polymers, preferably linear polymers. The polymer may be a polycation, polyanion, or non-ionic polymer. The bioactive agent, which may be a therapeutic agent, a diagnostic agent, or an adjuvant, preferably makes up at least 5%, 10%, 15%, 20%, 25%, 30%, or even 35% by weight of the conjugate. In certain embodiments, the rate of drug release is dependent primarily upon the rate of hydrolysis. In certain other embodiments, the rate of drug release is dependent primarily on enzymatic cleavage.

The present invention provides cyclodextrin-containing polymeric compounds for use in drug delivery of these therapeutic agents. The invention also provides compounds for use in controlled drug delivery which are capable of releasing a therapeutic agent in a targeted, predictable, and controlled rate.

Accordingly, one aspect of the present invention is a polymer conjugate comprising cyclodextrin moieties, a therapeutic agent, and an optional ligand targeting agent. The polymer may be linear or branched, and may be formed via polycondensation of cyclodextrin-containing monomers, copolymerization between one or more cyclodextrin-containing monomers and one or more comonomers which do not contain cyclodextrin moieties. Furthermore, the present invention also contemplates cyclodextrin-containing polymers formed by grafting cyclodextrin moieties to an already formed polymer. The cyclodextrin moieties contemplated by the present invention include, but are not limited to, $\alpha$, $\beta$, and $\gamma$ cyclodextrins and oxidized forms thereof. Depending on the drug/polymer ratio desired, the therapeutic agent may be attached to a monomer via an optional linker prior to the polymerization step, or may be subsequently grafted onto the polymer via an optional linker. Likewise, the targeting ligand may be attached to a monomer via an optional linker prior the polymerization step, or may be subsequently grafted onto the polymer via an optional linker, or may be attached to the polymer as an inclusion complex or host-guest interactions.

To illustrate further, one embodiment of the invention is a polymeric compound represented by Formula I:

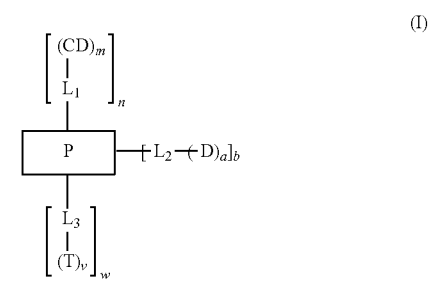

wherein

P represents a linear or branched polymer chain;

CD represents a cyclic moiety such as a cyclodextrin moiety;

$L_1$, $L_2$ and $L_3$, independently for each occurrence, may be absent or represent a linker group;

D, independently for each occurrence, represents a therapeutic agent or a prodrug thereof;

T, independently for each occurrence, represents a targeting ligand or precursor thereof;

a, m, and v, independently for each occurrence, represent integers in the range of 1 to 10 (preferably 1 to 8, 1 to 5, or even 1 to 3);

b represents an integer in the range of 1 to about 30,000 (preferably <25,000, <20,000, <15,000, <10,000, <5,000, <1,000, <500, <100, <50, <25, <10, or even <5); and n and w, independently for each occurrence, represents an integer in the range of 0 to about 30,000 (preferably <25,000, <20,000, <15,000, <10,000, <5,000, <1,000, <500, <100, <50, <25, <10, or even <5), wherein either the polymer chain comprises cyclodextrin moieties or n is at least 1.

Another embodiment of the present invention is a compound represented by Formula II:

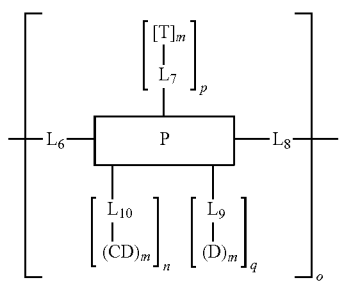

(II)

wherein

P represents a monomer unit of a polymer;

T, independently for each occurrence, represents a targeting ligand or a precursor thereof;

$L_6$, $L_7$, $L_8$, $L_9$ and $L_{10}$, independently for each occurrence, may be absent or represent a linker group;

CD, independently for each occurrence, represents a cyclic moiety such as a cyclodextrin moiety or a derivative thereof;

D, independently for each occurrence, represents a therapeutic agent or a prodrug form thereof;

m, independently for each occurrence, represents an integer in the range of 1 to 10 (preferably 1 to 8, 1 to 5, or even 1 to 3);

o represents an integer in the range of 1 to about 30,000 (preferably <25,000, <20,000, <15,000, <10,000, <5,000, <1,000, <500, <100, <50, <25, <10, or even <5); and p, n, and q, independently for each occurrence, represent an integer in the range of 0 to 10 (preferably 0 to 8, 0 to 5, 0 to 3, or even 0 to about 2), wherein CD and D are preferably each present at least 1 location (preferably at least 5, 10, 25, 50 or even >100 locations) in the compound.

Another embodiment of the present invention is a compound represented by Formula III:

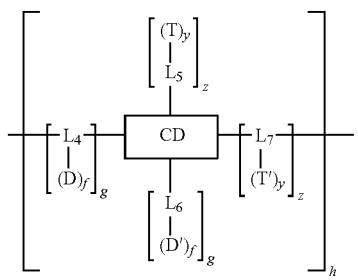

wherein

CD represents a cyclic moiety such as a cyclodextrin moiety, or derivative thereof;

$L_4$, $L_5$, $L_6$, and $L_7$, independently for each occurrence, may be absent or represent a linker group;

D and D', independently for each occurrence, represent the same or different therapeutic agent or prodrugs thereof;

T and T', independently for each occurrence, represent the same or different targeting ligand or precursor thereof;

f and y, independently for each occurrence, represent an integer in the range of 1 and 10 (preferably 1 to 8, 1 to 5, or even 1 to 3);

g and z, independently for each occurrence, represent an integer in the range of 0 and 10 (preferably 0 to 8, 0 to 5, 0 to 3, or even 0 to about 2); and h represents an integer in the range of 1 and 30,000 (preferably <25,000, <20,000, <15,000, <10,000, <5,000, <1,000, <500, <100, <50, <25, <10, or even <5), wherein at least one occurrence (and preferably at least 5, 10, or even at least 20, 50, or >100 occurrences) of g represents an integer greater than 0.

Another aspect of the present invention is a method for preparing the therapeutic cyclodextrin-containing polymeric conjugates described herein.

Another aspect of the present invention is a pharmaceutical composition comprising a compound or polymer as discussed above.

Another aspect of the present invention is a pharmaceutical dosage form comprising a polymeric conjugate as described herein.

Another aspect of the present invention is a method for treating a subject comprising administering a therapeutically effective amount of any of the polymeric conjugates described herein.

Another aspect of the present invention is a method of conducting a pharmaceutical business comprising manufacturing, licensing, or distributing kits containing or relating to any of the polymeric conjugates described herein.

In certain embodiments, these therapeutic polymer conjugates improve drug stability and/or solubility of the therapeutic agent when used in vivo. Furthermore, by selecting from a variety of linker groups, the polymer conjugates present methods for controlled release of the therapeutic and/or bioactive agents, or improve the in vivo safety and/or therapeutic efficacy of the therapeutic/bioactive agent. In certain embodiments, the polymer conjugates are bioerodable or biodegradable.

DETAILED DESCRIPTION OF THE INVENTION

I. Overview

Figure 1:
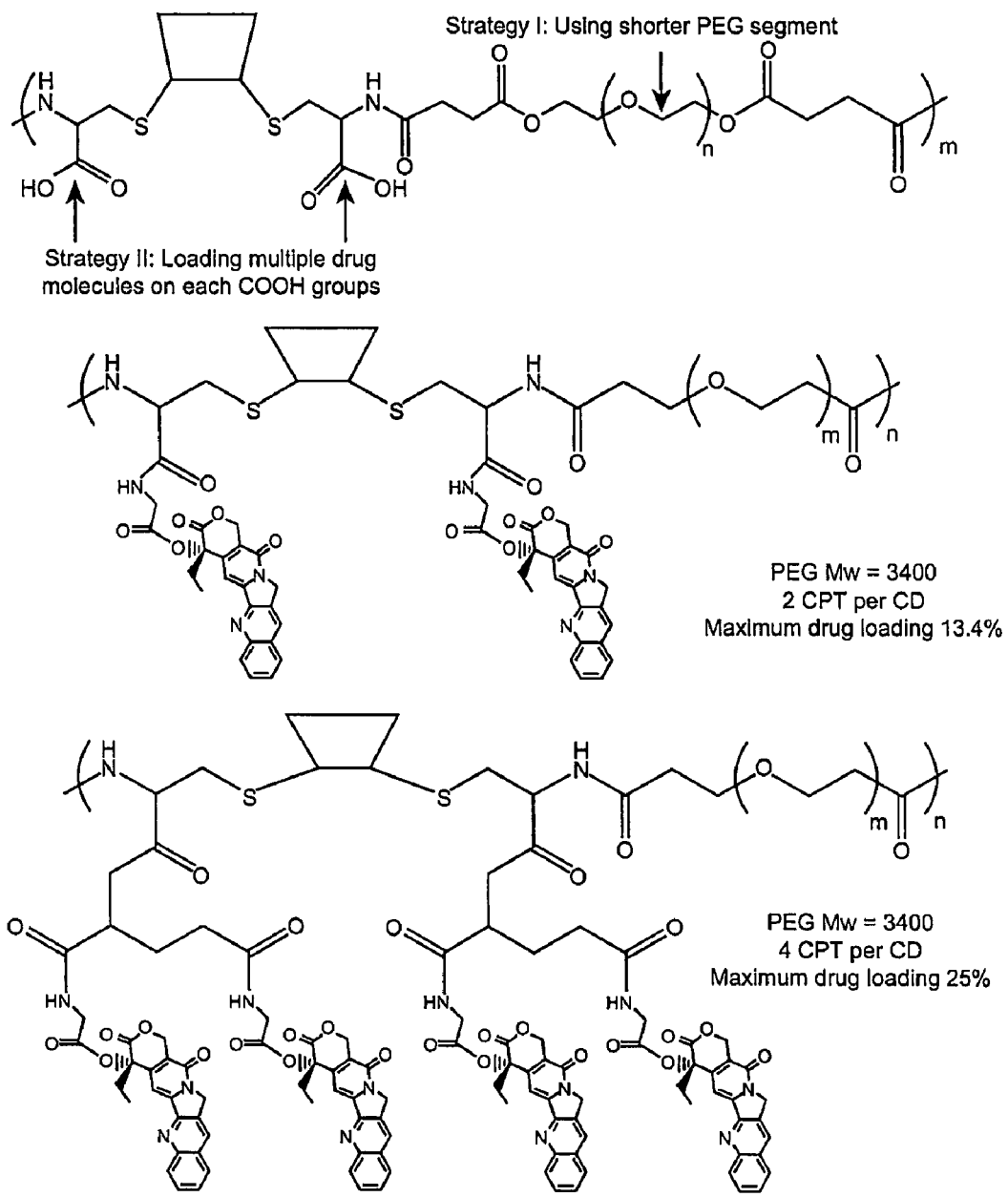
FIG. 1 shows strategies for varying polymer conjugates to tune their characteristics.

The present invention relates to novel compositions of therapeutic cyclodextrin-containing polymeric compounds designed for drug delivery of therapeutic agents. In certain embodiments, these cyclodextrin-containing polymers improve drug stability and/or solubility, and/or reduce toxicity, and/or improve efficacy of the small molecule therapeutic when used in vivo. In certain embodiments, the polymers can be used for delivery of therapeutics such as camptothecin, taxol, doxorubicin, and amphotericin. Furthermore, by selecting from a variety of linker groups, and/or targeting ligands, the rate of drug release from the polymers can be attenuated for controlled delivery. The invention also relates to methods of treating subjects with the therapeutic compositions described herein. The invention further relates to methods for conducting a pharmaceutical business comprising manufacturing, licensing, or distributing kits containing or relating to the polymeric compounds described herein.

More generally, the present invention provides water-soluble, biocompatible polymer conjugates comprising a water-soluble, biocompatible polymer covalently attached to bioactive moieties through attachments that are cleaved under biological conditions to release the bioactive moieties. In certain such embodiments, the polymer comprises cyclic moieties alternating with linker moieties that connect the cyclic structures, e.g., into linear or branched polymers, preferably linear polymers. The cyclic moieties may be any suitable cyclic structures, such as cyclodextrins, crown ethers (e.g., 18-crown-6, 15-crown-5, 12-crown-4, etc.), cyclic oligopeptides (e.g., comprising from 5 to 10 amino acid residues), cryptands or cryptates (e.g., cryptand[2.2.2], cryptand-2,1,1, and complexes thereof), calixarenes, or cavitands, or any combination thereof. Preferably, the cyclic structure is (or is modified to be) water-soluble. In certain embodiments, e.g., where a linear polymer is desired, the cyclic structure is selected such that under polymerization conditions, exactly two moieties of each cyclic structure are reactive with the linker moieties, such that the resulting polymer comprises (or consists essentially of) an alternating series of cyclic moieties and linker moieties, such as at least four of each type of moiety. Suitable difunctionalized cyclic moieties include many that are commercially available and/or amenable to preparation using published protocols. In certain embodiments, conjugates are soluble in water to a concentration of at least 0.1 g/mL, preferably at least 0.25 g/mL.

The polymer may be a polycation, polyanion, or non-ionic polymer. A polycationic or polyanionic polymer has at least one site that bears a positive or negative charge, respectively. In certain such embodiments, at least one of the linker moiety and the cyclic moiety comprises such a charged site, so that every occurrence of that moiety includes a charged site.

The bioactive agent, which may be a therapeutic agent, a diagnostic agent, or an adjuvant (such as a radiosensitizer, or a compound that lacks significant activity administered alone but that potentiates the activity of another therapeutic agent), preferably makes up at least 5%, 10%, 15%, 20%, 25%, 30%, or even 35% by weight of the conjugate. In preferred embodiments, administration of the polymer to a patient results in release of the bioactive agent over a period of at least 6 hours, preferably at least 12 or 18 hours. For example, the agent may be released over a period of time ranging from 6 hours to a month, 6 hours to two weeks, 6 hours to 3 days, etc. In certain embodiments, the rate of drug release is dependent primarily upon the rate of hydrolysis (as opposed to enzymatic cleavage), e.g., the rate of release changes by less than a factor of 5, preferably less than a factor of 2, in the presence of hydrolytic enzymes. In other embodiments, the rate of drug release may be dependent primarily on the rate of enzymatic cleavage.

Polymeric conjugates of the present invention may be useful to improve solubility and/or stability of a bioactive/therapeutic agent, reduce drug-drug interactions, reduce interactions with blood elements including plasma proteins, reduce or eliminate immunogenicity, protect the agent from metabolism, modulate drug-release kinetics, improve circulation time, improve drug half-life (e.g., in the serum, or in selected tissues, such as tumors), attenuate toxicity, improve efficacy, normalize drug metabolism across subjects of different species, ethnicities, and/or races, and/or provide for targeted delivery into specific cells or tissues. Poorly soluble and/or toxic compounds may benefit particularly from incorporation into polymeric compounds of the invention.

II. Definitions (a) General Terms

An 'adjuvant', as the term is used herein, is a compound that has little or no therapeutic value on its own, but increases the effectiveness of a therapeutic agent. Exemplary adjuvants include radiosensitizers, transfection-enhancing agents (such as chloroquine and analogs thereof), chemotactic agents and chemoattractants, peptides that modulate cell adhesion and/or cell mobility, cell permeabilizing agents, inhibitors of multidrug resistance and/or efflux pumps, etc.

The term "agonist", as used herein, is meant to refer to an agent that mimics or up-regulates (e.g., potentiates or supplements) the bioactivity of a protein of interest, or an agent that facilitates or promotes (e.g., potentiates or supplements) an interaction among polypeptides or between a polypeptide and another molecule (e.g., a steroid, hormone, nucleic acids, small molecules etc.). An agonist can be a wild-type protein or derivative thereof having at least one bioactivity of the wild-type protein. An agonist can also be a small molecule that up-regulates the expression of a gene or which increases at least one bioactivity of a protein. An agonist can also be a protein or small molecule which increases the interaction of a polypeptide of interest with another molecule, e.g., a target peptide or nucleic acid.

"Antagonist" as used herein is meant to refer to an agent that down-regulates (e.g., suppresses or inhibits) the bioactivity of a protein of interest, or an agent that inhibits/suppresses or reduces (e.g., destabilizes or decreases) interaction among polypeptides or other molecules (e.g., steroids, hormones, nucleic acids, etc.). An antagonist can also be a compound that down-regulates the expression of a gene of interest or which reduces the amount of the wild-type protein present. An antagonist can also be a protein or small molecule which decreases or inhibits the interaction of a polypeptide of interest with another molecule, e.g., a target peptide or nucleic acid.

The terms "biocompatible polymer" and "biocompatibility" when used in relation to polymers are art-recognized. For example, biocompatible polymers include polymers that are neither themselves toxic to the host (e.g., an animal or human), nor degrade (if the polymer degrades) at a rate that produces monomeric or oligomeric subunits or other byproducts at toxic concentrations in the host. In certain embodiments of the present invention, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible. Hence, a subject composition may comprise 99%, 98%, 97%, 96%, 95%, 90% 85%, 80%, 75% or even less of biocompatible polymers, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1 M NaOH at 37° C. until complete degradation is observed. The solution is then neutralized with 1 M HCl. About 200 µL of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers and formulations of the present invention may also be evaluated by well-known in vivo tests, such as subcutaneous implantations in rats to confirm that they do not cause significant levels of irritation or inflammation at the subcutaneous implantation sites.

The term "biodegradable" is art-recognized, and includes polymers, compositions and formulations, such as those described herein, that are intended to degrade during use. Biodegradable polymers typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to sidechain or that connects a side chain to the polymer backbone. For example, a therapeutic agent or other chemical moiety attached as a side chain to the polymer backbone may be released by biodegradation. In certain embodiments, one or the other or both general types of biodegradation may occur during use of a polymer.

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of an implant, and the mode and location of administration. For example, the greater the molecular weight, the higher the degree of crystallinity, and/or the greater the biostability, the biodegradation of any biodegradable polymer is usually slower. The term "biodegradable" is intended to cover materials and processes also termed "bioerodible".

In certain embodiments wherein the biodegradable polymer also has a therapeutic agent or other material associated with it, the biodegradation rate of such polymer may be characterized by a release rate of such materials. In such circumstances, the biodegradation rate may depend on not only the chemical identity and physical characteristics of the polymer, but also on the identity of material(s) incorporated therein. Degradation of the subject compositions includes not only the cleavage of intramolecular bonds, e.g., by oxidation and/or hydrolysis, but also the disruption of intermolecular bonds, such as dissociation of host/guest complexes by competitive complex formation with foreign inclusion hosts.

In certain embodiments, polymeric formulations of the present invention biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between 25 and 37° C. In other embodiments, the polymer degrades in a period of between about one hour and several weeks, depending on the desired application.

As used herein the term "bioerodable" refers to polymers which deliver sustained effective amounts of therapeutic agent to target tissue over desired extended periods of time. Thus, a polymer according to the invention in the biological environment of host tissue and the like, in one aspect, is subjected to hydrolytic enzymes and oxidative species under, and in proportion to, the host's inflammatory response. This results in release of the therapeutic agent via the breaking of the covalent linked bonds. Thus, in certain embodiments, the materials of the invention utilize the mammal's own wound-healing repair process in being degraded thereby, as hereinbefore described.

The biodegradable polymers polylactic acid, polyglycolic acid, and polylactic-glycolic acid copolymer (PLGA), have been investigated extensively for nanoparticle formulation. These polymers are polyesters that, upon implantation in the body, undergo simple hydrolysis. The products of such hydrolysis are biologically compatible and metabolizable moieties (e.g., lactic acid and glycolic acid), which are eventually removed from the body by the citric acid cycle. Polymer biodegradation products are formed at a very slow rate, and hence do not affect normal cell function. Several implant studies with these polymers have proven safe in drug delivery applications, used in the form of matrices, microspheres, bone implant materials, surgical sutures, and also in contraceptive applications for long-term effects. These polymers are also used as graft materials for artificial organs, and recently as basement membranes in tissue engineering investigations. Nature Med. 824-826 (1996). Thus, these polymers have been time-tested in various applications and proven safe for human use. Most importantly, these polymers are FDA-approved for human use.

When polymers are used for delivery of pharmacologically active agents in vivo, it is essential that the polymers themselves be nontoxic and that they degrade into non-toxic degradation products as the polymer is eroded by the body fluids. Many synthetic biodegradable polymers, however, yield oligomers and monomers upon erosion in vivo that adversely interact with the surrounding tissue. D. F. Williams, J. Mater. Sci. 1233 (1982). To minimize the toxicity of the intact polymer carrier and its degradation products, polymers have been designed based on naturally occurring metabolites. Probably the most extensively studied examples of such polymers are the polyesters derived from lactic or glycolic acid and polyamides derived from amino acids.

A number of bioerodable or biodegradable polymers are known and used for controlled release of pharmaceuticals. Such polymers are described in, for example, U.S. Pat. No. 4,291,013; U.S. Pat. No. 4,347,234; U.S. Pat. No. 4,525,495; U.S. Pat. No. 4,570,629; U.S. Pat. No. 4,572,832; U.S. Pat. No. 4,587,268; U.S. Pat. No. 4,638,045; U.S. Pat. No. 4,675,381; U.S. Pat. No. 4,745,160; and U.S. Pat. No. 5,219,980.

A biohydrolyzable bond (e.g., ester, amide, carbonate, carbamates, or imide) refers to a bond that is cleaved (e.g., an ester is cleaved to form a hydroxyl and a carboxylic acid) under physiological conditions. Physiological conditions include the acidic and basic environments of the digestive tract (e.g., stomach, intestines, etc.), acidic environment of a tumor, enzymatic cleavage, metabolism, and other biological processes, and preferably refer to physiological conditions in a vertebrate, such as a mammal.

As used herein the terms "comonomer A precursor", "linker", "linker group", and "linker moiety" refer to any straight chain or branched, symmetric or asymmetric compound which upon reaction with a cyclodextrin monomer precursor or other suitable cyclic moiety links two such moieties together. In certain embodiments, a comonomer A precursor is a compound containing at least two functional groups through which reaction and thus linkage of the cyclodextrin monomers can be achieved. Examples of functional groups, which may be the same or different, terminal or internal, of each comonomer A precursor include, but are not limited to, amino, acid, imidazole, hydroxyl, thio, acyl halide, —C=C—, or —C≡C— groups and derivatives thereof. In preferred embodiments, the two functional groups are the same and are located at termini of the comonomer. In certain embodiments, a comonomer A precursor contains one or more pendant groups with at least one functional group through which reaction and thus linkage of therapeutic agent or targeting ligand can be achieved, or branched polymerization can be achieved. Examples of functional groups, which may be the same or different, terminal or internal, of each comonomer A precursor pendant group include, but are not limited, to amino, acid, imidazole, hydroxyl, thiol, acyl halide, ethylene, and ethyne groups and derivatives thereof. In certain embodiments, the pendant group is a (un)substituted branched, cyclic or straight chain C1-C10 (preferably C1-C6) alkyl, or arylalkyl optionally containing one or more heteroatoms, e.g., N, O, S, within the chain or ring.

Upon copolymerization of a comonomer A precursor with a cyclodextrin monomer precursor, two cyclodextrin monomers may be linked together by joining the primary hydroxyl side of one cyclodextrin monomer with the primary hydroxyl side of another cyclodextrin monomer, by joining the secondary hydroxyl side of one cyclodextrin monomer with the secondary hydroxyl side of another cyclodextrin monomer, or by joining the primary hydroxyl side of one cyclodextrin monomer with the secondary hydroxyl side of another cyclodextrin monomer. Accordingly, combinations of such linkages may exist in the final copolymer. Both the comonomer A precursor and the comonomer A of the final copolymer may be neutral, cationic (e.g., by containing protonated groups such as, for example, quaternary ammonium groups), or anionic (e.g., by containing deprotonated groups, such as, for example, sulfate, phosphate, borinate or carboxylate). The charge of comonomer A of the copolymer may be adjusted by adjusting pH conditions. Examples of suitable comonomer A precursors include, but are not limited to succinimide (e.g., dithiobis(succinimidyl propionate) DSP, and dissucinimidyl suberate (DSS)), glutamates, and aspartates).

The cyclodextrin-containing polymers of the present invention may be linear, branched or grafted. As used herein, the term "linear cyclodextrin-containing polymer" refers to a polymer comprising (α, β, or γ) cyclodextrin molecules, or derivatives thereof which are inserted within a polymer chain. As used herein, the term "grafted cyclodextrin-containing polymer" refers to a polymer comprising (α, β, or γ) cyclodextrin molecules, or derivatives thereof which are pendant off of the polymer chain. The term "graft polymer" as used herein refers to a polymer molecule which has additional moieties attached as pendent groups along a polymer backbone. The term "graft polymerization" denotes a polymerization in which a side chain is grafted onto a polymer chain, which side chain consists of one or several other monomers. The properties of the graft copolymer obtained such as, for example, solubility, melting point, water absorption, wettability, mechanical properties, adsorption behavior, etc., deviate more or less sharply from those of the initial polymer as a function of the type and amount of the grafted monomers. The term "grafting ratio", as used herein, means the weight percent of the amount of the monomers grafted based on the weight of the polymer. As used herein, a branched cyclodextrin-containing polymer refers to a polymer backbone with a plurality of branch points, wherein each branch point is a starting point of yet another strand of the polymer backbone, and each section of polymer backbone may have a plurality of (α, β, or γ) cyclodextrin molecules, or derivatives thereof, inserted into or grafted onto the chain.

The term "cyclodextrin moiety" refers to (α, β, or γ) cyclodextrin molecules or derivatives thereof, which may be in their oxidized or reduced forms. Cyclodextrin moieties may comprise optional linkers. Optional therapeutic agents and/or targeting ligands may be further linked to these moieties via an optional linker. The linkage may be covalent (optionally via biohydrolyzable bonds, e.g., esters, amides, carbamates, and carbonates) or may be a host-guest complex between the cyclodextrin derivative and the therapeutic agent and/or targeting ligand or the optional linkers of each. Cyclodextrin moieties may further include one or more carbohydrate moieties, preferably simple carbohydrate moieties such as galactose, attached to the cyclic core, either directly (i.e., via a carbohydrate linkage) or through a linker group.

The term "$ED_{50}$" means the dose of a drug that produces 50% of its maximum response or effect.

An 'effective amount' of a subject compound, with respect to the subject method of treatment, refers to an amount of the therapeutic in a preparation which, when applied as part of a desired dosage regimen provides a benefit according to clinically acceptable standards for the treatment or prophylaxis of a particular disorder.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

"Instruction(s)" as used herein means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

"Kit" as used herein means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

The term "$LD_{50}$" means the dose of a drug that is lethal in 50% of test subjects.

A "patient" or "subject" to be treated by the subject method can mean either a human or non-human subject.

The "polymerizations" of the present invention include radical, anionic, and cationic mechanisms, as well as reactions of bifunctional molecules (analogous to the formation of nylon, e.g., reacting molecules each of which bears two or more different reactive moieties that react with each other (but, preferably, are disfavored from reacting intramolecularly by steric, conformational, or other constraints), or reacting two or more different compounds, each compound bearing two or more reactive moieties that react only with reactive moieties of different compounds (i.e., intermolecularly)), as well as metal-catalyzed polymerizations such as olefin metathesis, and other polymerization reactions known to those of skill in the art.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, where as if it is administered after manifestation of the unwanted condition, the treatment is therapeutic, (i.e., it is intended to diminish, ameliorate, or stabilize the existing unwanted condition or side effects thereof).

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the frequency of, or alternatively delaying, pain sensations experienced by subjects in a treated population versus an untreated control population.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. More particularly, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrhythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein the term "low aqueous solubility" refers to water insoluble compounds having poor solubility in water, that is <5 mg/ml at physiological pH (6.5-7.4). Preferably, their water solubility is <1 mg/ml, more preferably <0.1 mg/ml. It is desirable that the drug is stable in water as a dispersion; otherwise a lyophilized or spray-dried solid form may be desirable.

Examples of some preferred water-insoluble drugs include immunosuppressive agents such as cyclosporins including cyclosporine (cyclosporin A), immunoactive agents, antiviral and antifungal agents, antineoplastic agents, analgesic and anti-inflammatory agents, antibiotics, anti-epileptics, anesthetics, hypnotics, sedatives, antipsychotic agents, neuroleptic agents, antidepressants, anxiolytics, anticonvulsant agents, antagonists, neuron blocking agents, anticholinergic and cholinomimetic agents, antimuscarinic and muscarinic agents, antiadrenergic and antiarrhythmics, antihypertensive agents, hormones, and nutrients. A detailed description of these and other suitable drugs may be found in Remington's Pharmaceutical Sciences, 18th edition, 1990, Mack Publishing Co. Philadelphia, Pa.

The term "therapeutic index" refers to the therapeutic index of a drug defined as $LD_{50}/ED_{50}$.

A "therapeutically effective amount" of a compound, with respect to a method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

A "therapeutically effective daily dosage" of a compound, with respect to a method of treatment, refers to an amount of the compound(s) in a preparation which, when administered as part of a desired daily dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

(b) Chemical Terms

An aliphatic chain comprises the classes of alkyl, alkenyl and alkynyl defined below. A straight aliphatic chain is limited to unbranched carbon chain radicals. As used herein, the term "aliphatic group" refers to a straight chain, branched-chain, or cyclic aliphatic hydrocarbon group and includes saturated and unsaturated aliphatic groups, such as an alkyl group, an alkenyl group, and an alkylyl group.

Alkyl refers to a fully saturated branched or unbranched carbon chain radical having the number of carbon atoms specified, or up to 30 carbon atoms if no specification is made. For example, alkyl of 1 to 8 carbon atoms refers to radicals such as methyl, ethyl, propyl, butyl, pentyl, hexyl, heptyl, and octyl, and those radicals which are positional isomers of these radicals. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, a cyano, a nitro, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like. Exemplary substituted alkyls are described below. Cycloalkyls can be further substituted with alkyls, alkenyls, alkoxyls, alkylthios, aminoalkyls, carbonyl-substituted alkyls, —CF3, —CN, and the like.

Unless the number of carbons is otherwise specified, "lower alkyl", as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —(S)-alkyl, —(S)-alkenyl, —(S)-alkynyl, and —(S)—(CH2)m-R1, wherein m and R1 are defined below. Representative alkylthio groups include methylthio, ethylthio, and the like.

Alkenyl refers to any branched or unbranched unsaturated carbon chain radical having the number of carbon atoms specified, or up to 26 carbon atoms if no limitation on the number of carbon atoms is specified; and having 1 or more double bonds in the radical. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl and tetracosenyl, in their various isomeric forms, where the unsaturated bond(s) can be located anywhere in the radical and can have either the (Z) or the a) configuration about the double bond(s).

Alkynyl refers to hydrocarbyl radicals of the scope of alkenyl, but having 1 or more triple bonds in the radical.

The terms "alkoxyl" or "alkoxy" as used herein refers to an alkyl group, as defined below, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH2)m-R1, where m and R1 are described below.

The terms "amine" and "amino" are art-recognized and refer to both unsubstituted and substituted amines, e.g., a moiety that can be represented by the general formulae:

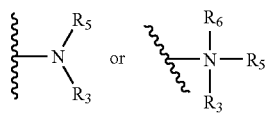

wherein R3, R5 and R6 each independently represent a hydrogen, an alkyl, an alkenyl, —(CH2)m-R1, or R3 and R5 taken together with the N atom to which they are attached complete a heterocycle having from 4 to 8 atoms in the ring structure; R1 represents an alkenyl, aryl, cycloalkyl, a cycloalkenyl, a heterocyclyl or a polycyclyl; and m is zero or an integer in the range of 1 to 8. In preferred embodiments, only one of R3 or R5 can be a carbonyl, e.g., R3, R5 and the nitrogen together do not form an imide. In even more preferred embodiments, R3 and R5 (and optionally R6) each independently represent a hydrogen, an alkyl, an alkenyl, or —(CH2)m-R1. Thus, the term "alkylamine" as used herein means an amine group, as defined above, having a substituted or unsubstituted alkyl attached thereto, i.e., at least one of R3 and R5 is an alkyl group. In certain embodiments, an amino group or an alkylamine is basic, meaning it has a pKa>7.00. The protonated forms of these functional groups have pK as relative to water above 7.00.

The term "carbonyl" is art-recognized and includes such moieties as can be represented by the general formula:

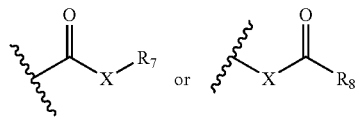

wherein X is a bond or represents an oxygen or a sulfur, and R7 represents a hydrogen, an alkyl, an alkenyl, —(CH2)m-R1 or a pharmaceutically acceptable salt, R8 represents a hydrogen, an alkyl, an alkenyl or —(CH2)m-R1, where m and R1 are as defined above. Where X is an oxygen and R7 or R8 is not hydrogen, the formula represents an "ester". Where X is an oxygen, and R7 is as defined above, the moiety is referred to herein as a carboxyl group, and particularly when R7 is a hydrogen, the formula represents a "carboxylic acid". Where X is an oxygen, and R8 is hydrogen, the formula represents a "formate". In general, where the oxygen atom of the above formula is replaced by sulfur, the formula represents a "thiocarbonyl" group. Where X is a sulfur and R7 or R8 is not hydrogen, the formula represents a "thioester" group. Where X is a sulfur and R7 is hydrogen, the formula represents a "thiocarboxylic acid" group. Where X is a sulfur and R8 is hydrogen, the formula represents a "thioformate" group. On the other hand, where X is a bond, and R7 is not hydrogen, the above formula represents a "ketone" group. Where X is a bond, and R7 is hydrogen, the above formula represents an "aldehyde" group.

The term "derivatized" refers to chemically modifying molecules. The chemical modifications may be artificial such as formation of drugs, natural such as formation of metabolites. The skilled artisan would readily recognize the variety of ways molecules may be modified, such as oxidations, reductions, electrophilic/nucleophilic substitutions, alkylations, ester/amide formations and the like. For example, cyclodextrins of the present invention may be chemically modified by amination, tosylation, or iodination prior to covalently attaching them to the polymeric matrix. Likewise, therapeutic agents may be chemically modified by preparing prodrugs (e.g., glycine-camptothecin).

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —CF3, —CN, or the like.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "hydrocarbyl" refers to a monovalent hydrocarbon radical comprised of carbon chains or rings of up to 26 carbon atoms to which hydrogen atoms are attached. The term includes alkyl, cycloalkyl, alkenyl, alkynyl and aryl groups, groups which have a mixture of saturated and unsaturated bonds, carbocyclic rings and includes combinations of such groups. It may refer to straight chain, branched-chain, cyclic structures or combinations thereof.

The term "hydrocarbylene" refers to a divalent hydrocarbyl radical. Representative examples include alkylene, phenylene, or cyclohexylene. Preferably, the hydrocarbylene chain is fully saturated and/or has a chain of 1-10 carbon atoms.

As used herein, the term "nitro" means —NO2; the term "halogen" designates —F, —Cl, —Br or —I; the term "sulfhydryl" means —SH; the term "hydroxyl" means —OH; and the term "sulfonyl" means —SO2-.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Ms represent methyl, ethyl, phenyl, and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including cis- and trans-isomers, (R)- and (S)-enantiomers, diastereomers, (d)-isomers, (l)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

III. Exemplary Applications of Method and Compositions (a) Exemplary Compositions The present invention includes polymer conjugates, such as cyclodextrin-containing polymer conjugates, wherein one or more therapeutic/bioactive agents are covalently attached. In certain embodiments, the therapeutic agent is a small molecule, a macromolecule, an antibody, a peptide, a protein, an enzyme, a nucleic acid, or a polymer that has therapeutic function. The polymers include linear or branched cyclodextrin-containing polymers and polymers grafted with cyclodextrin. Exemplary cyclodextrin-containing polymers that may be modified as described herein are taught in U.S. Pat. No. 6,509,323, published U.S. application No. 20020151523, and U.S. patent application Ser. Nos. 60/417,373, and 10/372,723. These polymers are useful as carriers for small molecule therapeutic delivery, and may improve drug stability and solubility when used in vivo.

Accordingly, one embodiment of present invention is a polymeric compound represented by Formula I:

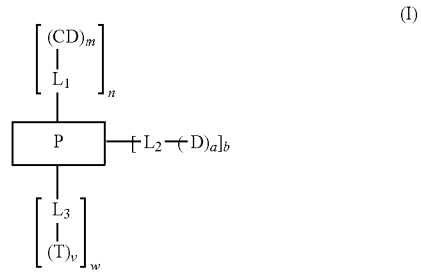

wherein

P represents a linear or branched polymer chain;

CD represents a cyclic moiety such as a cyclodextrin moiety;

$L_1$, $L_2$ and $L_3$, independently for each occurrence, may be absent or represent a linker group;

D, independently for each occurrence, represents a therapeutic agent or a prodrug thereof;

T, independently for each occurrence, represents a targeting ligand or precursor thereof;

a, m, and v, independently for each occurrence, represent integers in the range of 1 to 10 (preferably 1 to 8, 1 to 5, or even 1 to 3);

n and w, independently for each occurrence, represent an integer in the range of 0 to about 30,000 (preferably <25,000, <20,000, <15,000, <10,000, <5,000, <1,000, <500, <100, <50, <25, <10, or even <5); and b represents an integer in the range of 1 to about 30,000 (preferably <25,000, <20,000, <15,000, <10,000, <5,000, <1,000, <500, <100, <50, <25, <10, or even <5), wherein either P comprises cyclodextrin moieties or n is at least 1.

In certain embodiments, P contains a plurality of cyclodextrin moieties within the polymer chain as opposed to the cyclodextrin moieties being grafted on to pendant groups off of the polymeric chain. Thus in certain embodiments, the polymer chain of formula I further comprises n' units of U, wherein n' represents an integer in the range of 1 to about 30,000 (preferably <25,000, <20,000, <15,000, <10,000, <5,000, <1,000, <500, <100; <50, <25, <10, or even <5); and U is represented by the general formula:

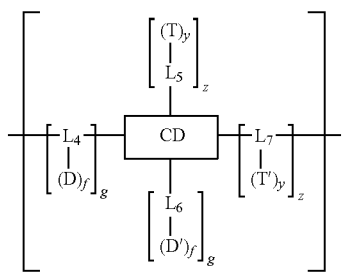

wherein

CD represents a cyclic moiety, such as a cyclodextrin moiety, or derivative thereof;

$L_4$, $L_5$, $L_6$, and $L_7$, independently for each occurrence, may be absent or represent a linker group;

D and D', independently for each occurrence, represent the same or different therapeutic agent or prodrug forms thereof;

T and T', independently for each occurrence, represent the same or different targeting ligand or precursor thereof;

f and y, independently for each occurrence, represent an integer in the range of 1 and 10; and g and z, independently for each occurrence, represent an integer in the range of 0 and 10.

In preferred embodiments, $L_4$ and $L_7$ represent linker groups.

In certain embodiments, the polymer may be selected from polysaccharides, and other non-protein biocompatible polymers, and combinations thereof, that contain at least one terminal hydroxyl group, such as polyvinylpyrrollidone, poly (oxyethylene) glycol (PEG), polysuccinic anhydride, polysebacic acid, PEG-phosphate, polyglutamate, polyethylenimine, maleic anhydride divinylether (DIVMA), cellulose, pullulans, inulin, polyvinyl alcohol (PVA), N-(2-hydroxypropyl) methacrylamide (APMA), dextran and hydroxyethyl starch (HES), and have optional pendant groups for grafting therapeutic agents, targeting ligands and/or cyclodextrin moieties. In certain embodiments, the polymer may be biodegradable such as poly(lactic acid), poly(glycolic acid), poly(alkyl 2-cyanoacrylates), polyanhydrides, and polyorthoesters, or bioerodible such as polylactide-glycolide copolymers, and derivatives thereof, non-peptide polyaminoacids, polyiminocarbonates, poly alpha-amino acids, polyalkyl-cyano-acrylate, polyphosphazenes or acyloxymethyl poly aspartate and polyglutamate copolymers and mixtures thereof.

Another embodiment of the invention is a polymeric compound represented by Formula II:

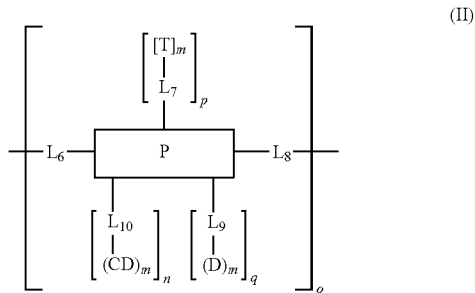

wherein

P represents a monomer unit of a polymer;

T, independently for each occurrence, represents a targeting ligand or a precursor thereof;

$L_6$, $L_7$, $L_8$, $L_9$, and $L_{10}$, independently for each occurrence, may be absent or represent a linker group;

CD, independently for each occurrence, represents a cyclodextrin moiety or a derivative thereof;

D, independently for each occurrence, represents a therapeutic agent, or a prodrug form thereof;

m, independently for each occurrence, represents an integer in the range of 1 to 10 (preferably 1 to 8, 1 to 5, or even 1 to 3);

o represents an integer in the range of 1 to about 30,000 (preferably <25,000, <20,000, <15,000, <10,000, <5,000, <1,000, <500, <100, <50, <25, <10, or even <5); and p, n, and q, independently for each occurrence, represent an integer in the range of 0 to 10 (preferably 0 to 8, 0 to 5, 0 to 3, or even 0 to about 2), wherein CD and D are preferably each present at least 1 location (preferably at least 5, 10, 25, or even 50 or 100 locations) in the compound.

Another embodiment of the invention is a compound represented by Formula III:

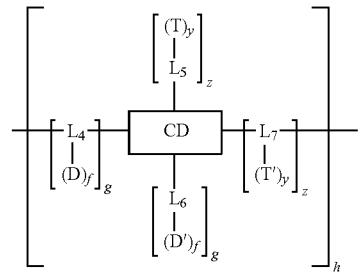

wherein

CD represents a cyclic moiety, such as a cyclodextrin moiety, or derivative thereof;

$L_4$, $L_5$, $L_6$, and $L_7$, independently for each occurrence, may be absent or represent a linker group;

D and D', independently for each occurrence, represent the same or different therapeutic agent or prodrugs thereof;

T and T', independently for each occurrence, represent the same or different targeting ligand or precursor thereof;

f and y, independently for each occurrence, represent an integer in the range of 1 and 10 (preferably 1 to 8, 1 to 5, or even 1 to 3);

g and z, independently for each occurrence, represent an integer in the range of 0 and 10 (preferably 0 to 8, 0 to 5, 0 to 3, or even 0 to about 2); and h represents an integer in the range of 1 and 30,000 (preferably <25,000, <20,000, <15,000, <10,000, <5,000, <1,000, <500, <100, <50, <25, <10, or even <5), wherein at least one occurrence (and preferably at least 5, 10, or even at least 20, 50, or 100 occurrences) of g represents an integer greater than 0.

In preferred embodiments, L4 and L7 represent linker groups.

In certain embodiments, the underlying polymers are linear cyclodextrin-containing polymers, e.g., the polymer backbone includes cyclodextrin moieties. For example, the polymer may be a water-soluble, linear cyclodextrin polymer produced by providing at least one cyclodextrin derivative modified to bear one reactive site at each of exactly two positions, and reacting the cyclodextrin derivative with a linker having exactly two reactive moieties capable of forming a covalent bond with the reactive sites under polymerization conditions that promote reaction of the reactive sites with the reactive moieties to form covalent bonds between the linker and the cyclodextrin derivative, whereby a linear polymer comprising alternating units of cyclodextrin derivatives and linkers is produced. Alternatively the polymer may be a water-soluble, linear cyclodextrin polymer having a linear polymer backbone, which polymer comprises a plurality of substituted or unsubstituted cyclodextrin moieties and linker moieties in the linear polymer backbone, wherein each of the cyclodextrin moieties, other than a cyclodextrin moiety at the terminus of a polymer chain, is attached to two of said linker moieties, each linker moiety covalently linking two cyclodextrin moieties. In yet another embodiment, the polymer is a water-soluble, linear cyclodextrin polymer comprising a plurality of cyclodextrin moieties covalently linked together by a plurality of linker moieties, wherein each cyclodextrin moiety, other than a cyclodextrin moiety at the terminus of a polymer chain, is attached to two linker moieties to form a linear cyclodextrin polymer.

The linker group(s) may be an alkylene chain, a polyethylene glycol (PEG) chain, polysuccinic anhydride, poly-L-glutamic acid, poly(ethyleneimine), an oligosaccharide, an amino acid chain, or any other suitable linkage. In certain embodiments, the linker group itself can be stable under physiological conditions, such as an alkylene chain, or it can be cleavable under physiological conditions, such as by an enzyme (e.g., the linkage contains a peptide sequence that is a substrate for a peptidase), or by hydrolysis (e.g., the linkage contains a hydrolyzable group, such as an ester or thioester). The linker groups can be biologically inactive, such as a PEG, polyglycolic acid, or polylactic acid chain, or can be biologically active, such as an oligo- or polypeptide that, when cleaved from the moieties, binds a receptor, deactivates an enzyme, etc. Various oligomeric linker groups that are biologically compatible and/or bioerodible are known in the art, and the selection of the linkage may influence the ultimate properties of the material, such as whether it is durable when implanted, whether it gradually deforms or shrinks after implantation, or whether it gradually degrades and is absorbed by the body. The linker group may be attached to the moieties by any suitable bond or functional group, including carbon-carbon bonds, esters, ethers, amides, amines, carbonates, carbamates, sulfonamides, etc.

In certain embodiments, the linker group(s) of the present invention represent a hydrocarbylene group wherein one or more methylene groups is optionally replaced by a group Y (provided that none of the Y groups are adjacent to each other), wherein each Y, independently for each occurrence, is selected from, substituted or unsubstituted aryl, heteroaryl, cycloalkyl, heterocycloalkyl, or —O—, C(=X) (wherein X is $NR_1$, O or S), —OC(O)—, —C(=O)O, —$NR_1$—, —$NR_1$CO—, —C(O) $NR_1$—, —S(O)$_n$— (wherein n is 0, 1, or 2), —OC(O)—$NR_1$, —$NR_1$—C(O)—$NR_1$—, —$NR_1$—C($NR_1$)—$NR_1$—, and —B(O$R_1$)—; and $R_1$, independently for each occurrence, represents H or a lower alkyl.

In certain embodiments, the linker group represents a derivatized or non-derivatized amino acid. In certain embodiments, linker groups with one or more terminal carboxyl groups may be conjugated to the polymer. In certain embodiments, one or more of these terminal carboxyl groups may be capped by covalently attaching them to a therapeutic agent, a targeting moiety, or a cyclodextrin moiety via an (thio) ester or amide bond. In still other embodiments, linker groups with one or more terminal hydroxyl, thiol, or amino groups may be incorporated into the polymer. In preferred embodiments, one or more of these terminal hydroxyl groups may be capped by covalently attaching them to a therapeutic agent, a targeting moiety, or a cyclodextrin moiety via an (thio) ester, amide, carbonate, carbamate, thiocarbonate, or thiocarbamate bond. In certain embodiments, these (thio) ester, amide, (thio) carbonate or (thio) carbamates bonds may be biohydrolyzable, i.e., capable of being hydrolyzed under biological conditions.

In certain embodiments, the polymers as described above have polydispersities less than about 3, or even less than about 2.

In certain embodiments, the therapeutic agent is a small molecule, a peptide, a protein, or a polymer that has therapeutic function. In certain embodiments, the agent is an anti-cancer (such as camptothecin or related derivatives), anti-fungal, anti-bacterial, anti-mycotic, or anti-viral therapeutic. In certain embodiments, the agent is a receptor agonist. In certain embodiments, the agent is a receptor antagonist. In certain embodiments, the therapeutic agent is a protease inhibitor. Furthermore, a polymer of the present invention may contain one kind of therapeutic agent, or may contain more than one kind of therapeutic agent. For instance, two or more different cancer drugs, or a cancer drug and an immunosuppressant, or an antibiotic and an anti-inflammatory agent may be grafted on to the polymer via optional linkers. By selecting different linkers for different drugs, the release of each drug may be attenuated to achieve maximal dosage and efficacy.

One embodiment of the present invention provides an improved delivery of certain hydrophobic small molecule therapeutics by covalently conjugating them to cyclodextrin containing polymers. Such conjugation improves the aqueous solubility and hence the bioavailability of the therapeutic agents. Accordingly, in one embodiment of the invention, the therapeutic agent is a hydrophobic compound with a log P>0.4, >0.6, >0.8, >1, >2, >3, >4, or even >5. In other embodiments, a hydrophobic therapeutic agent, such as camptothecin, may be conjugated to another compound, such as an amino acid, prior to covalently attaching the conjugate on to the polymer. Examples of amino acid derivatized camptothecin molecules are illustrated in Scheme V.

The polymer conjugates of the present invention preferably have molecular weights in the range of 10,000 to 500,000; 30,000 to 200,000; or even 70,000 to 150,000 amu.

In certain embodiments, the cyclodextrin moieties make up at least about 2%, 5% or 10% by weight, up to 20%, 30%, 50% or even 80% of the cyclodextrin-modified polymer by weight. In certain embodiments, the therapeutic agents, or targeting ligands make up at least about 1%, 5%, 10% or 15%, 20%, 25%, 30% or even 35% of the cyclodextrin-modified polymer by weight. Number-average molecular weight ($M_n$) may also vary widely, but generally fall in the range of about 1,000 to about 500,000 daltons, preferably from about 5000 to about 200,000 daltons and, even more preferably, from about 10,000 to about 100,000. Most preferably, $M_n$ varies between about 12,000 and 65,000 daltons. In certain other embodiments, $M_n$ varies between about 3000 and 150,000 daltons. Within a given sample of a subject polymer, a wide range of molecular weights may be present. For example, molecules within the sample may have molecular weights that differ by a factor of 2, 5, 10, 20, 50, 100, or more, or that differ from the average molecular weight by a factor of 2, 5, 10, 20, 50, 100, or more. Exemplary cyclodextrin moieties include cyclic-structures consisting essentially of from 7 to 9 saccharide moieties, such as cyclodextrin and oxidized cyclodextrin. A cyclodextrin moiety optionally comprises a linker moiety that forms a covalent linkage between the cyclic structure and the polymer backbone, preferably having from 1 to 20 atoms in the chain, such as alkyl chains, including dicarboxylic acid derivatives (such as glutaric acid derivatives, succinic acid derivatives, and the like), and heteroalkyl chains, such as oligoethylene glycol chains.

Cyclodextrins are cyclic polysaccharides containing naturally occurring D-(+)-glucopyranose units in an α-(1,4) linkage. The most common cyclodextrins are alpha ((α)-cyclodextrins, beta (β)-cyclodextrins and gamma (γ)-cyclodextrins which contain, respectively six, seven, or eight glucopyranose units. Structurally, the cyclic nature of a cyclodextrin forms a torus or donut-like shape having an inner apolar or hydrophobic cavity, the secondary hydroxyl groups situated on one side of the cyclodextrin torus and the primary hydroxyl groups situated on the other. Thus, using (β)-cyclodextrin as an example, a cyclodextrin is often represented schematically as follows.

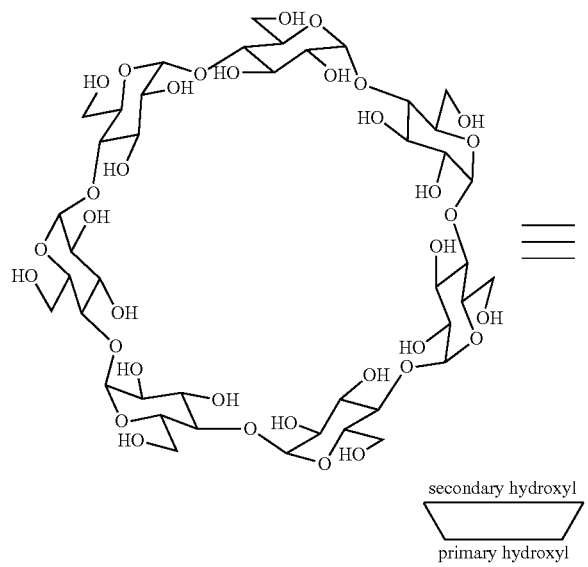

The side on which the secondary hydroxyl groups are located has a wider diameter than the side on which the primary hydroxyl groups are located. The present invention contemplates covalent linkages to cyclodextrin moieties on the primary and/or secondary hydroxyl groups. The hydrophobic nature of the cyclodextrin inner cavity allows for host-guest inclusion complexes of a variety of compounds, e.g., adamantane. (Comprehensive Supramolecular Chemistry, Volume 3, J. L. Atwood et al., eds., Pergamon Press (1996); T. Cserhati, Analytical Biochemistry, 225:328-332 (1995); Husain et al., Applied Spectroscopy, 46:652-658 (1992); FR 2 665 169). Additional methods for modifying polymers are disclosed in Suh, J. and Noh, Y., *Bioorg. Med. Chem. Lett.* 1998, 8, 1327-1330.

In certain embodiments, the present invention contemplates linear, water-soluble, cyclodextrin-containing polymer, wherein a plurality of bioactive moieties are covalently attached to the polymer through attachments that are cleaved under biological conditions to release the bioactive moieties, wherein administration of the polymer to a patient results in release of the bioactive agent over a period of at least 2, 3, 5, 6, 8, 10, 15, 20, 24, 36, 48 or even 72 hours.

In certain embodiments, the present invention contemplates attenuating the rate of release of the therapeutic agent by introducing various linking groups between the therapeutic agent and/or targeting ligand and the polymer. Thus, in certain embodiments, the polymeric therapeutics of the present invention are compositions for controlled delivery of therapeutic agents. One skilled in the art would also recognize that by labeling the therapeutic agent and/or targeting ligand with radionuclei, or by forming complexes of NMR active nuclei, e.g., technetium, gadolinium, or dysprosium, the polymers of the present invention can achieve a dual diagnostic/therapeutic utility.

In other embodiments, the polymeric compounds stabilize the bioactive form of a therapeutic agent which exists in equilibrium between an active and inactive form. For instance, conjugating the therapeutic agent to the polymers of the present invention may shift the equilibrium between two tautomeric forms of the agent to the bioactive tautomer. In other embodiment, the polymeric compounds may attenuate the equilibrium between lactonic and acid forms of a therapeutic agent.

One method to determine molecular weight is by gel permeation chromatography ("GPC"), e.g., mixed bed columns, $CH_2Cl_2$ solvent, light scattering detector, and off-line dn/dc. Other methods are known in the art.

In other embodiments, the polymer conjugate of the invention may be a flexible or flowable material. When the polymer used is itself flowable, the polymer composition of the invention, even when viscous, need not include a biocompatible solvent to be flowable, although trace or residual amounts of biocompatible solvents may still be present.

While it is possible that the biodegradable polymer or the biologically active agent may be dissolved in a small quantity of a solvent that is non-toxic to more efficiently produce an amorphous, monolithic distribution or a fine dispersion of the biologically active agent in the flexible or flowable composition, it is an advantage of the invention that, in a preferred embodiment, no solvent is needed to form a flowable composition. Moreover, the use of solvents is preferably avoided because, once a polymer composition containing solvent is placed totally or partially within the body, the solvent dissipates or diffuses away from the polymer and must be processed and eliminated by the body, placing an extra burden on the body's clearance ability at a time when the illness (and/or other treatments for the illness) may have already deleteriously affected it.

However, when a solvent is used to facilitate mixing or to maintain the flowability of the polymer conjugate of the invention, it should be non-toxic, otherwise biocompatible, and should be used in relatively small amounts. Solvents that are toxic should not be used in any material to be placed even partially within a living body. Such a solvent also must not cause substantial tissue irritation or necrosis at the site of administration.

Examples of suitable biocompatible solvents, when used, include N-methyl-2-pyrrolidone, 2-pyrrolidone, ethanol, propylene glycol, acetone, methyl acetate, ethyl acetate, methyl ethyl ketone, dimethylformamide, dimethylsulfoxide, tetra hydrofuran, caprolactam, oleic acid, or 1-dodecylazacylcoheptanone. Preferred solvents include N-methylpyrrolidone, 2-pyrrolidone, dimethylsulfoxide, and acetone because of their solvating ability and their biocompatibility.

In certain embodiments, the subject polymer conjugates are soluble in one or more common organic solvents for ease of fabrication and processing. Common organic solvents include such solvents as chloroform, dichloromethane, dichloroethane, 2-butanone, butyl acetate, ethyl butyrate, acetone, ethyl acetate, dimethylacetamide, N-methylpyrrolidone, dimethylformmamide, and dimethylsulfoxide.

One aspect of the present invention contemplates attaching a hydrophobic therapeutic agent such as (s)-20-camptothecin to linear or branched cyclodextrin-containing polymers for better delivery of the drug. (S)-20-camptothecin (CPT), an alkaloid isolated from *Camptitheca accuminata* in the late 1950's, was found to exhibit anticancer activity by inhibiting the action of topoisomerase I during the S-phase of the cell cycle. Its application in human cancer treatment, however, is limited due to several factors, especially its undesirable interactions with human serum albumin, instability of the bioactive lactone form, and poor aqueous solubility. In order to circumvent this problem, many CPT analogs have been developed to improve lactone stability and aqueous solubility. Topotecan and irinotecan are analogs of CPT that have already been approved by FDA for human cancer treatment. The present invention discloses various types of linear, branched, or grafted cyclodextrin-containing polymers wherein (S)-20-camptothecin is covalently bound to the polymer. In certain embodiments, the drug is covalently linked via a biohydrolyzable bond selected from an ester, amide, carbamates, or carbonate.

An exemplary synthetic scheme for covalently bonding a derivatized CD to 20(S)-camptothecin is shown in Scheme I.

Scheme I

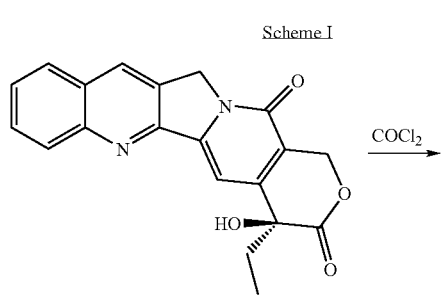

Without intending to limit the scope of the invention, a general strategy for synthesizing linear, branched or grafted cyclodextrin-containing polymers (CD Polymer) for loading a therapeutic agent such as camptothecin, and an optional targeting ligand is shown in Scheme II.

Scheme II

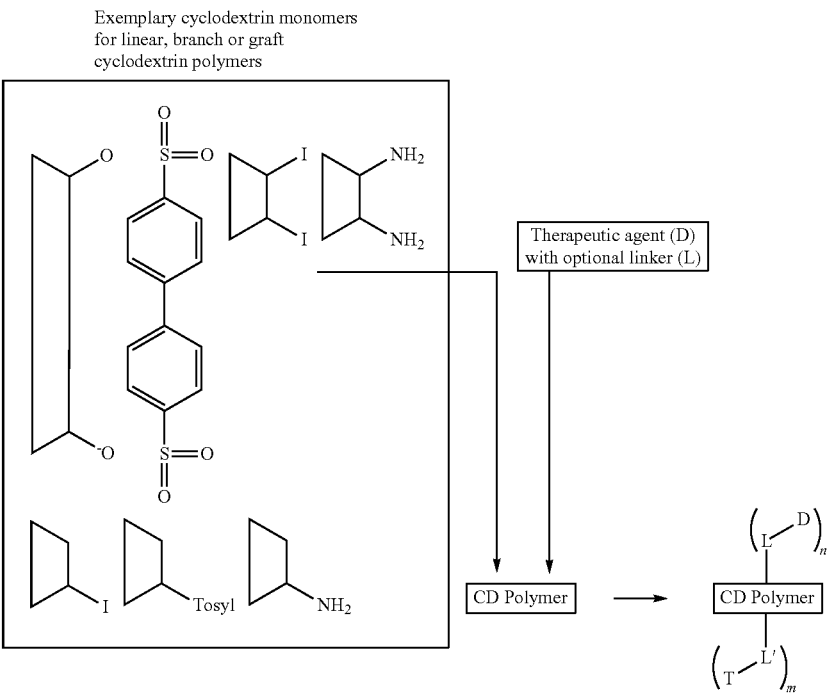

-continued

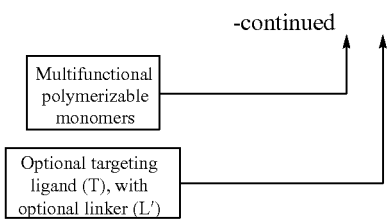

To illustrate further, without intending to be limiting, comonomer A precursors, cyclodextrin moieties, therapeutic agents, and/or targeting ligands may be assembled as shown in Schemes IIa-IIb. Note that in schemes IIa-b, in any given reaction there may be more than one comonomer A precursor, cyclodextrin moiety, therapeutic agent or targeting ligand that is of the same type or different. Furthermore, prior to polymerization, one or more comonomer A precursor, cyclodextrin moiety, therapeutic agent or targeting ligand may be covalently linked with each other in one or more separate step.

Scheme IIa: General scheme for graft polymers. The comonomer A precursor cyclodextrin moiety, therapeutic agent and targeting ligand are as defined above. Furthermore, one skilled in the art may choose from a variety of reactive groups, e.g., hydroxyls, carboxyls, halides, amines, and activated ethenes, ethynes, or aromatic groups in order achieve polymerization. For further examples of reactive groups are disclosed in Advanced Organic Chemistry: Reactions, Mechanisms, and Structure, 5th Edition 2000.

Scheme IIa: General scheme for graft polymers. The comonomer A precursor, cyclodextrin moiety, therapeutic agent and targeting ligand are as defined above. Furthermore, one skilled in the art may choose from a variety of reactive groups, e.g., hydroxyls, carboxyls, halides, amines, and activated ethenes, ethynes, or aromatic groups in order achieve polymerization. For further examples of reactive groups are disclosed in Advanced Organic Chemistry: Reactions, Mechanisms, and Structure, 5th Edition, 2000.

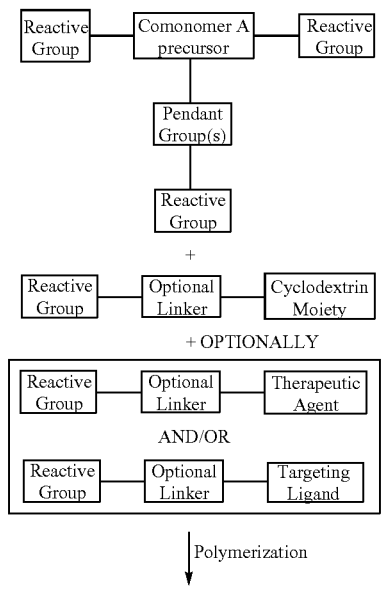

-continued

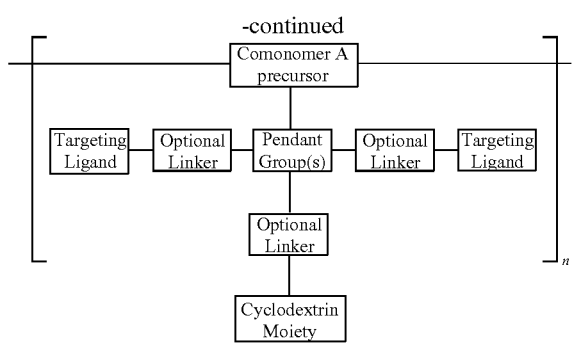

Scheme IIb: General scheme of preparing linear cylcodextrin-containing polymers. One skilled in the art would recognize that by choosing a comonomer A precursor that has multiple reactive groups polymer branching can be achieved.

Scheme IIb: General scheme of preparing linear cyclodextrin-containing polymers. One skilled in the art would recognize that by choosing a comonomer A precursor that has multiple reactive groups polymer branching can be achieved.

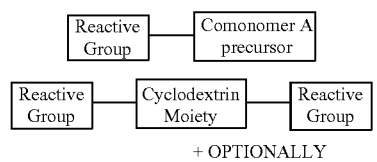

+ OPTIONALLY

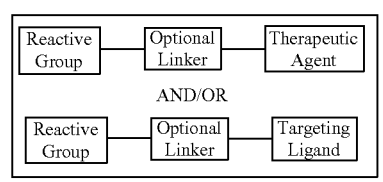

↓ Polymerization

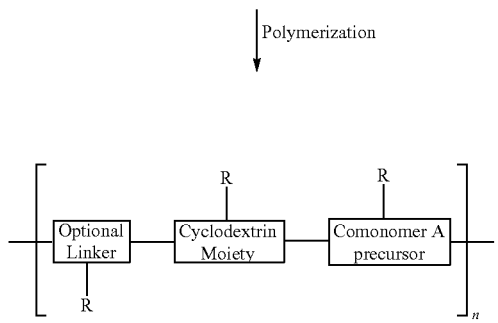

Wherein R is a therapeutic agent and/or targeting ligand which may be absent or present.

Examples for different ways of synthesizing linear cyclo-dextrin-CPT polymers are shown in Schemes III-VIII.
Scheme III
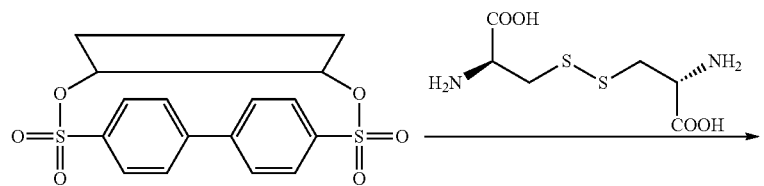
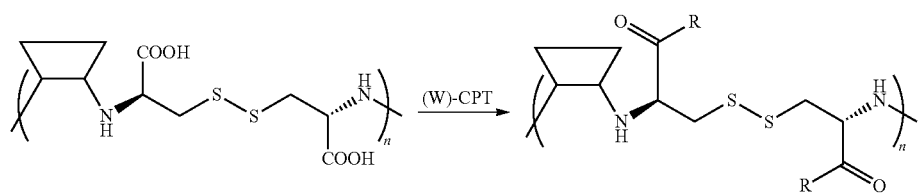
wherein
W represents an potional linking group; and
R represents W-CPT or O.
Scheme IV
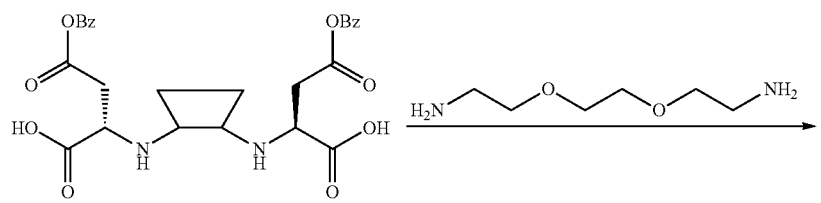
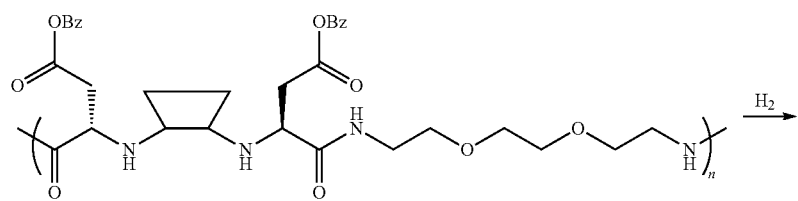

-continued
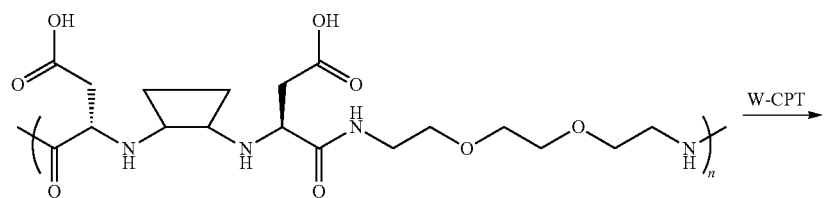
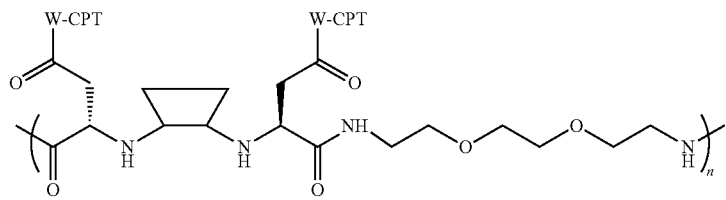
wherein
W represents an optional linking group
Scheme V
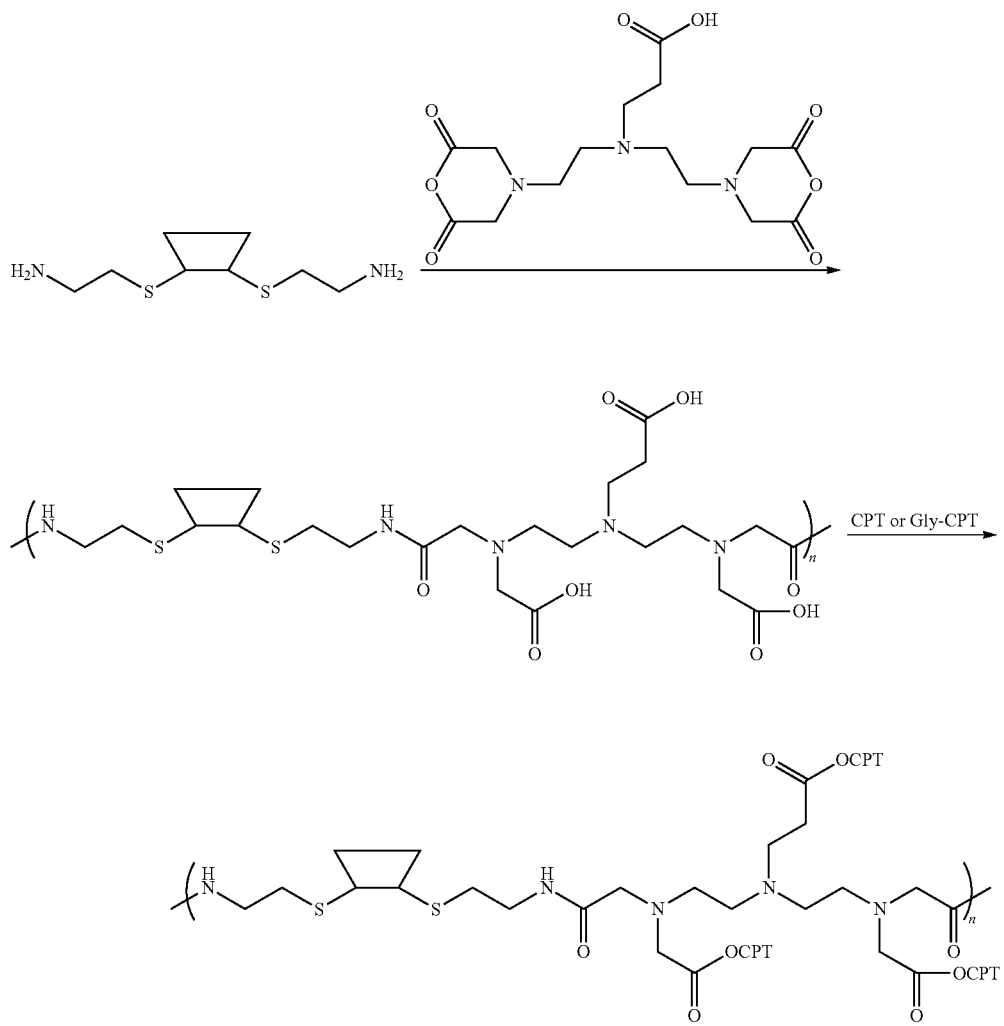

-continued
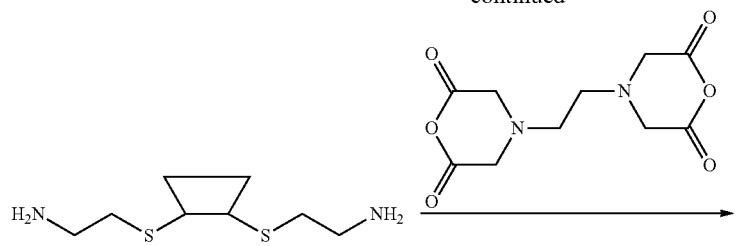
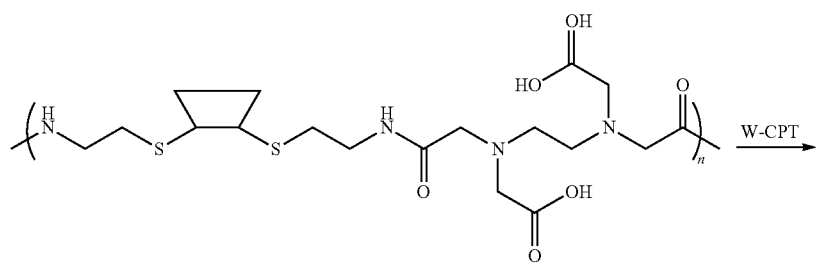
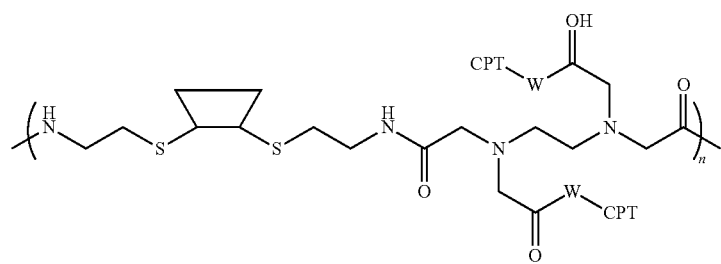
wherein
W represents an optional linking group, e.g., glycyl residue Scheme VI
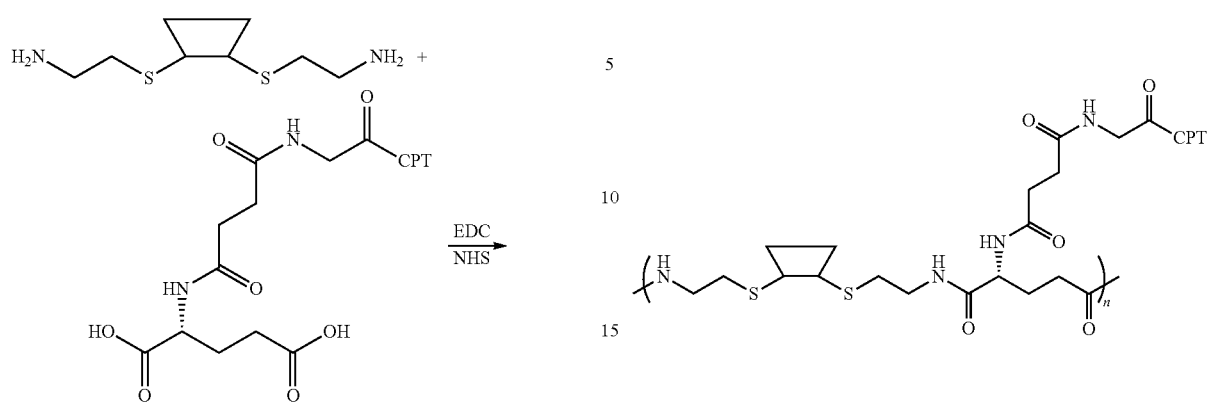
Scheme VII
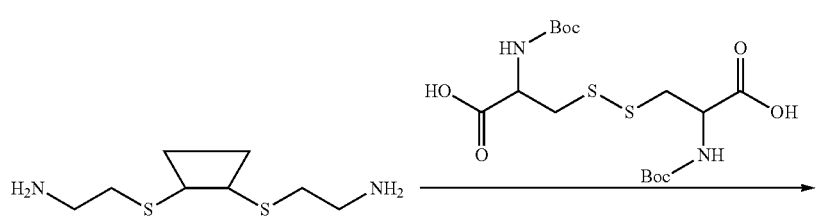
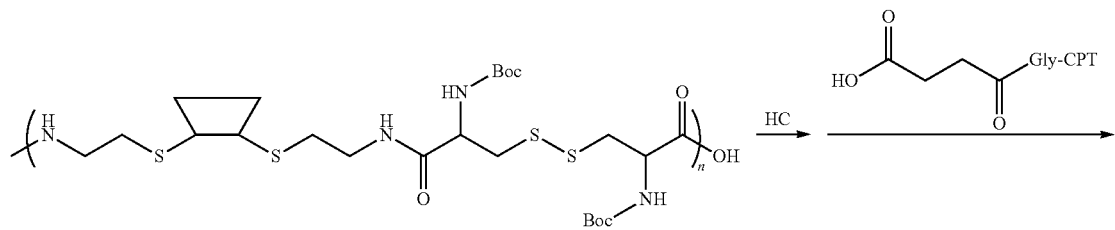
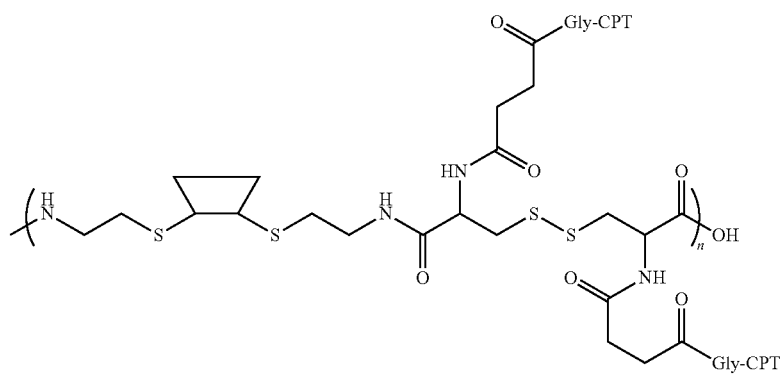

Scheme VIII

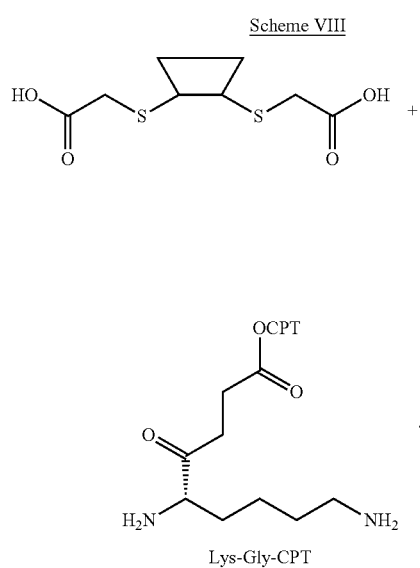

Examples for grafting cyclodextrins on to side-chains of CPT-containing polymers subunits are shown in Schemes IX-XII. Each subunit may repeat any number of times, and one subunit may occur with substantially the same frequency, more often, or less often than another subunit, such that both subunits may be present in approximately the same amount, or in differing amounts, which may differ slightly or be highly disparate, e.g., one subunit is present nearly to the exclusion of the other.

In certain instances, the polymers are random copolymers, in which the different subunits and/or other monomeric units are distributed randomly throughout the polymer chain. Thus, where the formula $X_m$—$Y_n$-$Z_o$ appears, wherein X, Y and Z are polymer subunits, these subunits may be randomly interspersed throughout the polymer backbone. In part, the term "random" is intended to refer to the situation in which the particular distribution or incorporation of monomeric units in a polymer that has more than one type of monomeric units is not directed or controlled directly by the synthetic protocol, but instead results from features inherent to the polymer system, such as the reactivity, amounts of subunits and other characteristics of the synthetic reaction or other methods of manufacture, processing, or treatment.

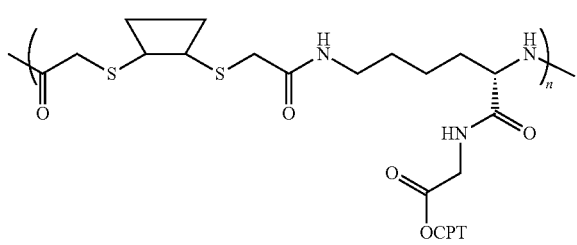

Scheme IX

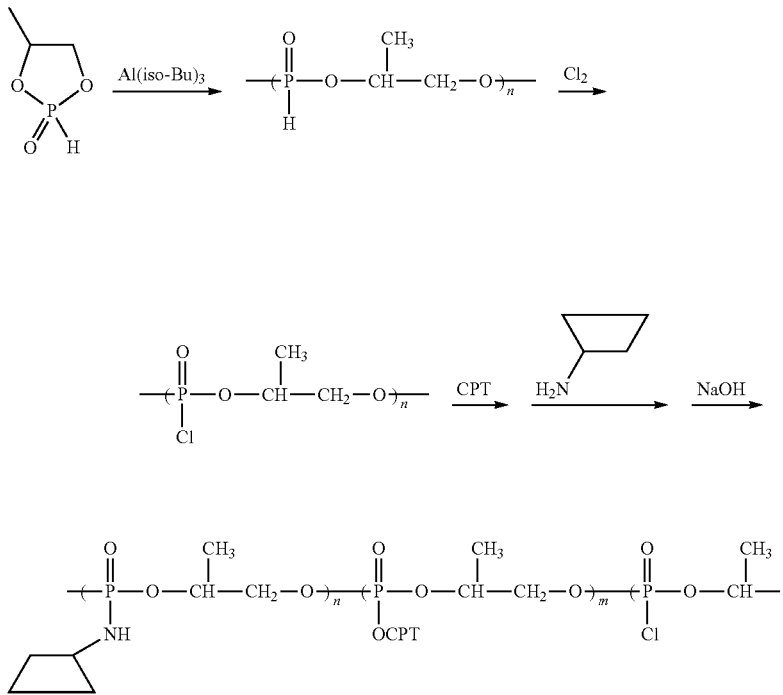

Scheme X
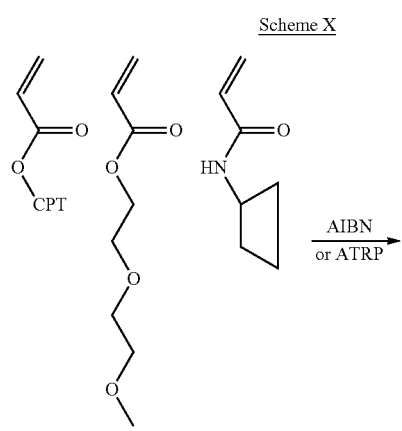
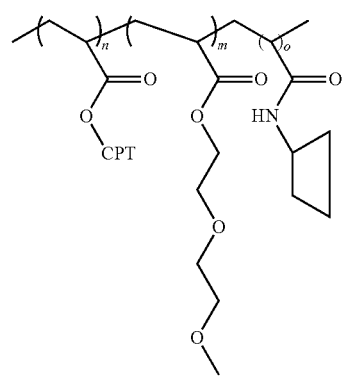
Scheme XI
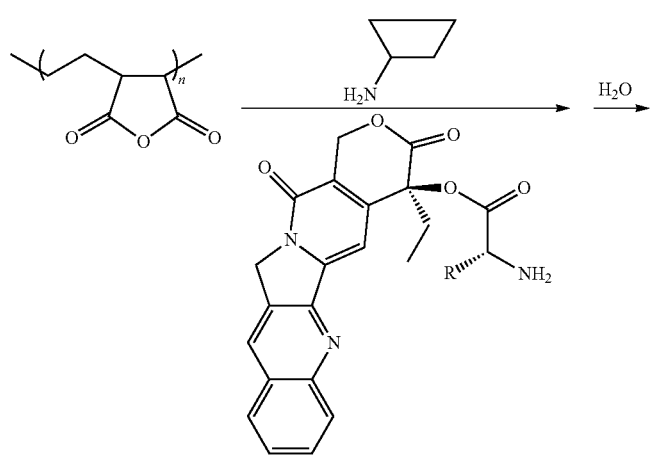
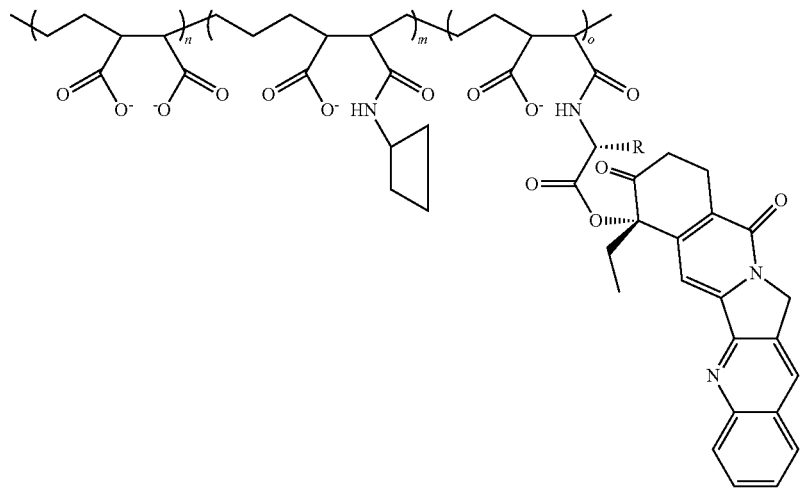

Scheme XII
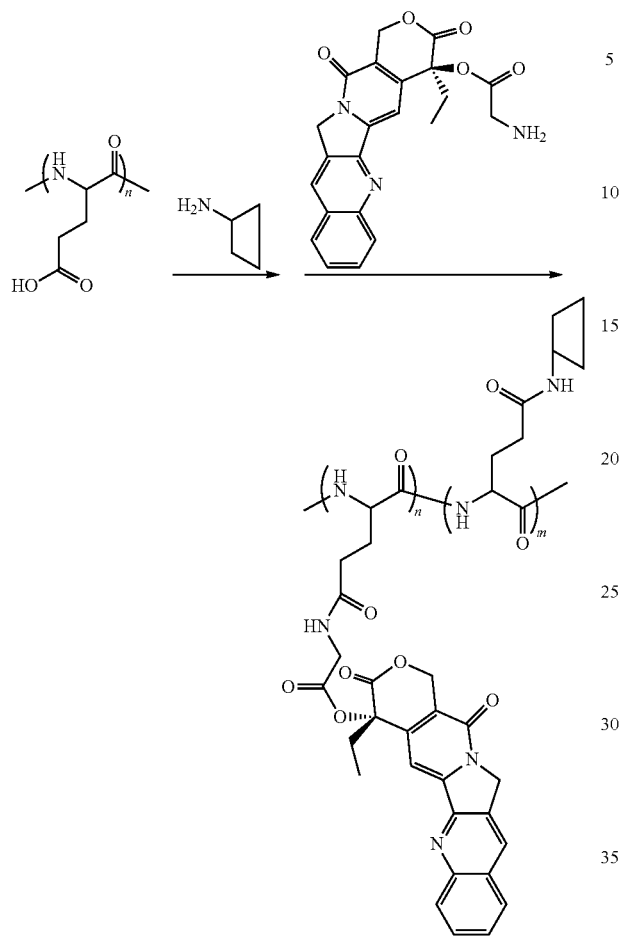
The present invention further contemplates CD-polymers synthesized using CD-biscysteine monomer and a di-NHS ester such as PEG-DiSPA or PEG-BTC as shown in Schemes XIII-XIV.
Scheme XIII
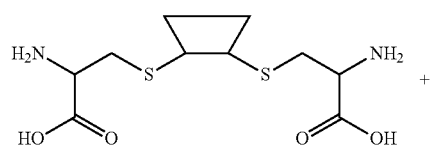 +
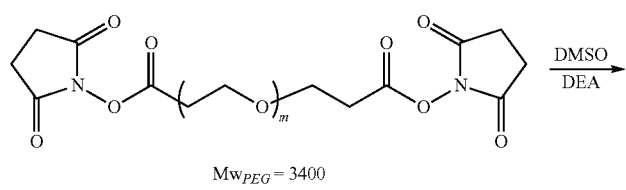

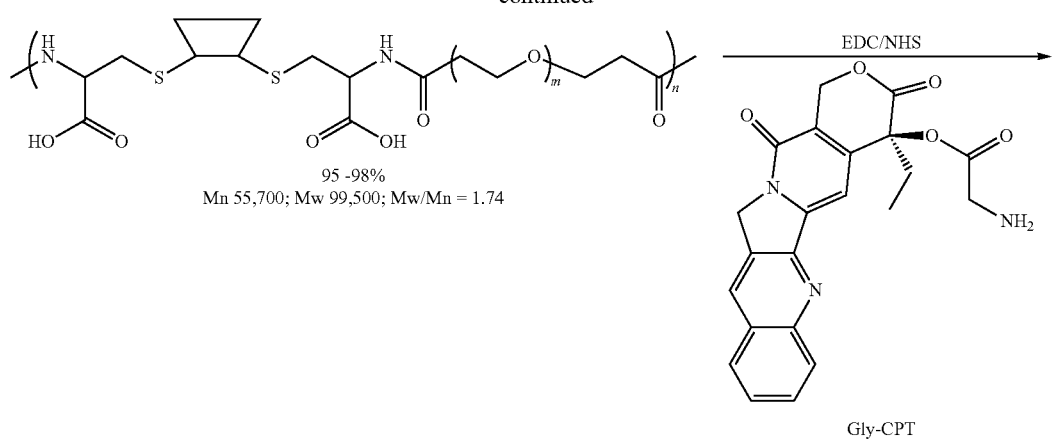
Gly-CPT
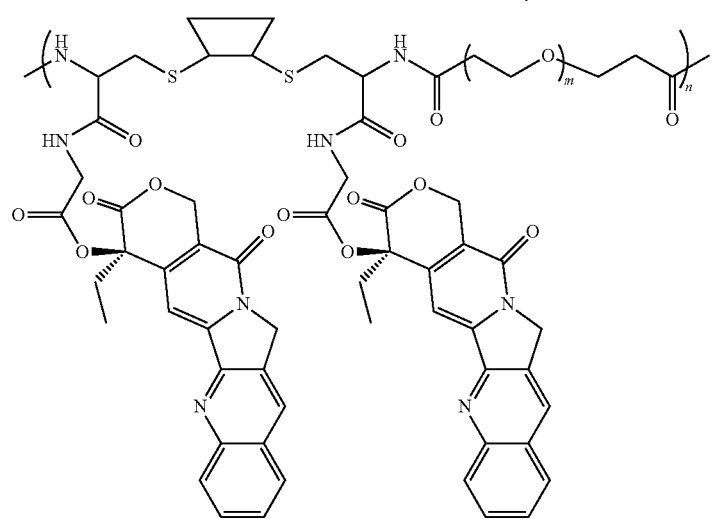
Scheme XIV
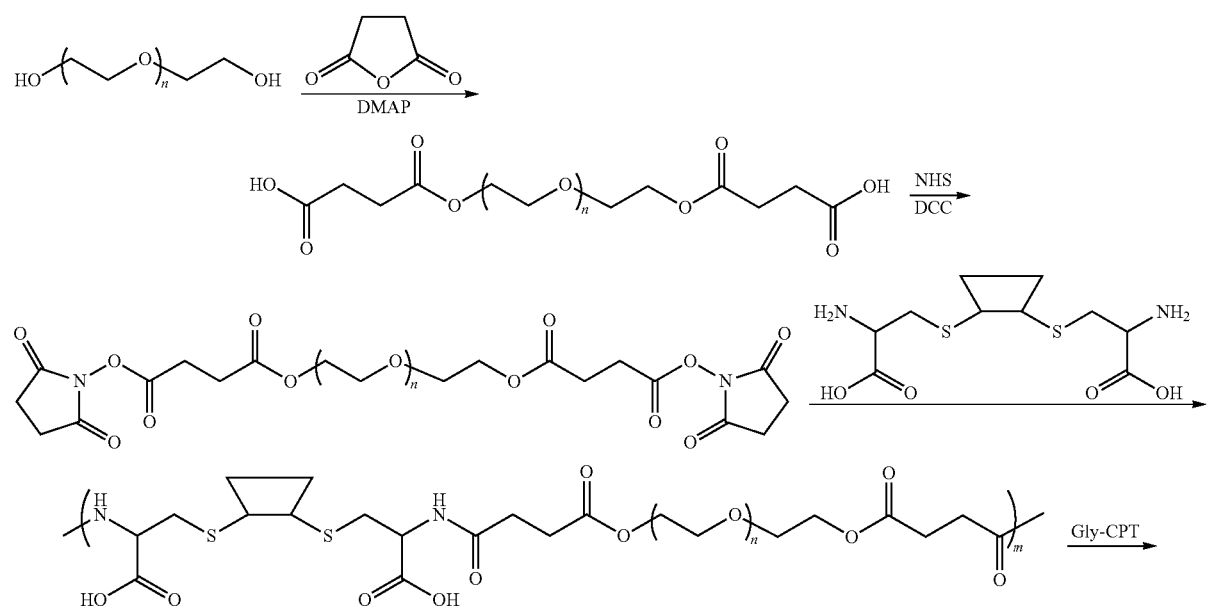
Gly-CPT

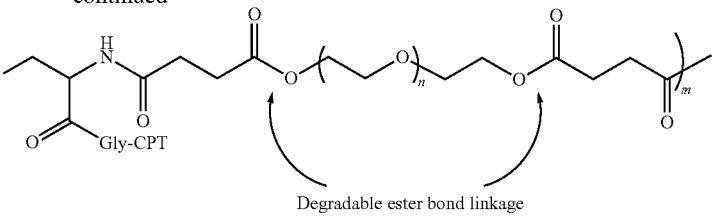

Degradable ester bond linkage

In certain embodiments, the present invention discloses several strategies to increase drug loading as shown in FIG. 1.

(b) Targeting Ligand

As mentioned above, one aspect of the present invention contemplates attaching a therapeutic agent to the polymer conjugates described herein.

In certain embodiments, the polymer conjugate further comprises a targeting ligand. Thus in certain embodiments, a receptor, cell, and/or tissue-targeting ligand, or a precursor thereof is coupled to a polymer conjugate. As used herein the term "targeting ligand" refers to any material or substance which may promote targeting of receptors, cells, and/or tissues in vivo or in vitro with the compositions of the present invention. The targeting ligand may be synthetic, semi-synthetic, or naturally-occurring. Materials or substances which may serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, small molecules, vitamins, steroids, steroid analogs, hormones, cofactors, bioactive agents, and genetic material, including nucleosides, nucleotides, nucleotide acid constructs and polynucleotides. As used herein, the term "precursor" to a targeting ligand refers to any material or substance which may be converted to a targeting ligand. Such conversion may involve, for example, anchoring a precursor to a targeting ligand. Exemplary targeting precursor moieties include maleimide groups, disulfide groups, such as ortho-pyridyl disulfide, vinylsulfone groups, azide groups, and α-iodo acetyl groups. The attachment of the targeting ligand or precursor thereof to the polymer may be accomplished in various ways including but not limited to chelation, covalent attachment, or formation of host-guest complexes. In certain embodiments, an optional linker group may be present between the targeting ligand or precursor thereof and the polymer, wherein the linker group is attached to the polymer via chelation, covalent attachment or form host guest complexes. For example, the one terminal end of a linker group may be attached to the targeting ligand while the other may be attached to an adamantane group, or other such hydrophobic moiety, which forms a host guest complex with a cyclodextrin moiety. Thus the targeting ligand may be attached to a grafted cyclodextrin moiety, to a cyclodextrin moiety within the polymeric chain, or to the polymeric chain itself. The number of targeting ligands per polymeric chain may vary according to various factors including but not limited to the identity of the therapeutic agent, nature of the disease, type of polymer chain. Structures of possible linker groups are the same as linker groups defined elsewhere in this application.

(c) Pharmaceutical Compositions, Formulations and Dosages

In part, a biocompatible polymer composition of the present invention includes a biocompatible and optionally biodegradable polymer, such as one having the recurring monomeric units shown in one of the foregoing formulas, optionally including any other biocompatible and optionally biodegradable polymer mentioned above or known in the art. In certain embodiments, the compositions are non-pyrogenic, e.g., do not trigger elevation of a patient's body temperature by more than a clinically acceptable amount.

The subject compositions may contain a "drug", "therapeutic agent," "medicament," or "bioactive substance," which are biologically, physiologically, or pharmacologically active substances that act locally or systemically in the human or animal body. For example, a subject composition may include any of the other compounds discussed above.

Various forms of the medicaments or biologically active materials may be used which are capable of being released from the polymer matrix into adjacent tissues or fluids. They may be hydrophobic molecules, neutral molecules, polar molecules, or molecular complexes capable of hydrogen bonding. They may be in the form of ethers, esters, amides and the like, including prodrugs which are biologically activated when injected into the human or animal body, e.g., by cleavage of an ester or amide. A therapeutic agent in a subject composition may vary widely with the purpose for the composition.

Plasticizers and stabilizing agents known in the art may be incorporated in polymers of the present invention. In certain embodiments, additives such as plasticizers and stabilizing agents are selected for their biocompatibility. In certain embodiments, the additives are lung surfactants, such as 1,2-dipalmitoylphosphatidycholine (DPPC) and L-α-phosphatidylcholine (PC).

A composition of this invention may further contain one or more adjuvant substances, such as fillers, thickening agents or the like. In other embodiments, materials that serve as adjuvants may be associated with the polymer matrix. Such additional materials may affect the characteristics of the polymer matrix that results.

For example, fillers, such as bovine serum albumin (BSA) or mouse serum albumin (MSA), may be associated with the polymer matrix. In certain embodiments, the amount of filler may range from about 0.1 to about 50% or more by weight of the polymer matrix, or about 2.5, 5, 10, 25, or 40 percent. Incorporation of such fillers may affect the biodegradation of the polymeric material and/or the sustained release rate of any encapsulated substance. Other fillers known to those of skill in the art, such as carbohydrates, sugars, starches, saccharides, celluloses and polysaccharides, including mannitose and sucrose, may be used in certain embodiments of the present invention.

In other embodiments, spheronization enhancers facilitate the production of subject polymeric matrices that are generally spherical in shape. Substances such as zein, microcrystalline cellulose or microcrystalline cellulose co-processed with sodium carboxymethyl cellulose may confer plasticity to the subject compositions as well as implant strength and integrity. In particular embodiments, during spheronization, extrudates that are rigid, but not plastic, result in the formation of dumbbell shaped implants and/or a high proportion of fines, and extrudates that are plastic, but not rigid, tend to agglomerate and form excessively large implants. In such embodiments, a balance between rigidity and plasticity is desirable. The percent of spheronization enhancer in a formulation typically range from 10 to 90% (w/w).

In certain embodiments, a subject composition includes an excipient. A particular excipient may be selected based on its melting point, solubility in a selected solvent (e.g., a solvent that dissolves the polymer and/or the therapeutic agent), and the resulting characteristics of the microparticles.

Excipients may comprise a few percent, about 5%, 10%, 15%, 20%, 25%, 30%, 40%, 50%, or higher percentage of the subject compositions.

Buffers, acids and bases may be incorporated in the subject compositions to adjust their pH. Agents to increase the diffusion distance of agents released from the polymer matrix may also be included.

Disintegrants are substances that, in the presence of liquid, promote the disruption of the subject compositions. Disintegrants are most often used in implants, in which the function of the disintegrant is to counteract or neutralize the effect of any binding materials used in the subject formulation. In general, the mechanism of disintegration involves moisture absorption and swelling by an insoluble material.

Examples of disintegrants include croscarmellose sodium and crospovidone which, in certain embodiments, may be incorporated into the polymeric matrices in the range of about 1-20% of total matrix weight. In other cases, soluble fillers such as sugars (mannitol and lactose) may also be added to facilitate disintegration of implants.

Other materials may be used to advantage or to control the desired release rate of a therapeutic agent for a particular treatment protocol. For example, if the sustained release is too slow for a particular application, a pore-forming agent may be added to generate additional pores in the matrix. Any biocompatible water-soluble material may be used as the pore-forming agent. They may be capable of dissolving, diffusing or dispersing out of the formed polymer system whereupon pores and microporous channels are generated in the system. The amount of pore-forming agent (and size of dispersed particles of such pore-forming agent, if appropriate) within the composition should affect the size and number of the pores in the polymer system.

Pore-forming agents include any pharmaceutically acceptable organic or inorganic substance that is substantially miscible in water and body fluids and will dissipate from the forming and formed matrix into aqueous medium or body fluids or water-immiscible substances that rapidly degrade to water-soluble substances.

Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and PVP. The size and extent of the pores may be varied over a wide range by changing the molecular weight and percentage of pore-forming agent incorporated into the polymer system.

The charge, lipophilicity or hydrophilicity of any subject polymeric matrix may be modified by attaching in some fashion an appropriate compound to the surface of the matrix. For example, surfactants may be used to enhance wettability of poorly soluble or hydrophobic compositions. Examples of suitable surfactants include dextran, polysorbates and sodium lauryl sulfate. In general, surfactants are used in low concentrations, generally less than about 5%.

Binders are adhesive materials that may be incorporated in polymeric formulations to bind and maintain matrix integrity. Binders may be added as dry powder or as solution. Sugars and natural and synthetic polymers may act as binders.

Materials added specifically as binders are generally included in the range of about 0.5%-15% w/w of the matrix formulation. Certain materials, such as microcrystalline cellulose, also used as a spheronization enhancer, also have additional binding properties.

Various coatings may be applied to modify the properties of the matrices.

Three exemplary types of coatings are seal, gloss and enteric coatings. Other types of coatings having various dissolution or erosion properties may be used to further modify subject matrices behavior, and such coatings are readily known to one of ordinary skill in the art.

The seal coat may prevent excess moisture uptake by the matrices during the application of aqueous based enteric coatings. The gloss coat generally improves the handling of the finished matrices. Water-soluble materials such as hydroxypropylcellulose may be used to seal coat and gloss coat implants. The seal coat and gloss coat are generally sprayed onto the matrices until an increase in weight between about 0.5% and about 5%, often about 1% for a seal coat and about 3% for a gloss coat, has been obtained.

Enteric coatings consist of polymers which are insoluble in the low pH (less than 3.0) of the stomach, but are soluble in the elevated pH (greater than 4.0) of the small intestine. Polymers such as EUDRAGIT™, RohmTech, Inc., Malden, Mass., and AQUATERIC™, FMC Corp., Philadelphia, Pa., may be used and are layered as thin membranes onto the implants from aqueous solution or suspension or by a spray drying method. The enteric coat is generally sprayed to a weight increase of about 1% to about 30%, preferably about 10 to about 15% and may contain coating adjuvants such as plasticizers, surfactants, separating agents that reduce the tackiness of the implants during coating, and coating permeability adjusters.

The present compositions may additionally contain one or more optional additives such as fibrous reinforcement, colorants, perfumes, rubber modifiers, modifying agents, etc. In practice, each of these optional additives should be compatible with the resulting polymer and its intended use. Examples of suitable fibrous reinforcement include PGA microfibrils, collagen microfibrils, cellulosic microfibrils, and olefinic microfibrils. The amount of each of these optional additives employed in the composition is an amount necessary to achieve the desired effect.

The therapeutic polymer conjugates as described herein can be administered in various pharmaceutical formulations, depending on the disorder to be treated and the age, condition and body weight of the patient, as is well known in the art. For example, where the compounds are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the therapeutic agent is recommended for an adult human patient, and this may be administered in a single dose or in divided doses.

The precise time of administration and/or amount of therapeutic polymer conjugate that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those therapeutic polymer conjugates, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" refers to the relatively non-toxic, inorganic and organic acid addition salts of the therapeutic polymer conjugates. These salts can be prepared in situ during the final isolation and purification of the therapeutic polymer conjugates, or by separately reacting a purified polymer in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19)

In other cases, the therapeutic polymer conjugates useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of the polymer(s). These salts can likewise be prepared in situ during the final isolation and purification of the polymer(s), or by separately reacting the purified polymer(s) in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including ophthalmic, otic, buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a therapeutic polymer conjugate(s) with the carrier and, optionally, one or more accessory ingredients. In general, the formulations are prepared by uniformly and intimately bringing into association a therapeutic polymer conjugate with liquid carriers, or finely divided solid carriers, or both, and then, if necessary, shaping the product.

Formulations suitable for oral administration may be in the form of capsules, cachets, pills, tablets, gums, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a therapeutic polymer conjugate(s) as an active ingredient. A compound may also be administered as a bolus, electuary or paste.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetra hydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active therapeutic polymer conjugates may contain suspending agents as, for example, ethoxylated isostearyl alcohols, polyoxyethylene sorbitol and sorbitan esters, microcrystalline cellulose, aluminum meta hydroxide, bentonite, agar-agar and tragacanth, and mixtures thereof.

Formulations for rectal or vaginal administration may be presented as a suppository, which may be prepared by mixing one or more therapeutic polymer conjugates with one or more suitable nonirritating excipients or carriers comprising for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of a therapeutic polymer conjugate(s) include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to ligand(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a therapeutic polymer conjugate(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The therapeutic polymer conjugate(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic polymer conjugate(s) to the body. Such dosage forms can be made by dissolving or dispersing the agent in the proper medium. Absorption enhancers can also be used to increase the flux of the ligand across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic polymer conjugate(s) in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of therapeutic polymer conjugate(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the therapeutic polymer conjugate(s) of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of agents may be given orally, parenterally, topically, or rectally. They are of course given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a therapeutic polymer conjugate, drug or other material other than directly into the central nervous system, such that it enters the patient's system and, thus, is subject to metabolism and other like processes, for example, subcutaneous administration.

These therapeutic polymer conjugate(s) may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the therapeutic polymer conjugate(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

(c) Physical Structures of the Subject Compositions

The subject polymers may be formed in a variety of shapes. For example, in certain embodiments, subject polymer matrices may be presented in the form of microparticles or nanoparticles. Microspheres typically comprise a biodegradable polymer matrix incorporating a drug. Microspheres can be formed by a wide variety of techniques known to those of skill in the art. Examples of microsphere forming techniques include, but are not limited to, (a) phase separation by emulsification and subsequent organic solvent evaporation (including complex emulsion methods such as oil in water emulsions, water in oil emulsions and water-oil-water emulsions); (b) coacervation-phase separation; (c) melt dispersion; (d) interfacial deposition; (e) in situ polymerization; (f) spray drying and spray congealing; (g) air suspension coating; and (h) pan and spray coating. These methods, as well as properties and characteristics of microspheres are disclosed in, for example, U.S. Pat. No. 4,652,441; U.S. Pat. No. 5,100,669; U.S. Pat. No. 4,526,938; WO 93/24150; EPA 0258780 A2; U.S. Pat. No. 4,438,253; and U.S. Pat. No. 5,330,768, the entire disclosures of which are incorporated by reference herein.

To prepare microspheres of the present invention, several methods can be employed depending upon the desired application of the delivery vehicles. Suitable methods include, but are not limited to, spray drying, freeze drying, air drying, vacuum drying, fluidized-bed drying, milling, co-precipitation and critical fluid extraction. In the case of spray drying, freeze drying, air drying, vacuum drying, fluidized-bed drying and critical fluid extraction; the components (stabilizing polyol, bioactive material, buffers, etc.) are first dissolved or suspended in aqueous conditions. In the case of milling, the components are mixed in the dried form and milled by any method known in the art. In the case of co-precipitation, the components are mixed in organic conditions and processed as described below. Spray drying can be used to load the stabilizing polyol with the bioactive material. The components are mixed under aqueous conditions and dried using precision nozzles to produce extremely uniform droplets in a drying chamber. Suitable spray drying machines include, but are not limited to, Buchi, NIRO, APV and Lab-plant spray driers used according to the manufacturer's instructions.

The shape of microparticles and nanoparticles may be determined by scanning electron microscopy. Spherically shaped nanoparticles are used in certain embodiments, for circulation through the bloodstream. If desired, the particles may be fabricated using known techniques into other shapes that are more useful for a specific application.

In addition to intracellular delivery of a therapeutic agent, it also possible that particles of the subject compositions, such as microparticles or nanoparticles, may undergo endocytosis, thereby obtaining access to the cell. The frequency of such an endocytosis process will likely depend on the size of any particle.

In certain embodiments, solid articles useful in defining shape and providing rigidity and structural strength to the polymeric matrices may be used. For example, a polymer may be formed on a mesh or other weave for implantation. A polymer may also be fabricated as a stent or as a shunt, adapted for holding open areas within body tissues or for draining fluid from one body cavity or body lumen into another. Further, a polymer may be fabricated as a drain or a tube suitable for removing fluid from a post-operative site, and in some embodiments adaptable for use with closed section drainage systems such as Jackson-Pratt drains and the like as are familiar in the art.

The mechanical properties of the polymer may be important for the processability of making molded or pressed articles for implantation. For example, the glass transition temperature may vary widely but must be sufficiently lower than the temperature of decomposition to accommodate conventional fabrication techniques, such, as compression molding, extrusion, or injection molding.

(d) Biodegradability and Release Characteristics

In certain embodiments, the polymers and blends of the present invention, upon contact with body fluids, undergo gradual degradation. The life of a biodegradable polymer in vivo depends upon, among other things, its molecular weight, crystallinity, biostability, and the degree of crosslinking. In general, the greater the molecular weight, the higher the degree of crystallinity, and the greater the biostability, the slower biodegradation will be.

If a subject composition is formulated with a therapeutic agent or other material, release of such an agent or other material for a sustained or extended period as compared to the release from an isotonic saline solution generally results. Such release profile may result in prolonged delivery (over, say 1 to about 2,000 hours, or alternatively about 2 to about 800 hours) of effective amounts (e.g., about 0.0001 mg/kg/hour to about 10 mg/kg/hour) of the agent or any other material associated with the polymer.

A variety of factors may affect the desired rate of hydrolysis of polymers of the subject invention, the desired softness and flexibility of the resulting solid matrix, rate and extent of bioactive material release. Some of such factors include the selection/identity of the various subunits, the enantiomeric or diastereomeric purity of the monomeric subunits, homogeneity of subunits found in the polymer, and the length of the polymer. For instance, the present invention contemplates heteropolymers with varying linkages, and/or the inclusion of other monomeric elements in the polymer, in order to control, for example, the rate of biodegradation of the matrix.

To illustrate further, a wide range of degradation rates may be obtained by adjusting the hydrophobicities of the backbones or side chains of the polymers while still maintaining sufficient biodegradability for the use intended for any such polymer. Such a result may be achieved by varying the various functional groups of the polymer. For example, the combination of a hydrophobic backbone and a hydrophilic linkage produces heterogeneous degradation because cleavage is encouraged where as water penetration is resisted.

One protocol generally accepted in the field that may be used to determine the release rate of any therapeutic agent or other material loaded in the polymer matrices of the present invention involves degradation of any such matrix in a 0.1 M PBS solution (pH 7.4) at 37° C., an assay known in the art. For purposes of the present invention, the term "PBS protocol" is used herein to refer to such protocol.

In certain instances, the release rates of different polymer systems of the present invention may be compared by subjecting them to such a protocol. In certain instances, it may be necessary to process polymeric systems in the same fashion to allow direct and relatively accurate comparisons of different systems to be made. For example, the present invention teaches several different means of formulating the polymeric, matrices of the present invention. Such comparisons may indicate that any one polymeric system releases incorporated material at a rate from about 2 or less to about 1000 or more times faster than another polymeric system.

Alternatively, a comparison may reveal a rate difference of about 3, 5, 7, 10, 25, 50, 100, 250, 500 or 750 times. Even higher rate differences are contemplated by the present invention and release rate protocols.

In certain embodiments, when formulated in a certain manner, the release rate for polymer systems of the present invention may present as mono- or bi-phasic.

Release of any material incorporated into the polymer matrix, which is often provided as a microsphere, may be characterized in certain instances by an initial increased release rate, which may release from about 5 to about 50% or more of any incorporated material, or alternatively about 10, 15, 20, 25, 30 or 40%, followed by a release rate of lesser magnitude.

The release rate of any incorporated material may also be characterized by the amount of such material released per day per mg of polymer matrix. For example, in certain embodiments, the release rate may vary from about 1 ng or less of any incorporated material per day per mg of polymeric system to about 500 or more ng/day/mg. Alternatively, the release rate may be about 0.05, 0.5, 5, 10, 25, 50, 75, 100, 125, 150, 175, 200, 250, 300, 350, 400, 450, or 500 ng/day/mg. In still other embodiments, the release rate of any incorporated material may be 10,000 ng/day/mg, or even higher. In certain instances, materials incorporated and characterized by such release rate protocols may include therapeutic agents, fillers, and other substances.

In another aspect, the rate of release of any material from any polymer matrix of the present invention may be presented as the half-life of such material in the matrix.

In addition to the embodiment involving protocols for in vitro determination of release rates, in vivo protocols, whereby in certain instances release rates for polymeric systems may be determined in vivo, are also contemplated by the present invention. Other assays useful for determining the release of any material from the polymers of the present system are known in the art.

(e) Implants and Delivery Systems

In its simplest form, a biodegradable delivery system for a therapeutic agent consists of a dispersion of such a therapeutic agent in a polymer matrix. In other embodiments, an article is used for implantation, injection, or otherwise placed totally or partially within the body, the article comprising the subject compositions. It is particularly important that such an article result in minimal tissue irritation when implanted or injected into vasculated tissue.

Biodegradable delivery systems, and articles thereof, may be prepared in a variety of ways known in the art. The subject polymer may be melt-processed using conventional extrusion or injection molding techniques, or these products may be prepared by dissolving in an appropriate solvent, followed by formation of the device, and subsequent removal of the solvent by evaporation or extraction.

Once a system or implant article is in place, it should remain in at least partial contact with a biological fluid, such as blood, internal organ secretions, mucus membranes, cerebrospinal fluid, and the like to allow for sustained release of any encapsulated therapeutic agent.

(f) Methods of Manufacturing

Generally, compounds of the present invention can be prepared in one of two ways: monomers bearing therapeutic agents, targeting ligands, and/or cyclodextrin moieties can be polymerized, or polymer backbones can be derivatized with therapeutic agents, targeting ligands, and/or cyclodextrin moieties.

Thus, in one embodiment, the present invention contemplates the synthesis of compounds of the invention by reacting monomers M-L-CD and M-L-D (and, optionally, M-L-T), wherein CD represents a cyclic moiety, such as a cyclodextrin molecule, or derivative thereof;

L, independently for each occurrence, may be absent or represents a linker group;

D, independently for each occurrence, represents the same or different therapeutic agent or prodrugs thereof;

T, independently for each occurrence, represents the same or different targeting ligand or precursor thereof; and M represents a monomer subunit bearing one or more reactive moieties capable of undergoing a polymerization reaction with one or more other M in the monomers in the reaction mixture, under conditions that cause polymerization of the monomers to take place.

In certain embodiments, the reaction mixture may further comprise monomers that do not bear CD, T, or D moieties, e.g., to space the derivatized monomer units throughout the polymer.

In an alternative embodiment, the invention contemplates synthesizing a compound of the present invention by reacting a polymer P (the polymer bearing a plurality of reactive groups, such as carboxylic acids, alcohols, thiols, anines, epoxides, etc.) with grafting agents X-L-CD and Y-L-D (and, optionally, Z-L-T), wherein CD represents a cyclic moiety, such as a cyclodextrin molecule, or derivative thereof;

L, independently for each occurrence, may be absent or represents a linker group;

D, independently for each occurrence, represents the same or different therapeutic agent or prodrugs thereof;

T, independently for each occurrence, represents the same or different targeting ligand or precursor thereof;

X, independently for each occurrence, represents a reactive group, such as carboxylic acids, alcohols, thiols, amimes, epoxides, etc., capable of forming a covalent bond with a reactive group of the polymer; and Y and Z, independently for each occurrence, represent inclusion hosts or reactive groups, such as carboxylic acids, alcohols, thiols, amines, epoxides, etc., capable of forming a covalent bond with a reactive group of the polymer or inclusion complexes with CD moieties grafted to the polymer, under conditions that cause the grafting agents to form covalent bonds and/or inclusion complexes, as appropriate, with the polymer or moieties grafted to the polymer.

For example, if the polymer includes alcohols, thiols, or amines as reactive groups, the grafting agents may include reactive groups that react with them, such as isocyanates, isothiocyanates, acid chlorides, acid anhydrides, epoxides, ketenes, sulfonyl chlorides, activated carboxylic acids (e.g., carboxylic acids treated with an activating agent such as PyBrOP, carbonyldiimidazole, or another reagent that reacts with a carboxylic acid to form a moiety susceptible to nucleophilic attack), or other electrophilic moieties known to those of skill in the art. In certain embodiments, a catalyst may be needed to cause the reaction to take place (e.g., a Lewis acid, a transition metal catalyst, an amine base, etc.) as will be understood by those of skill in the art.

In certain embodiments, the different grafting agents are reacted with the polymer simultaneously or substantially simultaneously (e.g., in a one-pot reaction), or are reacted sequentially with the polymer (optionally with a purification and/or wash step between reactions).

Another aspect of the present invention is a method for manufacturing the linear or branched cyclodextrin-containing polymers represented by formulae I-III. While the discussion below focuses on the preparation of linear cyclodextrin molecules, one skilled in the art would readily recognize that the methods described can be adapted for producing branched polymers by choosing an appropriate comonomer A precursor.

Accordingly, one embodiment of the invention is a method of preparing a linear cyclodextrin copolymer. According to the invention, a linear cyclodextrin copolymer of the invention may be prepared by copolymerizing a cyclodextrin monomer precursor disubstituted with an appropriate leaving group with a comonomer A precursor capable of displacing the leaving groups. The leaving group, which may be the same or different, may be any leaving group known in the art which may be displaced upon copolymerization with a comonomer A precursor. In a preferred embodiment, a linear cyclodextrin copolymer may be prepared by iodinating a cyclodextrin monomer precursor to form a diiodinated cyclodextrin monomer precursor and copolymerizing the diiodinated cyclodextrin monomer precursor with a comonomer A precursor to form a linear cyclodextrin copolymer having a repeating unit of formula II or III, or a combination thereof, each as described above. While examples presented below discuss iodinated cyclodextrin moieties, one skilled in the art would readily recognize that the present invention contemplates and encompasses cyclodextrin moieties wherein other leaving groups such as alkyl and aryl sulfonate may be present instead of iodo groups. In a preferred embodiment, a method of preparing a linear cyclodextrin copolymer of the invention by iodinating a cyclodextrin monomer precursor as described above to form a diiodinated cyclodextrin monomer precursor of formula IVa, IVb, IVc or a mixture thereof:

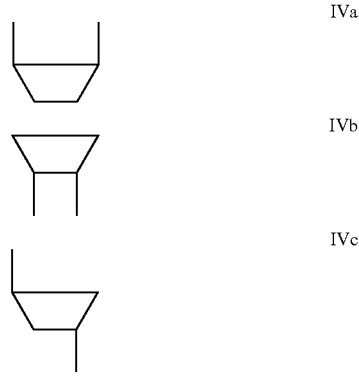

The diiodinated cyclodextrin may be prepared by any means known in the art. (Tabushi et al. J. Am. Chem. 106, 5267-5270 (1984); Tabushi et al. J. Am. Chem. 106, 4580-4584 (1984)). For example, β-cyclodextrin may be reacted with biphenyl-4,4'-disulfonyl chloride in the presence of anhydrous pyridine to form a biphenyl-4,4'-disulfonyl chloride capped β-cyclodextrin which may then be reacted with potassium iodide to produce diiodo-β-cyclodextrin. The cyclodextrin monomer precursor is iodinated at only two positions. By copolymerizing the diiodinated cyclodextrin monomer precursor with a comonomer A precursor, as described above, a linear cyclodextrin polymer having a repeating unit of Formula Ia, Ib, or a combination thereof, also as described above, may be prepared. If appropriate, the iodine or iodo groups may be replaced with other known leaving groups.

Also according to the invention, the iodo groups or other appropriate leaving group may be displaced with a group that permits reaction with a comonomer A precursor, as described above. For example, a diiodinated cyclodextrin monomer precursor of formula IVa, IVb, IVc or a mixture thereof may be aminated to form a diaminated cyclodextrin monomer precursor of formula Va, Vb, Vc or a mixture thereof:

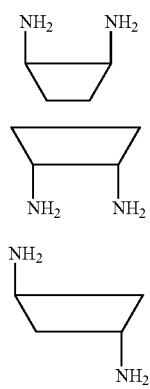

The diaminated cyclodextrin monomer precursor may be prepared by any means known in the art. (Tabushi et al. Tetrahedron Lett. 18:11527-1530 (1977); Mungall et al., J. Org. Chem. 16591662 (1975)). For example, a diiodo-β-cyclodextrin may be reacted with sodium azide and then reduced to form a diamino-β-cyclodextrin). The cyclodextrin monomer precursor is aminated at only two positions. The diaminated cyclodextrin monomer precursor may then be copolymerized with a comonomer A precursor, as described above, to produce a linear cyclodextrin polymer having a repeating unit of formula II-III or a combination thereof, also as described above. However, the amino functionality of a diaminated cyclodextrin monomer precursor need not be directly attached to the cyclodextrin moiety. Alternatively, the amino functionality or another nucleophilic functionality may be introduced by displacement of the iodo or other appropriate leaving groups of a cyclodextrin monomer precursor with amino group containing moieties such as, for example, $HSCH_2CH_2NH_2$ (or a di-nucleophilic molecule more generally represented by $HW—(CR_1R_2)_n—WH$ wherein W, independently for each occurrence, represents O, S, or $NR_1$; $R_1$ and $R_2$, independently for each occurrence, represent H, (un)substituted alkyl, (un)substituted aryl, (un)substituted heteroalkyl, (un)substituted heteroaryl) with an appropriate base such as a metal hydride, alkali or alkaline carbonate, or tertiary amine to form a diaminated cyclodextrin monomer precursor of formula Vd, Ve, Vf or a mixture thereof:

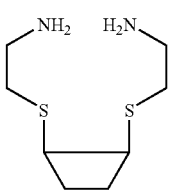

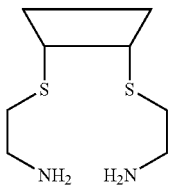

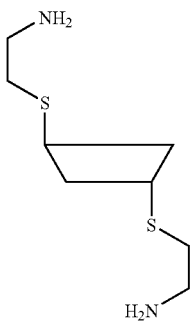

A linear oxidized cyclodextrin-containing copolymer of the invention may also be prepared by oxidizing a reduced linear cyclodextrin-containing copolymer of the invention as described below. This method may be performed as long as the comonomer A does not contain an oxidation sensitive moiety or group such as, for example, a thiol.

According to the invention, a linear cyclodextrin copolymer of the invention may be oxidized so as to introduce at least one oxidized cyclodextrin monomer into the copolymer such that the oxidized cyclodextrin monomer is an integral part of the polymer backbone. A linear cyclodextrin copolymer which contains at least one oxidized cyclodextrin monomer is defined as a linear oxidized cyclodextrin copolymer or a linear oxidized cyclodextrin-containing polymer. The cyclodextrin monomer may be oxidized on either the secondary or primary hydroxyl side of the cyclodextrin moiety. If more than one oxidized cyclodextrin monomer is present in a linear oxidized cyclodextrin copolymer of the invention, the same or different cyclodextrin monomers oxidized on either the primary hydroxyl side, the secondary hydroxyl side, or both may be present. For illustration purposes, a linear oxidized cyclodextrin copolymer with oxidized secondary hydroxyl groups has, for example, at least one unit of formula VIa or VIb:

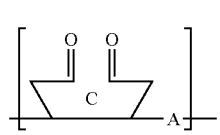

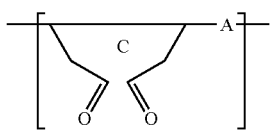

VIb

In formulae VIa and VIb, C is a substituted or unsubstituted oxidized cyclodextrin monomer and A is a comonomer bound, i.e., covalently bound, to the oxidized cyclodextrin C. Also in formulae VIa and VIb, oxidation of the secondary hydroxyl groups leads to ring opening of the cyclodextrin moiety and the formation of aldehyde groups.

A linear oxidized cyclodextrin copolymer may be prepared by oxidation of a linear cyclodextrin copolymer as discussed above. Oxidation of a linear cyclodextrin copolymer of the invention may be accomplished by oxidation techniques known in the art. (Hisamatsu et al., Starch 44:188-191 (1992)). Preferably, an oxidant such as, for example, sodium periodate is used. It would be understood by one of ordinary skill in the art that under standard oxidation conditions that the degree of oxidation may vary or be varied per copolymer. Thus in one embodiment of the invention, a linear oxidized copolymer of the invention may contain one oxidized cyclodextrin monomer. In another embodiment, substantially all cyclodextrin monomers of the copolymer would be oxidized.

Another method of preparing a linear oxidized cyclodextrin copolymer of the invention involves the oxidation of a diiodinated or diaminated cyclodextrin monomer precursor, as described above, to form an oxidized diiodinated or diaminated cyclodextrin monomer precursor and copolymerization of the oxidized diiodinated or diaminated cyclodextrin monomer precursor with a comonomer A precursor. In a preferred embodiment, an oxidized diiodinated cyclodextrin monomer precursor of formula VIIa, VIIb, VIIc, or a mixture thereof:

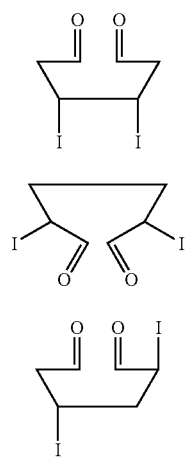

VIIa

VIIb

VIIc may be prepared by oxidation of a diiodinated cyclodextrin monomer precursor of formulae IVa, IVb, IVc, or a mixture thereof, as described above. In another preferred embodiment, an oxidized diaminated cyclodextrin monomer precursor of formula VIIIa, VIIIb, VIIIc or a mixture thereof:

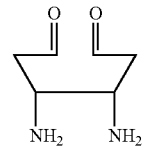

VIIIa

VIIIb

VIIIc may be prepared by amination of an oxidized diiodinated cyclodextrin monomer precursor of formulae VIIa, VIIb, VIIc, or a mixture thereof, as described above. In still another preferred embodiment, an oxidized diaminated cyclodextrin monomer precursor of formula IXa, IXb, IXc or a mixture thereof:

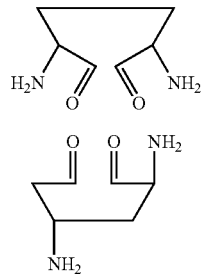

IXa

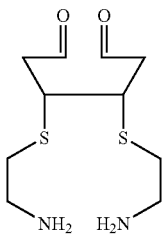

IXb

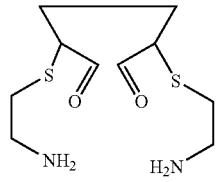

IXc may be prepared by displacement of the iodo or other appropriate leaving groups of an oxidized cyclodextrin monomer precursor disubstituted with an iodo or other appropriate leaving group with the amino or other nucleophilic group containing moiety such as, e.g. $HSCH_2CH_2NH_2$ (or a di-nucleophilic molecule more generally represented by HW—$(CR_1R_2)_n$—WH wherein W, independently for each occurrence, represents O, S, or $NR_1$; $R_1$ and $R_2$, independently for each occurrence, represent H, (un)substituted alkyl, (un)substituted aryl, (un)substituted heteroalkyl, (un)substituted heteroaryl) with an appropriate base such as a metal hydride, alkali or alkaline carbonate, or tertiary amine.

Alternatively, an oxidized diiodinated or diaminated cyclodextrin monomer precursor, as described above, may be prepared by oxidizing a cyclodextrin monomer precursor to form an oxidized cyclodextrin monomer precursor and then diiodinating and/or diaminating the oxidized cyclodextrin monomer, as described above. As discussed above, the cyclodextrin moiety may be modified with other leaving groups other than iodo groups and other amino group containing functionalities. The oxidized diiodinated or diaminated cyclodextrin monomer precursor may then be copolymerized with a comonomer A precursor, as described above, to form a linear oxidized cyclodextrin copolymer of the invention.

A linear oxidized cyclodextrin copolymer may also be further modified by attachment of at least one ligand to the copolymer. The ligand is as described above.

According to the invention, a linear cyclodextrin copolymer or linear oxidized cyclodextrin copolymer may be attached to or grafted onto a substrate. The substrate may be any substrate as recognized by those of ordinary skill in the art. In another preferred embodiment of the invention, a linear cyclodextrin copolymer or linear oxidized cyclodextrin copolymer may be crosslinked to a polymer to form, respectively, a crosslinked cyclodextrin copolymer or a crosslinked oxidized cyclodextrin copolymer. The polymer may be any polymer capable of crosslinking with a linear or linear oxidized cyclodextrin copolymer of the invention (e.g., polyethylene glycol (PEG) polymer, polyethylene polymer). The polymer may also be the same or different linear cyclodextrin copolymer or linear oxidized cyclodextrin copolymer. Thus; for example, a linear cyclodextrin copolymer may be crosslinked to any polymer including, but not limited to, itself, another linear cyclodextrin copolymer, and a linear oxidized cyclodextrin copolymer. A crosslinked linear cyclodextrin copolymer of the invention may be prepared by reacting a linear cyclodextrin copolymer with a polymer in the presence of a crosslinking agent. A crosslinked linear oxidized cyclodextrin copolymer of the invention may be prepared by reacting a linear oxidized cyclodextrin copolymer with a polymer in the presence of an appropriate crosslinking agent. The crosslinking agent may be any crosslinking agent known in the art. Examples of crosslinking agents include dihydrazides and disulfides. In a preferred embodiment, the crosslinking agent is a labile group such that a crosslinked copolymer may be uncrosslinked if desired.

A linear cyclodextrin copolymer and a linear oxidized cyclodextrin copolymer of the invention may be characterized by any means known in the art. Such characterization methods or techniques include, but are not limited to, gel permeation chromatography (GPC), matrix assisted laser desorption ionization-time of flight mass spectrometry (MALDI-TOF Mass spec), $^1$H and $^{13}$C NMR, light scattering and titration.

The invention also provides a cyclodextrin composition containing at least one linear cyclodextrin copolymer and at least one linear oxidized cyclodextrin copolymer of the invention as described above. Accordingly, either or both of the linear cyclodextrin copolymer and linear oxidized cyclodextrin copolymer may be crosslinked to another polymer and/or bound to a ligand as described above. Therapeutic compositions according to the invention contain a therapeutic agent and a linear cyclodextrin copolymer or a linear oxidized cyclodextrin copolymer, including crosslinked copolymers, of the invention. A linear cyclodextrin copolymer, a linear oxidized cyclodextrin copolymer and their crosslinked derivatives are as described above. The therapeutic agent may be any synthetic or naturally occurring biologically active therapeutic agent including those known in the art. Examples of suitable therapeutic agents include, but are not limited to, antibiotics, steroids, polynucleotides (e.g., genomic DNA, cDNA, mRNA, double-stranded RNA, and antisense oligonucleotides), plasmids, peptides, peptide fragments, small molecules (e.g., doxorubicin) and other biologically active macromolecules such as, for example, proteins and enzymes.

(g) Business Methods

Other aspects of the invention provides for certain methods of doing business. In particular, practicing the methods of the invention may enable novel therapeutic compositions and improved formulations thereof. This technical step, when combined with one or more additional steps, provides for novel approaches to conduct a pharmaceutical, or preferably a life-science business. For example, such therapeutic prepared by the method of the invention may be tested for efficacy as therapeutics in a variety of disease models, the potential therapeutic compositions then tested for toxicity and other safety-profiling before formulating, packaging and subsequently marketing the resulting formulation for the treatment of disease. Alternatively, the rights to develop and market such formulations or to conduct such steps may be licensed to a third party for consideration.

Accordingly, in certain embodiments, the present invention provides a method for conducting a pharmaceutical business, comprising:

a. manufacturing a formulation or kit including a pharmaceutical composition of any of the compounds of claims 1-4; and b. marketing to healthcare providers the benefits of using the formulation or kit in the treatment of a disease or disorder.

In other embodiments, the present invention discloses a method for conducting a pharmaceutical business, comprising:

a. providing a distribution network for selling a pharmaceutical composition of any of the compounds of claims 1-4; and b. providing instruction material to patients or physicians for using the preparation in the treatment of a disease or disorder.

In certain embodiments, the present invention provides a method for conducting a pharmaceutical business, comprising:

a. determining an appropriate formulation and dosage of a pharmaceutical composition of any of the compounds of claims 1-4;

b. conducting therapeutic profiling of formulations identified in step (a), for efficacy and toxicity in animals; and c. providing a distribution network for selling a preparation or preparations identified in step (b) as having an acceptable therapeutic profile.

An additional step of the embodiment comprises providing a sales group for marketing the preparation to healthcare providers.

In still other embodiments, the present invention provides a method for conducting a pharmaceutical business, comprising:

a. determining an appropriate formulation and dosage of a pharmaceutical composition of any of the compounds of claims 1-4; and b. licensing, to a third party, the rights for further development and sale of the formulation.

EXEMPLIFICATION

Materials. β-Cyclodextrin, "β-CD", (Cerestar USA, Inc. of Hammond, Ind.) was dried in vacuo (<0.1 mTorr) at 120° C. for 12 h before use.

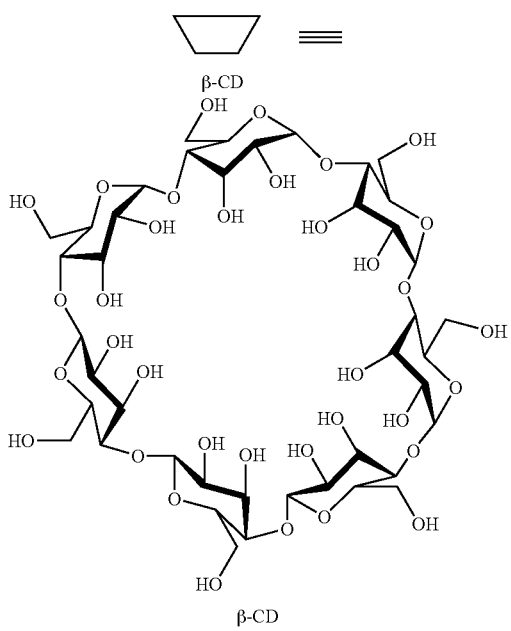

All the anhydrous solvents, HPLC grade solvents and other common organic solvents were purchased from commercial suppliers and used without further purification. Biphenyl-4, 4'-disulfonyl chloride (Aldrich Chemical Company, Inc. of Milwaukee, Wis.) was recrystallized from chloroform/hexanes. Potassium iodide was powdered with a mortar and pestle and dried in an oven at 200° C. Polyethylene glycol dipropanoicsuccinimide (PEG-DiSPA, MW 3400), polyethylene glycol dibutanoicsuccinimide (PEG-DiSBA, MW 3400), and polyethylene glycol dibenzotrizolecarbonate (PEG-DiBTC, MW 3400) were purchased from Nektar (Huntsville, Ala.). Polyethylene glycol di-p-nitrophenolcarbonate (PEG-DiNPC, MW 3400) was acquired from Sigma (St. Louis, Mo.). CPT was purchased from Boehringer Ingelheim (Ingelheim, Germany). Human plasma was purchased from Sigma and reconstituted with DI water. Mouse plasma was prepared by centrifuge removal of blood cells of fresh blood samples collected from BALB/C female mice (Charles River). $6^A,6^D$-diiodo-$6^A,6^D$-dideoxy-β-cyclodextrin (CDDI, Scheme 2) was synthesized according to previous reported procedure by Hwang et. al (Bioconjugate Chem. 12, 280-290). Deionized water (18-MΩ-cm) was obtained by passing in-house deionized water through a Barnstead E-pure purification system. NMR spectra were recorded on a Bruker AMX 500 MHz or a Varian 300 MHz spectrometer. Mass spectral (MS) analysis was performed using either an electrospray mass spectrometer equipped with LCQ ion trap (Thermo Finnigan) and fitted with an electrospray ionization source or a MALDI-TOF mass spectrometer (Voyager DE-PRO, Applied Biosystems). MWs of the polymer samples were analyzed on a GPC system equipped with a Hitachi L-6200 Intelligent Pump, an Anspec RI detector (ERC-7512, Erma, Inc.), a Precision Detectors DLS detector (PD 2020), and double gel permeation columns (PL-aquagel-OH-40 8 μm 300 mm×7.5 mm, Polymer Laboratory) calibrated using polyethylene glycol standard and eluded using PBS (1×) at a concentration of 20-50 mg/mL and at a 0.7 mL/min flow rate at ambient temperature. CD derivatives were analyzed with a C-18 reverse phase column on a HPLC system equipped with an UV detector (System Gold 168 Detector, Beckman Coulter) and an evaporative light scattering (ELS) detector (Sedex 75, Sedere, France). CPT, CPT derivatives, and polymer-CPT conjugates were analyzed on HPLC systems with a C-18 reverse phase column (HIRPB-4438, 4.6×150 mm, Richard Scientific) equipped with a fluorescence detector (FD-500, GTI/Spectro Vision, Groton Technology, Inc.) using a gradient of potassium phosphate buffer (pH 4.1) and acetonitrile. Excitation and emission wavelengths of the fluorescence detector were set at 370 nm and 440 nm, respectively.

Example 1

Biphenyl-4,4'-disulfonyl-A,D-Capped β-Cyclodextrin, 1 (Tabushi et al. *J. Am. Chem. Soc.* 106, 5267-5270 (1984))

Scheme XV

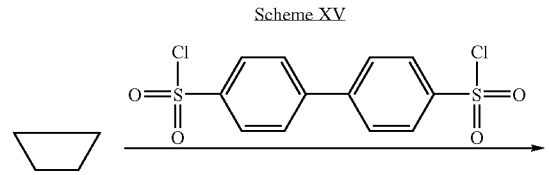

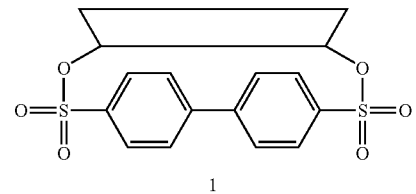

1

A 500 mL round bottom flask equipped with a magnetic stirbar, a Schlenk adapter and a septum was charged with 7.92 g (6.98 mmol) of dry β-cyclodextrin and 250 mL of anhydrous pyridine (Aldrich Chemical Company, Inc.). The resulting solution was stirred at 50° C. under nitrogen while 2.204 g (6.28 mmol) of biphenyl-4,4'-disulfonyl chloride was added in four equal portions at 15 min intervals. After stirring at 50° C. for an additional 3 h, the solvent was removed in vacuo and the residue was subjected to reversed-phase column chromatography using a gradient elution of 0-40% acetonitrile in water. Fractions were analyzed by high performance liquid chromatography (HPLC) and the appropriate fractions were combined. After removing the bulk of the acetonitrile on a rotary evaporator, the resulting aqueous sus-

Example 2

$6^A,6^D$-Diiodo-$6^A,6^D$-Dideoxy-β-cyclodextrin, 2
(Tabushi et al. *J. Am. Chem.* 106, 4580-4584 (1984))

Scheme XVI

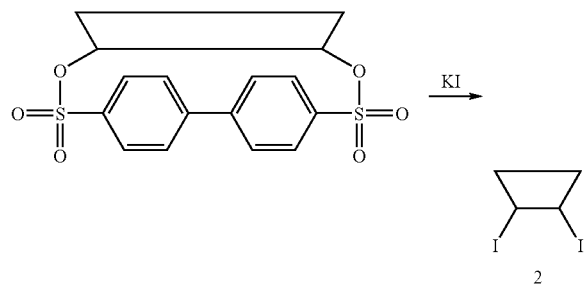

A 40 mL centrifuge tube equipped with a magnetic stirbar, a Schlenk adapter and a septum was charged with 1.02 g (7.2 mmol) of 1, 3.54 g (21.3 mmol) of dry, powdered potassium iodide (Aldrich) and 15 mL of anhydrous N, N-dimethylformamide (DMF) (Aldrich). The resulting suspension was stirred at 80° C. under nitrogen for 2 h. After cooling to room temperature, the solids were separated by filtration and the supernatant was collected. The solid precipitate was washed with a second portion of anhydrous DMF and the supernatants were combined and concentrated in vacuo. The residue was then dissolved in 14 mL of water and cooled in an ice bath before 0.75 mL (7.3 mmol) of tetrachloroethylene (Aldrich) was added with rapid stirring. The precipitated product was filtered on a medium glass frit and washed with a small portion of acetone before it was dried under vacuum over $P_2O_5$ for 14 h. This afforded 0.90 g (92%) of 2 as a white solid.

Example 3

$6^A,6^D$-Bis-(2-aminoethylthio)-$6^A,6^D$-dideoxy-β-cyclodextrin, 3 (Tabushi, I: Shimokawa, K; Fugita, K. *Tetrahedron Lett.* 1977, 1527-1530)

Scheme XVII

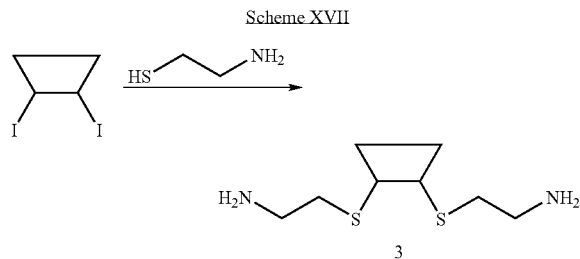

A 25 mL Schlenk flask equipped with a magnetic stirbar and a septum was charged with 0.91 mL (7.37 mmol) of a 0.81 M solution of sodium 2-aminoethylthiolate in ethanol. (Fieser, L. F.; Fieser, M. *Reagents for Organic Synthesis*; Wiley: New York, 1967; Vol. 3, pp. 265-266). The solution was evaporated to dryness and the solid was redissolved in 5 mL of anhydrous DMF (Aldrich). $6^A,6^D$-Diiodo-$6^A,6^D$-dideoxy-β-cyclodextrin (2) (100 mg, $7.38 \times 10^{-5}$ mol) was added and the resulting suspension was stirred at 60° C. under nitrogen for 2 h. After cooling to room temperature, the solution was concentrated in vacuo and the residue was redissolved in water. After acidifying with 0.1 N HCl, the solution was applied to a Toyopearl SP-650M ion-exchange column ($NH_4^+$ form) and the product was eluted with a 0 to 0.4 M ammonium bicarbonate gradient. Appropriate Fractions were combined and lyophilized to dryness. This afforded 80 mg (79%) of 3 as a white powder.

Alternative Synthesis of dicysteamine β-CD 3.

To a solution of 4.69 g (3.17 mmol) of 2 in 100 mL of degassed water was added 0.489 g (6.34 mmol) of freshly sublimed cysteamine. The solution was stirred under reflux for 2 h. After cooling to room temperature and acidifying with 1 N HCl, the solution was applied to a Toyopearl SP-650M ion-exchange column ($NH_4^+$ form) and the product was eluted with a 0 to 0.2 M ammonium bicarbonate gradient. Appropriate fractions were combined and lyophilized to dryness. This procedure gave 1.87 g (39% yield) of a white solid. The solid was characterized by TLC (silica gel, n-PrOH—AcOEt-$H_2O$—$NH_3$ aq 5/3/3/1, detection by ninhydrin) and exhibited a major spot corresponding to 3. Matrix-assisted laser desorption/ionization (MALDI) time-of flight (TOF) mass spectrum was recorded on 2 meter ELITE instrument supplied by PerSeptive Biosystems, Inc. MALDI-TOF m/z calcd for 3:1252. found: 1253.5 $[M+H]^+$, 1275.5 $[M+Na]^+$, 1291.4 $[+K]^+$. $^{13}$C NMR (Bruker 500 Mhz, $D_2O$) δ ppm: 32.1 (S—$CH_2$) and 38.8 ($CH_2$—$NH_2$), 32.9 (C6 adjacent to S), 60.2 (C6 adjacent to OH), 70.8, 71.4, 72.5 (C2, C3, C5), 81.8 (C4), 101.7 (C1).

Example 4

$6^A,6^D$-Bis-(2-amino-2-carboxylethylthio)-$6^A6^D$-dideoxy-β-cyclodextrin, 4 (CD-Bis Cys)

Scheme XVIII

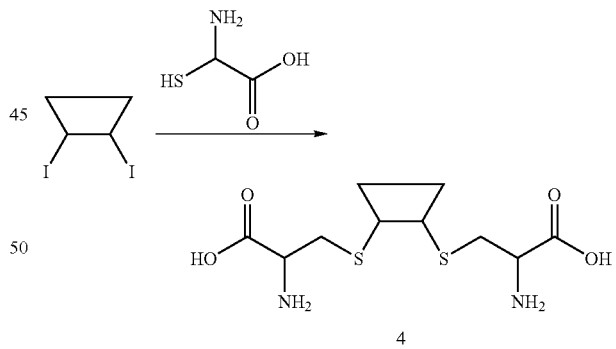

167 mL of 0.1 M sodium carbonate buffer were degassed for 45 minutes in a 500 mL 2-neck round bottom flask equipped with a magnetic stir bar, a condenser and septum. To this solution were added 1.96 g (16.2 mmol) of L-cysteine and 10.0 g (73.8 mmol) of diiodo, deoxy-β-cyclodextrin 2. The resulting suspension was heated at a reflux temperature for 4.5 h until the solution turned clear (color less). The solution was then cooled to room temperature and acidified to pH 3 using 1N HCl. The product was precipitated by slow addition of acetone (3 times weight ratio of the solution). This afforded 9.0 g crude material containing CD-biscysteine (90.0%), unreacted cyclodextrin, CD-mono-cysteine and cystine. The resulting solid was subjected to anionic exchange column chromatography (SuperQ650M, Tosoh Bioscience) using a gradient elution of 0-0.4M ammonium bicarbonate. All fractions were analyzed by HPLC. The desired fractions were combined and the solvent was reduced to 100 mL under vacuum. The final product was either precipitated by adding acetone or by adding methanol (3 times weight ratio of the solution). 4 was obtained in 60-90% yield. $^1$H NMR (D$_2$O) δ 5.08 (m, 7H, CD-2-CH), 3.79-3.94 (m, 30H, CD-3,4-CH, CD-CH$_2$, Cys-CH), 3.49-3.62 (m, 14H, CD-5, 6-CH), 2.92-3.30 (m, 4H, Cys-CH$_2$). $^{13}$C NMR (D$_2$O) δ 172.3, 101.9, 83.9, 81.6, 81.5, 73.3, 72.2, 72.0, 60.7, 54.0, 34.0, 30.6. ESI/MS (m/z): 1342 [M]$^+$, 1364 [M+Na]$^+$. Purity of 4 was confirmed by HPLC.

Example 5

$6^A,6^D$-Bis-(carboxylmethylthio)-$6^A,6^D$-dideoxy-β-cyclodextrin, 5 (CDDM)

Scheme XIX

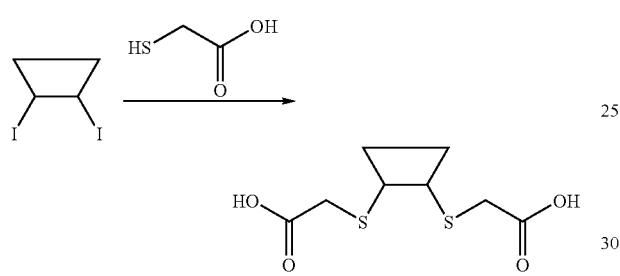

A 50 mL of 0.1 M sodium carbonate solution was degassed for 2 h in a 100 mL 3-neck round bottom flask equipped with a magnetic stir bar, a condenser and septa. Mercaptoacetic acid (0.46 mL, 6.64 mmol) was syringed into the flask and pH of the solution was adjusted to 9.3 with 1N sodium hydroxide. To this resulting solution was added 3.00 g (2.21 mmol) of di-iodo-β-cyclodextrin 2 and heated at 80° C. for an hour. The solution temperature was increased 10° C. every hour until it reached 100° C. After 3 h. at the reflux temperature, the clear color less solution was cooled to room temperature and acidified to pH 3.5 using 1 N HCl. The crude product was crashed out by slow addition of acetone (3 times weight ratio of the solution). The resulting solid was subjected to anionic exchange column chromatography using a gradient elution of 0-0.4 M ammonium bicarbonate solution. This afforded 1.8 g (63.4%) of 5 as a color less solid. ESI/MS (m/z): 1281 [M]$^-$. Purity of this compound was confirmed with HPLC.

Example 6

CD-Bis(Glutamic acid-γ-Benzyl ester) 6

Scheme XX

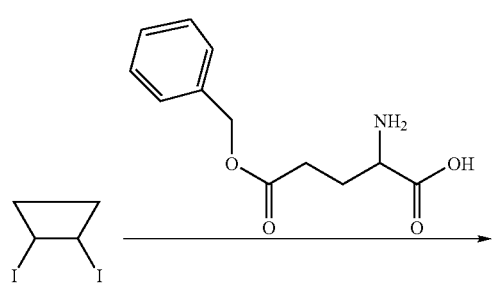

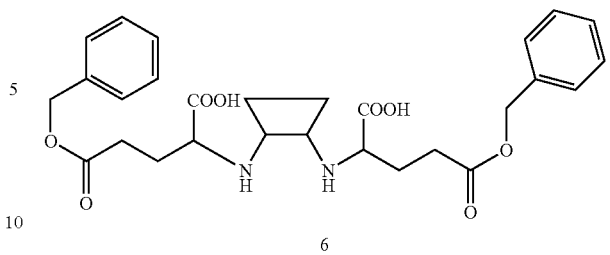

A 50 mL round bottom flask equipped with a magnetic stirbar and a condenser and a septum was charged with 0.101 g (0.425 mmol) of H-Glu(Obzl)-OH and 0.15 g (0.106 mmol) of dio-iodo β cyclodextrin 2 in 5 mL of degassed 0.1 M sodium carbonate solution. The solution mixture was heated at 100° C. for 2 h. The solution was then cooled to room temperature and acidified to pH 4 before dialyzing in MWCO 500 membranes for 24 h. The yield of 6 was 0.142 g (83.6%).

Example 7

CD-BisLys(Z) 7

Scheme XXI

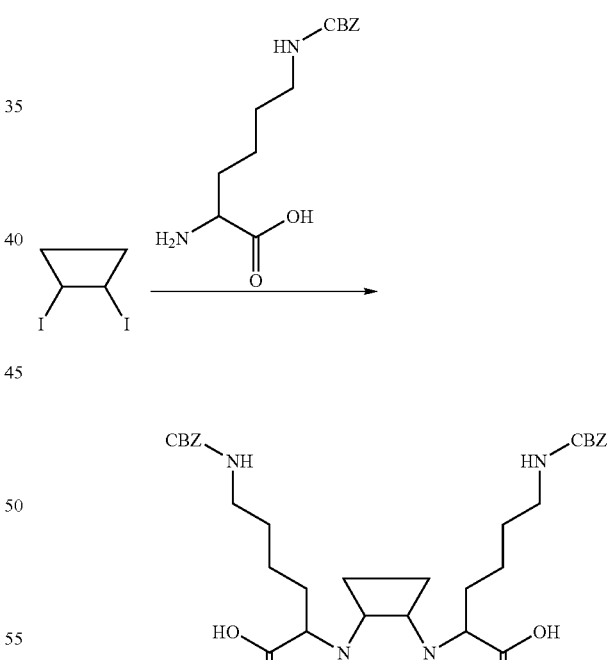

A 50 mL round bottom flask equipped with a magnetic stirbar and a condenser and a septum was charged with 0.124 g (0.443 mmol) of H-Lysine(Z)-OH and 0.15 g (0.111 mmol) of di-iodo-β-cyclodextrin 2 in 5 mL of degassed 0.1M sodium carbonate solution. The solution mixture was heated at 100° C. for 4 h. The solution was then filtered and the pH of the filtrate is adjusted to 8.5 before dialyzing in MWCO 500 membranes for 24 h. The yield of 7 was 0.124 g (68.9%).

Example 8

Synthesis of β-cyclodextrin-Tosylate, 8 (Melton, L. D., and Slessor, K. N., *Carbohydrate Research*, 18, p. 29 (1971))

Scheme XXII

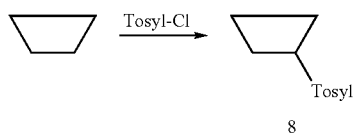

8

A 500 mL round-bottom flask equipped with a magnetic stirbar, a vacuum adapter and a septum was charged with a solution of dry β-cyclodextrin (8.530 g, 7.51 mmol) and 200 mL of dry pyridine. The solution was cooled to 0° C. before 1.29 g (6.76 mmol) of tosyl chloride was added. The resulting solution was allowed to warm to room temperature overnight. The pyridine was removed as much as possible in vacuo. The resulting residue was then recrystallized twice from 40 mL of hot water to yield 7.54 (88%) of a white crystalline solid 8.

Example 9

Synthesis of Iodo-β-cyclodextrin, 9

Scheme XXIII

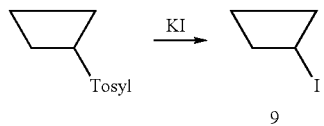

9

A round bottom flask with a magnetic stirbar and a Schlenk adapter is charged with 8, 15 equivalents of potassium iodide, and DMF. The resulting mixture is heated at 80° C. for 3 h, after which the reaction is allowed to cool to room temperature. The mixture is then filtered to remove the precipitate and the filtrate evaporated to dryness and redissolved in water at 0° C. Tetrachloroethylene is added and the resulting slurry stirred vigorously at 0° C. for 20 minutes. The solid 9 is collected on a medium glass frit, triturated with acetone and stored over $P_2O_5$.

Example 10

Synthesis of Cysteamine-β-Cyclodextrin, 10

Scheme XXIV

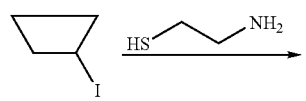

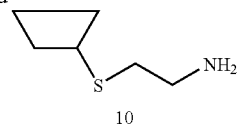

10

To a solution of 9 in 100 mL of degassed water is added 1 eq. of freshly sublimed cysteamine. The solution is stirred under reflux for 2 h. After cooled to room temperature and acidified with 1 N HCl, the solution is applied to a Toyopearl SP-650M ion-exchange column ($NH_4^+$ form) and the product is eluted with an ammonium bicarbonate gradient. Appropriate fractions are combined and lyophilized to dryness to yield 10.

Example 11

Synthesis of Gly-CPT 11 (Greenwald et al., *Bioorg. Med. Chem.*, 1998, 6, 551-562)

Scheme XXV

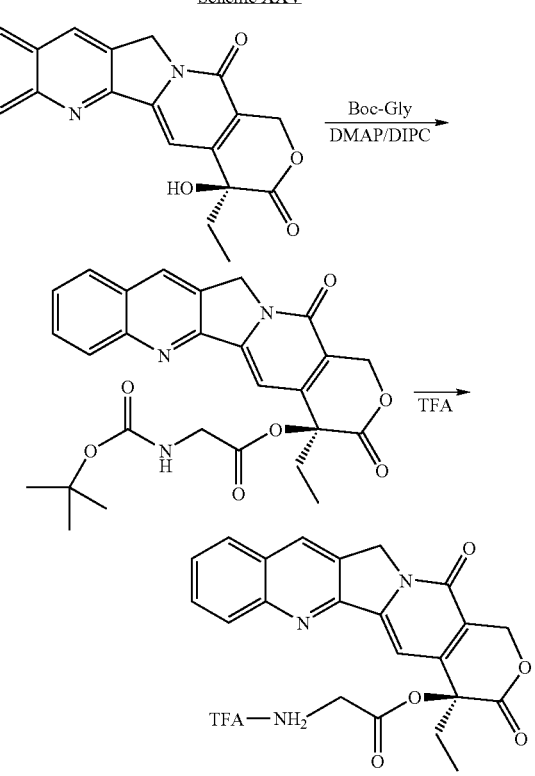

11 t-Boc-glycine (0.9 g, 4.7 mmol) was dissolved in 350 mL of anhydrous methylene chloride at room temperature, and to this solution were added DIPC (0.75 mL, 4.7 mmol), DMAP (382 mg, 3.13 mmol) and camptothecin (0.55 g, 1.57 mmol) at 0° C. The reaction mixture was allowed to warm to room temperature and left for 16 h. The solution was washed with 0.1 N HCl, dried and evaporated under reduced pressure to yield a white solid, which was recrystallized from methanol to give camptothecin-20-ester of t-Boc-glycine: $^1$H NMR (DMSO-$d_6$) 7.5-8.8 (m), 7.3 (s), 5.5 (s), 5.3 (s), 4 (m), 2.1 (m), 1.6 (s), 1.3 (d), 0.9 (t). Camptothecin-20-ester of t-Boc-glycine (0.595 g, 1.06 mmol) was dissolved in a mixture of methylene chloride (7.5 mL) and TFA (7.5 mL) and stirred at room temperature for 1 h. Solvent was removed and the residue was recrystallized from methylene chloride and ether to give 0.45 g of 11. $^1$H NMR (DMSO-d$_6$) δ7.7-8.5 (m); 7.2 (s), 5.6 (s), 5.4 (s), 4.4 (m), 2.2 (m), 1.6 (d), 1.0 (t), $^{13}$C NMR (DMSO-d$_6$) δ168.6, 166.6, 156.5, 152.2, 147.9, 146.2, 144.3, 131.9, 130.6, 129.7, 128.8, 128.6, 128.0, 127.8, 119.0, 95.0, 77.6, 66.6, 50.5, 47.9, 30.2, 15.9, 7.9. ESI/MS (m/z) expected 405. Found 406 (M+H).

Example 12

Synthesis of GlyGlyGly-CPT 12

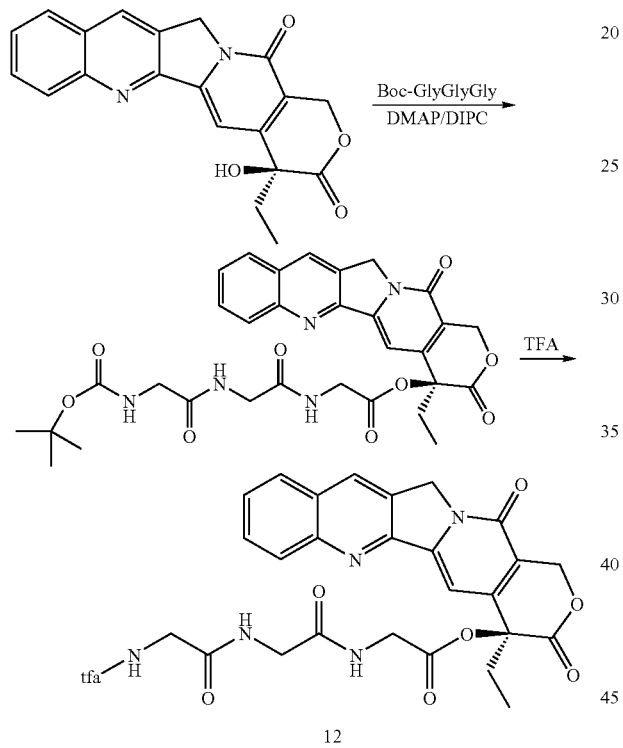

t-Boc-GlyGlyGly (1.359 g, 4.7 mmol) was dissolved in 350 mL of anhydrous methylene chloride at room temperature and to this solution were added DIPC (0.75 mL, 4.7 mmol), DMAP (382 mg, 3.13 mmol) and camptothecin (0.55 g, 1.57 mmol) at 0° C. The reaction mixture was allowed to warm to room temperature and left for 16 h. The solution was washed with 0.1 N HCl, dried and evaporated under reduced pressure to yield a white solid, which was recrystallized from methanol to give camptothecin-20-ester of t-Boc-GlyGlyGly: $^1$H NMR (DMSO-d$_6$) δ 8.40 (s), 8.25 (d), 7.91 (d), 7.78 (m), 7.65 (t), 7.26 (s), 7.05 (br, s), 5.65 (d), 5.40 (d), 5.25 (s), 5.10 (br, s), 3.75-4.42 (m), 2.15-2.35 (m), 1.45 (s), 0.95 (t) Camptothecin-20-ester of t-Boc-GlyGlyGly (1.5 g, 1.06 mmol) was dissolved in a mixture of methylene chloride (10 mL) and TFA (10 mL) and stirred at room temperature for 1 h. Solvent was removed under vacuum and the residue was re-dissolved in methylene chloride. The solution was poured into ether to give instant precipitate (yellow). The precipitate was filtered and washed with cold ether to give 1.31 g of 12.

$^1$H NMR (DMSO-d$_6$) δ 8.79 (s), 7.75-8.61 (m), 7.10 (s), 5.55 (s), 3.90-4.37 (m), 3.86 (s), 3.54 (s), 2.11-2.23 (m), 0.95 (t). ESI/MS (m/z) expected 519. Found 520 (M+H).

Figure 2:
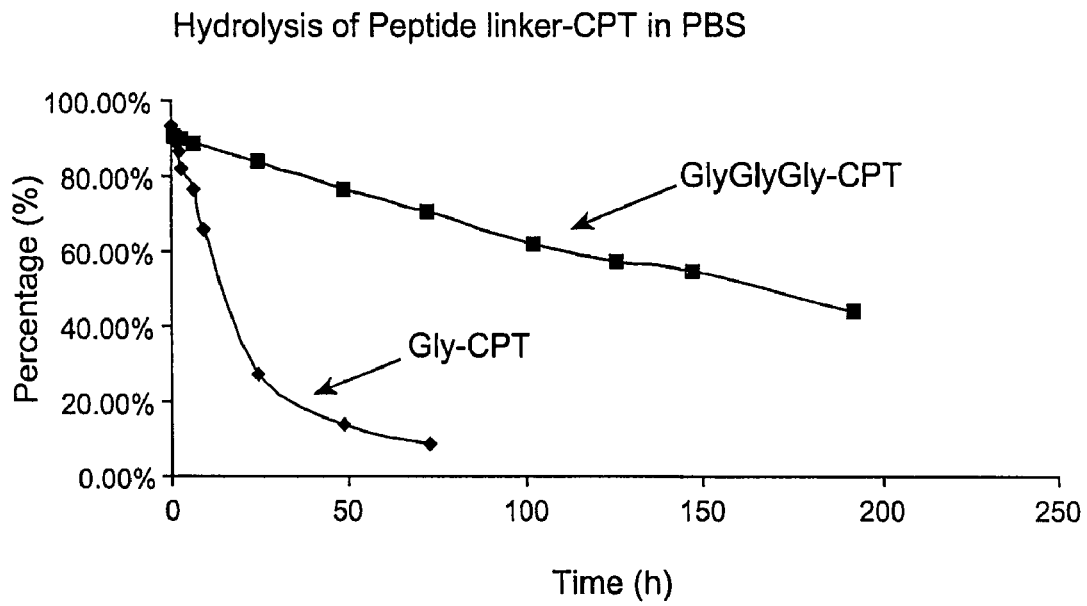
FIG. 2 demonstrates the effect of peptide tether length on drug release rate for drug-loaded CD polymer.

Stability of CPT-Peptide Ester Bond 11 and 12 were dissolved in PBS buffer (pH 7.4) at room temperature to prepare a solution about 500 μg/mL. This solution was further diluted in 8.5% H$_3$PO$_4$ to 10 μg/mL. Hydrolysis rate was analyzed using HPLC equipped with a C$_{18}$ RP (reverse phase) column and a fluorescence detector using a 50/50 (v/v) of acetonitrile/potassium phosphate buffer (pH 4.1). The peaks of 11 (or 12) and the released CPT (lactone form) were integrated. The stability of the ester bond in aqueous solution is peptide-length dependant. Thus the drug release rate (hydrolysis rate) can be tuned by adjusting the peptide length. See FIG. 2.

Lactone Stability of CPT, 11 and 12 in Phosphate Buffered Saline (PBS)

CPT, 11 or 12 was dissolved in DMSO at 1 mg/mL and then diluted to 1 μg/mL with PBS (1×, pH 7.4). 30 μL of solution were injected into the HPLC at room temperature at selected time intervals. The peak area from the CPT lactone form of CPT, 11 or 12) were integrated.

Figure 3:
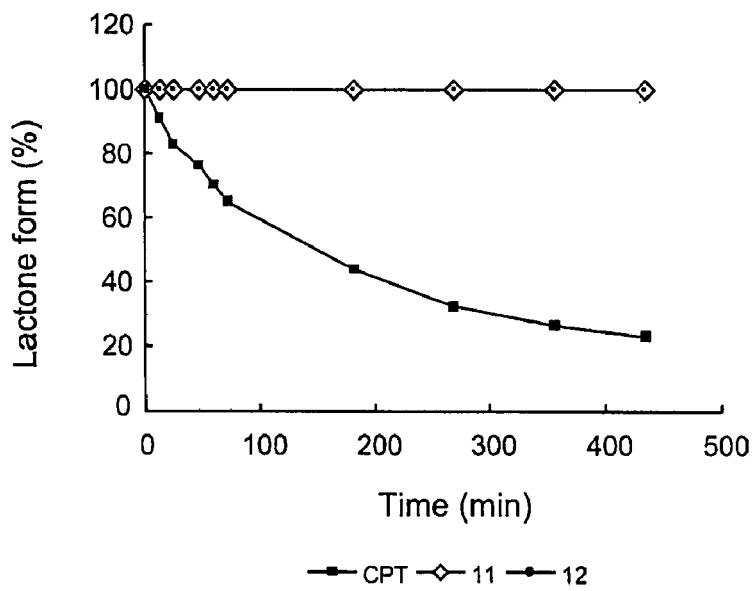
FIG. 3 presents the effect that tethering camptothecin has on enhancing camptothecin stability, e.g., inhibiting lactone ring-opening.

The rate of lactone ring opening for 11, 12 and CPT were studied in PBS buffer (pH 7.4). Both 11 and 12 were very stable against ring-opening and no carboxylate forms of 11 and 12 were detected throughout the study (7 hours). On the other hand, more than 60% of the CPT lactone form was transformed to its carboxylate form in the same period of time. (See FIG. 3)

Example 13

Synthesis of Lys(Bis CBZ)-CPT 13

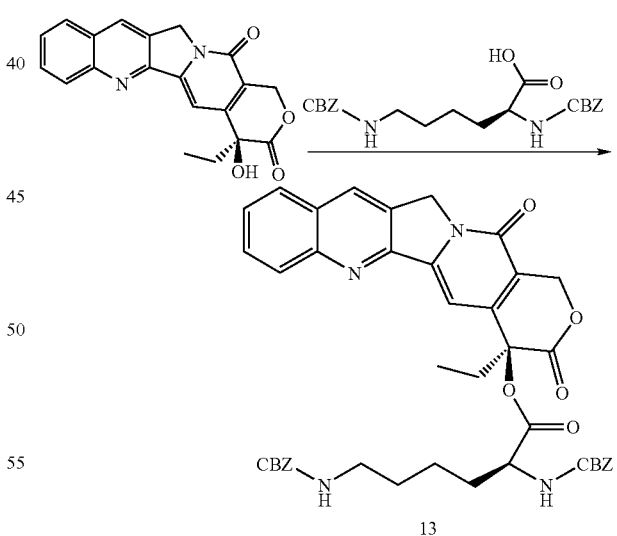

N,N-Bis CBZ-Lysine (311 mg, 0.75 mmol) was dissolved in 56 mL of anhydrous methylene chloride at room temperature. To this solution were added DIPC (0.12 mL, 0.75 mmol), DMAP (0.61 mg, 0.5 mmol) and camptothecin (0.087 g, 0.25 mmol) at 0° C. The reaction mixture was allowed to warm to room temperature and left for 16 h. The solution was washed with 0.1 N HCl, dried and evaporated under reduced pressure to yield a light yellow solid, which was recrystallized from methanol to give camptothecin-20-ester of N,N-Bis CBZ-Lys 13. Purification of 13 was satisfactory based on TLC and HPLC analysis.

Hydrolysis of 13 in aqueous solution is very slow and cannot be detected using HPLC equipped with a UV detector. Hydrolysis rate of the ester bond of CPT-peptide linker can be tuned not only by adjusting the length of peptide, as shown in Example 12, but also by using different amino acid linked directly with CPT's 20-OH.

Figure 4:
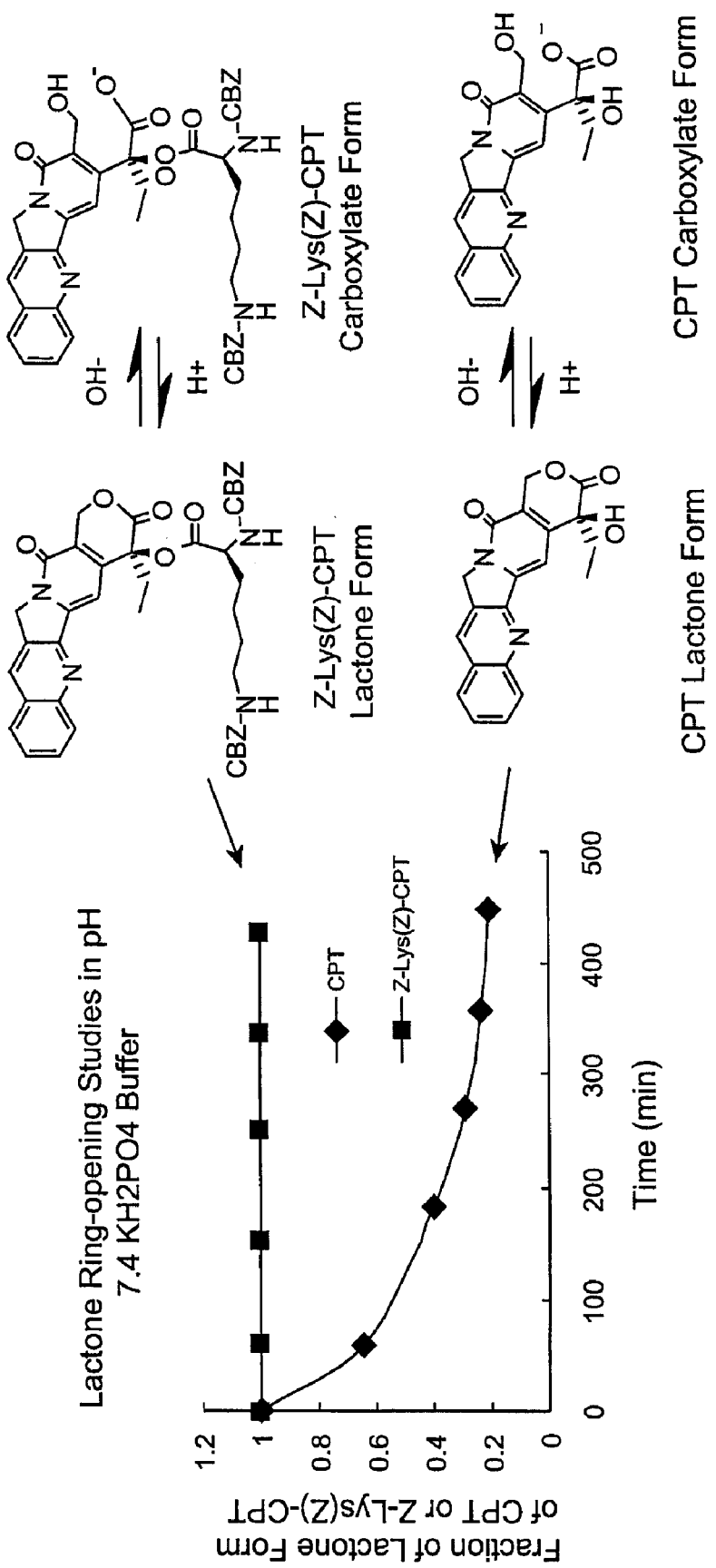
FIG. 4 shows lactone ring opening studies in pH 7.4 KH2PO4 buffer.

The transformation of lactone form to carboxylate form of CPT and 13 were also tested in PBS buffer. It was found that the transformation of lactone form to carboxylate form of compound 13 was much slower than that of free CPT, indicating that lactone form (drug active form) can be stabilized by forming an ester with the —OH of CPT at its 20 position. (See FIG. 4)

Example 14

Synthesis Lys-Gly-CPT 14

11 is dissolved in chloroform. N,N-DiBoc-Lys-NHS, (1.0 eq) is added followed by triethylamine (1.0 eq). The mixture is stirred at rt for 16 hours and extracted twice with water and then dried with MgSO4. Solvent is removed under high vacuum to yield N,N-DiBoc-Lys-Gly-CPT. To this compound is added a mixture of equal volume CH$_2$Cl$_2$ and TFA and stirred at rt for 1 h. The solvent is then removed under vacuum. The residue is redissolved in CHCl$_3$. Ether is added to the solution to crash out the product 14. The precipitate is washed several times with ether and then dried under vacuum. It is purified using a silica gel column chromatography to yield 14 in pure TFA salt form.

Example 15

Synthesis of Suc-Gly-CPT 15

A solution of succinic anhydride is mixed with 11 (1 eq) in dry CHCl$_3$ in the presence of a catalytic amount of DMAP and DIEA (1 eq). The mixture is stirred at rt for 24 hours to yield 15. 15 is purified by crystallization.

Example 16

Synthesis of Glu-Suc-Gly-CPT 16

15 is converted to its NHS ester using traditional DCC/NHS method. The NHS ester of 15 is then reacted with glutamic acid (1.0 eq) in DMSO in the presence of triethylamine. The solution is added to ether to precipitate 16. 16 is purified by crystallization.

Example 17

Synthesis of Glu-Bis(GlyCPT) 17

11 and Boc-Glu(NHS)—NHS (0.4 eq) are mixed in CHCl$_3$ under argon before triethylamine (1 eq) is added to the mixture. The solution is stirred at rt for 16 h and then washed with acidic water. The organic layer is dried and then solvent is removed under vacuum. The resulting compound is purified using a silica gel column chromatography. The purified compound is then dissolved in an equal volume mixture of TFA and CH$_2$Cl$_2$. The mixture is stirred at rt for 1 h and then poured into ether. The precipitate 17 is washed with ether and dried under vacuum.

Example 18

Synthesis of Cyclodextrin-Camptothecin 18

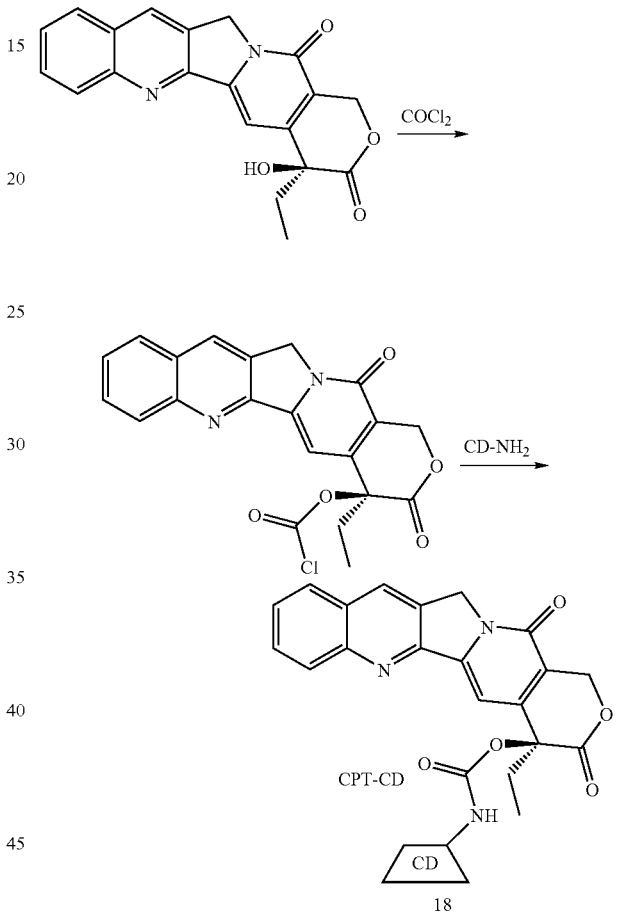

CPT (197 mg, 0.566 mmol) was vacuumed for 30 minutes. Dry chloroform (100 mL) was added under argon. Phosgene (1.34 mL, 20% in toluene solution) was added at 0° C. Ice bath was removed and the solution was warmed up to room temperature. Two hours later solvent was removed under high vacuum. Dry DMSO (50 mL) was added to the residue, followed by 200 mg CD-NH$_2$ (Cyclodextrin Technology, Inc.) and triethylamine (4 mL, excess). 16 hours later, the solution was poured into 200 mL ether. Precipitate was washed with ether extensively and then dried. 167 mg yellow powder (18) was obtained (62% yield). TLC analysis (silica gel) of 18: R$_f$=0 (developed with CHCl$_3$/MeOH v/v=5/1). TLC analysis of CPT: R$_f$=0.65 (developed with CHCl$_3$/MeOH v/v=5/1). Solubility: >10 mg/mL in water. This indicates that solubility of CPT in water can be substantially increased when it is covalently attached to cyclodextrin molecule (free CPT solubility in water <0.004 mg/mL).

Example 19
Synthesis of CDDC-Dianhydride Copolymer 19, 21 and its CPT Conjugate 20, 22
Scheme XXIX
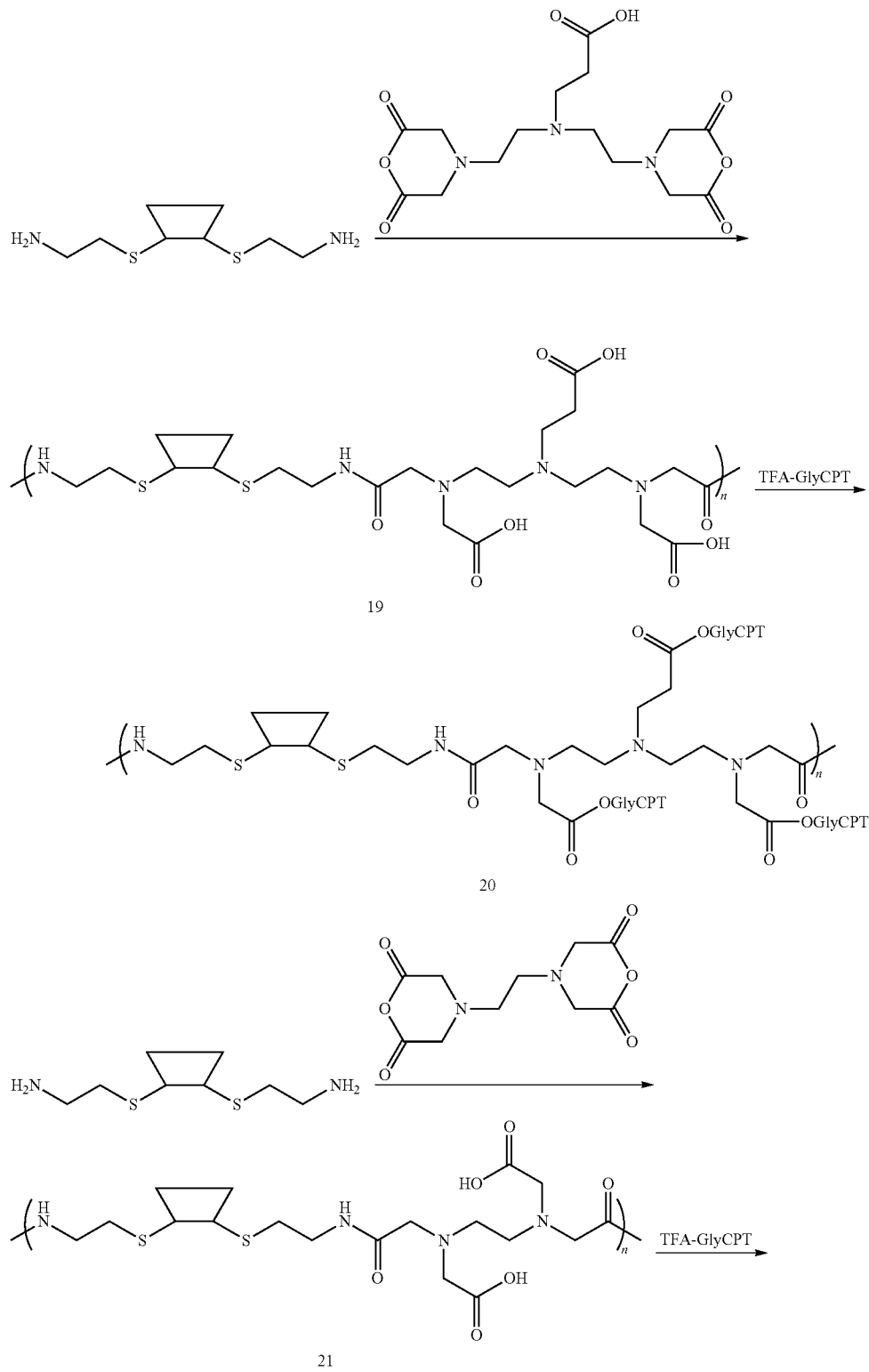

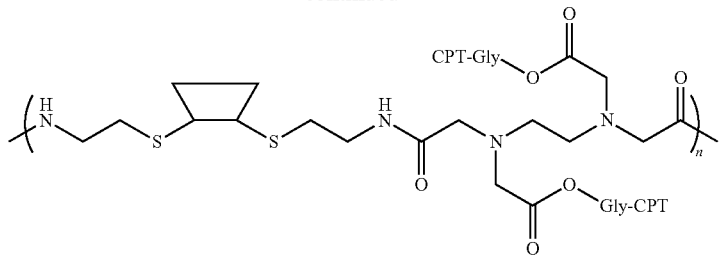

22

A: Ethylenediamine tetraacetic dianhydride (25.6 mg, 0.1 mmol) and CDDC (3, 125.3 mg, 0.1 mmol) were dissolved in 2 mL of dry DMSO. The solution was heated at 50° C. for 72 h. Water was added to the mixture, followed by addition of 1 N NaOH to pH around 12. The polymer was dialyzed in 10,000 MWCO membrane for 24 h. Precipitation was observed in the dialysis membrane. The solid was removed and the remaining solution was dialyzed again in 10,000 MWCO membrane for 24 h. A white powder 19 (75 mg) was obtained after lyophilization.

11 is added to the polymer (19)/DMSO solution in the presence of EDC (2 eq), NHS (1 eq), and DIEA (1.0 eq). The solution is stirred for 16 h and then poured into ether. The precipitate is washed with CH$_2$Cl$_2$ extensively until no free drug is observed in the washing solution. Compound 20 is obtained after drying under high vacuum.

B: Diethylenetriamine pentaacetic dianhydride (8.5 mg, 0.024 mmol) and CDDC, 3 (30 mg, 0.024 mmol) were dissolved in 1-methyl-2 pyridin one (2 mL). The mixture was stirred at 64° C. for 4 days and then dialyzed in 10,000 MWCO membrane for 2 days. A white powder 21 (3 mg) was obtained after lyophilization.

11 is added to the polymer (21)/DMSO solution in the presence of EDC (2 eq), NHS (1 eq), and DIEA (1.0 eq). The solution is stirred for 16 h and then precipitated in ether. The precipitate is washed with CH$_2$Cl$_2$ extensively until no free drug is observed in the washing solution. Compound 22 is obtained after drying under high vacuum.

Example 20

Synthesis of CCD-Cys Copolymer 23 and its CPT conjugate 24

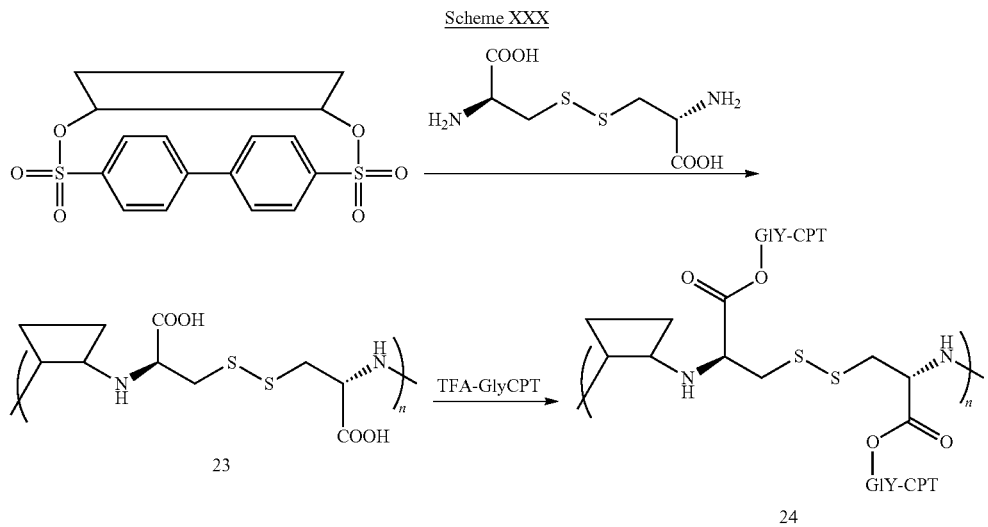

CCD 1 (141.3 mg, 0.1 mmol) and cystine (24 mg, 0.1 mmol) were dissolved in dry DMSO (0.3 mL) and pyridine (0.1 mL). The mixture was stirred under argon for overnight at 72° C. Water (10 mL) was added. Precipitate was filtered and the filtrate was dialyzed in 10,000 MWCO membrane (Spectra/Por 7) for 48 h. A white powder 23 (8 mg) was obtained.

11 is mixed with 23 in DMSO. EDC (2 eq), NHS (1 eq), and DIEA (1.0 eq) are added to the solution. The solution is stirred for 16 h and then precipitated with ether. The precipitate is washed with CH$_2$Cl$_2$ extensively until no free drug is observed in the washing solution. Compound 24 is obtained after drying under high vacuum.

Example 21

Synthesis of CD-BisGlu-Diamine Copolymer 25 and its CPT conjugate 26

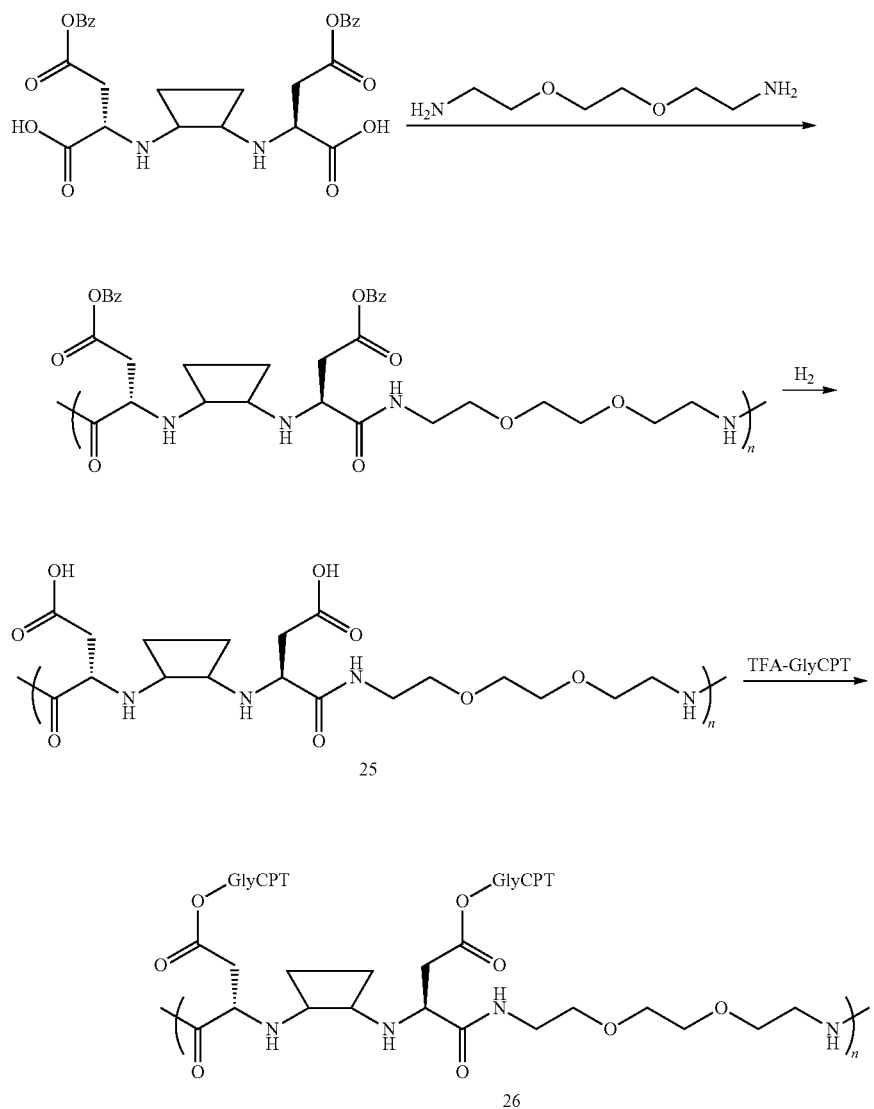

CD-Bis(Glutamic acid-γ-Benzyl ester) 6 and ethyleneglycolbisethylamine are dissolved in dry DMSO. EDC (3 eq) and Sulfo-NHS (2 eq) are added to the mixture. The solution is stirred under argon for 2 days at rt. The solution is then transferred to a 10,000 MWCO dialysis membrane and dialyzed for 48 hours. After lyophilization a white powder is obtained. The solid is then dissolved in DMSO and methanol solvent mixture and treated with $H_2$ in the presence of 10% Pd/C catalyst for 24 hours. The solution is poured into ether to crash out the product. 25 is obtained after drying under vacuum.

11 is mixed with 25 in DMSO solution. EDC (2 eq), NHS (1 eq), and DIEA (1.0 eq) are added to the solution. The solution is stirred for 16 hrs and then precipitated with ether. The precipitate is washed with $CH_2Cl_2$ extensively until no free drug is observed in the washing solution. Compound 26 is obtained after drying under high vacuum.

Example 22

Synthesis of CDDM-Lys(GlyCPT) Polymer 27

Scheme XXXII

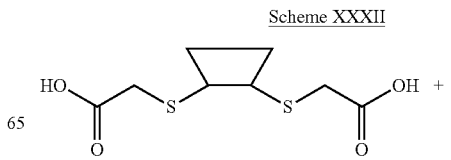

83
-continued
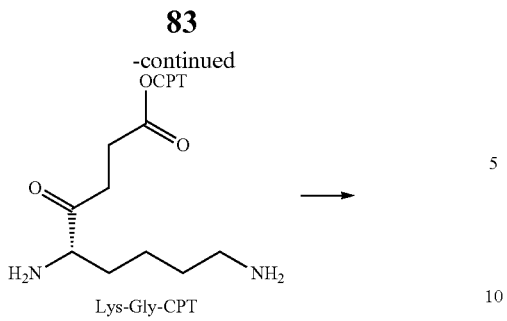
Lys-Gly-CPT
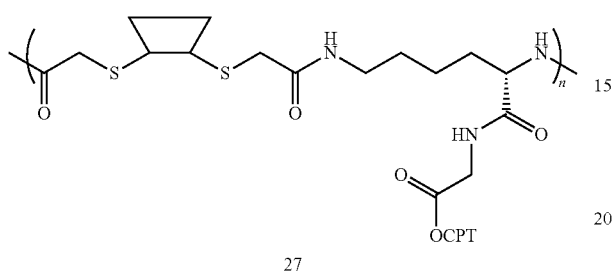
27
CDDM, 5, and Lys-Gly-CPT, 14, are dissolved in dry DMSO. EDC (3 eq) and Sulfo-NHS (2 eq) are added to the mixture. The solution was stirred under argon for 2 days at rt. The solution is then poured into ether. The precipitate 27 is dried under vacuum.
Example 23
Synthesis of CDDC-Cys(Boc) Copolymer 28, CDDC-CysCopolymer 29 and its CPT Conjugate 30
Scheme XXXIII
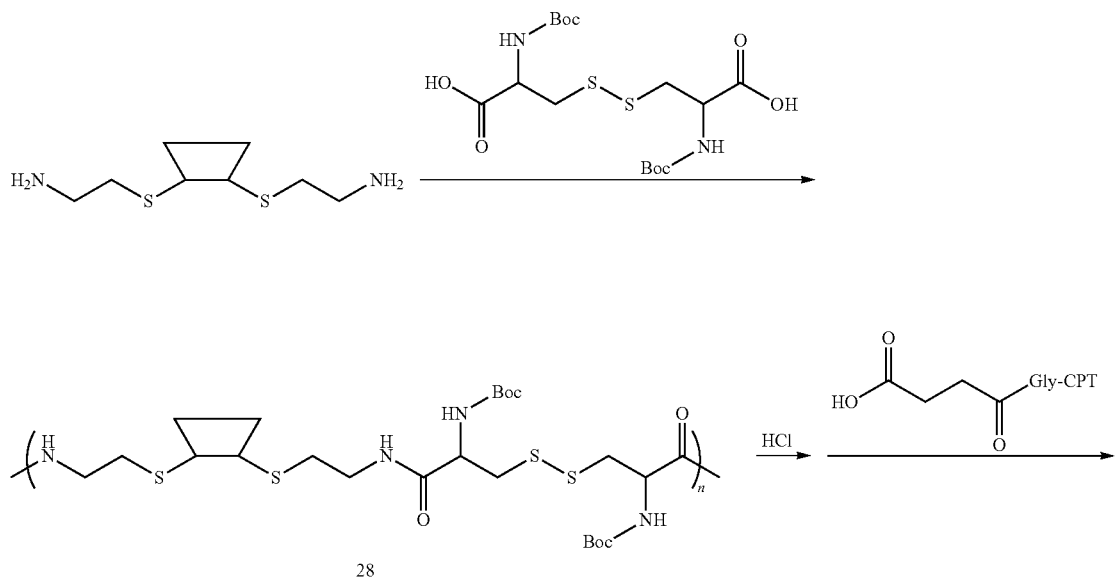
28
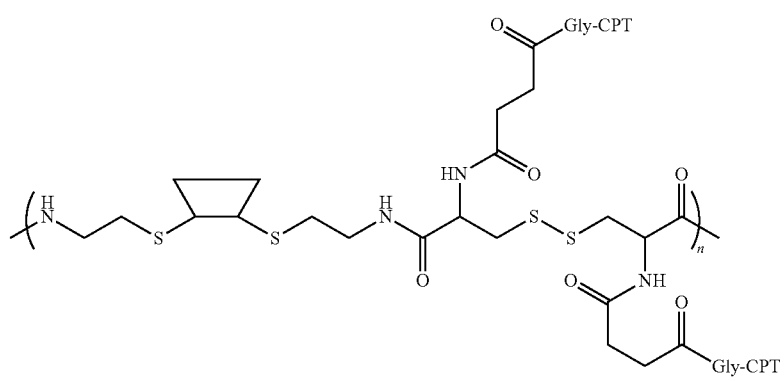
30

CDDC (3) and N, N-DiBoc-Cystine are dissolved in dry DMSO. EDC (3 eq) and Sulfo-NHS (2 eq) were added to the mixture. The solution was stirred under argon for 2 days at rt. The solution is then transferred to a 10,000 MWCO dialysis membrane and dialyzed for 48 hours. After lyophilization a white powder, CDDC-Cys(Boc) polymer 28, is obtained. To the white powder 28 is added a mixture of HCl and DMSO solution. The solution is stirred at rt for 1 h and then dialyzed against water for 24 h using 10,000 MWCO membrane. 29 is obtained as a white solid.

Suc-Gly-CPT 15 is mixed with 29 in DMSO solution. EDC (2 eq), NHS (1 eq), and DIEA (1.0 eq) are added to the solution. The solution is stirred for 16 h under argon and then precipitated with ether. The precipitate is washed with ether until no free drug is observed in the washing solution. Compound 30 is obtained after drying under high vacuum.

Example 24

Synthesis of Biodegradable CD-Polyphosphoester Polymer 31 and its CPT Conjugates 32

Scheme XXXIV

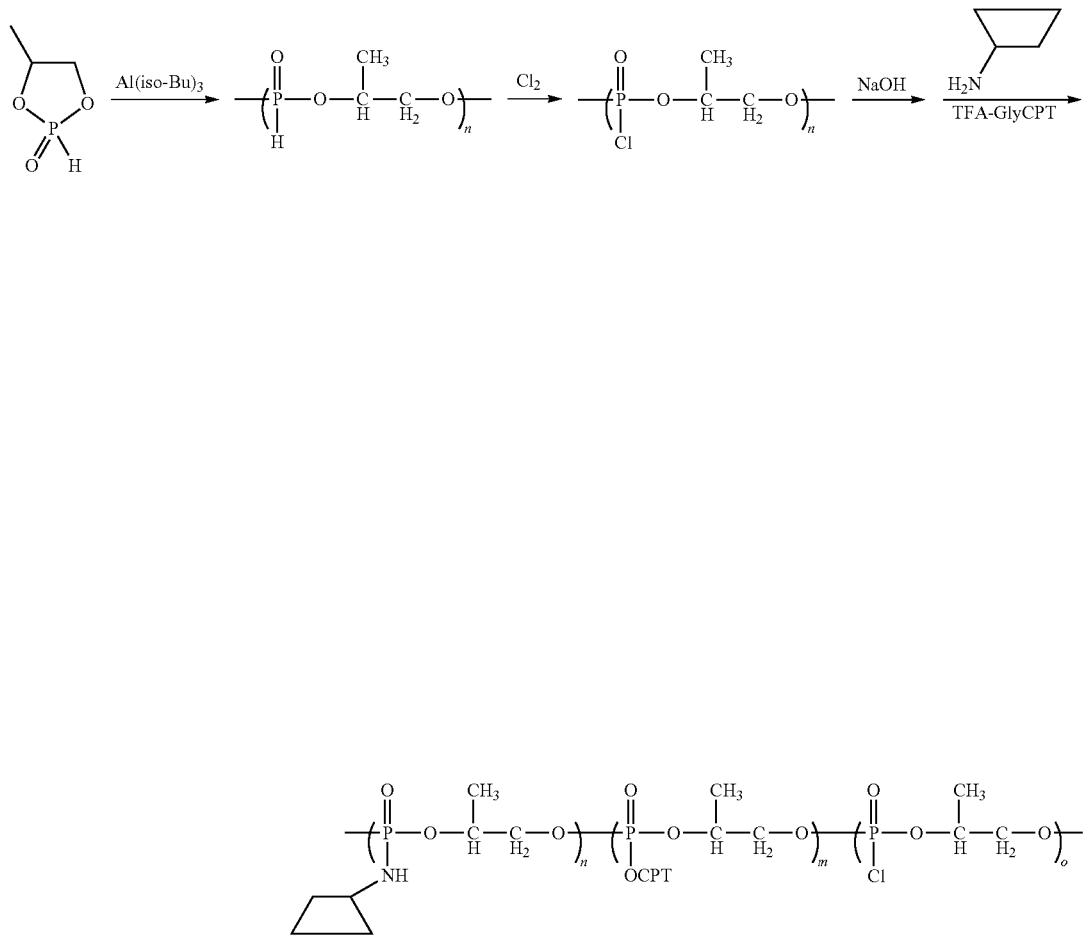

32

Synthesis of the biodegradable polyphosphoester can be found in Wang J et al, *JACS,* 2001, 123, 9480-9481.

Polyphosphoester is mixed with 10 (0.5 eq of repeat unit) in DMSO. EDC (2 eq), NHS (1 eq), and DIEA (1.0 eq) are added to the solution. The solution is stirred for 16 hrs and then precipitated with ether. The obtained CD-polyphosphoester 31 is dissolved in DMSO. To the solution is added 11 (0.5 eq of repeat unit), EDC (2 eq), NHS (1 eq), and DIEA (1.0 eq). The solution is stirred for 16 h and then precipitated with ether. The precipitate is washed with ether extensively until no free drug is observed in the washing solution. Compound 32 is obtained after drying under high vacuum.

Example 25

Synthesis of CD Copolymer-CPT Conjugate 33 with Polyethylene Backbone Via Radical Polymerization

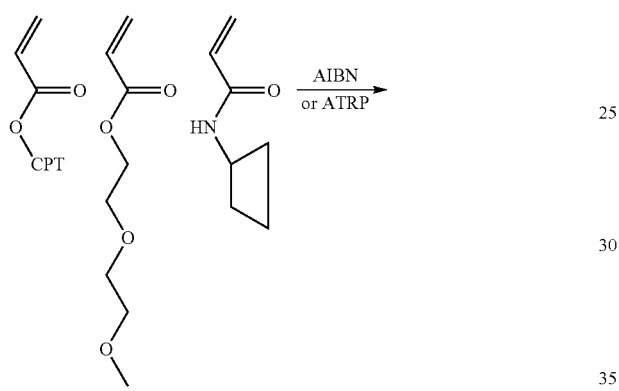

Acrylate monomers of CPT, triethyleneglycol monomethylether, and CD-monocystamine can be synthesized from N-Acryloxysuccinimide (Polysciences, Inc.).

These monomers are mixed in 1:1:1 ratio in dry DMSO. AIBN is added to the mixture under argon. The solution is stirred at rt for 24-48 hrs until the solution becomes viscous. Polymer-CPT conjugate 33 is precipitated with ether and dried under vacuum.

Example 26

Synthesis of CD-graft-poly(ethylene-alt-maleic anhydride)-GlyGlyGlyCPT 34

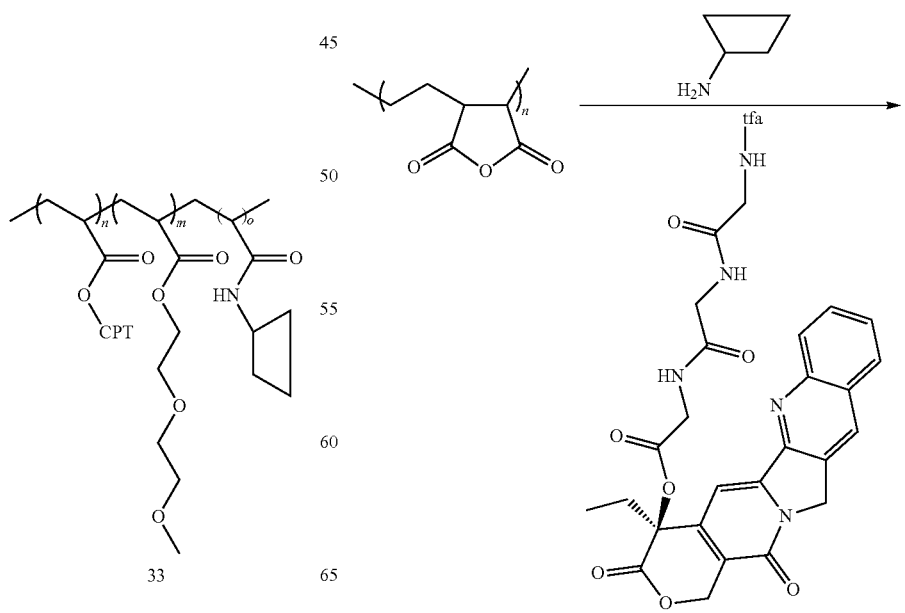

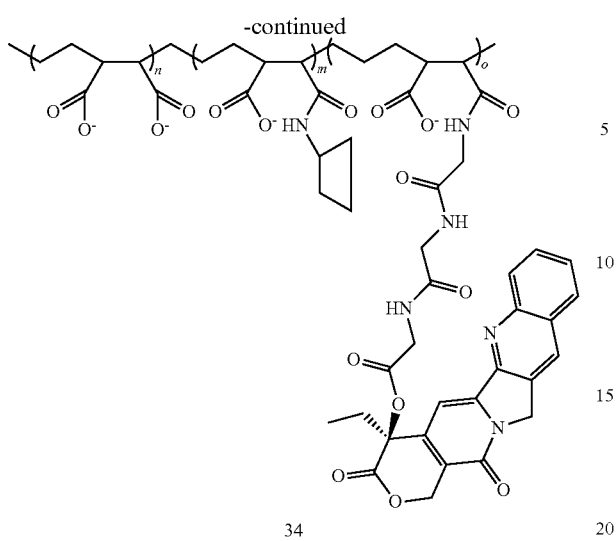

34

Poly(ethylene-alt-maleic anhydride) (Aldrich) is dissolved in DMSO. 10 (0.4 eq of repeat unit) and 12 (0.4 eq of repeat) are added. The solution is heated at 70° C. for 16 hrs and then precipitated with ether. The obtained CD-graft-poly(ethylene-alt-maleic anhydride)-GlyGlyGlyCPT 34 is dried under high vacuum.

Example 27

Synthesis of Polyglutamate-CD-CPT Conjugate 35

Scheme XXXVII

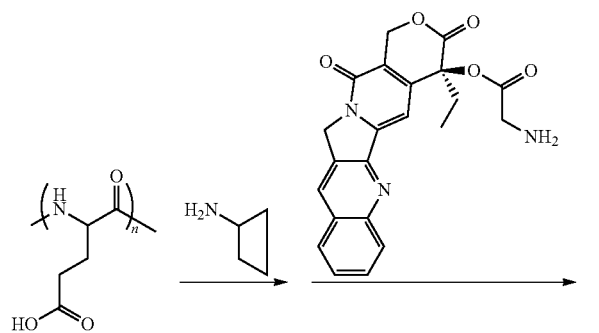

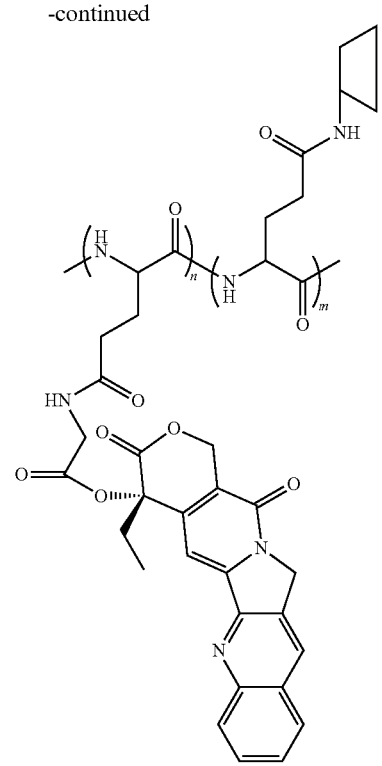

35

Polyglutamate (from Sigma-Aldrich) is mixed with 10 (0.5 eq of repeat unit) and 11 (0.5 eq of repeat unit) in DMSO. EDC (3 eq), NHS (2 eq), and DIEA (1.0 eq) are added to the solution. The solution is stirred for 16 hr and then precipitated with ether. After drying under high vacuum, polyglutamate-CD-CPT conjugate 35 is obtained.

Example 28

Synthesis and Characterization of CD-Bis Cys-Peg3400 Copolymers 36 and Their CPT Conjugates 37

A. Synthesis and Characterization of CD-Bis Cys-Peg3400 Copolymers 36

Scheme XXXVIIIa

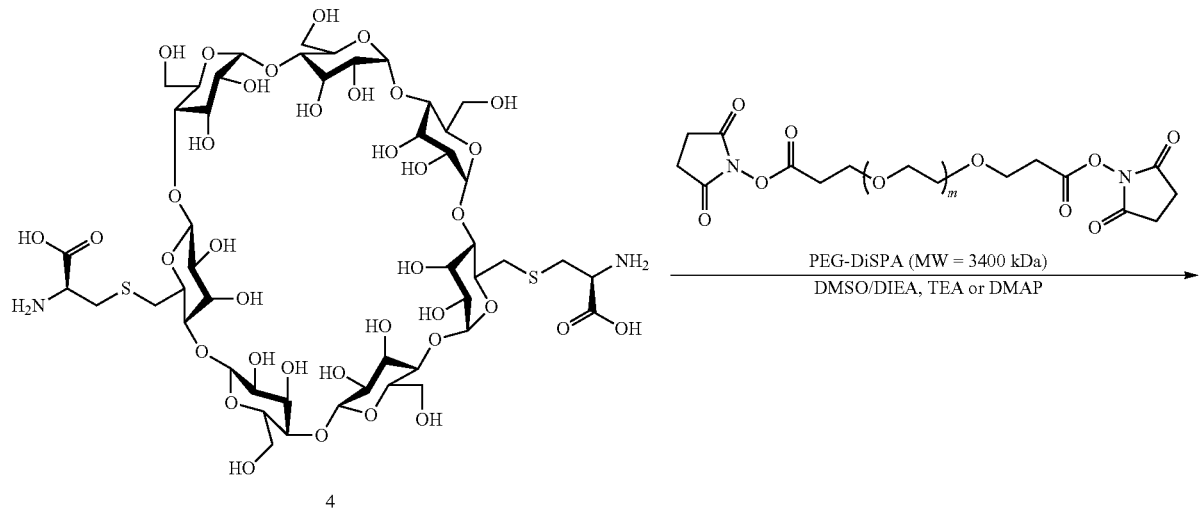

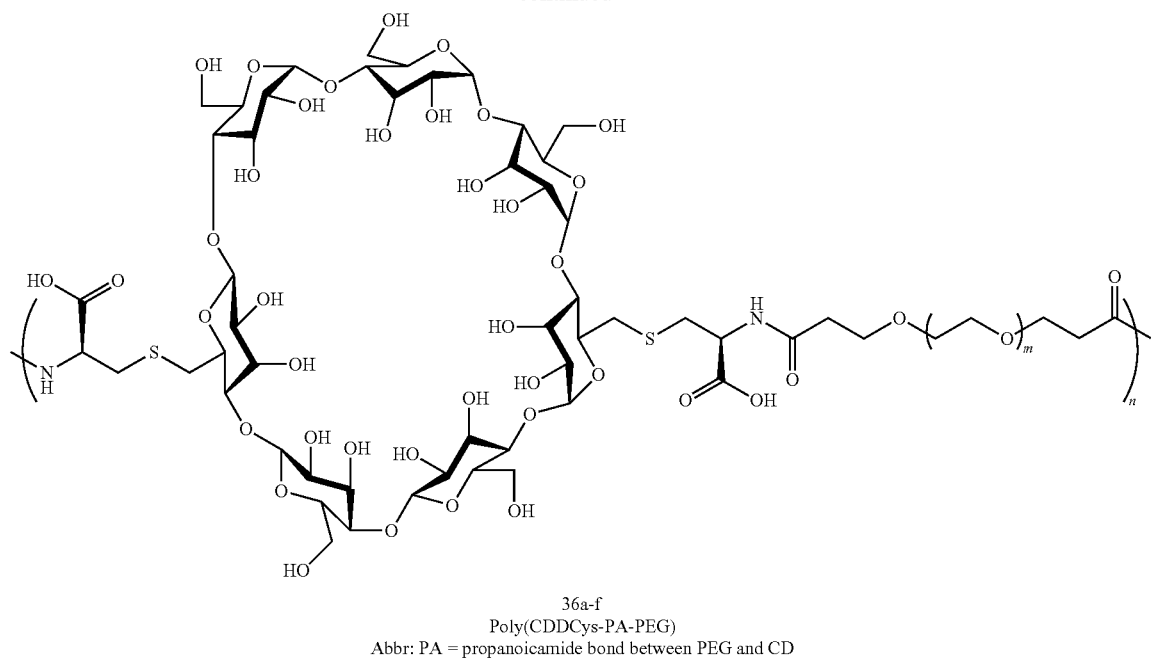
36a-f
Poly(CDDCys-PA-PEG)
Abbr: PA = propanoicamide bond between PEG and CD
Scheme XXXVIIIb
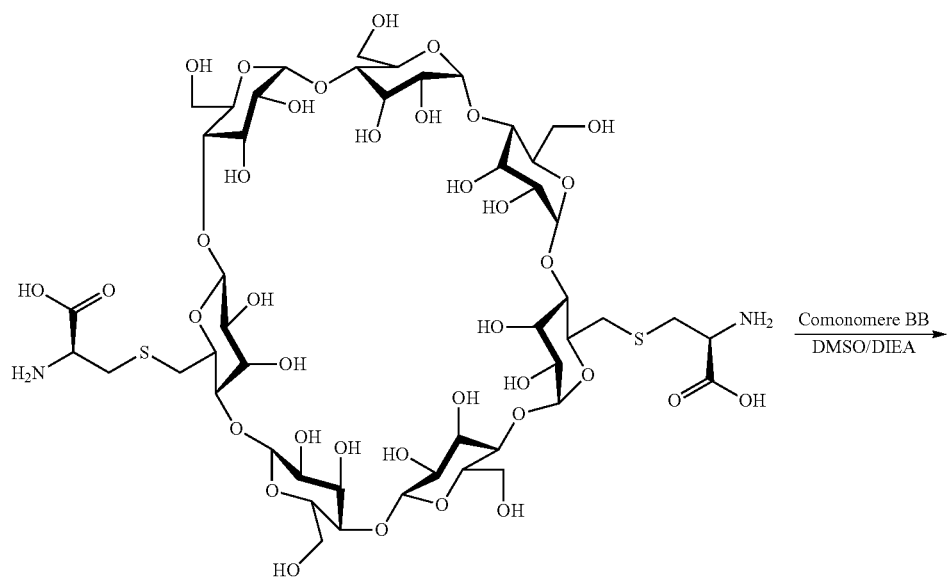

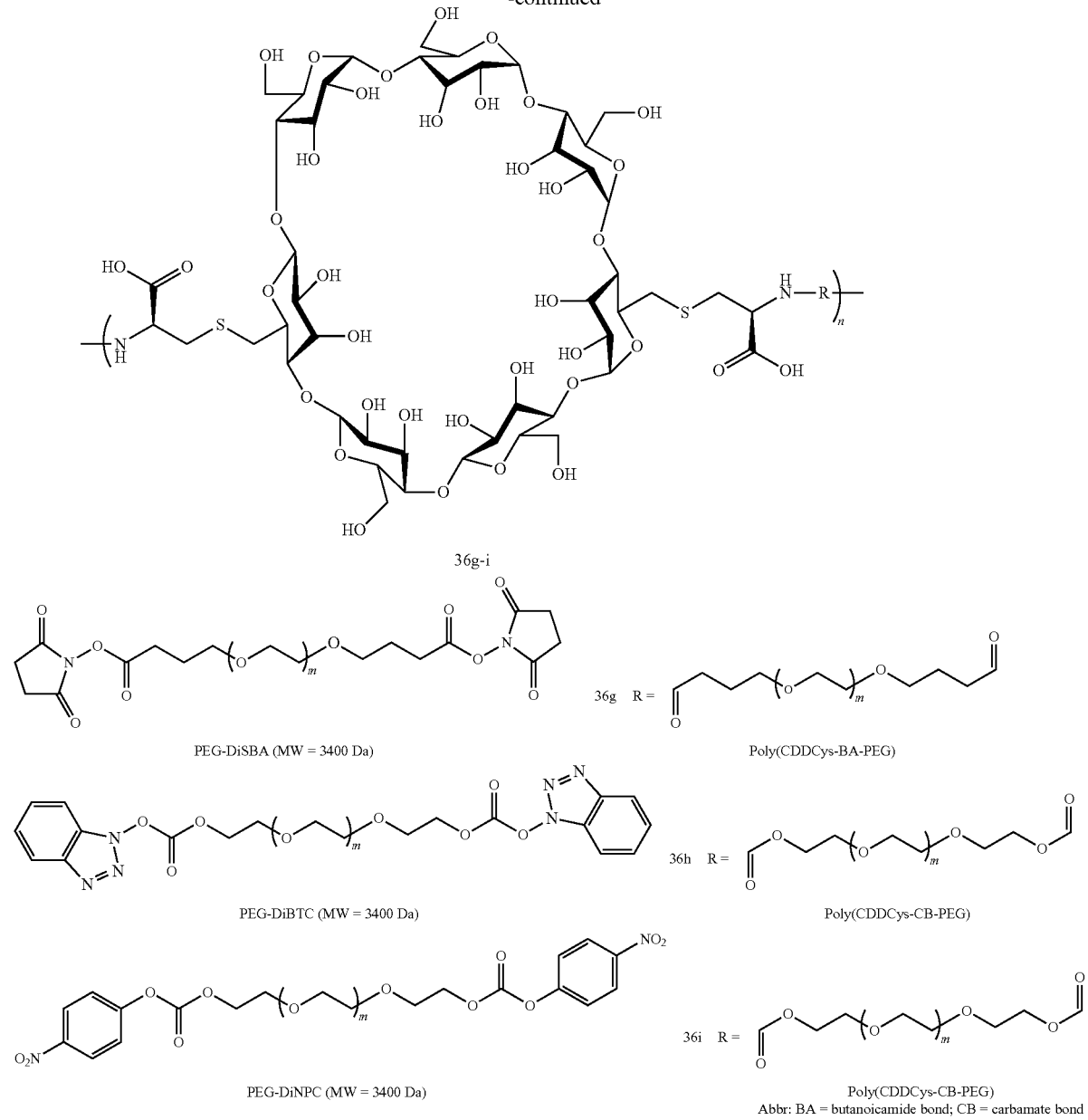

Synthesis of Poly(CDDCys-PA-PEG), 36a 4 (after precipitation with acetone, 63 mg, 0.047 mmol) and PEG-DiSPA (MW 3400, 160 mg, 0.047 mmol) were dried under vacuum for 8 hours. Anhydrous DMSO (1.26 mL) was added to the mixture under argon. After 10 minutes of stirring, anhydrous diisopropylethylamine (DIEA, 19 μL, 2.3 eq.) was added under argon. The reaction mixture was stirred under argon for 120 h. The polymer containing solution was dialyzed using a 10,000 MWCO membrane (Spectra/Por 7) against water for 48 h and lyophilized to yield 196 mg 36a (90%, Table 1). $M_w$=57.4 kDa, $M_n$=41.7 kDa, $M_w/M_n$=1.38. $^1$H NMR (D$_2$O) δ 5.08 (m, CD-2-H), 4.27 (m, Cys-CH), 2.72-3.76 (m, CD-3,4,5,6-CH, CD-CH$_2$, PEG-CH$_2$), 2.44 (m, Cys-CH$_2$).

Synthesis of other poly(CDDCys-PA-PEG) (36b-f), Poly(CDDCys-BA-PEG) (36g) Poly(CDDCys-CB-PEG) (36h-i) were achieved under polymerization condition similar to that of 36a. Details for the polymerization conditions, monomer selection, polymer molecular weight, polydispersity and yields are listed in Table 1. 36g: $^1$H NMR (D$_2$O) δ 5.10 (m, CD-2-H), 4.25-4.37 (m, Cys-CH), 2.72-3.86 (m, CD-3,4,5,6-CH, CD-CH$_2$, PEG-CH$_2$), 2.21 (m, Cys-CH$_2$). 36h-i: $^1$H NMR (D$_2$O) δ 5.05 (m, CD-2-H), 4.56 (m, Cys-CH), 2.70-3.93 (m, CD-3,4,5,6-CH, CD-CH$_2$, PEG-CH$_2$), 2.38 (m, —OCH$_2$CH$_2$CH$_2$C(O)—NH—), 2.34 (m, Cys-CH$_2$), 1.90 (m, —OCH$_2$CH$_2$CH$_2$C(O)—NH—).

Addition of a non-nucleophilic organic base (such as DIEA) was essential for this polymerization as no viscosity changes of the polymerization solutions were observed after 48 hours if no base was added. When 2.3 eq. of DIEA were added, the viscosity of the polymerization solution increased dramatically after 4-6 hours of reaction. DIEA deprotonates the amino groups of 4 to render them more nucleophilic for coupling with PEG-DiSPA. There were essentially no differences in the polymerizations if other bases, such as TEA or DMAP, were used (36b-c, Table 1). Polymerization using 4 recovered by the two different precipitation methods (acetone and methanol) produced polymers with different MWs. 4 that was purified by the methanol-precipitation method (contains no free cystine) gave higher MW polymer (36d-e) as compared to the less pure 4 that was obtained from the acetone-precipitation method (36a). Polymerization of 4 with PEG-DiSPA typically produced polymer yields greater than 90%.

4 was polymerized with other activated monomers such as PEG-DiSBA, PEG-DiBTC, and PEG-DiNPC. Reaction of 4 with PEG-DiSBA gave polymer 36g with similar linkages as 36a-f (amide bond, but one more $CH_2$ group than 36a-f at the linker) with $M_w$ over 100 kDa, while reaction of 4 with PEG-DiBTC and PEG-DiNPC generated polymers 36h and 36i, respectively, with connecting carbamate moiety and $M_w$'s over 50 kDa (Table 1).

TABLE 1

Polymerization of 4 with difunctionalized PEG

| CDP | PEG Comonomer | Base | Polymerization time (h) | $M_w$ (kDa) | $M_n$ (kDa) | $M_w/M_n$ | Yield (%) |
|---|---|---|---|---|---|---|---|
| 36a[a] | PEG-DiSPA | DIEA | 120 | 57.4 | 41.7 | 1.38 | 90 |
| 36b[a] | PEG-DiSPA | DMAP | 120 | 54.2 | 38.1 | 1.42 | 91 |
| 36c[a] | PEG-DiSPA | TEA | 120 | 57.4 | 42.6 | 1.35 | 91 |
| 36d[b] | PEG-DiSPA | DIEA | 120 | 93.6 | 58.0 | 1.48 | 96 |
| 36e[b] | PEG-DiSPA | DIEA | 144 | 97.3 | 58.0 | 1.67 | 94 |
| 36f[b] | PEG-DiSPA | DIEA | 2 | 35.3 | 25.6 | 1.38 | 95 |
| 36g | PEG-DiSBA | DIEA | 120 | 114.7 | 77.9 | 1.47 | 96 |
| 36h | PEG-DiBTC | DIEA | 120 | 67.6 | 39.4 | 1.47 | 95 |
| 36i | PEG-DiNPC | DIEA | 120 | 86.5 | 57.2 | 1.51 | 96 |

[a] 4 was washed with acetone before polymerization.
[b] 4 was washed with methanol before polymerization.

Polymers 36a-i are highly soluble in aqueous solution. They can be easily dissolved in water or phosphate buffered saline (PBS) solution at concentrations of at least 200 mg/mL. Solubility of these polymers in aqueous solution at concentrations higher than 200 mg/ml was not attempted due to the high viscosity. These polymers were also soluble in DMF, DMSO and methanol, slightly soluble in $CH_3CN$ and $CHCl_3$, but insoluble in THF and ethyl ether.

Molecular Weight Control of CD Polymers 4 (after precipitation with methanol) (56.2 mg, 0.0419 mmol) and PEG-DiSPA (147 mg, 0.0419 mmol) were dried under vacuum for 4-8 hours. To the mixture was added dry DMSO (1.1 mL) under argon. After 10 minutes stirring, DIEA (16 µL, 2.2 eq) was added under argon. A portion of polymerization solution (150 µL) was removed and precipitated with ether at selected times (2 h, 18 h, 43 h, 70 h, 168 h and 288 h). MWs of the precipitated polymers were determined as described above.

Figure 5A:
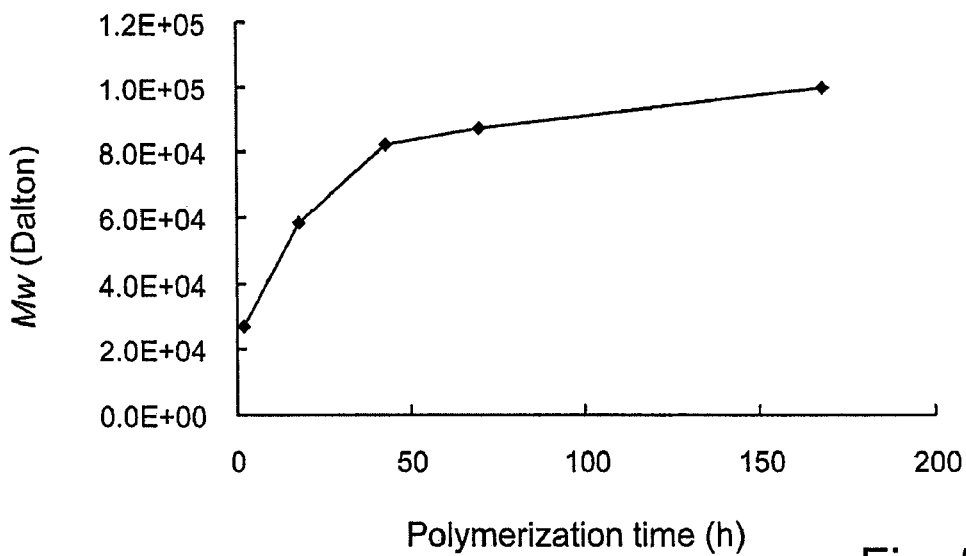
FIGS. 5a and 5b show polymerization control by adjusting polymerization time.
Figure 5B:
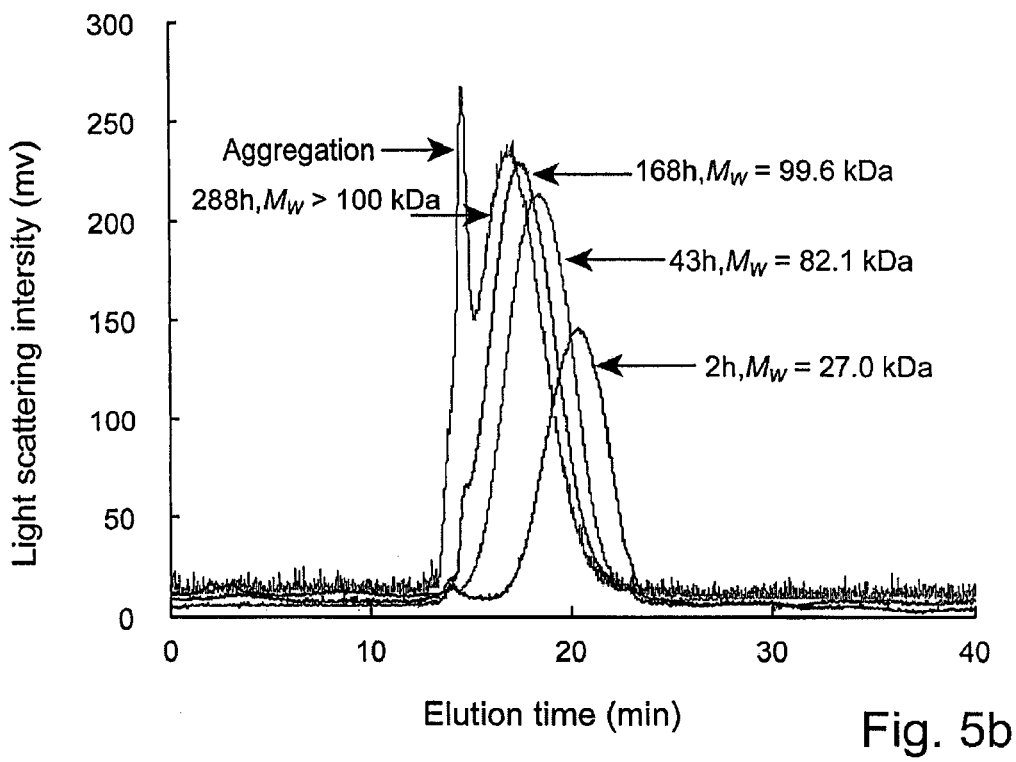

As shown in FIGS. 5a and 5b, molecular weights of 36 can be controlled by adjusting polymerization time.

B. Synthesis of Poly(CDDCys-PA-PEG)-CPT Conjugates (HGGG6, LGGG10, HG6, HGGG10).

Scheme XXXIX

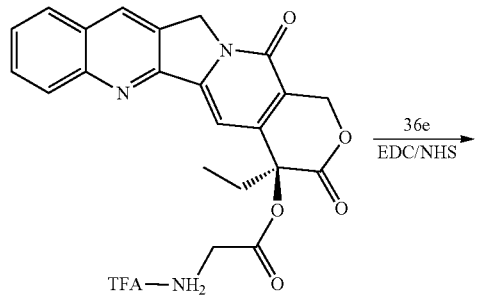

-continued
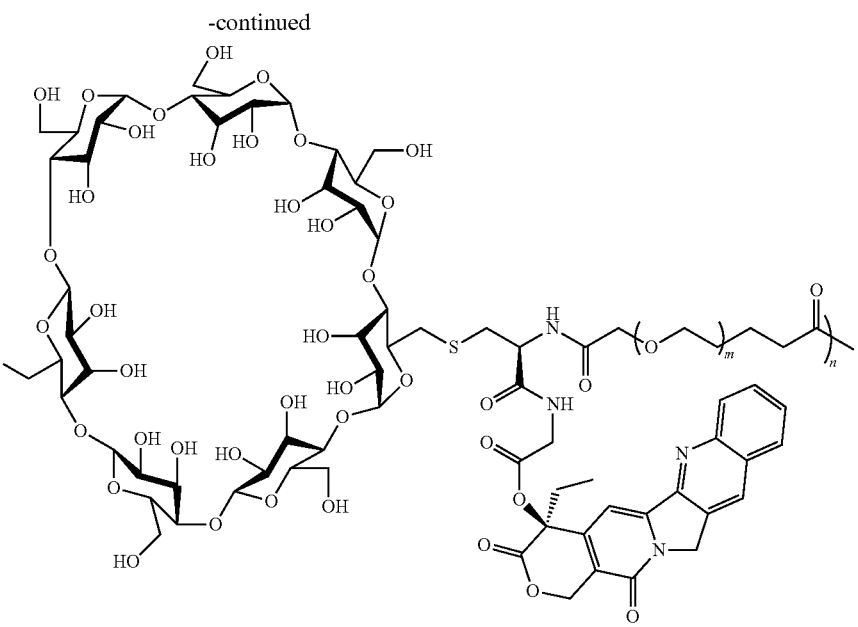
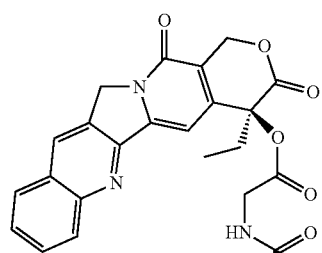
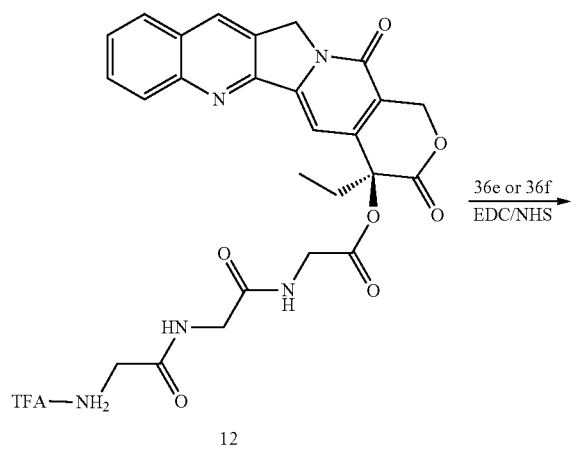
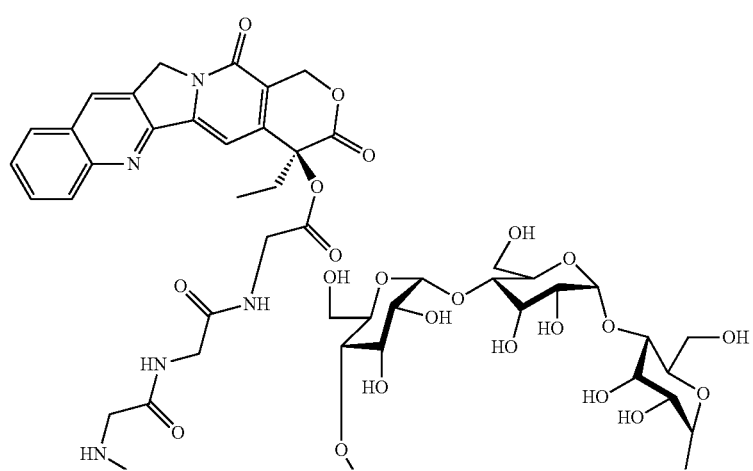

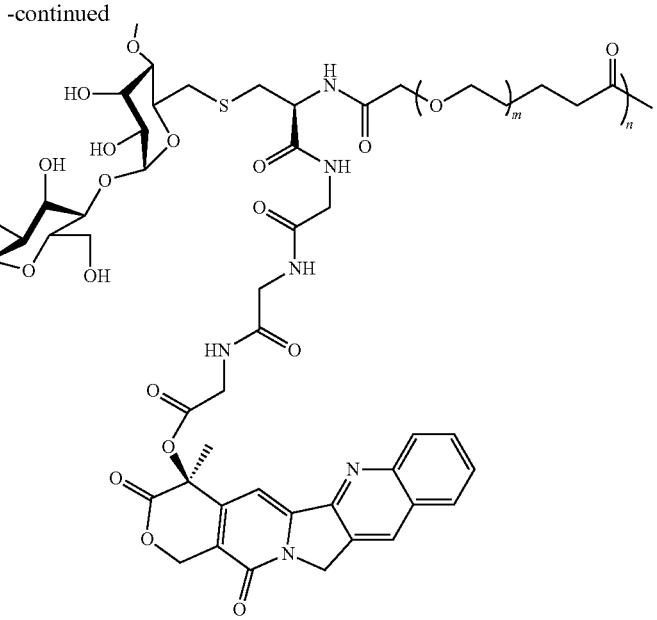

Synthesis of Poly(CDDCys-PA-PEG)-GlyGlyGly-CPT (HGGG6) 36e (1.37 g, 0.30 mmol of repeat unit) was dissolved in dry DMSO (136 mL). The mixture was stirred for 10 minutes. 12 (419 mg, 0.712 mmol, 2.36 eq), DIEA (0.092 mL, 0.712 mmol, 2.36 eq), EDC (172 mg, 0.903 mmol, 3 eq), and NHS (76 mg, 0.662 mmol, 2.2 eq) were added to the polymer solution and stirred for ca. 15 hours. The polymer was precipitated with ethyl ether (1 L). The ether was poured out and the precipitate was washed with $CH_3CN$ (3×100 mL). The precipitate was dissolved in water 600 mL. Some insoluble solid was filtered through 0.2 μm filters. The solution was dialyzed using 25,000 MWCO membrane (Spectra/Por 7) for 10 h at 10-15° C. in DI water. Dialysis water was changed every 60 minutes. The polymer-drug conjugate solution was sterilized by passing it through 0.2 μM filters. The solution was lyophilized to yield a yellow solid HGGG6 (1.42 g, 85% yield).

Synthesis of Poly(CDDCys-PA-PEG)-GlyGlyGly-CPT (LGGG10) Conjugation of 12 to 36f was performed in a manner similar to that used to produce HGGG6 except that-this conjugate was dialyzed with 10,000 MWCO membrane (Spectra/Por 7) instead of with 25,000 MWCO membrane. The yield of LGGG10 was 83%.

Synthesis of Poly(CDDCys-PA-PEG)-Gly-CPT (HG6) Conjugation of 11 to 36e was performed in a manner similar to that used to produce HGGG6. The yield of HG6 was 83%.

Synthesis of Poly(CDDCys-PA-PEG)-GlyGlyGly-CPT (HGGG10) 36e (1.5 g, 0.33 mmol of repeat unit) was dissolved in dry DMSO (150 mL). The mixture was stirred for 10 minutes. 12 (941 mg, 1.49 mmol, 4.5 eq), DIEA (0.258 mL, 1.49 mmol, 4.5 eq), EDC (283 mg, 1.49 mmol, 4.5 eq), and NHS (113 mg, 0.99 mmol, 3 eq) was added to the polymer solution and stirred for ca. 24 hours. Another portion of EDC (142 mg, 0.75 mmol, 2.3 eq) and NHS (56 mg, 0.5 mmol, 1.5 eq) were added to the conjugation solution. The polymer was stirred for an additional 22 hours. The workup procedure was the same as that for the synthesis of HGGG6. The yield of HGGG10 was 77%.

Determination of wt % CPT on the Conjugates Stock solutions of HGGG6, LGGG10, HG6 and HGGG10 were prepared at a concentration of 10 mg/mL in DMSO. An aliquot of corresponding stock solution was diluted to 100 μg/mL using 1 N NaOH. CPT was completely hydrolyzed in this basic solution and transformed to its carboxylate form within 2 h at room temperature. An aliquot of this solution was diluted to 10 μg/mL using 8.5% $H_3PO_4$, and the CPT carboxylate form was transformed to its lactone form. 30 μL of this solution was injected into the HPLC. The peak area from the CPT lactone form was integrated and compared to a standard curve.

11 and 12 were conjugated to 36e or 36f (Table 2) using conventional coupling methods. Due to the instability of the ester linker of 11 and 12 in aqueous solution, the conjugation was conducted in anhydrous DMSO under argon. An organic base was required to deprotonate the TFA salts of 11 and 12 to facilitate the coupling. For polymer conjugation with 12, the weight percent (wt %) drug loading was around 6-10%. The theoretical maximum drug loading is around 13% using PEG with MW of 3400 Da; maximum values can be increased by decreasing the MW of the PEG segments. Solubilities of all conjugates in water or PBS were more than 200 mg/mL (equivalent to a 12-20 mg CPT/mL for 6-10 wt % drug loading, respectively). Details for the HGGG6, LGGG10, HG6, and HGGG10 are summarized in Table 2.

TABLE 2

Properties of polymer-CPT conjugates.

| Conjugate[a] | $M_w$ of parent polymer (×10$^{-3}$) | $M_w/M_n$[b] | Linker | CPT (wt %) |
|---|---|---|---|---|
| HGGG6 | 97 | 1.7 | triglycine | 6.1 |
| LGGG10 | 35 | 1.6 | triglycine | 10.2 |
| HG6 | 97 | 1.7 | glycine | 6.8 |
| HGGG10 | 97 | 1.7 | triglycine | 9.6 |

[a]Abbreviations: H = High $M_w$ polymer (97 kDa), L = Low $M_w$ polymer (35 kDa), GGG = triglycine linker, G = glycine linker, 6 = drug loading around 6 wt %, 10 = drug loading around 10 wt %.
[b]Polymer polydispersity as measured by light scattering techniques(26)

C. Release of CPT from HGGG6 and HG6

Release of CPT in PBS HGGG6 and HG6 were prepared at 1 mg/mL in PBS (1×, pH 7.4). A 100 µL aliquot of the solution was transferred to a 1.5 mL Eppendorf tube and incubated at 37° C. The incubated samples were quenched at selected time intervals and stored at −80° C. until the analysis. Each solution was diluted with 8.5% $H_3PO_4$ to a 5 mL total volume in a volumetric flask. 30 mL of such solution was injected into the HPLC. The peak area from the CPT lactone form was integrated and compared to a standard curve.

Analysis for the release of CPT from HGGG6 and HG6 in PBS containing acetyl cholinesterase (an esterase, 100 units/mL), in $KH_2PO_4$ buffer (pH 6.1, 0.1 M) and in the $KH_2PO_4$ buffer (pH 6.1, 0.1 M) containing cathepsin B (a cysteine proteinase, 200 µM, preactivated on ice for 30 minutes in this buffer containing 2 mM DTT and 1 mM EDTA) were performed in a manner similar to that described above for PBS alone.

Release of CPT in Human Plasma An aliquot of HGGG6 and HG6 stock solution were diluted to give final concentration of 0.5 mg/nL in PBS (1×, pH 7.4). This solution was added to a lyophilized powder of human plasma to reconstitute 100% human plasma by the recommended amount. The solution was divided into equal volume (250 µL) to 1.5 mL Eppendorf tubes, incubated at 37° C., and stopped at selected time point. Samples were stored at −80° C. until the analysis. Samples were separated from plasma by solid phase extraction columns. The solid phase extraction cartridge (Oasis HLB 1 cc cartridge from Waters) was pre-conditioned with 1 mL of acetonitrile and then with 1 mL of 8.5% $H_3PO_4$ before loading. Samples were acidified with equal volume of 8.5% $H_3PO_4$ prior to loading. After the acidified solution was loaded on the cartridge, the bed was washed with 3×1 mL of water. Released CPT and polymer conjugate w ere eluted with 3×1 mL of a solution mixture of acetonitrile and potassium phosphate buffer (pH 4.1) (60/40 v/v). The eluted solution was diluted to 5 mL total volume in a 5 mL volumetric flask. 30 µL of such solution was injected into the HPLC. The peak area from the CPT lactone form was integrated and compared to a standard curve.

Release of CPT from HGGG6 and HG6 in PBS containing 4% human plasma (PBS/reconstituted human plasma solution=96/4 (v/v)), in mouse plasma and in reconstituted human albumin (PBS solution) were performed in a manner similar to that described above for pure human plasma.

In PBS (1×, pH 7.4), the half-lives ($t_{1/2}$) for releasing CPT from HG6 and HGGG6 were 59 h and 32 h, respectively. The half-lives decreased to 25 h and 22 h, respectively, in the presence of 4% human plasma, and to 1.7 h and 1.6 h, respectively, in 100% human plasma ("HP") and 2.6 h and 2.2 h, respectively, in 100% mouse plasma ("MP"). CPT release rates for both HG6 and HGGG6 in the presence of albumin ("Alb") or acetyl-cholinesterase ("Ac Cho") were on the same order of magnitude as in PBS. In a buffer solution at a pH lower than PBS (pH 6.1) with or without the enzyme cathepsin B (active at pH 6.1), less than 50% of total conjugated CPT was released from both HG6 and HGGG6 for times up to 144 h (Table 3).

TABLE 3

Half-life ($t_{1/2}$, in hour) of the release of CPT from HG6 and HGGG6[a]

| Conjugate | PBS[b] | 4% HP[c] | HP[d] | MP[e] | Alb[f] | Ac Cho[g] | pH 6.1 buffer[h] | Cath B (pH 6.1)[i] |
|---|---|---|---|---|---|---|---|---|
| HG6 | 59 | 25 | 1.7 | 2.6 | 62 | 33 | >144 | >144 |
| HGGG6 | 32 | 22 | 1.6 | 2.2 | 73 | 43 | >144 | >144 |

[a]$t_{1/2}$ is defined as time (hours) for the release of half of the total conjugated CPT.
Abbreviations: HP means human plasma, MP means mouse plasma.
[b]pH 7.4 PBS 1× buffer.
[c]Reconstituted human plasma mixed with PBS (v/v = 4/96).
[d]Reconstituted human plasma
[e]Fresh mouse plasma
[f]In reconstituted human albumin PBS buffer
[g]In the presence of acetyl cholinesterase PBS solution (100 units/mL).
[h]pH 6.1 phosphate buffer (0.1M)
[i]pH 6.1 phosphate buffer in the presence of Cathepsin B Release of CPT in Solution at Different pH. HGGG6 and HG6 were prepared at 1 mg/mL in buffer solution with pHs ranging from acidic (pH 1.2) to basic (pH=13.1) and incubated at 37° C. for 24 h. An aliquot of each solution was diluted with 8.5% $H_3PO_4$ to about 100 µg/mL. 30 µL of such solution was injected into HPLC. The peak area from the CPT lactone form was integrated and compared to a standard curve.

Figure 6:
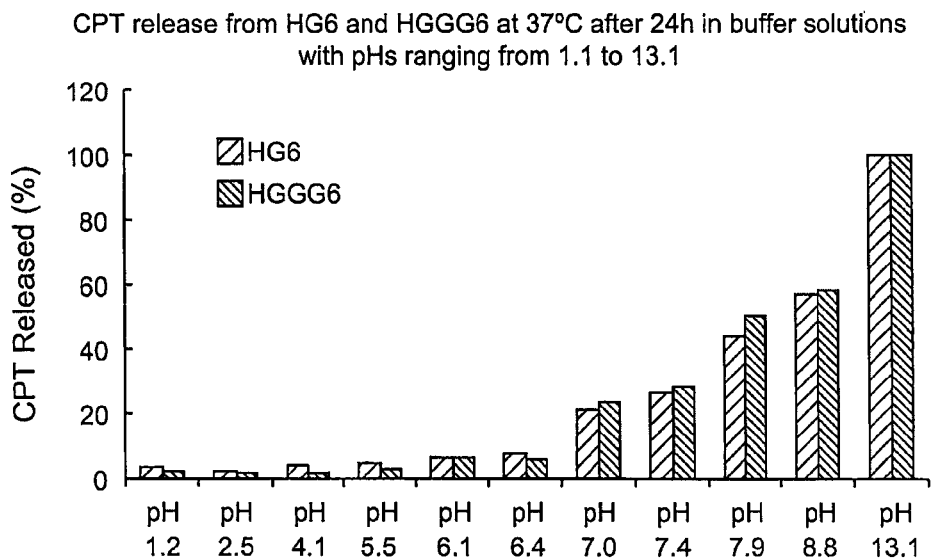
FIG. 6 illustrates CPT release from HG6 and HGGG6 at 37° C. after 24 h in buffer solutions with pHs ranging from 1.1 to 13.1.

The pH of aqueous solution has a significant effect on the CPT release rates from both HG6 and HGGG6. The amounts of CPT released from HG6 and HGGG6 at 37° C. after 24 h in buffer solutions with pHs ranging from 1.1 to 13.1 are illustrated in FIG. 6. The glycinyl-CPT ester bonds of both HG6 and HGGG6 were very stable in acidic pH (1.1 to 6.4) as less than 7% of CPT were released in 24 h.

$IC_{50}$ via MTT Assay The human ovarian carcinoma A2780 cell line was obtained from the European Collection of Cell Cultures (Salisbury, Wiltshire, UK). The human colorectal adenocarcinoma HT29, human prostate carcinoma PC-3, and human colonic adeoncarcinoma LS174T cell lines were obtained from the American Type Culture Collection (Rockville, Md.). Cells were seeded in 96-well plates at 5000 cells/well and grown in medium containing 10% fetal bovine serum at 37° C. for 24 h in a humidified 5% $CO_2$ atmosphere. The medium was replaced with fresh medium containing CPT, 36e, HGGG6 or HG6 in concentrations ranging from 1 nM to 10 µM of CPT and 36e (CPT equivalent for HGGG6 and HG6). At each concentration three wells per plate were treated. The effect of the compounds on cell growth was measured by the MTT assay after 72 h. The medium was removed, the cells were rinsed with PBS, MTT solution was added at a concentration of 0.5 mg/mL, and the plates were incubated for 4 h at 37° C. The medium was removed and the formazan crystals were solubilized in DMSO. Absorbance was measured at 560 nm using a SPECTRAFluor Plus plate reader (Tecan, Durham, N. C.). The percentage of cell survival was calculated relative to untreated cells, and $IC_{50}$'s were determined from plots of dose versus cell survival. IC50 data of CPT, 36e, HGGG6 or HG6 are listed in Table 4.

TABLE 4

IC$_{50}$ of CPT, unconjugated polymer 36e and CPT conjugates HG6 and HGGG6 in various cell lines

| Cell Line | 36e (μM) | CPT (μM) | HG6 (μM) | HGGG6 (μM) |
|---|---|---|---|---|
| LS174T | >300 | 0.005 | 0.050 | 0.010 |
| HT29 | 300 | 0.020 | 0.050 | 0.030 |
| A2780 | 100 | 0.007 | 0.025 | 0.020 |
| PC3 | >300 | 0.075 | 0.25 | 0.15 |

Example 29

Poly-CD-Bis Cys-Peg3400-Ala-CPT 37

36e (54 mg, 0.012 mmol of repeat unit) was dissolved in dry DMSO (226 mL) and stirred for 10 minutes. TFA-Ala-CPT which is prepared similar to 11 (15 mg, 0.028 mmol, 2.36 eq), DIEA (4.88 mL, 0.028 mmol, 2.36 eq), DCC (24.52 mg, 0.12 mmol, 10 eq), and NHS (13.6 mg, 0.12 mmol, 10 eq) were added to the polymer solution. The mixture was stirred for about 16 hours. The polymer was precipitated with ether (40 mL) and washed with ether (2×30 μL) and with CH$_3$CN (2×10 mL). It was then redissolved in pH 4 aqueous solution (10 mL) and dialyzed at room temperature for 48 h using 25,000. MWCO membrane. The solution was then passed through a sterilized 0.2 μm filter and then lyophilized to yield 37 (46 mg, 85%). Weight percent of drug loading was calculated to be 5.5% using HPLC equipped with a fluorescence detector after releasing CPT from 37 using base. Free CPT in 37 is <1%.

Example 30

Poly-CD-Bis Cys-Peg3400-Leu-CPT 38

36e (54 mg, 0.012 mmol of repeat unit) was dissolved in dry DMSO (226 mL) and stirred for 10 minutes. TFA-Leu-CPT which is prepared similar to 11 (16 mg, 0.028 mmol, 2.36 eq), DEA (4.88 mL, 0.028 mmol, 2.36 eq), DCC (24.52 mg, 0.12 mmol, 10 eq), and NHS (13.6 mg, 0.12 mmol, 10 eq) were added to the polymer solution. The mixture was stirred for about 16 hours. The polymer was precipitated with ether (40 mL) and washed with ether (2×30 mL) and with CH$_3$CN (2×10 mL). It was then redissolved in pH 4 aqueous solution (10 mL) and dialyzed at room temperature for 48 h using 25,000 MWCO membrane. The solution was then passed through a sterilized 0.2 μm filter and then lyophilized to yield 38 (42 mg, 78%). Weight percent of drug loading was calculated to be 5.0% using HPLC equipped with a fluorescence detector after releasing CPT from 38 using base. Free CPT in 38 is <1%.

Example 31

Synthesis of CD-Bis Cys-Bis Peg-FITC 39

Scheme XXXX

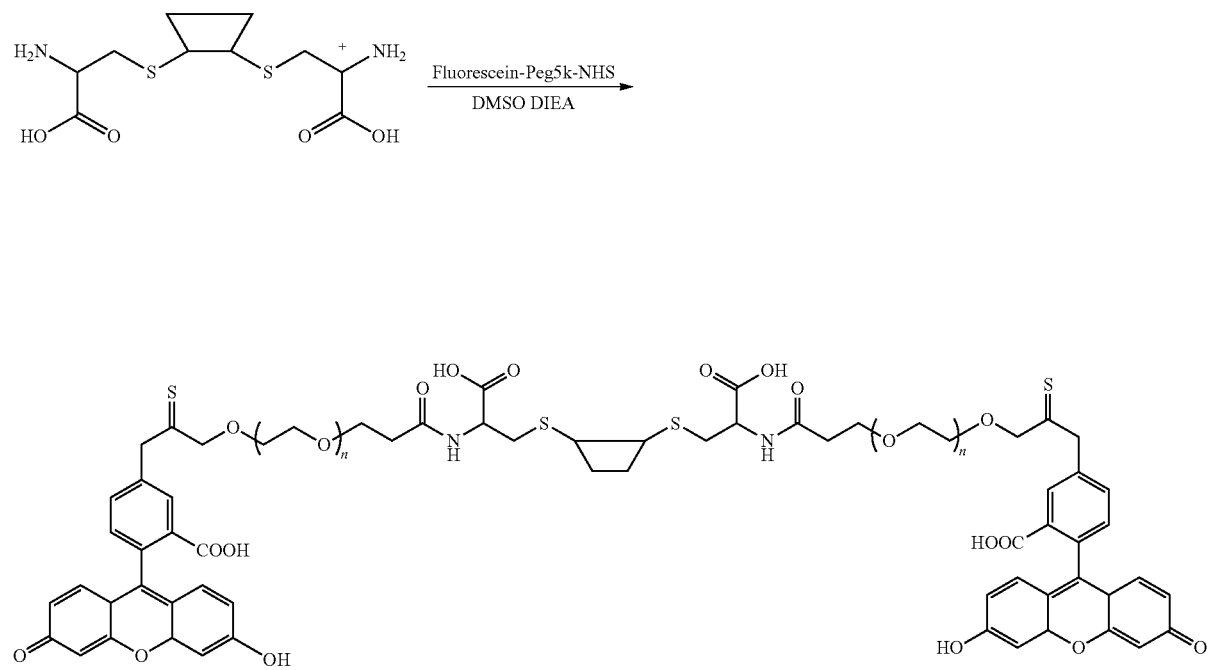

39

4 (25 mg, 0.0186 mmol) and FITC-Peg5000-NHS (Shearwater, 186 mg, 0.0373 mmol) were dissolved in dry DMSO (2 mL). DIEA (0.0094 mL, 0.056 mmol, 3 eq) was added to the mixture. The mixture was kept in dark and stirred for 24 hours. Water (10 mL) was then added and the solution was dialyzed in dark using 10,000 MWCO for about 48 hours. After lyophilization a yellow polymer 39 was obtained. Polymer was characterized by MS and $^1$H NMR.

Example 32

Synthesis of Bis-succinimidyl succinatePeg3400 (Bis-SS-PEG) (40a) and Biodegradable CD-Bis Cys-SS-Peg3400 (40b) and its CPT Conjugate 41

This resulted in 9.6 g of bis-succinimidyl Peg3400 at a yield of 90.6%. The product was analyzed by reverse-phase columned High Performance Liquid Chromatography.

A 100 mL round bottom flask equipped with a magnetic stirbar and a septum was charged with 2 g (0.56 mmol) of bis-succinimidyl Peg3400 and 10 mL of anhydrous dichloromethane. To this solution was added 0.324 g (2.82 mmol) of N-hydroxyl succinimide. The solution mixture was then cooled in an ice bath and added 0.58 g (2.82 mmol) of 1,3-dicyclohexylcarbodiimide. After leaving at room temperature for 24 h, the solution was filtered and precipitated out in 150 mL of diethyl ether. Dissolution in 10 mL dichloromethane and precipitation in diethyl ether was repeated two times. This

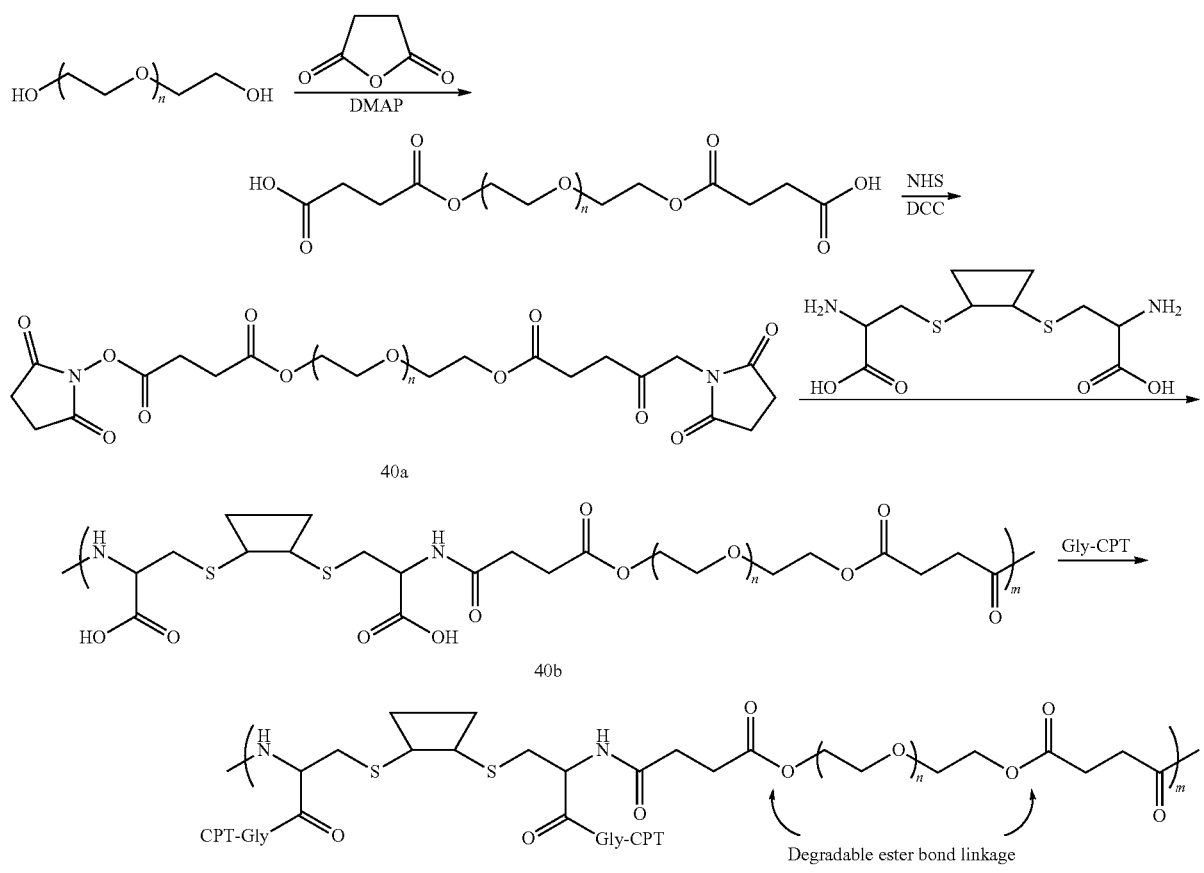

Scheme XXXXI

A 100 mL round bottom flask equipped with a magnetic stirbar and a septum was charged with 10 g (2.99 mmol) of polyethylene glycol Mw 3350, 2.0 g (20 mmol) of succinic anhydride and 50 mL of anhydrous pyridine. After stirring the solution at 50° C. for 16 h, the solvent was removed by rotary evaporator. The residue was redissolved in 30 mL of water and extracted with 10 mL of chloroform three times. The organic layer was dried over MgSO$_4$ and filtered. The solvent was then concentrated and precipitated out in diethyl ether.

afforded 1.74 g (82.9%) of Bis-SS-PEG 40a. It was analyzed by reverse-phase columned High Performance Liquid Chromatography.

CD-Bis Cys-SS-Peg3400 Polymer 40b

A 50-mL pearl shaped flask was charged with 100 mg (0.0746 mmol) of 4 and 254 mg (0.0746 mmol) of 40a. The combined solids were dried under vacuum for 24 hours before the addition of mL of anhydrous DMSO and 2.2 equivalents (0.164 mmol) of DIEA. The solution mixture was stirred at room temperature for 3 days and then precipitated out in diethyl ether. This yielded 100% of 40b. Molecular weight was analyzed on a Hitachi HPLC system equipped with an Anspec R1 detector, a Precision Detectors DLS detector, and a Progel-TSK G3000$_{PWXL}$ column using 0.1 M PBS as eluant at a 0.7 mL min$^{-1}$ flow rate. $M_w$=93,000, $M_n$=61,000 and $M_w/M_n$=1.5.

CD-Bis Cys-SS-Peg3400-GlyGlyGly-CPT Conjugate 41

40b (201.8 mg, 0.044 mmol of repeat unit), TFA-GlyGlyGly-CPT 12 (66 mg, 0.105 mmol, 2.36 eq), EDC (25.5 mg, 0.133 mmol, 3 eq), and NHS (11 mg, 0.0977 mmol, 2.2 eq) were dissolved in dry DMSO (6 mL) and stirred for 30 minutes. DIEA (19 μL, 0.105 mmol, 2.36 eq), added to the polymer solution. The mixture was stirred for about 41 hours. The polymer was crashed out with diethyl ether (250 mL) and washed with acetonitrile (3×25 μL). It was then re-dissolved in pH 4 water (10 mg/mL) and dialyzed at room temperature for 24 hours using 10,000 MWCO membrane. The solution was then passed through a sterilized 0.2 μm filter and then lyophilized to yield 41 (128 mg, 52%). Weight percent of drug loading was calculated to be 6.95% using HPLC equipped with a fluorescence detector after releasing CPT from 41 using base.

Hydrolysis of 41 was set up in human plasma (100% solution) at 1 mg/mL. Aliquot solutions (100 μL) were placed in 1.5 mL eppendorf tubes and incubated in 37° C. water bath.

Then, the samples were acidified with 100 μL of 8.5% $H_3PO_4$ and loaded on pre-conditioned solid phase extraction cartridge. It was eluted with 60:40 (v/v) acetonitrile: $KH_2PO_4$ buffer. Free CPT (lactone form) was analyzed on HPLC/ Fluorescence detector using acetonitrile/$KH_2PO_4$ buffer. Half-life was determined to be 3 h.

Figure 7:
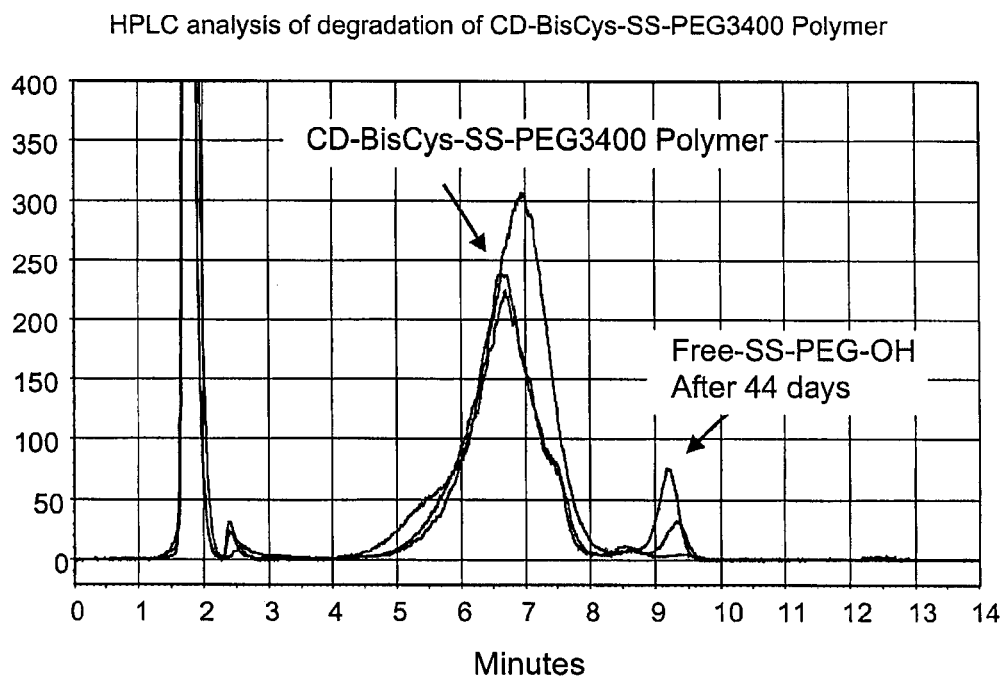
FIG. 7 Displays HPLC analysis of degradation of CD-Bis Cys-SS-Peg3400 Polymer

Degradation of CD-Bis Cys-SS-Peg3400 Polymer 40b 50 mg/mL of 40b solution was prepared in human plasma reconstituted in PBS (pH 7.4) solution. 100 μL aliquots were incubated at 37° C. Each sample tube was taken out at a specific time point and crashed out in 900 μL cold methanol. The solution was centrifuged and the supernatant was analyzed on a HPLC/ELS detector. The resulting spectrum is shown in FIG. 7.

Methods for Increasing Drug Weight Percent Loading

Method I. Synthesis of CD-Bis Cys-Peg Copolymer with a Short Peg Linkage and its GlyCPT Conjugate Example 33

Synthesis of CD-Bis Cys-Peg (Short PEG, e.g., Peg200-Peg2000) and its CPT Conjugate 42

Scheme XXXXII

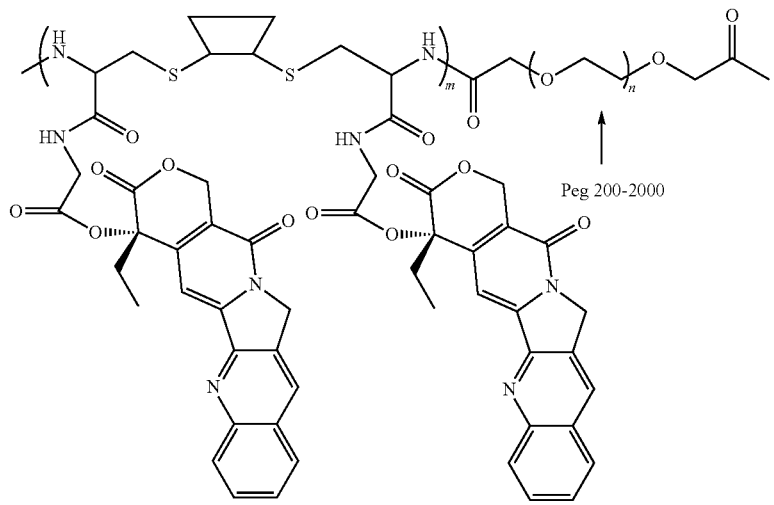

42

Synthesis of polymer and drug conjugate 42 are same as 36, 37, and 38 in Example 28.
Method II. Synthesis of CD-Bis Cys-Peg Copolymer with Multiple Drug Molecules on Each Loading Site.
Example 34
Synthesis of CD-Bis Cys-Peg and its GluBis(GlyCPT) Conjugate 43
Scheme XXXXIII
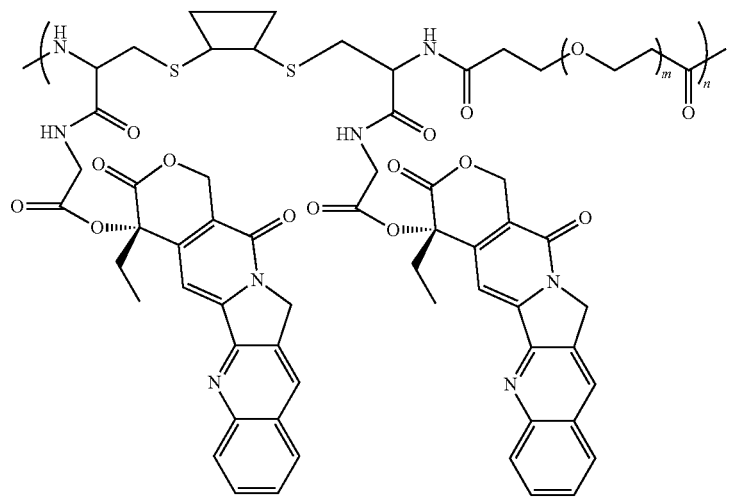
PEG Mw = 3400
2 CPT per CD
Maximum drug loading 13.4%
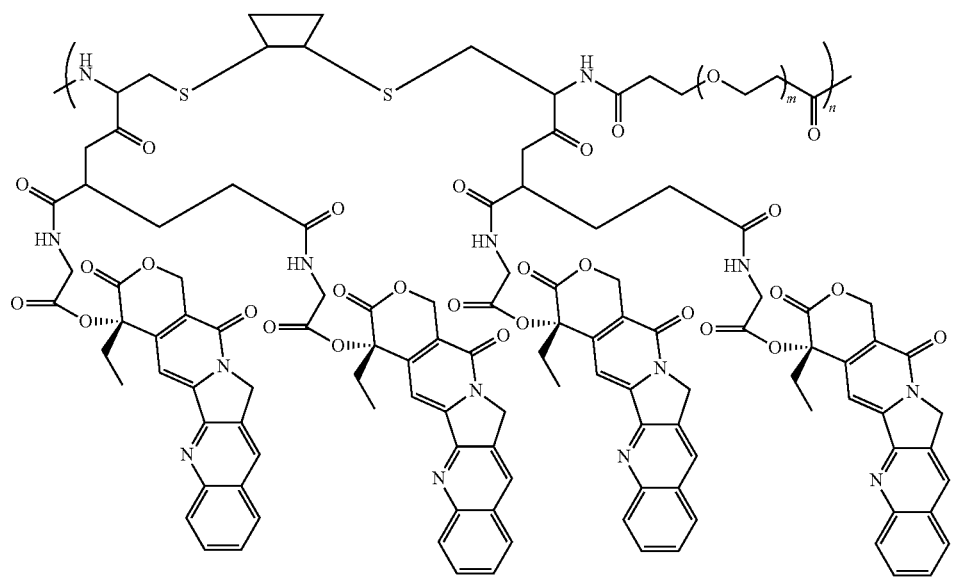
43
PEG Mw = 3400
4 CPT per CD
Maximum drug loading 25%

36 and Glu-Bis(Gly-CPT) 17 are dissolved in DMSO. EDC (3 eq), NHS (2.2 eq), and DIEA (2.2 eq) are added to the solution. CD-BisCys-Peg-GluBis(GlyCPT) 43 is precipitated with CH₃CN and washed with the same solvent until no free drug is detected using UV or TLC. 43 is dried under high vacuum.

Example 35

Synthesis of PEI-CD-CPT Conjugate 44 (Branched CD-Polymer with CPT Conjugates)

A: Synthesis of Branched PEI-Cyclodextrin Polymer

Scheme XXXXIV

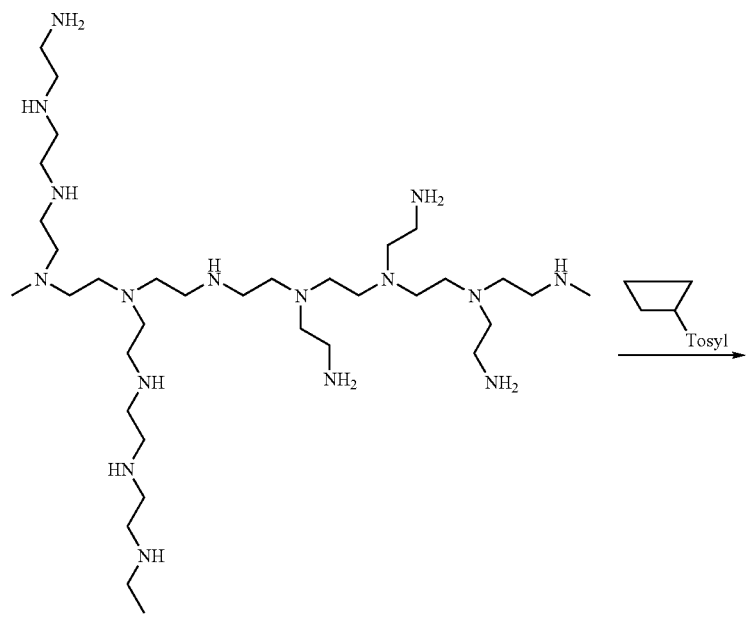

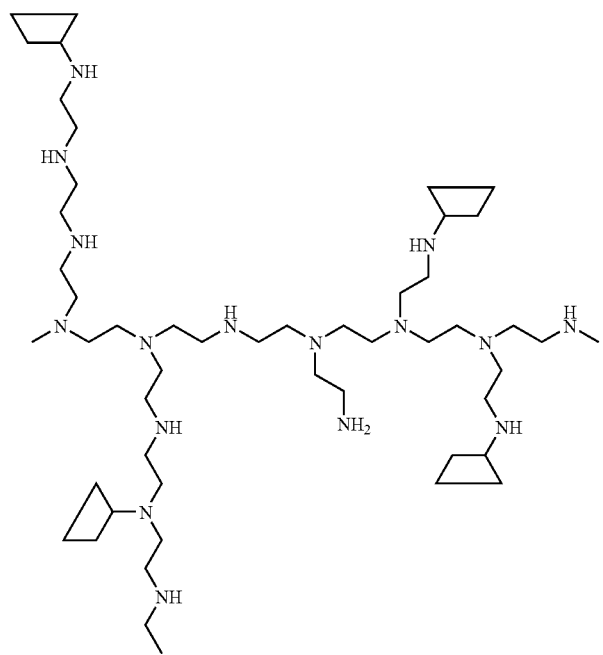

PEI (29 mg, Aldrich Mw 25,000) was dissolved in dry DMSO (2 mL). Cyclodextrin monotosylate (448 mg, Cyclodextrin Technologies Development, Inc.) was added to the solution under $N_2$. The cloudy solution turned clear after the mixture was stirred at 70° C. for about 1 hour. The solution turned slightly yellow after 48 hours at such temperature under $N_2$.

The solution was transferred to a Spectra/Por MWCO 10,000 membrane and dialyzed against water for 4 days. Water was then removed by lyophilization. A white powder was obtained (120-140 mg) after the solution was lyophilized. Cyclodextrin/PEI ratio was calculated based on the proton integration of $^1$H NMR.

B: Synthesis of Branched PEI-CD-CPT Conjugate

Scheme XXXXV

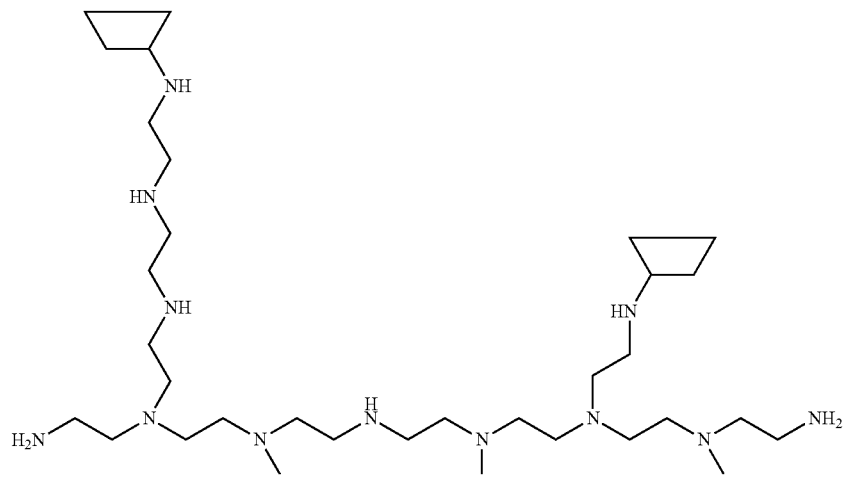

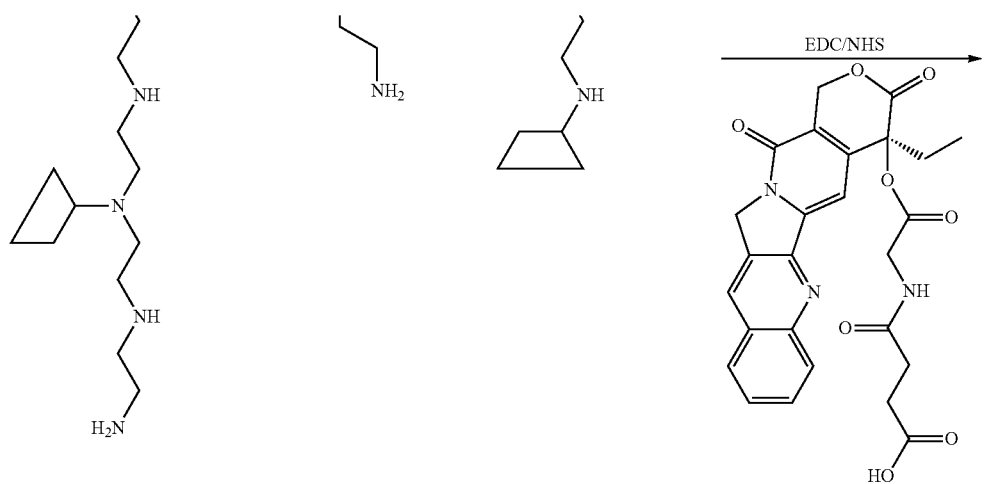

-continued
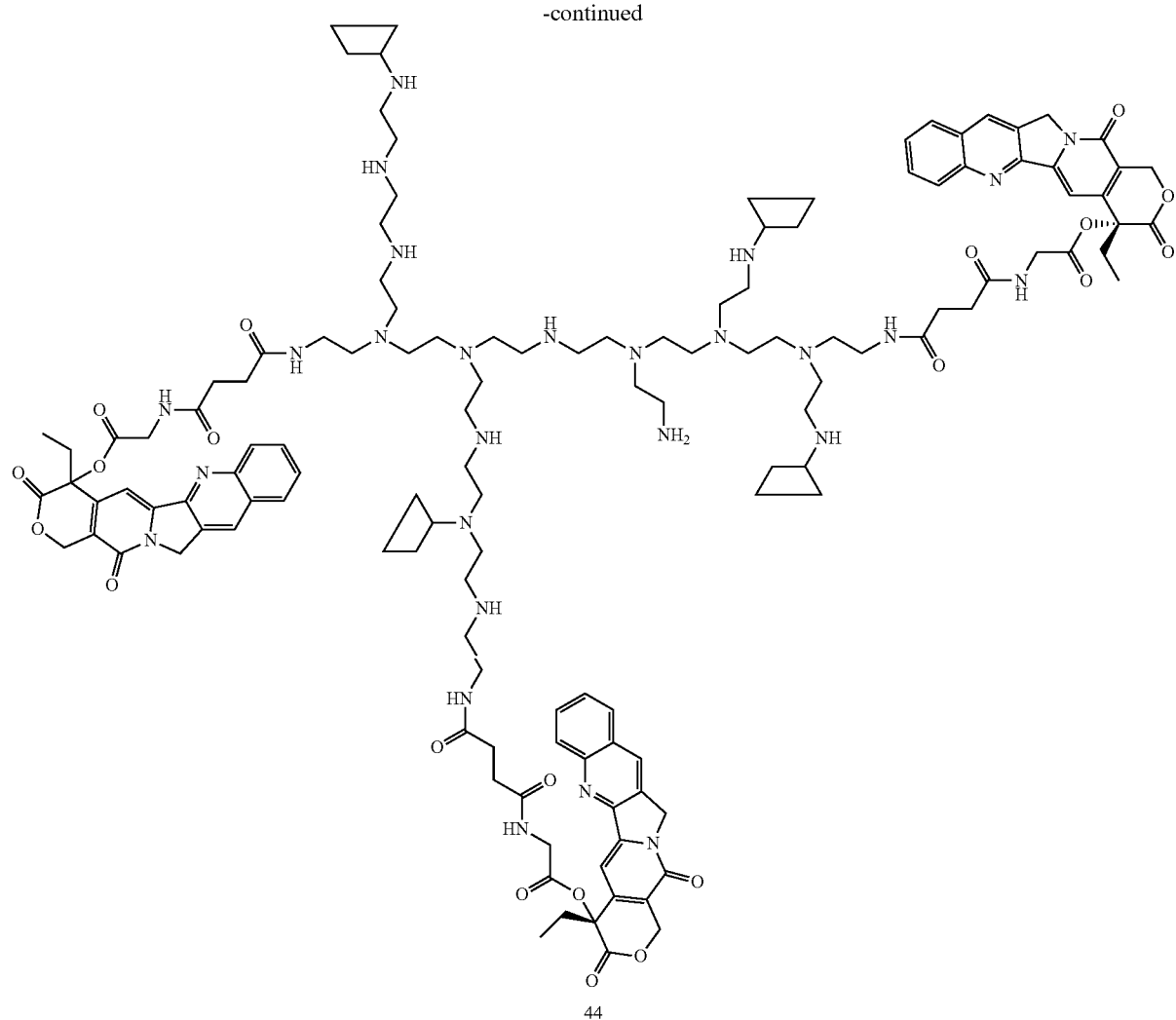
44
PEI-CD and Suc-Gly-CPT 15 (1.0 eq) are dissolved in DMSO. EDC (3 eq), NHS (2.2 eq), and DIEA (1 eq) are added to the solution. PEI-CD-Gly-CPT 44 is precipitated with ether, washed extensively with this solvent, and dried under high vacuum.
Example 36
Synthesis of Ad-PEG$_{3400}$-Ad 45
Scheme XXXXVI
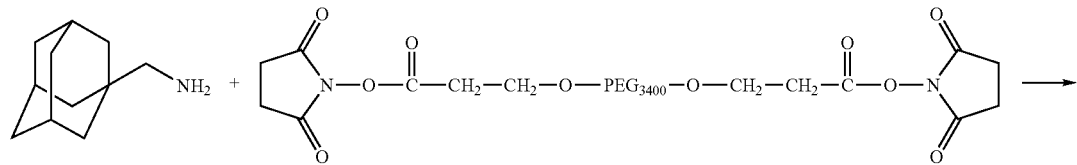

-continued

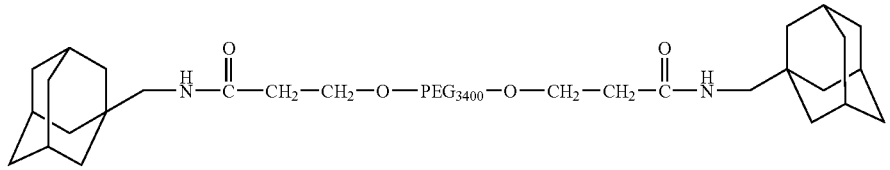

45

240 mg of 1-aminoadamantane (1.60 mmol, Aldrich) and 272 mg of PEG$_{3400}$(SPA)$_2$ (0.080 mmol, Shearwater Polymers) was added to a glass vial equipped with a stirbar. To this was added 5 mL of dichloromethane, and the solution was stirred overnight. The next day, the solution was filtered to remove the n-hydroxysuccinimide byproduct and the dichloromethane was removed in vacuo. The residue was dissolved in water and centrifuged to remove excess 1-aminoadamantane. The supernatant was then dialyzed overnight in Pierce's Slide-A-Lyzer with MWCO=3500. The solution was then lyophilized to afford 248 mg of a white fluffy solid of Ad-PEG$_{3400}$-Ad 45.

Example 37

Synthesis of DiCyclodextrin PEG 46

362 mg of CD-NH$_2$ (0.32 mmol, Cyclodextrin Technology, Inc.) and 436 mg of PEG$_{3400}$(SPA)$_2$ (0.128 mmol, Shearwater Polymers) were added to a glass vial equipped with a stirbar. To this vial was added 4.36 mL of DMSO, and the solution was stirred for 72 hrs. The solution was dialyzed using 2000 MWCO membrane for 4 days in water. 46 (603 mg, 86%) was obtained as a white powder after lyophilization.

Example 38

Synthesis of Inclusion Polymer 47 Using DiAD-Peg45 and DiCD-PEG 46

46 (54.6 mg, 0.01 mmol) and 45 (34 mg, 0.01 mmol) were mixed in water (0.27 μL) and stirred for overnight. The solution is very viscous. Polymer 47 was crashed out with ether and dried under vacuum Example 39

Synthesis of Inclusion Polymer CPT-Conjugate 48 between DiCD-PEG 46 and a CPT-Di-AD compound Synthesis of Diadamantane Crosslinker: Bis-(2(1-adamantyl)ethyl)phosphate (Zhang et al., *J. Am. Chem. Soc.* 1997, 119, 1676-1681)

Scheme XXXXVII

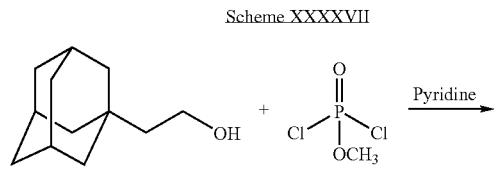

-continued

Anhydrous pyridine (10 mL, Aldrich, Milwaukee, Wis.) was cooled in an ice bath and methyl dichlorophosphate (1.488 g, 10 mmol, Aldrich, Milwaukee, Wis.) was added dropwise. The mixture was kept cold for a further 15 min. During this period a precipitate of N-methylpyridinium dichlorophosphate formed. 1-Adamantane ethanol (4.758 g, 26.4 mmol, Aldrich, Milwaukee, Wis.) was added, and the sealed mixture was stirred overnight at room temperature. It was then poured into 10% NaHCO$_3$ solution (50 mL) and the pyridine was evaporated under vacuum. The slightly yellow solid was dissolved in 1 L of water and extracted with ether (three 150 mL portions). The aqueous phase was acidified with 2 N HCl to pH 1, and then extracted with three 150 mL portions of CHCl$_3$: n-BuOH (7:3). The combined organic layer (ether and CHCl$_3$: n-BuOH) was washed with water and a slightly yellow precipitate was formed in the mixed solvents, at which point the solvents were evaporated under vacuum. A slightly yellow solid was formed and was recrystallized from acetone/hexane. The solid was dried under vacuum, yield 60%.

Scheme XXXXVIII

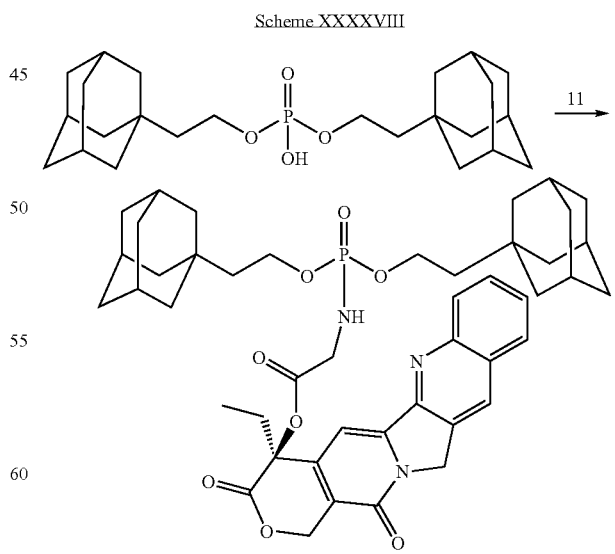

Bis-(2(1-adamantyl) ethyl) phosphate and 11 are mixed in DMSO. EDC (3 eq), NHS (2.2 eq), and DEA (1 eq) are added to the solution. Solution is stirred under argon for 16 hours.

Bis-(2(1-adamantyl) ethyl) phosphate-Gly-CPT is precipitated with ether, washed extensively with this solvent, and dried under high vacuum. This compound and Di-CD-PEG 46 are mixed in DMSO to form inclusion polymer-CPT conjugate 48.

Example 40

Synthesis of AD-Peg-Folate 49

The following procedure is the synthesis of AD-Peg$_{5000}$-Folate. This method can be adapted for the synthesis of any Guest molecule-Linker-Ligand tri-component molecules.
1. Synthesis of AD-Peg-NH$_2$ 266 mg of FMOC-PEG$_{5000}$-NHS (78.2 µmol, Shearwater Polymers, Huntsville Ala.) were added to a glass vial equipped with a magnetic stirbar. 10 eq. of 1-adamantane-methylamine (1.5 mmol, Aldrich) dissolved in 3 mL of dichloromethane were then added and the solution stirred overnight at room temperature. The solvent was removed in vacuo and water was added to the remaining solution to dissolve the PEG product. The solution was centrifuged at 20K rcf for 10 minutes, whereupon the adamantane-methylamine phase-separated as a denser liquid. The aqueous portion was collected and water removed in vacuo. The remaining viscous liquid was redissolved in 20% piperidine in DMF for FMOC deprotection and stirred for 30 minutes at room temperature. The solvent was removed in vacuo, washed several times with DMF, redissolved in water, and run on an anionic exchange column to remove unreacted PEG. The first fractions were collected and lyophilized to yield 222 mg of a white, fluffy powder (76% yield) of the desired product which was confirmed by MALDI-TOF analysis.
2. Synthesis of N-Hydroxysuccinimide-folate (NHS-folate)

Scheme XXXXIX

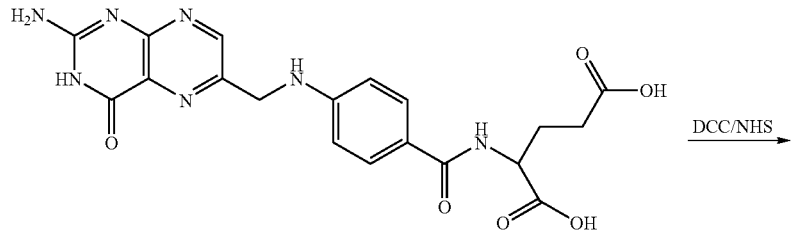

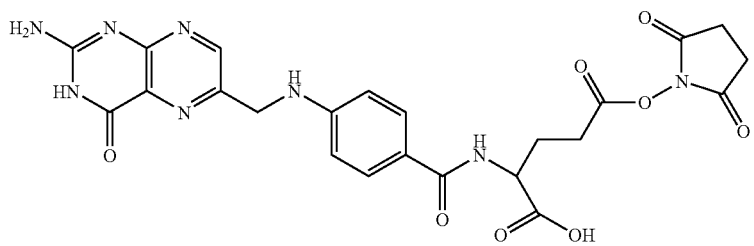

Scheme L

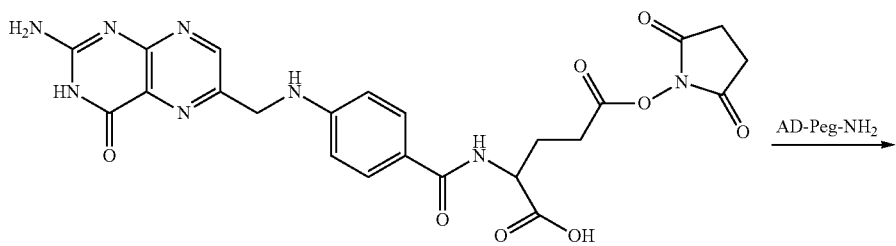

NHS-folate is synthesized according to the method of Lee and Low (Lee, R. J; Low, P. S. *J. Biol. Chem.* 1994, 269, 3198-3204). Folic acid (5 g, 11.3 mmol; Sigma) is dissolved in DMS (100 ml) and triethylamine (2.5 ml) and reacted with N-hydroxysuccinimide (2.6 g, 22.6 mmol) and dicyclohexylcarbodiimide (4.7 g, 22.7 mmol) over-night at room temperature. The solution is filtered and concentrated under reduced pressure. NHS-folate is precipitated using diethyl ether (yellow-orange precipitate), and washed 2-3 times in anhydrous ether, dried under vacuum, and stored at −20° C.

3. AD-Peg$_{5000}$-Folate

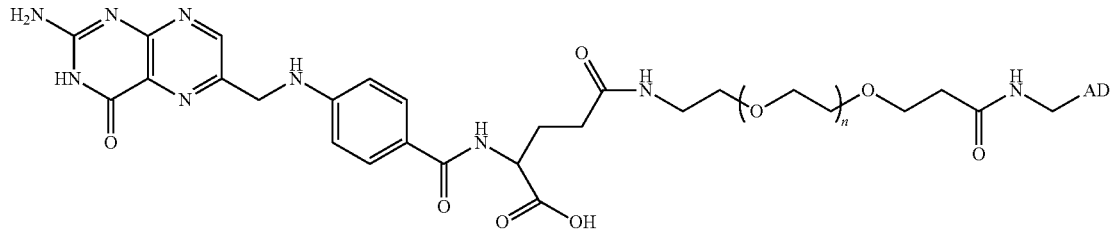

AD-Peg5000-NH$_2$ and NHS-Folate are mixed at 1:1 eq. in DMSO solution. DIEA (2 eq) is added. The mixture is allowed to stir at room temperature for overnight. The DMSO solution is then dialyzed against 3500 MWCO (Spectra/Por 7) membrane for 48 hours. AD-Peg5000-Folate 49 is obtained after lyophilization.

Example 41

Formulation of the AD-Peg-Folate and a CD-Polymer-CPT Conjugate

A typical procedure: A CD-polymer CPT conjugate is dissolved in a DSW buffer. A D5W solution containing 0.1-1 eq (mols of repeat unit) of AD-Peg-Folate solution is added to polymer solution. Particle sizes of polymer are measured before and after adding of AD-Peg-Folate using light scattering. This solution is used for either in vitro or in vivo test for the analysis of folate targeting effects.

Example 42

Covalent Linking a Targeting Ligand (e.g., Folate) to a CD-CPT Polymer Conjugate (eg PEI-CD-GlyCPT)

Scheme LI

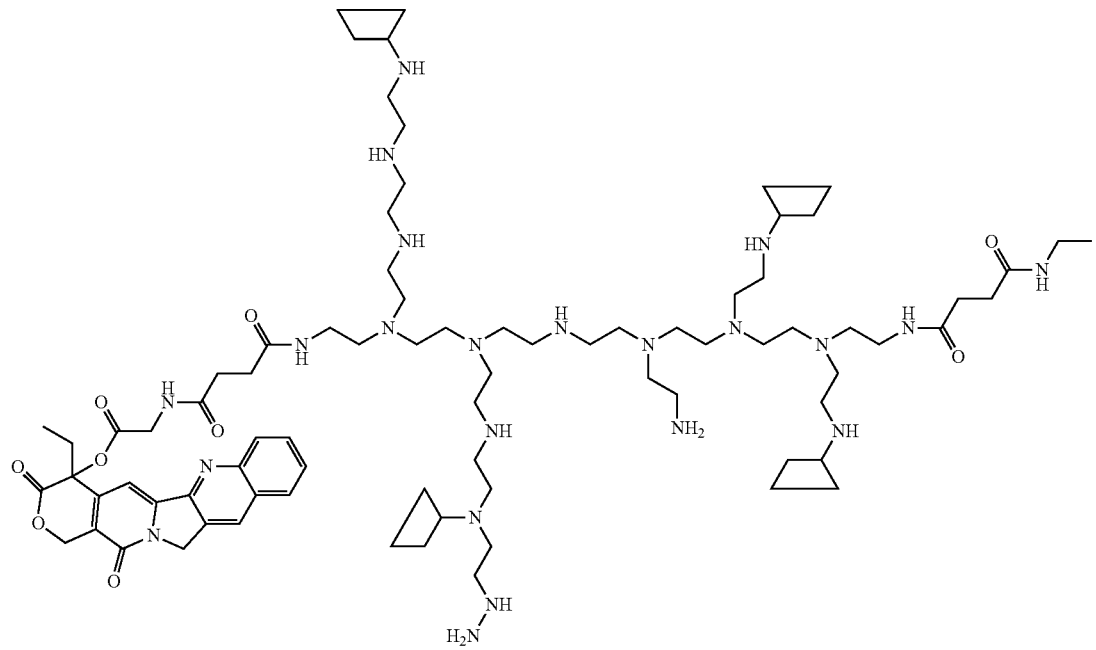

123 124
-continued
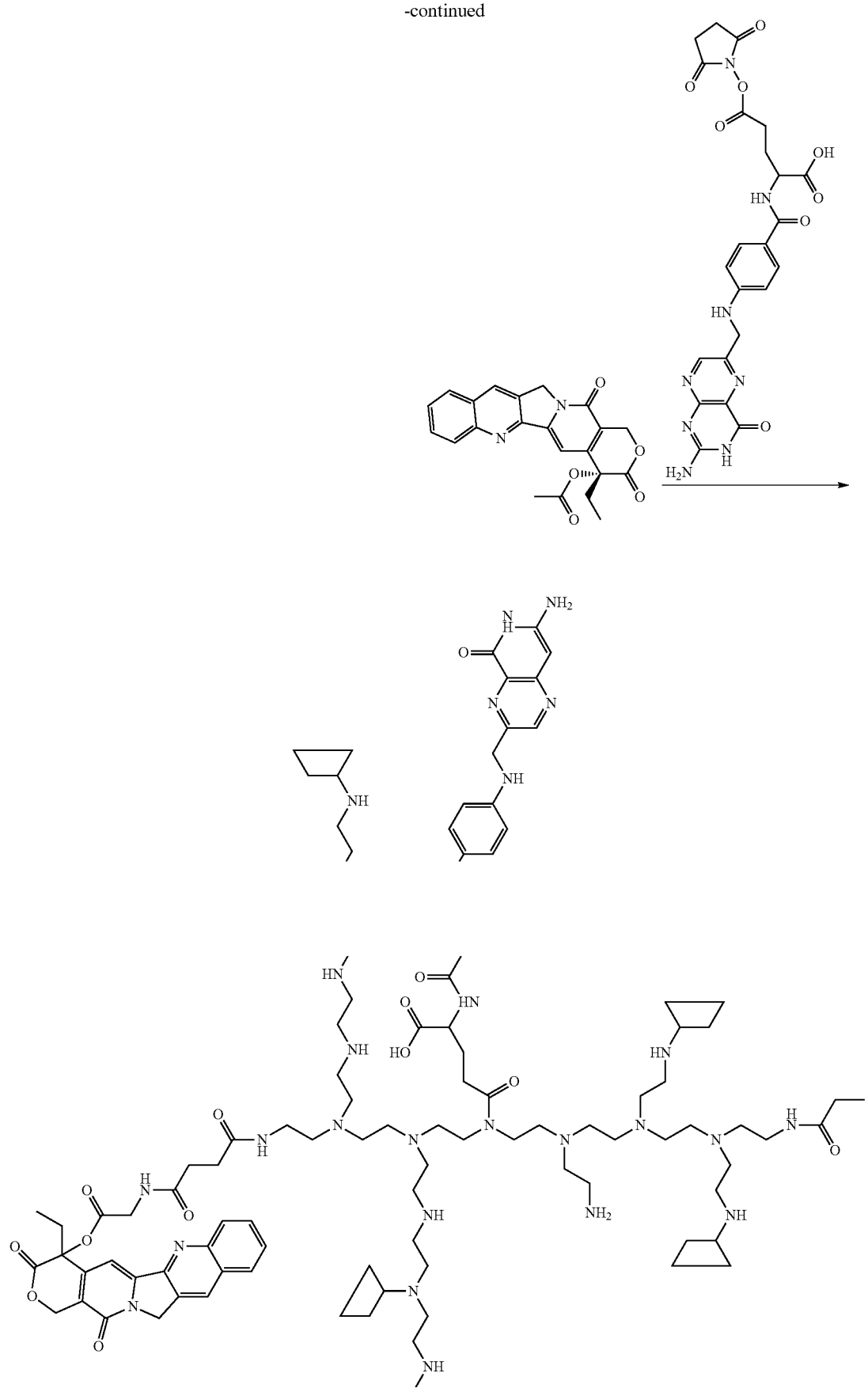

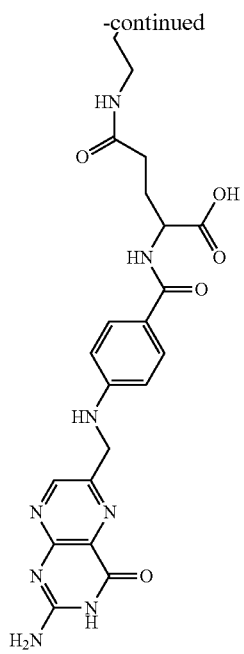

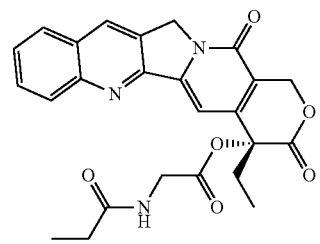

PEI-CD-GlyCPT 44 and Folate-NHS (0.1-0.5 eq) are mixed in DMSO and stirred for 24 hours. The polymer is crashed out with ether and washed extensively with this solvent until no free folate molecule can be detected. The resulting CD-polymer-CPT-Folate conjugate 50 is dried under vacuum.

Example 43

Crosslinking of CD-CPT Polymer Using Ad-Peg-Ad. 51

A typical procedure: AD-Peg-AD 45 (0.01-0.1 eq of CD-polymer repeat unit) and CD-polymer CPT conjugate are mixed in a minimum amount of DMSO. The resulting viscous solution is precipitated with ether and dried under vacuum to yield lightly crosslinked polymer 51. 51 should still maintain small particle size in solution, have good water solubility, and have higher molecular weight than parent CD-polymer CPT conjugate.

Example 44

In Vivo Tests of Camptothecin Polymer Conjugates HGGG6, LGGG10, HG6, and HGGG10 (Synthesized According to Example 28)

A. In Vivo Toxicity and Blood Chemistry Analysis from Dosing with Parent Polymer 36e The toxicity of 36e and its effects on blood chemistry were evaluated in female Charles River nude mice (13-14 weeks old). Four treatment groups of six mice each were treated with a D5W solution of 36e at a dose of 240 mg/kg, 160 mg/kg, 80 mg/kg or D5W alone by i.v. tail vein injection on Days 1, 5, and 9, respectively. Dosing volume was determined based upon a ratio of 200 µl for a 20 g mouse, and was scaled appropriately according to the actual BW of the mice. The BWs of the mice were followed daily for the first 5 days and then twice a week, thereafter. Blood samples (150-200 µl) were collected from each mouse by retro-orbital bleeding under isofluorane on Day 12. Samples from three mice in each group were used for complete blood count (CBC) analyses, while blood samples from the remaining three mice in each group were processed for blood chemistry analyses. The study was stopped at Day 23. All mice were euthanized by cardiac puncture under $CO_2$, and blood from each mouse was collected for CBC and blood chemistry analysis in the same manner as on Day 12.

There was no significant difference in BW loss, CBC or blood chemistry data between any of the 36e treated groups and D5W control group throughout the study, and no time dependent effects were observed over 23 days' for all the treated groups. 36e was well tolerated by mice at the maximum dose treated (240 mg/kg).

B. Determination of Maximum Tolerable Dose (MTD) for CDP-CPT Conjugates.

The MTD was determined using female Charles River nude mice (15-16 weeks old) for HG6, LGGG10, HGGG10. A 5% (w/v) of dextrose solution (D5W) of the polymer-CPT conjugates was freshly prepared before each injection. Doses for the treatment groups ranged from 2.25 mg CPT/kg to 54 mg CPT/kg. Dosing was administered intravenously (i.v.) by tail vein injection on Days 1, 5, and 9. The dosing volume was determined based upon a ratio of 200 μl for a 20 g mouse, and was scaled appropriately according to actual body weight (BW) of the mice. Three to five mice were used in each treatment group. The BWs of the mice were followed daily for the first 5 days and then twice a week, thereafter. The MTD was defined as the highest administered dose that resulted in a decrease of mean group BW of less than 20% or the highest administered dose that did not result in death of any animal in that group. The maximum mean body weight loss and treatment related deaths for all treated groups are listed in Table 5.

TABLE 5

Treatment response for the MTD study. Nude mice (n = 3-6) were treated i.v. by tail vein injection.

| Agent | mg/kg[a] | Max % BW loss; Day[b] | $N_{TR}/N$[c] |
|---|---|---|---|
| D5W | — | −2.5%; Day 3 | 0/6 |
| 36e | 240 | −2.0%; Day 3 | 0/6 |
| 36e | 160 | −3.5%; Day 13 | 0/6 |
| 36e | 80 | −2.3%; Day 3 | 0/6 |
| LGGG10 | 54 | −20.6%; Day 3 | 3/3 |
| LGGG10 | 36 | −9.3%; Day 13 | 0/3 |
| LGGG10 | 18 | 0 | 0/3 |
| LGGG10 | 9 | 0 | 0/5 |
| LGGG10 | 4.5 | −0.8%; Day 13 | 0/5 |
| HG6 | 54 | −28.5%; Day 3 | 3/3 |
| HG6 | 36 | −23.9%; Day 3 | 3/3 |
| HG6 | 18 | −22.1%; Day 3 | 3/3 |
| HG6 | 9 | −6.1%; Day 9 | 0/5 |
| HG6 | 4.5 | −4.4%; Day 5 | 0/5 |
| HG6 | 2.25 | −2.9%; Day 9 | 0/5 |
| HGGG10 | 54 | — | 3/3 |
| HGGG10 | 36 | −34%; Day 5 | 3/3 |
| HGGG10 | 18 | −16%; Day 3 | 1/3 |
| HGGG10 | 9 | −3.3%; Day 9 | 0/5 |
| HGGG10 | 4.5 | −2.5%; Day 9 | 0/5 |

[a]Mg CDP/kg for the CDP polymer and mg CPT/kg for the three conjugates tested.
[b]Maximum body weight (BW) loss observed post injection
[c]Number of treatment-related deaths ($N_{TR}$) to the number of mice treated (N)

The MTD of LGGG110, HG6, and HGGG10 were determined to be 36 mg CPT/kg, 9 mg CPT/kg, and 9 mg CPT/kg, respectively. Based on the structural similarities between HGGG6 and HGGG10, it is expected that the MTD for these two groups are similar. Therefore, the MTD of HGGG6 (not tested) was assumed to be 9 mg CPT/kg.

C. Antitumor Efficacy Study.

The antitumor efficacy study was performed using female Charles River nude mice (15-16 weeks old). A fragment (1 mm 3) of human LS174T colon carcinoma tissue was implanted subcutaneously (s.c.) into the right flank of each test mouse approximately 14-18 days before dosing. The tumor volume was determined by measuring the tumor in two dimensions with calipers and calculated using the formula: tumor volume=(length×width 2)/2. Tumor volume was converted to tumor weight assuming 1 mm³ is equal to 1 mg tumor in weight. Treatment was initialized when mean tumor size reached approximately 60-100 mg (Day 1). The animals were sorted into twelve groups. Each group consisted of seven mice with tumor sizes ranging from 62.5-144.0 mg with group mean tumor sizes of 88.6-90.7 mg. Mice in each group were treated according to the protocol listed in Table 6. All conjugate treatments were administered intravenously by tail vein injection. Tumor sizes were measured twice a week for the duration of the experiment. At the end of study, tumors from each euthanized mouse were harvested and frozen at −80° C.

TABLE 6

Dosing protocol for efficacy study.[a]

| Group | Agent | Dose (mg CPT/kg)[b] | Route[c] | Schedule[d] |
|---|---|---|---|---|
| 1 | D5W | | i.v. | Q4D × 3 |
| 2 | CPT | 9 | i.p. | Q4D × 2[e] |
| 3 | Irinotecan | 100[f] | i.p. | Qwk × 3 |
| 4 | HGGG6 | 9 | i.v. | Q4D × 3 |
| 5 | HGGG6 | 4.5 | i.v. | Q4D × 3 |
| 6 | LGGG10 | 36 | i.v. | Q4D × 3 |
| 7 | LGGG10 | 18 | i.v. | Q4D × 3 |
| 8 | LGGG10 | 9 | i.v. | Q4D × 3 |
| 9 | HG6 | 9 | i.v. | Q4D × 3 |
| 10 | HG6 | 4.5 | i.v. | Q4D × 3 |
| 11 | HGGG10 | 9 | i.v. | Q4D × 3 |
| 12 | HGGG10 | 4.5 | i.v. | Q4D × 3 |

[a]Seven mice were used in each group
[b]Doses are equivalent of CPT except for group 3
[c]i.p. = intraperitoneal, i.v. = intravenous
[d]Administration schedules were abbreviated as: Q4D × 3 = three injection with four-day intervals, Qwk × 3 = three injection with one-week interval, first dose was initialized on day 1 for all groups.
[e]The scheduled third dose was not given due to the emerging toxicity
[f]100 mg irinotecan/kg Each animal was euthanized when tumor weight reached the predetermined endpoint size (1,500 m g). The time-to-endpoint (TTE) for each mouse was calculated from the equation: TTE=(log(endpoint-b))/m, where b and m are the intercept and the slope, respectively, of the line obtained by linear regression of a log-transformed tumor growth data set comprised of the first observation that exceeded the study endpoint volume and the three consecutive observations that immediately preceded the attainment of the endpoint volume. Animals that do not reach the endpoint were assigned a TTE value equal to the last day of the study (114 days). Animals classified as treatment-related deaths (TR) were assigned a TTE value equal to the day of death. Animals classified as non-treatment-related death (NTR) are excluded from TTE calculations. Tumor growth delay (TGD), defined as the increase in the median time to endpoint (TTE) in a treatment group compared to the control group, was one parameter investigated to evaluate treatment efficacy. TGD is calculated as the difference between the median TTE for a treatment group and the median TTE of the control group (TGD=T−C) and is expressed in days, and as a percentage of the median TTE of the control group; % TGD=(T−C)/C where T is equal to median TTE for a treatment groups and C is equal to median TTE for the control, Group 1.

Toxicity. Animals were weighed daily on Days 1-5, then twice weekly thereafter. Mice were examined frequently for overt signs of any adverse, drug-related side effects. Acceptable toxicity for cancer drugs in mice is defined by the NCI as a group mean body-weight loss of less than 20% during the study, and not more than one toxic death among seven treated animals.

Results for this efficacy study that include median TTE values, median tumor burden on day 114, treatment response and deaths are summarized in Table 7.

TABLE 7

| Group | Median TTE[a] | T − C[b] | % TGD[c] | Median Tumor Burden in mg (N$_s$[d]) | N$_{TR}$[e]/ N$_{NTR}$[f]/ N$_{EU}$[g] | P vs D5W[h] | P vs CPT[i] |
|---|---|---|---|---|---|---|---|
| 1 | 34.9 | — | — | — (0) | 0/1/6 | — | — |
| 2 | 51.4 | 16.5 | 47% | — (0) | 2/0/5 | 0.2128 | — |
| 3 | 68.7 | 33.8 | 97% | 1152 (3) | 0/0/4 | 0.0002 | 0.0253 |
| 4 | 114.0 | 79.1 | 227% | 256 (5) | 1/0/1 | 0.0040 | 0.0115 |
| 5 | 65.6 | 30.7 | 88% | 566 (2) | 0/1/4 | 0.0046 | 0.1369 |
| 6 | 100.0 | 65.1 | 187% | 666 (3) | 4/0/0 | 0.0272 | 0.0289 |
| 7 | 75.6 | 40.7 | 117% | 221 (3) | 0/0/4 | 0.0018 | 0.0601 |
| 8 | 63.2 | 28.3 | 81% | 700 (1) | 1/0/5 | 0.0006 | 0.1064 |
| 9 | 114.0 | 79.1 | 227% | 394 (4) | 0/0/3 | 0.0002 | 0.0028 |
| 10 | 74.2 | 39.3 | 113% | 668 (2) | 1/1/3 | 0.0016 | 0.0673 |
| 11 | 114.0 | 79.1 | 227% | 500 (5) | 1/0/1 | 0.0040 | 0.0050 |
| 12 | 78.0 | 43.1 | 123% | 1010 (2) | 0/0/6 | 0.0006 | 0.0392 |

[a] TTE = Time (Days) to endpoint (1500 mg)
[b] T − C = Difference between TTE (Days) of treated versus control group
[c] % TGD = [(T − C)/C]
[d] Mice surviving
[e] N$_{TR}$ = Number of treatment-related death
[f] N$_{NTR}$ = Number of non-treatment-related death
[g] N$_{EU}$ = Number of mice euthanized after reaching endpoint
[h] P value versus the D5W treatment group (Group 1)
[i] P value versus the CPT treatment group (Group 2)

One NTR death on day 72 was observed in the control animals treated with D5W. Tumors in the other six control mice grew to the 1500 mg endpoint size, yielding a median TTE of 34.9 days (Table 7).

Two treatment-related deaths were reported on Day 9 for CPT at 9 mg/kg. Thus, CPT must be considered to be toxic at this dose in this experiment. The median TTE for this group was 51.4 days, corresponding to a 16.5 day T-C and a 47% TGD, relative to untreated control mice (not significant). No animal in Group 2 survived to Day 114.

Group 3 received irinotecan i.p. at 100 mg/kg (Qwk×3). The median TTE for Group 3 was 68.7 days, corresponding to a significant 33.8 day T-C and a 97% TGD, relative to control mice (P<0.01). Three animals survived to Day 114 with a median tumor burden of 1,152 mg. No regressions were recorded.

Groups 4 and 5 received HGGG6 i.v. Q4D×3 at 9 and 4.5 mg CPT/kg, respectively. One treatment-related death was observed on Day 16 in Group 4, and one NTR death was recorded on Day 37 in Group 5. The median TTE for Group 4 was 114 days, the maximum possible value in this study. This TTE value corresponds to a significant 79.1 day T-C and a 227% TGD, relative to control (P<0.01). Tumors in five mice of Group 4 did not reach the 1,500 mg endpoint. These five mice had a median tumor burden of 256 mg on Day 114. The median TTE for Group 5 was 65.6 days, and corresponds to a significant 30.7 day T-C and an 88% TGD, relative to control (P<0.01).

Groups 6-8 were treated with LGGG10 i.v. Q4D×3 at 36, 18, and 9 mg CPT/kg, respectively. Although no death was observed in MTD study using this conjugate in non-tumor bearing mice at 36 mg CPT/kg (Table 5), four treatment-related deaths were recorded in Group 6 when tumor-bearing mice were given at this dose, two on Day 16 and one each on Days 75 and 100. These results indicate that 36 mg CPT/kg is probably over the MTD of LGGG10. As shown in Table 5, no significant body weight loss was recorded in the MTD study when the mice were dosed at 18 mg CPT/kg, indicating that this dose is below the MTD. Therefore, the MTD of LGGG10 lies somewhere between 18 to 36 mg CPT/kg. The median TTE for Group 7 (18 mg CPT/kg) was 75.6 days. This TTE value corresponds to a significant 40.7 day T-C and a 117% TGD, relative to control mice (P<0.01). Three mice in this group had a median tumor burden of 221 mg on Day 114. One late TR death was recorded on Day 103 in Group 8 (9 mg CPT/kg). The median TTE for Group 8 was 63.2 days. This TTE value corresponds to a significant 28.3 day T-C and an 81% TGD, relative to untreated control mice (P<0.01). The remaining mouse in this group had a tumor burden of 700 mg on Day 114.

Groups 9 and 10 were dosed with HG6 i.v. Q4D×3 at 9 and 4.5 mg CPT/kg, respectively. One TR and one NTR death were recorded in Group 10 on Days 47 and 84, respectively. The median TTE for Group 9 was the maximum, 114 days. This TTE value corresponds to a significant 79.1 day T-C and a 227% TGD, relative to untreated control mice (P<0.01). Four mice in Group 9 had a median tumor burden of 394 mg on Day 114. The median TTE for Group 10 was 74.2 days. This TTE value corresponds to a significant 39.3 day T-C and a 113% TGD, relative to control mice (P<0.01). The remaining two mice in Group 10 had a median tumor burden of 668 mg on Day 114.

Groups 11 and 12 were dosed with HGGG10 i.v. Q4D×3 at 9 and 4.5 mg CPT/kg, respectively. One treatment-related death was recorded on Day 16 in Group 11. The median TTE for Groups 11 and 12 were 114 days and 78 days, respectively. The TTE value for Group 11 corresponds to a significant 79.1 day T-C and a 227% TGD, relative to control mice (P<0.01). Tumors in five mice in Group 11 did not reach the endpoint; these five mice had a median tumor burden of 500 mg on Day 114. The TTE value of Group 12 corresponds to a significant 43.1 day T-C and a 123% TGD, relative to control mice (P<0.01). The remaining two mice in this group had a median tumor burden of 1,010 mg on Day 114.

Figure 8:
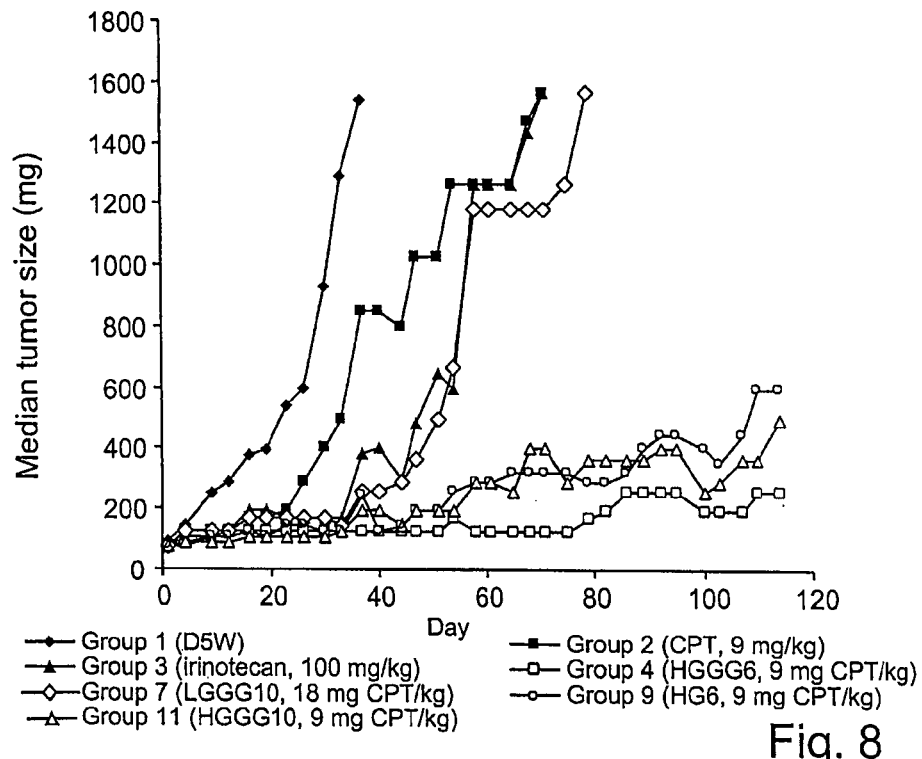
FIG. 8 Shows the tumor growth curve as a function of time for the D5W, CPT, irinotecan, LGGG10 at its highest non-toxic dose tested (18 mg CPT/kg), and the other three conjugates with high MW polymer (HGGG6, HG6, HGGG10) at their MTDs in xenograft mice.
Figure 9:
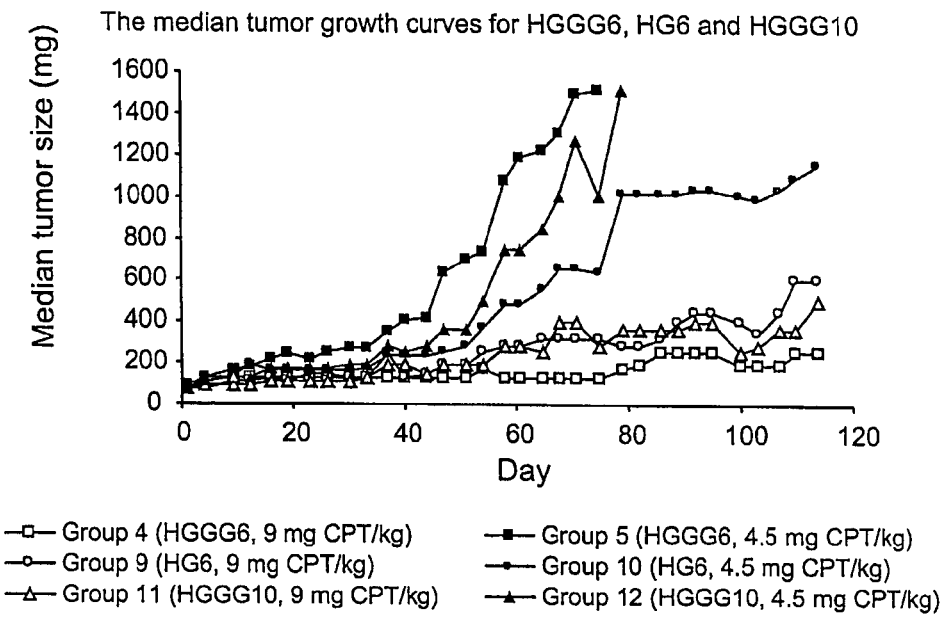
FIG. 9 presents the median tumor growth curves for HGGG6, HG6 and HGGG10 in xenograft mice.
Figure 10:
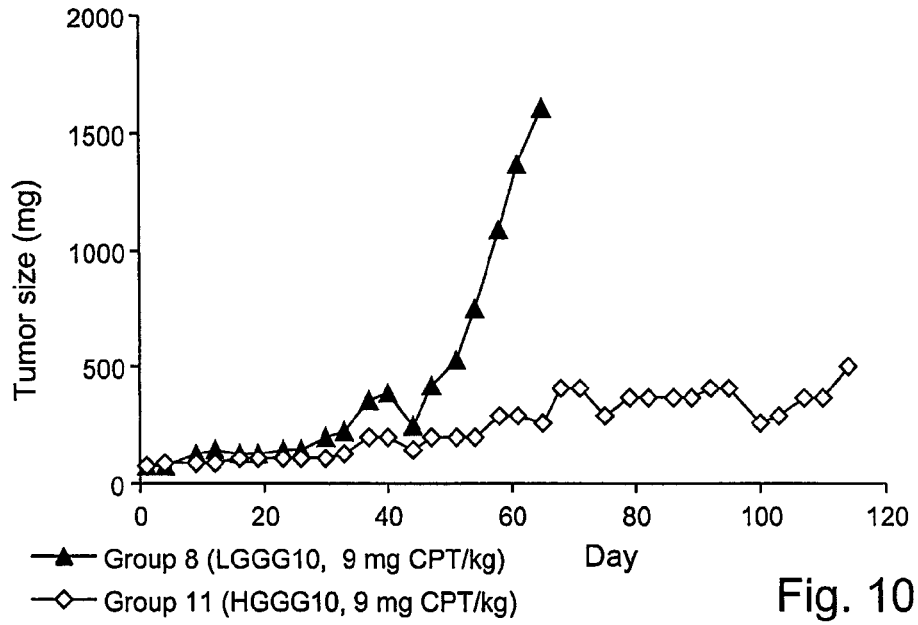
FIG. 10 presents the medium tumor growth curves for LGGG10 and HGGG10 each dosed at 9 mg CPT/kg in xenograft mice.

The tumor growth curve as a function of time for the D5W, CPT, irinotecan, LGGG10 at its highest non-toxic dose tested (18 mg CPT/kg), and the other three conjugates with high MW polymer (HGGG6, HG6, HGGG10) at their MTDs are shown in FIG. 8. The three high MW conjugates administered at their MTDs displayed more prolonged tumor growth inhibition compared to D5W, CPT and irinotecan. The median tumor growth curves for HGGG6, HG6 and HGGG10 that are illustrated in FIG. 9 show that there is a distinct dose response for all three of these polymers when dosed as their MTD and at half of their MTD. The medium tumor growth curves for LGGG10 and HGGG10 each dosed at 9 mg CPT/kg as illustrated in FIG. 10 demonstrate that high MW polymer-drug conjugate has greater antitumor effect when compared to the low MW conjugates presumably due to the enhanced accumulation (EPR effect) and reduced renal clearance.

Figure 11:
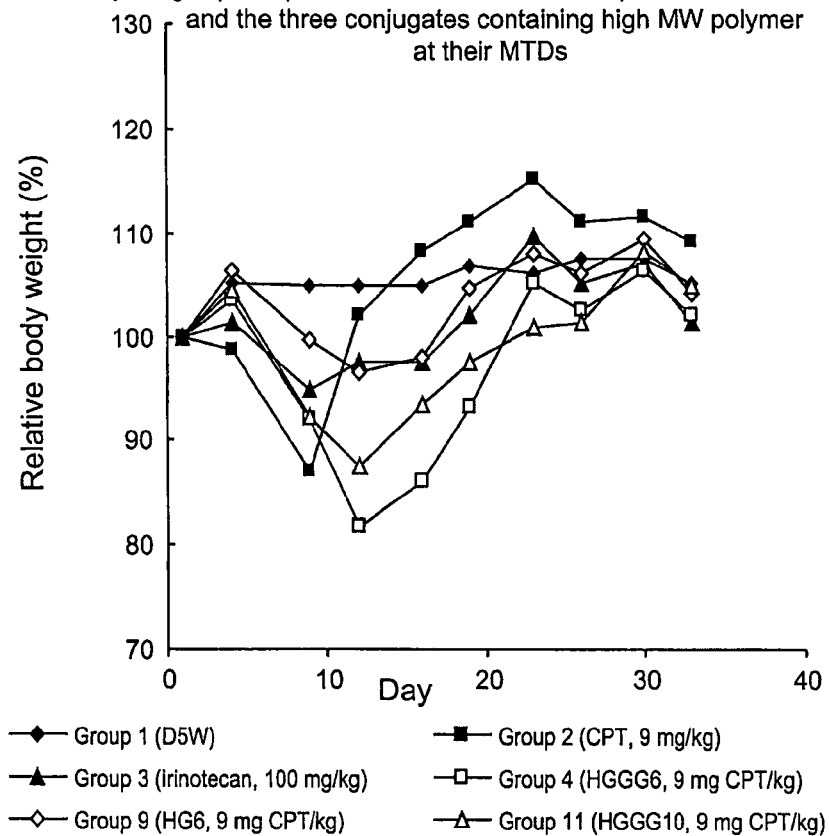
FIG. 11 presents the mean body weight (MBW) losses as a function of time plotted for D5W, CPT, irinotecan and the three conjugates containing high MW polymer at their MTDs in xenograft mice.

Mean Body Weight Loss of Mice. Mean body weight (MBW) losses as a function of time are plotted for D5W, CPT, irinotecan and the three conjugates containing high MW polymer at their MTDs (FIG. 11). Maximum MBW losses observed in Group 2 (CPT) and the two conjugates with the triglycine linker dosed at their MTDs (Groups 4 and 11) were 13.1%, 18.3%, and 12.6%, respectively. Maximum MBW loss of HG6 (3.4%), the only conjugate with a glycine linker, was similar to the maximum MBW loss recorded for irinotecan (5.0%). Negligible (<5%) maximum group mean body-weight losses were recorded in all the other treatment groups and in the D5W group. Mean body weight returned to baseline levels for all treatment groups following cessation of therapy.

D Correlation of Tumor Size of Enthanized Mouse and the CPT Concentration in Corresponding Tumor.

Figure 12:
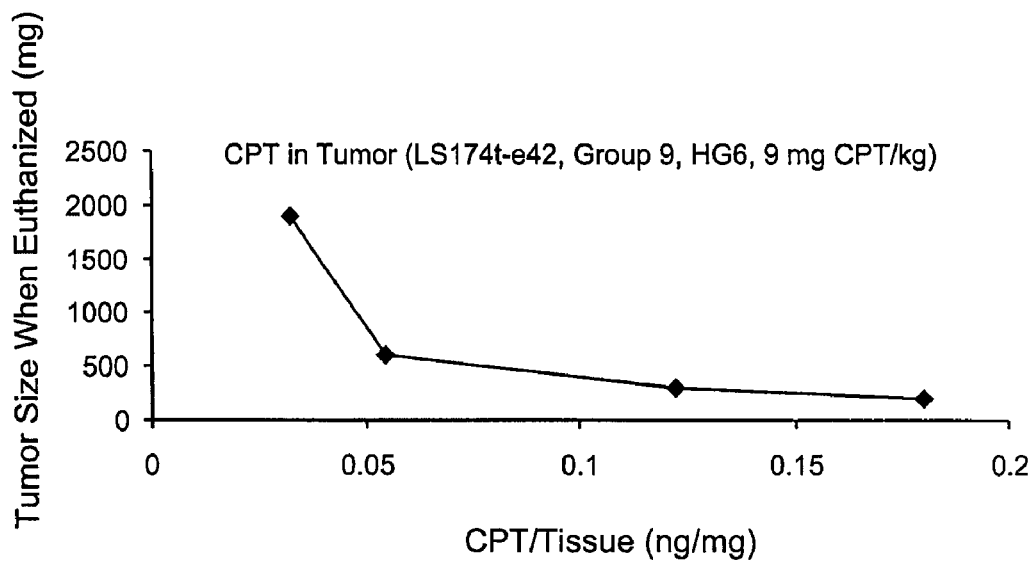
FIG. 12 shows the correlation of CPT concentration (ng/mg tissue) to tumor size (in mg) in xenograft mice.

Each tumor harvested from mice at the completion of the LS174t xenograft mouse study was thawed and placed in a 2 ml lysis tube (Lysing Matrix D, Qbiogen). 300 μL of lysis reagent (Cellytic—MT Mommalian Tissue Lysis/Extraction reagent) was added to each tube. The tissue was homogenized on a FastPrep FP12 homogenizer (Qbiogen) at 5 m/s for 40 sec. Homogenization was repeated six times with a 10 min interval between successive homogenization. The homogenized solution was centrifuged at 14000 g for 15 min at 10° C. 90 proof the solution was syringed out to which 10 μL 1 N NaOH was added. An aliquot of 400 μL MeOH was added to this solution after allowing the homogenized solution to stand for 2 h at room temperature. The solution was centrifuged for 15 min at 14000 g. The supernatant (270 μL) was mixed with 30 μL 1N HCl and injected into an HPLC for analysis. The correlation of CPT concentration (ng/mg tissue) to tumor size (in mg) is illustrated in FIG. 12. CPT concentration was inversely correlated to tumor size.

Example 45

Synthesis of Poly(CDDC-PEG)-Amphotericin B 52 Via Amide Linker

Scheme LII

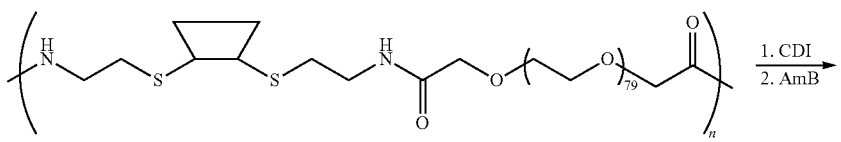

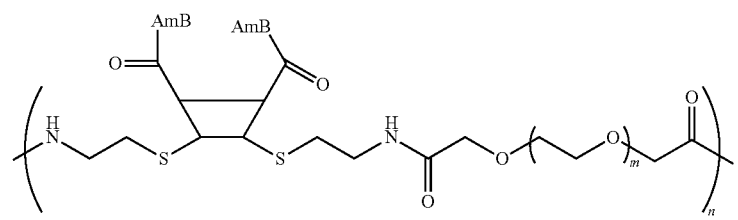

52

Poly(CDDC-PEG) (788 mg) and 1,1'-carbonyl diimidazole (CDI, 1.45 g, 50 eq.) were stirred in anhydrous DMSO (10 mL) in the presence of DMAP (429 mg, 20 eq) for 16 h. Ether (200 mL) was added to the mixture to precipitate poly (CDDC-PEG)-carbonyl-imidazole. The resulting yellow solid was washed with ether 2×200 mL and dried under vacuum. The solid was dissolved in anhydrous DMSO (15 mL), followed by adding AmB (332 mg, 2 eq) and DMAP (43.0 mg, 2 eq). The solution was stirred in dark for 48 h and dialyzed in water using 25000 MWCO membrane for 3 days. The solution was then filtered using 0.2 μm filter and lyophilized. A yellow solid (920 mg) 52 was obtained. The wt % of AniB is around 13%.

Example 46

Synthesis of Poly(CDDC-PEG)-Amphotericin B 53 via imine linker

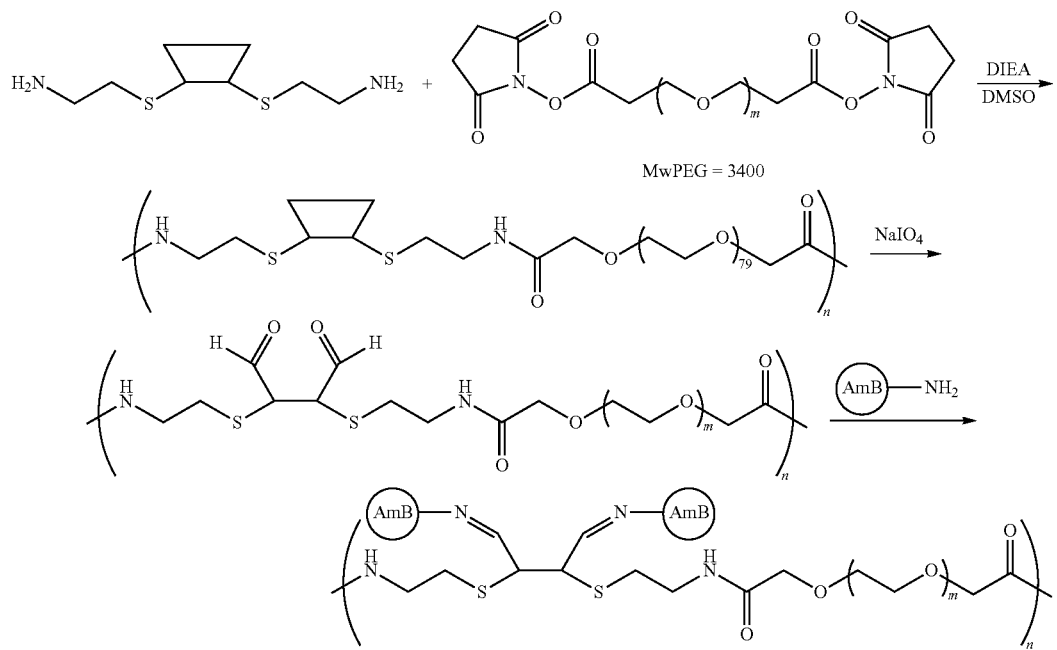

3 and PEG-DiSPA (1:1 ratio) were dried under vacuum at room temperature. DMSO (10 mg of 3/mL DMSO) was added to the solid and followed by adding of DIEA (2 eq) to the mixture. Polymer was crashed out with excess ether 5 days later and dialyzed using 25000 MWCO membrane for 48 h. The yield of poly(CDDC-PEG) is 80-95%. The Mw of polymer was determined using GPC to be 70-100 kDa.

Poly(CDDC-PEG) (1.124 g, 0.25 mmol) was dissolved in water (55 mL). NaIO$_4$ (0.264 g, 5 eq.) was added. The solution was stirred in dark at room temperature for 20 min and stored at 4° C. for 24 h in dark. BaCl$_2$ solution was added (5.05 eq) to the solution to give immediate precipitation of Ba(IO$_4$)$_2$. The precipitate was filtered. Saturated Na$_2$CO$_3$ solution was added to adjust pH to 11. Amphotericin B (343 mg, 1.5 eq) was then added to solution and stirred at rt in dark for 48 h. The pH of solution was maintained to be 11 by adding NaOH (0.1N) throughout the reaction. The solution was dialyzed at 4° C. for 48 h using 25000 MWCO and lyophilized to give 1.03 g polymer-AmB conjugate 53 as a yellow powder. The wt % of AmB is determined to be 18 using UV spectrometer at 405 nm.

D. References

Additional cyclodextrin-containing polymers that can be modified according to the teachings of the present invention, as well as methods of preparing such polymers, are disclosed in U.S. patent application Ser. Nos. 09/203,556, 09/339,818, 09/453,707, 10/021,294, and 10/021,312, all of which are hereby incorporated herein by reference in their entireties.

All of the references, patents, and publications cited herein are hereby incorporated by reference.

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims.

We claim:

1. A polymer having the following formula:

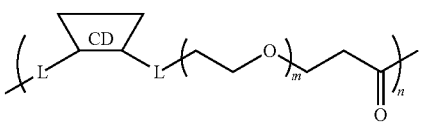

wherein each L is independently a linker comprising an amino acid or a derivative thereof;

wherein the group

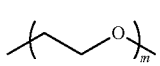

has a Mw of 3.4 kDa or less and n is at least 4.

2. The polymer of claim 1, wherein

is alpha, beta or gamma cyclodextrin.

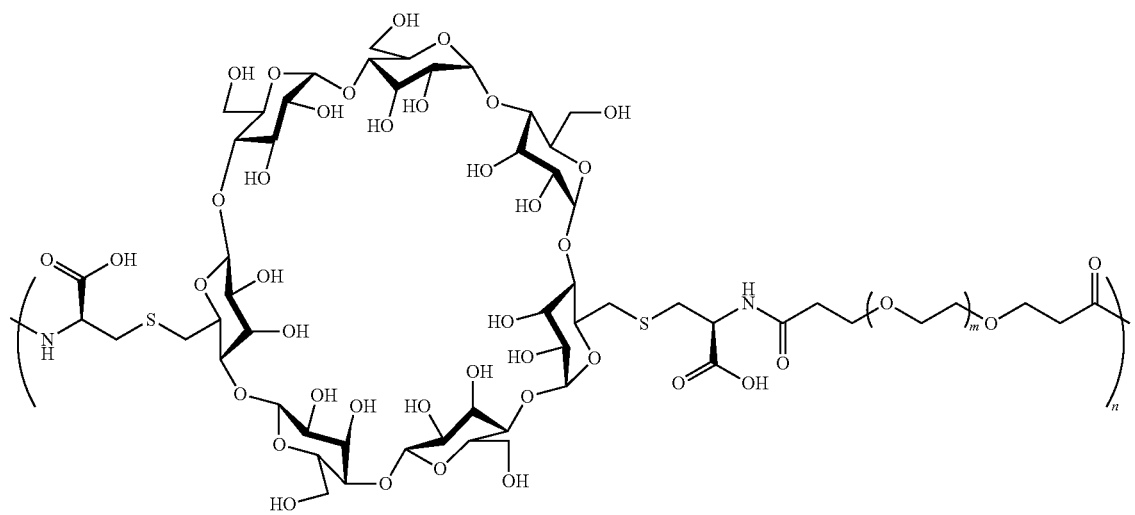

3. The polymer of claim 2, wherein

is beta cyclodextrin.

4. The polymer of claim 1, wherein at least one L comprises cysteine or a derivative thereof.

5. The polymer of claim 4, wherein each L comprises cysteine.

6. The polymer of claim 5, wherein each L is cysteine and the cysteine is connected to the CD by way of a thiol linkage.

7. The polymer of claim 1, having the following formula:

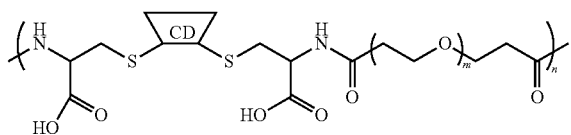

wherein the group

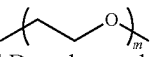

has a Mw of 3.4 kDa or less and n is at least 4.

8. The polymer of claim 7, wherein

is alpha, beta or gamma cyclodextrin.

9. The polymer of claim 8, wherein

is beta cyclodextrin.

10. A polymer having the following formula

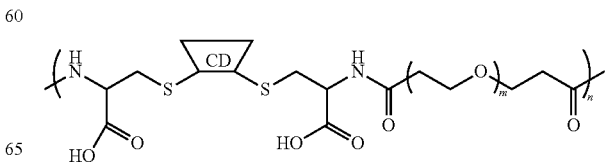

wherein the group

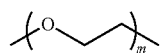

has a Mw of 3.4 kDa or less and n is at least 4.

11. The polymer of claim 10 wherein the group

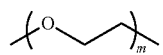

has a Mw of 3.4 kDa and the Mw of the compound as a whole is from 27 kDa to 99.6 kDa.

12. A method of making a polymer of the following formula:

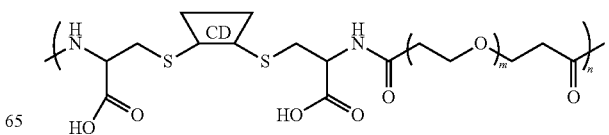

the method comprising:
providing a compound of formula A and formula B:

Formula A

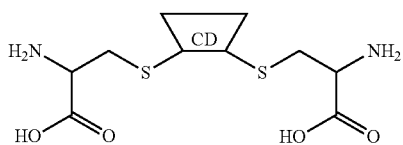

and

Formula B

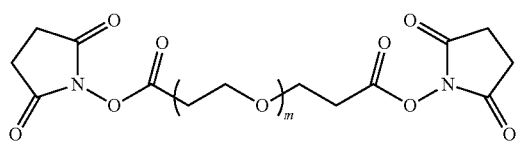

and contacting the compounds under conditions that allow for the formation of a covalent bond between the compounds of formula A and B, to form a polymer of the following formula:

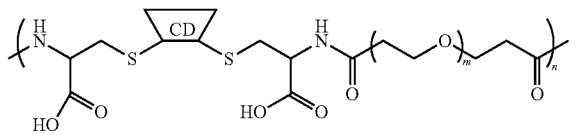

wherein the group

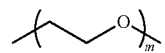

has a Mw of 3.4 kDa or less and n is at least four.

13. The method of claim 12, wherein the group

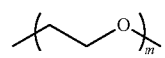

has a Mw of 3.4 kDa and the Mw of the polymer is from 27 kDa to 99.6 kDa.

14. The method of claim 12, wherein the compounds of formula A and formula B are contacted in the presence of a base.

15. The method of claim 14, wherein the base is an amine containing base.

16. The method of claim 15, wherein the base is DEA.

17. A method of making a polymer of the following formula:

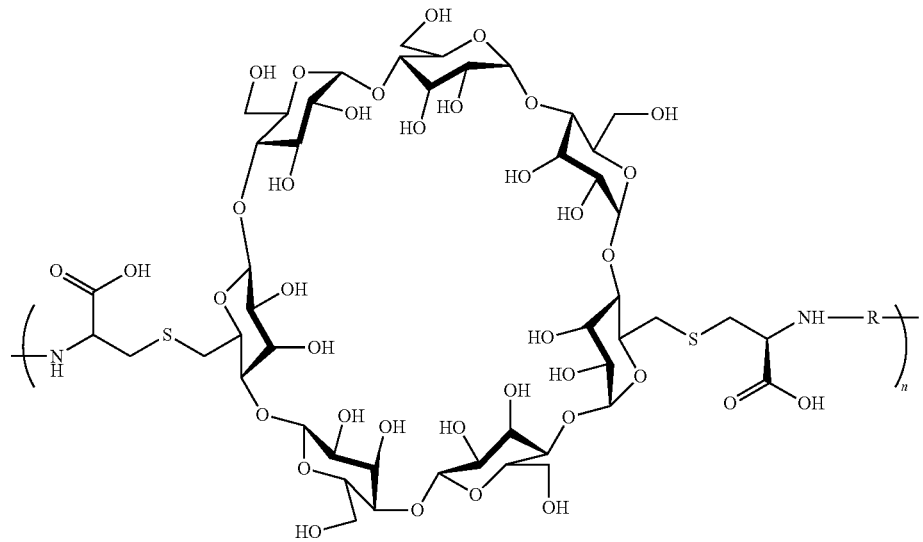

wherein R is of the form:

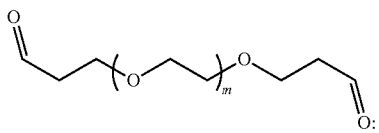

comprising the steps of:
reacting a compound of the formula below:

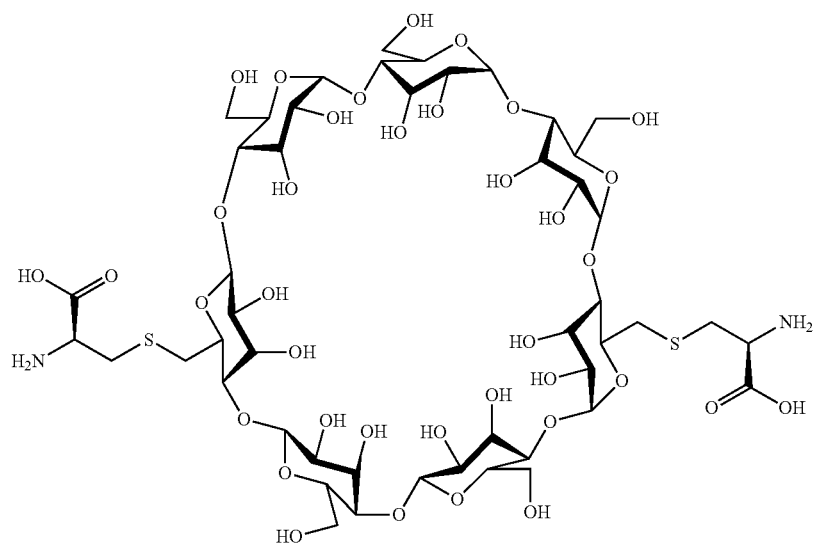

with a compound of the formula below:

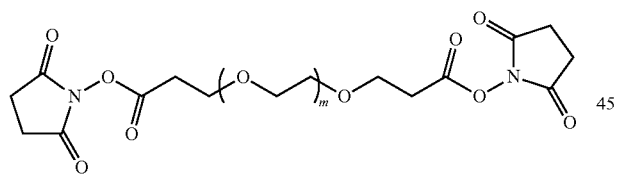

wherein the group

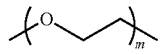

has a Mw of 3.4 kDa or less and n is at least four, in the presence of a non-nucleophilic organic base in a solvent.

18. The method of claim 17, wherein the solvent is a polar aprotic solvent.

19. The method of claim 18, wherein the solvent is DMSO.

20. The method of claim 17, further comprising the steps of dialysis; and lyophilization.

21. A method of making the polymer of the formula below:
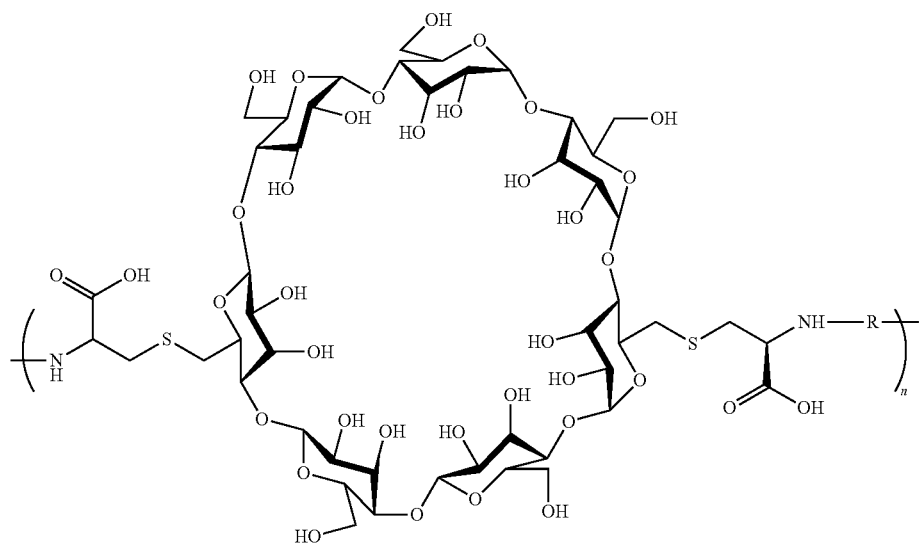
wherein R is of the form:
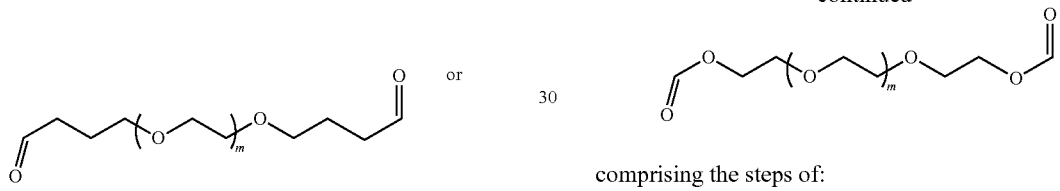
comprising the steps of:
reacting a compound of the formula below:
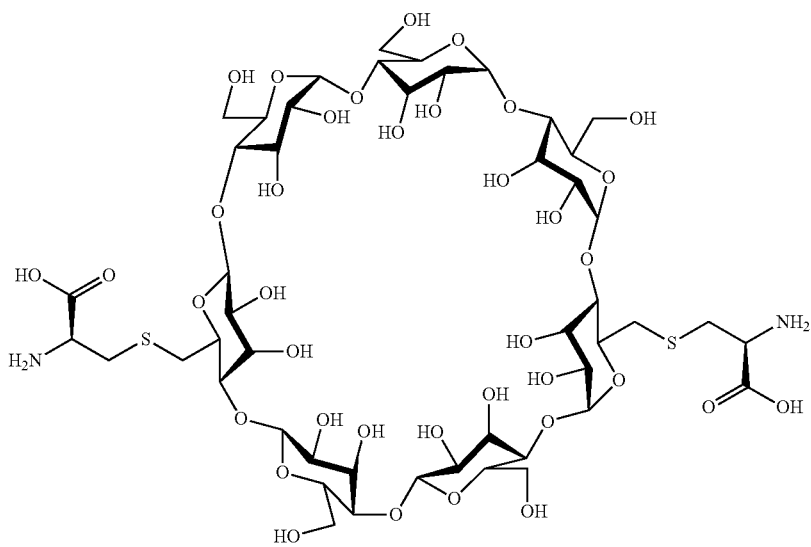

with a compound of the formula below:
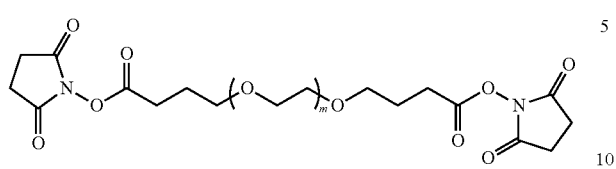
wherein the group
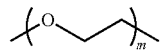
has a Mw of 3.4 kDa or less and n is at least four, or with a compound provided below:
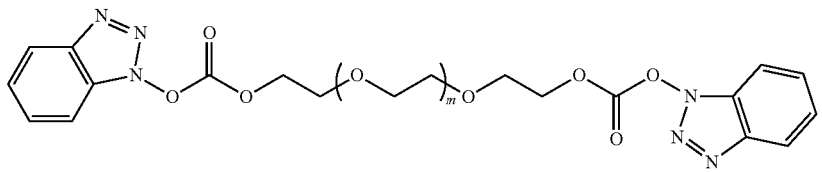
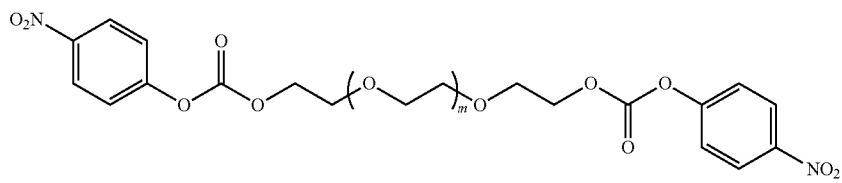
wherein the group
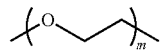
has a Mw of 3.4 kDa;
in the presence of a non-nucleophilic organic base in DMSO;
and dialyzing and lyophilizing the following polymer
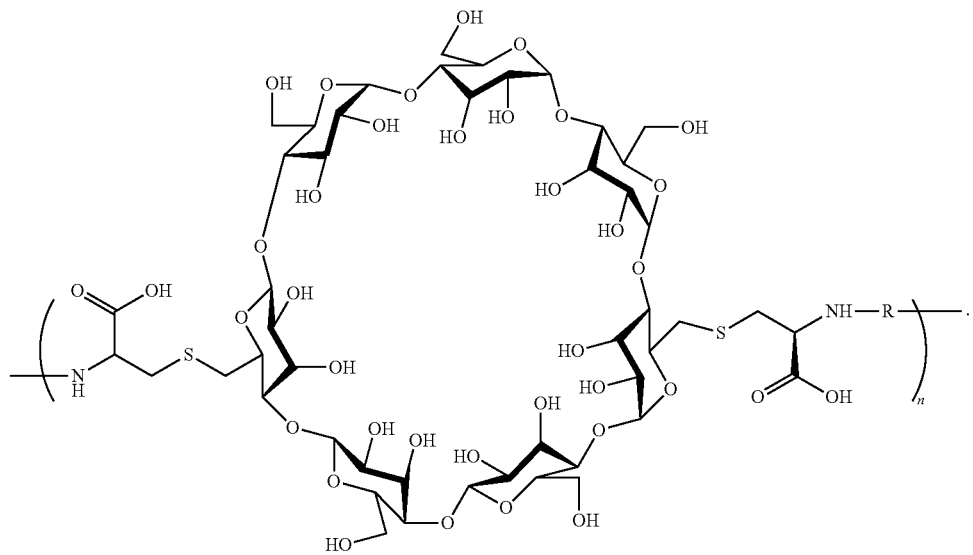

22. A water soluble linear polymer conjugate comprising:
   a linear polymer comprising cyclodextrin moieties and comonomers which do not contain cyclodextrin moieties (comonomers); and
   therapeutic agents covalently linked to the comonomers of the linear polymer, wherein the therapeutic agents are cleaved from the water soluble linear polymer conjugate under biological conditions to release therapeutic agents; and
   wherein the water soluble linear polymer conjugate comprises at least four cyclodextrin moieties and at least four comonomers.

23. The water soluble linear polymer conjugate of claim 22, wherein the least four cyclodextrin moieties and at least four comonomers alternate in the water soluble linear polymer conjugate.

24. The water soluble linear polymer conjugate of claim 22, wherein therapeutic agents are attached via linkers.

25. The water soluble linear polymer conjugate of claim 22, wherein the comonomer comprises residues of at least two functional groups through which reaction and linkage of the cyclodextrin monomers was achieved.

26. The water soluble linear polymer conjugate of claim 25, wherein the functional groups, which may be the same or different, terminal or internal, of each comonomer comprise an amino acid, imidazole, hydroxyl, thio, acyl halide, —HC=CH—, —C≡C— group, or derivative thereof.

27. The water soluble linear polymer conjugate of claim 25, wherein the two functional groups are the same and are located at termini of the comonomer precursor.

28. The water soluble linear polymer conjugate of claim 22, wherein the cyclodextrin moiety comprises an alpha, beta, or gamma cyclodextrin moiety.

29. The water soluble linear polymer conjugate of claim 22, wherein the therapeutic agent is at least 5%, 10%, 15%, 20%, 25%, 30%, or 35% by weight of the water soluble linear polymer conjugate.

30. The water soluble linear polymer conjugate of claim 29, wherein the comonomer comprises a polyethylene glycol, the cyclodextrin moiety comprises beta-cyclodextrin, and the therapeutic agent is (S)-20-camptothecin.

31. The water soluble linear polymer conjugate of claim 22, wherein a therapeutic agent is an antineoplastic agent.

32. The water soluble linear polymer conjugate of claim 22, wherein the therapeutic agent is an inhibitor of the S phase of the cell cycle.

33. The water soluble linear polymer conjugate of claim 22, wherein the therapeutic agent is a topoisomerase I inhibitor.

34. The water soluble linear polymer conjugate of claim 22, wherein the therapeutic agent is (S)-20-camptothecin.

35. The water soluble linear polymer conjugate of claim 22, wherein the therapeutic agent is a (S)-20-camptothecin analog.

36. The water soluble linear polymer conjugate of claim 35, wherein the (S)-20-camptothecin analog is topotecan.

37. The water soluble linear polymer conjugate of claim 35, wherein the (S)-20-camptothecin analog is irinotecan.

38. The water soluble linear polymer conjugate of claim 22, wherein the therapeutic agent is paclitaxel.

39. The water soluble linear polymer conjugate of claim 22, wherein the therapeutic agent is doxorubicin.

40. The water soluble linear polymer conjugate of claim 22, wherein the therapeutic agent is poorly soluble in water.

41. The water soluble linear polymer conjugate of claim 22, wherein the solubility of the therapeutic agent is <5 mg/ml at physiological pH.

42. The water soluble linear polymer conjugate of claim 22, wherein the therapeutic agent is a hydrophobic compound with a log P>0.4, >0.6, >0.8, >1, >2, >3, >4, or >5.

43. The water soluble linear polymer conjugate of claim 22, wherein the therapeutic agent is hydrophobic and is attached via a second compound.

44. The water soluble linear polymer conjugate of claim 22, wherein administration of the water soluble linear polymer conjugate to a patient results in release of the therapeutic agent over a period of at least 6 hours.

45. The water soluble linear polymer conjugate of claim 22, wherein administration of the water soluble linear polymer conjugate to a patient results in release of the therapeutic agent over a period of 6 hours to a month.

46. The water soluble linear polymer conjugate of claim 22, wherein, upon administration of the water soluble linear polymer conjugate to a patient the rate of therapeutic agent release is dependent primarily upon the rate of hydrolysis as opposed to enzymatic cleavage.

47. The water soluble linear polymer conjugate of claim 22, having a molecular weight of 10,000-500,000 amu.

48. The water soluble linear polymer conjugate of claim 22, wherein the cyclodextrin moieties make up at least about 2%, 5%, 10%, 20%, 30%, 50% or 80% of the polymer by weight.

49. The water soluble linear polymer conjugate of claim 22, made by a method comprising providing cyclodextrin moiety precursors modified to bear one reactive site at each of exactly two positions, and reacting the cyclodextrin moiety precursors with comonomer precursors having exactly two reactive moieties capable of forming a covalent bond with the reactive sites under polymerization conditions that promote reaction of the reactive sites with the reactive moieties to form covalent bonds between the comonomers and the cyclodextrin moieties, whereby a water soluble linear polymer comprising alternating units of a cyclodextrin moiety and a comonomer is produced.

50. The water soluble linear polymer conjugate of claim 22, wherein a comonomer comprises a group selected from the following:
   an alkylene chain,
   polysuccinic anhydride,
   poly-L-glutamic acid,
   poly(ethyleneimine),
   an oligosaccharide, or
   an amino acid chain.

51. The water soluble linear polymer conjugate of claim 22, wherein a comonomer comprises a polyethylene glycol chain.

52. The water soluble linear polymer conjugate of claim 22, wherein a comonomer comprises a group selected from the following:
   polyglycolic acid or polylactic acid chain.

53. The water soluble linear polymer conjugate of claim 22, wherein a comonomer comprises a hydrocarbylene group wherein one or more methylene groups is optionally replaced by a group Y (provided that none of the Y groups are adjacent to each other), wherein each Y, independently for each occurrence, is selected from, substituted or unsubstituted aryl, heteroaryl, cycloalkyl, heterocycloalkyl, or —O—, C(=X) (wherein X is $NR_1$, O or S), —OC(O)—, —C(=O)O, —$NR_1$—, —$NR_1$CO—, —C(O)$NR_1$—, —S(O)$_n$— (wherein n is 0, 1, or 2), —OC(O)—$NR_1$, —$NR_1$—C(O)—

NR$_1$—, —NR$_1$1-C(NR$_1$)—NR$_1$—, and —B(OR$_1$)—; and R$_1$, independently for each occurrence, represents H or a lower alkyl.

54. A polymer having attached thereto a plurality of D moieties of the following formula:

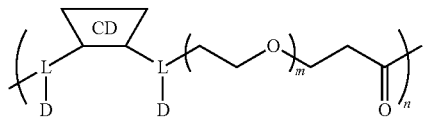

wherein each L is independently a linker, and each D is independently a therapeutic agent, a prodrug derivative thereof, or absent; and
wherein the group

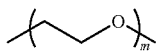

has a Mw of 3.4 kDa or less and n is at least 4.

55. The polymer of claim 54, wherein each L independently comprises an amino acid or a derivative thereof.
56. The polymer of claim 54, wherein each L independently comprises a plurality of amino acids or derivatives thereof.
57. The polymer of claim 54, wherein each L is independently a dipeptide or derivative thereof.
58. A polymer having attached thereto a plurality of L-D moieties of the following formula:

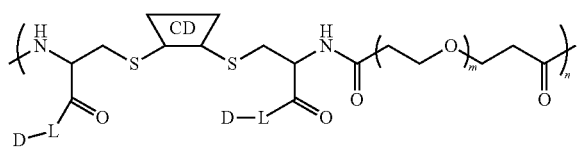

wherein each L is independently a linker or absent and each D is independently a therapeutic agent, a prodrug derivative thereof, or —OH and wherein the group

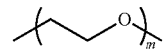

has a Mw of 3.4 kDa or less and n is at least 4.

59. The polymer of claim 58, wherein each L independently comprises an amino acid or derivative thereof.
60. The polymer of claim 59, wherein each L is glycine or a derivative thereof.
61. The polymer of claim 58, having the following formula:

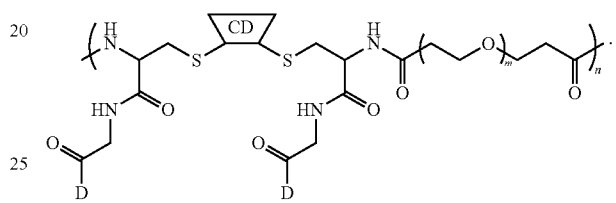

62. The polymer of claim 58, wherein each D is independently selected from an anti-fungal, anti-bacterial, anti-mycotic, or anti-viral therapeutic agent.
63. The polymer of claim 58, wherein each D is independently an anti-cancer agent or —OH.
64. The polymer of claim 58, wherein each D is independently —OH or selected from the group consisting of paclitaxel, doxorubicin, and amphotericin.
65. The polymer of claim 58, wherein each D is independently camptothecin or —OH.
66. The polymer of claim 58, wherein each D is independently a camptothecin analog or —OH.
67. A polymer having the following formula:

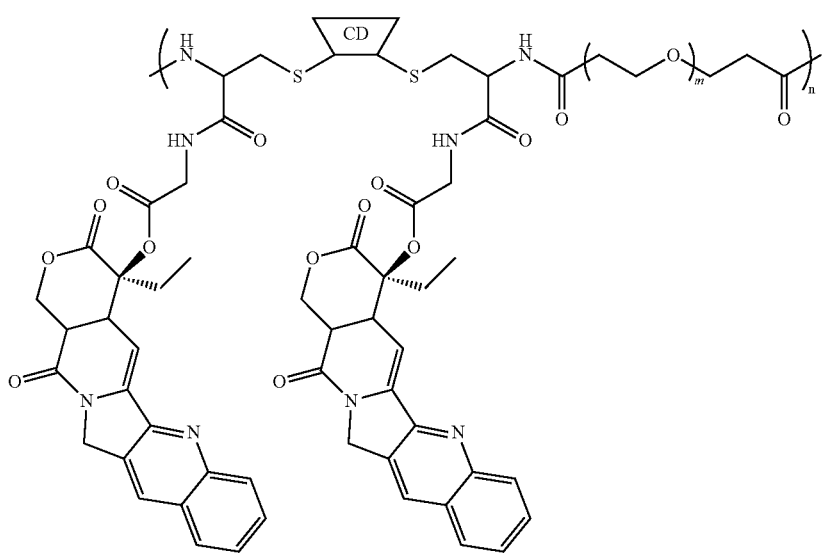

wherein the group

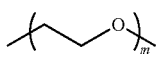

has a Mw of 3.4 kDa or less and n is at least 4.

68. A polymer having the following formula:

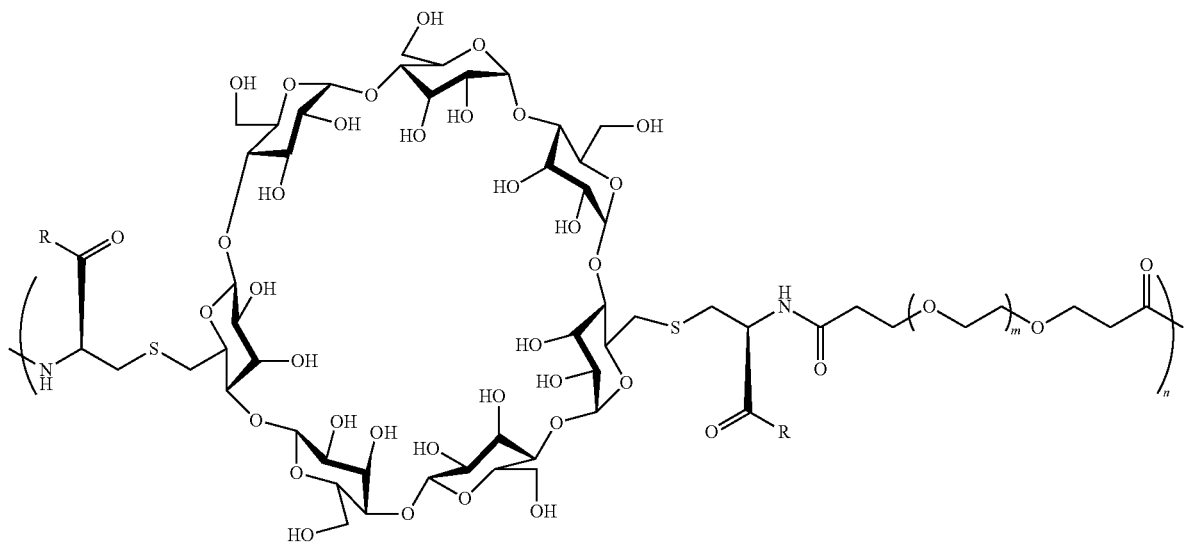

wherein each R is independently OH or a therapeutic agent or prodrug derivative thereof, provided that the loading of R when R is a therapeutic agent is from about 6% to about 10% by weight of the total polymer; and wherein the group

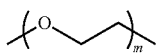

has a Mw of 3.4 kDa or less and n is at least 4.

69. The polymer of claim 68, wherein when R is a therapeutic agent, R is

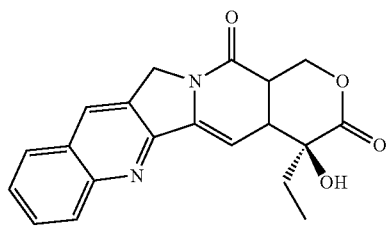

or a prodrug derivative thereof.

70. The polymer of claim 68, wherein R is

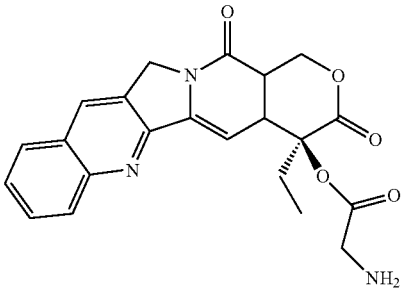

or a prodrug derivative thereof.

71. A method of making a water soluble linear polymer conjugate comprising therapeutic agents comprising:

providing a water soluble linear polymer comprising cyclodextrin moieties and comonomers which do not contain cyclodextrin moieties (comonomers), wherein the cyclodextrin moieties and comonomers alternate in the water soluble linear polymer and wherein the water soluble linear polymer comprises at least four cyclodextrin moieties and at least four comonomers; and covalently attaching therapeutic agents to comonomers of the water soluble linear polymer, wherein the therapeutic agents are cleaved from the water soluble linear polymer conjugate under biological conditions to release therapeutic agents, thereby making a water soluble linear polymer conjugate.

72. The method of claim 71, wherein a therapeutic agent is attached via a linker.

73. The method of claim 71, wherein the water soluble linear polymer conjugate is made by a process comprising:

providing cyclodextrin moiety precursors, providing comonomer precursors, and
copolymerizing said cyclodextrin moiety precursors and comonomer precursors to thereby make a water soluble linear polymer conjugate comprising cyclodextrin moieties and comomomers.

74. The method of claim 71, comprising providing cyclodextrin moiety precursors modified to bear one reactive site at each of exactly two positions, and reacting the cyclodextrin moiety precursors with comonomer precursors having exactly two reactive moieties capable of forming a covalent bond with the reactive sites under polymerization conditions that promote reaction of the reactive sites with the reactive moieties to form covalent bonds between the comonomers and the cyclodextrin moieties, whereby a water soluble linear polymer comprising alternating units of a cyclodextrin moiety and a comonomer is produced.

75. The method of claim 71, wherein the therapeutic agent makes up at least 5%, 10%, 15%, 20%, 25%, 30%, or even 35% by weight of the water soluble linear polymer conjugate.

76. The method of claim 72, wherein the comonomer comprises a polyethylene glycol, the cyclodextrin moiety comprises beta-cyclodextrin, and the therapeutic agent is (S)-20-camptothecin.

77. The method of claim 73, wherein the comonomer precursor is a compound containing at least two functional groups through which reaction and thus linkage of the cyclodextrin moieties is achieved.

78. The method of claim 77, wherein the functional groups, which may be the same or different, terminal or internal, of each comonomer precursor comprise an amino acid, imidazole, hydroxyl, thio, acyl halide, —HC=CH—, —C≡C— group, or derivative thereof.

79. The method of claim 77, wherein the two functional groups are the same and are located at termini of the comonomer precursor.

80. The method of claim 71, wherein a comonomer contains one or more pendant groups with at least one functional group through which reaction and thus linkage of a therapeutic agent is achieved.

81. The method of claim 80, wherein the functional groups, which may be the same or different, terminal or internal, of each comonomer pendant group comprise an amino acid, imidazole, hydroxyl, thiol, acyl halide, ethylene, ethyne group, or derivative thereof.

82. The method of claim 80, wherein the pendant group is a substituted or unsubstituted branched, cyclic or straight chain C1-C10 alkyl, or arylalkyl optionally containing one or more heteroatoms within the chains or rings.

83. The method of claim 71, wherein the cyclodextrin moiety comprises an alpha, beta, or gamma cyclodextrin moiety.

84. The method of claim 71, wherein the therapeutic agent is an antineoplastic agent.

85. The method of claim 71, wherein the therapeutic agent is an inhibitor of the S phase of the cell cycle.

86. The method of claim 71, wherein the therapeutic agent is a topoisomerase I inhibitor.

87. The method of claim 71, wherein the therapeutic agent is (S)-20-camptothecin.

88. The method of claim 71, wherein the therapeutic agent is (S)-20-camptothecin analog.

89. The method of claim 88, wherein the (S)-20-camptothecin analog is topotecan.

90. The method of claim 88, wherein the (S)-20-camptothecin analog is irinotecan.

91. The method of claim 71, wherein the therapeutic agent is paclitaxel.

92. The method of claim 71, wherein the therapeutic agent is doxorubicin.

93. The method of claim 71, wherein the therapeutic agent is poorly soluble in water.

94. The method of claim 71, wherein the solubility of the therapeutic agent is <5 mg/ml at physiological pH.

95. The method of claim 71, wherein the therapeutic agent is a hydrophobic compound with a log P>0.4, >0.6, >0.8, >1, >2, >3, >4, or >5.

96. The method of claim 71, wherein the therapeutic agent is hydrophobic and is attached via a second compound.

97. The method of claim 71, wherein administration of the water soluble linear polymer conjugate to a patient results in release of the therapeutic agent over a period of at least 6 hours.

98. The method of claim 71, wherein administration of the water soluble linear polymer conjugate to a patient results in release of the therapeutic agent over a period of 6 hours to a month.

99. The method of claim 71, wherein, upon administration of the water soluble linear polymer conjugate to a patient the rate of therapeutic agent release is dependent primarily upon the rate of hydrolysis as opposed to enzymatic cleavage.

100. The method of claim 71, wherein the water soluble linear polymer conjugate has a molecular weight of 10,000-500,000 amu.

101. The method of claim 71, wherein the cyclodextrin moieties make up at least about 2%, 5%, 10%, 20%, 30%, 50% or 80% of the polymer by weight.

102. The method of claim 71, wherein a comonomer comprises a group selected from the following:

an alkylene chain, polysuccinic anhydride, poly-L-glutamic acid, poly(ethyleneimine), an oligosaccharide, or an amino acid chain.

103. The method of claim 71, wherein a comonomer comprises a polyethylene glycol chain.

104. The method of claim 71, wherein a comonomer comprises a group selected from the following:

polyglycolic acid or polylactic acid chain.

105. The method of claim 71, wherein a comonomer comprises a hydrocarbylene group wherein one or more methylene groups is optionally replaced by a group Y (provided that none of the Y groups are adjacent to each other), wherein each Y, independently for each occurrence, is selected from, substituted or unsubstituted aryl, heteroaryl, cycloalkyl, heterocycloalkyl, or —O—, C(=X) (wherein X is $NR_1$, O or S), —OC(O)—, —C(=O)O, —$NR_1$—, —$NR_1$CO—, —C(O)$NR_1$—, —S(O)$_n$— (wherein n is 0, 1, or 2), —OC(O)—$NR_1$, —$NR_1$—C(O)—$NR_1$—, —$NR_1$—C($NR_1$)—$NR_1$—, and —B(O$R_1$)—; and $R_1$, independently for each occurrence, represents H or a lower alkyl.

106. A method of making a polymer having the following formula:

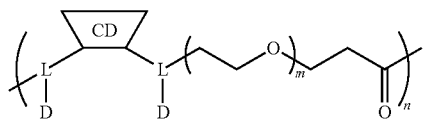

the method comprising:
providing a polymer of the formula below:

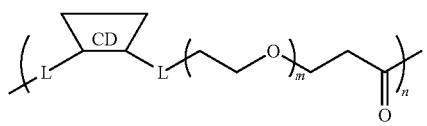

and coupling the polymer with a plurality of D moieties to provide:

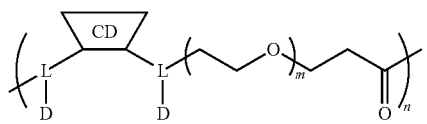

wherein each L is independently a linker, and each D is independently a therapeutic agent, a prodrug derivative thereof, or absent and the group

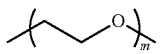

has a Mw of 3.4 kDa or less and n is at least 4.

107. A method of making a polymer having the following formula:

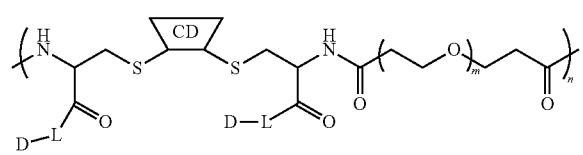

the method comprising:
providing a polymer below:

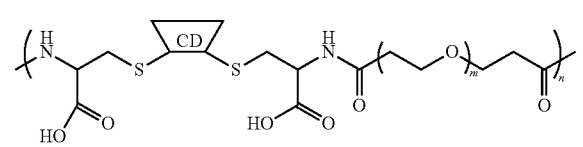

and coupling the polymer with a plurality of L-D moieties to provide:

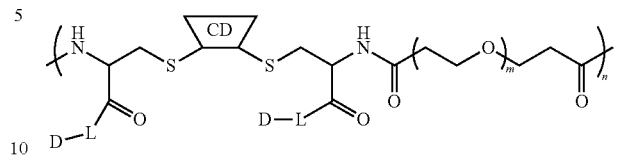

wherein each L is independently a linker, and each D is independently a therapeutic agent, a prodrug derivative thereof, or —OH and the group

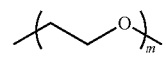

has a Mw of 3.4 kDa or less and n is at least 4.

108. The method of claim 107, wherein L of L-D is absent.

109. The method of claim 107, wherein L is an amino acid or derivative thereof.

110. The method of claim 107, wherein the coupling of the polymer with the plurality of L-D moieties results in the formation of a plurality of amide bonds.

111. The method of claim 107, wherein each D is independently selected from an anti-fungal, anti-bacterial, anti-mycotic, or anti-viral therapeutic agent.

112. The method of claim 107, wherein each D is independently an anti-cancer agent.

113. The method of claim 107, wherein each D is independently selected from the group consisting of paclitaxel, doxorubicin, and amphotericin.

114. The method of claim 107, wherein each D is independently camptothecin or —OH.

115. The method of claim 107, wherein each D is independently a camptothecin analog or —OH.

116. A pharmaceutical preparation comprising the water soluble linear polymer conjugate of claim 22.

117. A pharmaceutical preparation comprising a pharmaceutical excipient and a water soluble linear polymer conjugate of claim 22, or a pharmaceutically acceptable ester, salt, or hydrate thereof.

118. A pharmaceutical preparation comprising the polymer of claim 54, 58, 67, or 68.

119. A pharmaceutical preparation comprising a pharmaceutical excipient and a polymer of claim 54, 58, 67, or 68 or a pharmaceutically acceptable ester, salt, or hydrate thereof.

120. A reaction mixture comprising the polymer of any of claims 1 and 10 and a solvent.

121. The reaction mixture of claim 120, further comprising a therapeutic agent optionally coupled to a linker.

122. A compound of the following formula:

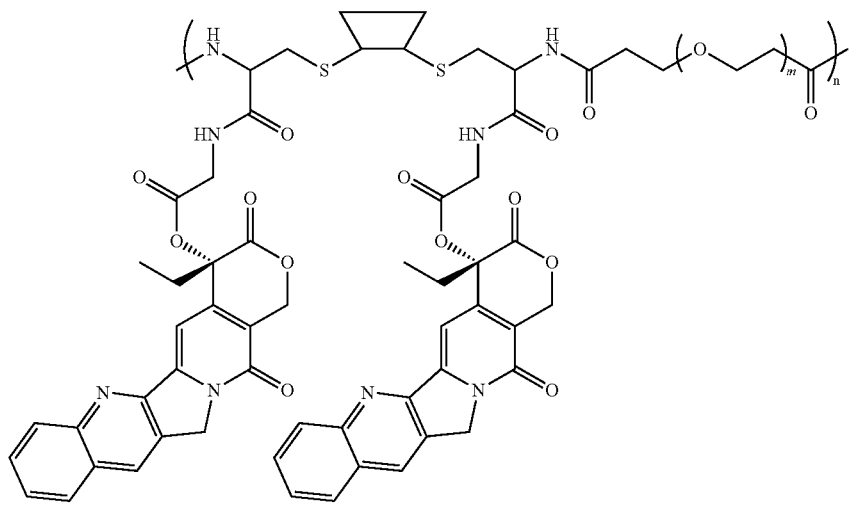

wherein, m is a number such that the molecular weight of the PEG is 3400, n is a number such that the molecular weight of the compound is 10,000 to 500,000 amu; and

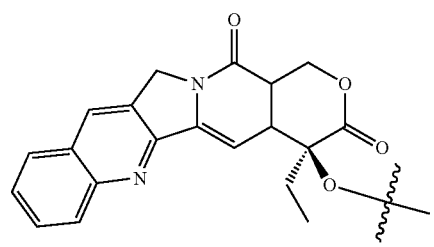

makes up at least about 5% of the compound by weight.

123. The compound of claim 122, wherein the molecular weight of the compound is 30,000 to 200,000 amu.

124. The compound of claim 122, wherein the

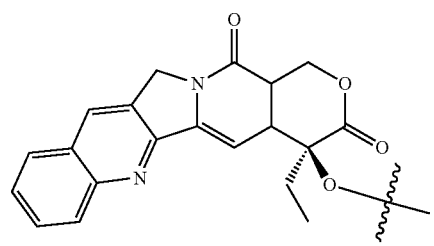

makes up at least about 10% of the compound by weight.

125. A compound of the following formula:

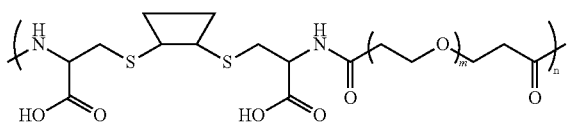

wherein, m is a number such that the molecular weight of the PEG is 3400, n is a number such that the molecular weight of the compound is 10,000 to 500,000 amu.

126. The compound of claim 125, wherein the molecular weight of the compound is 30,000 to 200,000 amu.

127. A linear polymer comprising beta cyclodextrin moieties which may be formed via poly condensation of beta cyclodextrin containing monomers and comonomers which do not contain beta cyclodextin moieties, and therapeutic agents covalently attached to one or more of the comonomers, wherein the therapeutic agents are cleaved from the linear polymer under biological conditions to release therapeutic agents.

128. The linear polymer of claim 127, wherein therapeutic agents are grafted onto the polymer via an optional linker subsequent to polymerization.

129. The linear polymer of claim 127, wherein the therapeutic agent is selected from camptothecin, paclitaxel, doxorubicin, and cyclosporine A.

130. The linear polymer of claim 127, wherein the therapeutic agent is an antineoplastic agent.

131. The linear polymer of claim 127, wherein the therapeutic agent is a camptothecin derivative.

132. The linear polymer of claim 127, wherein the therapeutic agent is topotecan.

133. The linear polymer of claim 127, wherein the therapeutic agent is irinotecan.

134. A subunit of a polymeric compound, the subunit having the following formula:

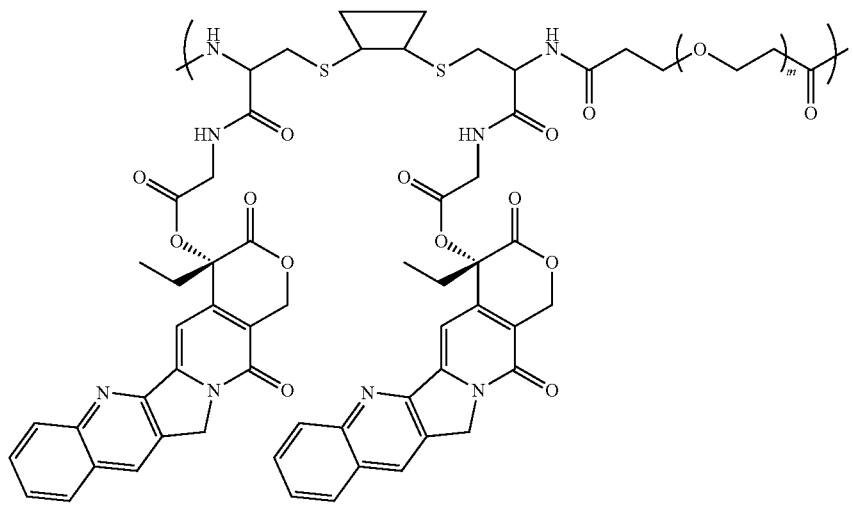

wherein,
m is a number such that the molecular weight of the PEG is 3400; and

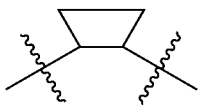

is a cyclodextrin.

135. The polymer of claim 59, wherein each L independently comprises a glycine or a derivative thereof.

136. The polymer of claim 59, wherein each L is triglycine or a derivative thereof.

137. The pharmaceutical preparation of claim 116 or 117, wherein therapeutic agents are attached via linkers.

138. The pharmaceutical preparation of claim 116 or 117, wherein the therapeutic agent is at least 5%, 10%, 15%, 20%, 25%, 30%, or 35% by weight of the water soluble linear polymer conjugate.

139. The pharmaceutical preparation of claim 138, wherein the comonomer comprises a polyethylene glycol, the cyclodextrin moiety comprises beta-cyclodextrin, and the therapeutic agent is (S)-20-camptothecin.

140. The water soluble linear polymer conjugate of claim 29, wherein the therapeutic agent is at least 5% by weight of the water soluble linear polymer conjugate.

141. The water soluble linear polymer conjugate of claim 29, wherein the therapeutic agent is at least 10% by weight of the water soluble linear polymer conjugate.

142. The water soluble linear polymer conjugate of claim 29, wherein the therapeutic agent is at least 15% by weight of the water soluble linear polymer conjugate.

143. The water soluble linear polymer conjugate of claim 29, wherein the therapeutic agent is at least 20% by weight of the water soluble linear polymer conjugate.

144. The water soluble linear polymer conjugate of claim 29, wherein the therapeutic agent is at least 25% by weight of the water soluble linear polymer conjugate.

145. The water soluble linear polymer conjugate of claim 22, wherein the therapeutic agent is an anti-inflammatory agent.

146. The water soluble linear polymer conjugate of claim 22, wherein the therapeutic agent is a peptide.

147. The method of claim 75, wherein the therapeutic agent makes up at least 5% by weight of the water soluble linear polymer conjugate.

148. The method of claim 75, wherein the therapeutic agent makes up at least 10% by weight of the water soluble linear polymer conjugate.

149. The method of claim 75, wherein the therapeutic agent makes up at least 15% by weight of the water soluble linear polymer conjugate.

150. The method of claim 75, wherein the therapeutic agent makes up at least 20% by weight of the water soluble linear polymer conjugate.

151. The method of claim 75, wherein the therapeutic agent makes up at least 25% by weight of the water soluble linear polymer conjugate.

152. The method of claim 71, wherein the therapeutic agent is an anti-inflammatory agent.

153. The method of claim 71, wherein the therapeutic agent is a peptide.

154. The pharmaceutical preparation of claim 138, wherein the therapeutic agent is at least 5% by weight of the water soluble linear polymer conjugate.

155. The pharmaceutical preparation of claim 138, wherein the therapeutic agent is at least 10% by weight of the water soluble linear polymer conjugate.

156. The pharmaceutical preparation of claim 138, wherein the therapeutic agent is at least 15% by weight of the water soluble linear polymer conjugate.

157. The pharmaceutical preparation of claim 138, wherein the therapeutic agent is at least 20% by weight of the water soluble linear polymer conjugate.

158. The pharmaceutical preparation of claim 138, wherein the therapeutic agent is at least 25% by weight of the water soluble linear polymer conjugate.

159. The pharmaceutical preparation of claim 138, wherein administration of the water soluble linear polymer conjugate to a patient results in release of the therapeutic agent over a period of at least 6 hours.

160. The pharmaceutical preparation of claim 138, wherein administration of the water soluble linear polymer conjugate to a patient results in release of the therapeutic agent over a period of 6 hours to a month.

161. The linear polymer of claim 129, wherein the therapeutic agent is camptothecin.

162. The polymer of claim 54, wherein the therapeutic agent is an anti-inflammatory agent.

163. The polymer of claim 54, wherein the therapeutic agent is a peptide.

164. The polymer of claim 58, wherein the therapeutic agent is an anti-inflammatory agent.

165. The polymer of claim 58, wherein the therapeutic agent is a peptide.

* * * * *

UNITED STATES PATENT AND TRADEMARK OFFICE
CERTIFICATE OF CORRECTION

PATENT NO. : 8,110,179 B2
APPLICATION NO. : 11/881325
DATED : February 7, 2012
INVENTOR(S) : Jianjun Cheng et al.

Page 1 of 5

It is certified that error appears in the above-identified patent and that said Letters Patent is hereby corrected as shown below:

In Columns 97 to 98, at the bottom, and in Columns 99 to 100, at the top, in Scheme XXXIX, the structure of the conjugate has been split into three pieces,

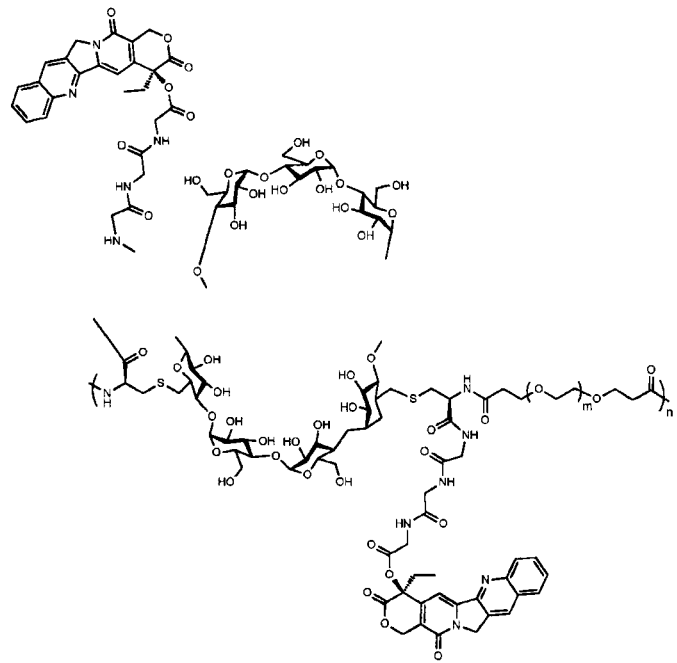

delete " "

Signed and Sealed this
Twenty-second Day of January, 2013

David J. Kappos
*Director of the United States Patent and Trademark Office*

CERTIFICATE OF CORRECTION (continued)
U.S. Pat. No. 8,110,179 B2

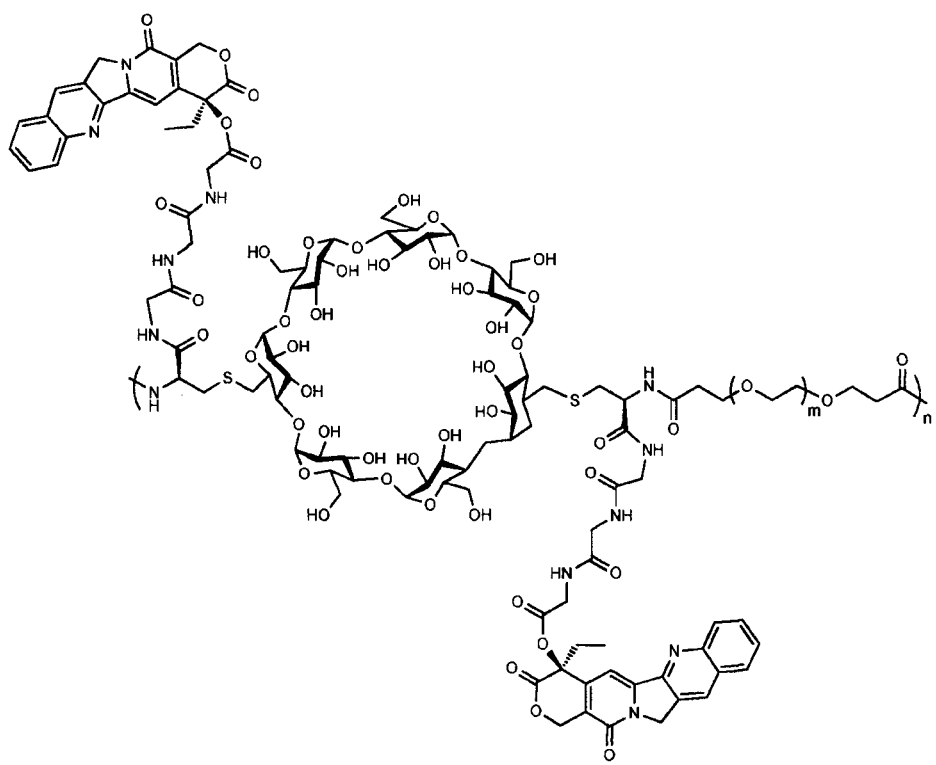

and insert --                                                                 --

In Columns 113 to 114, in Scheme XXXXV, the structure of PEI-CD has been split into four pieces,

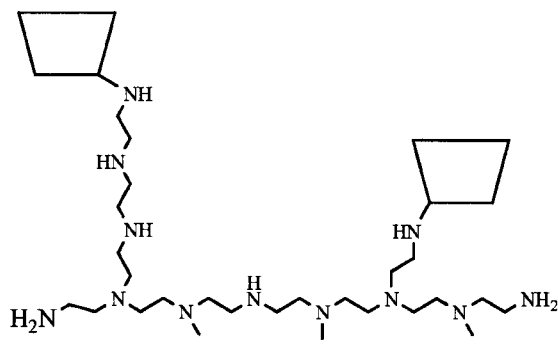

delete " 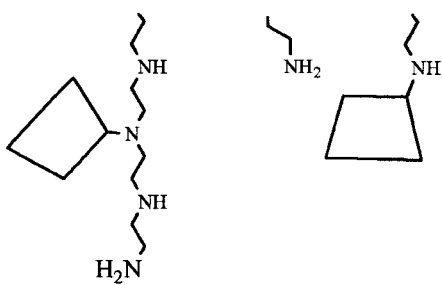 "

CERTIFICATE OF CORRECTION (continued)
U.S. Pat. No. 8,110,179 B2 and insert --
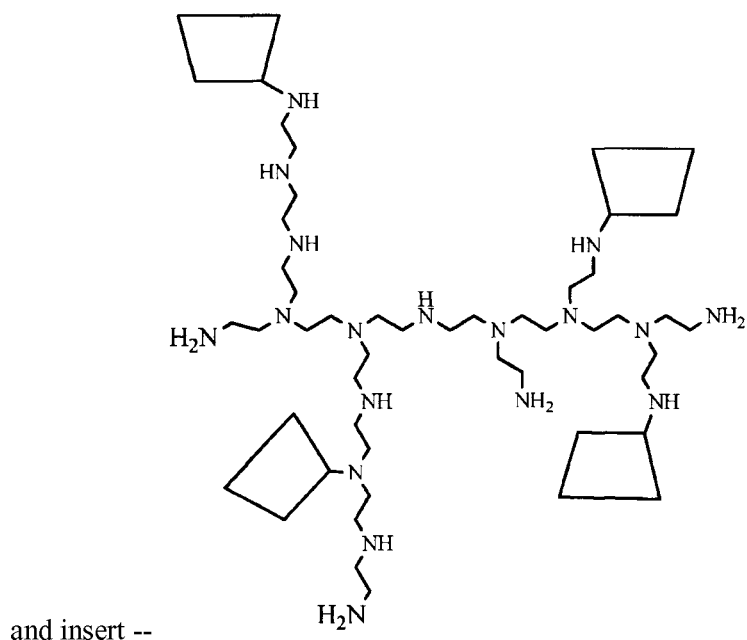
--

In Columns 123 to 124, at the bottom, and in Columns 125 to 126, at the top, in Scheme L1, the structure of PEI-CD-GlyCPT has been split into five pieces, delete "
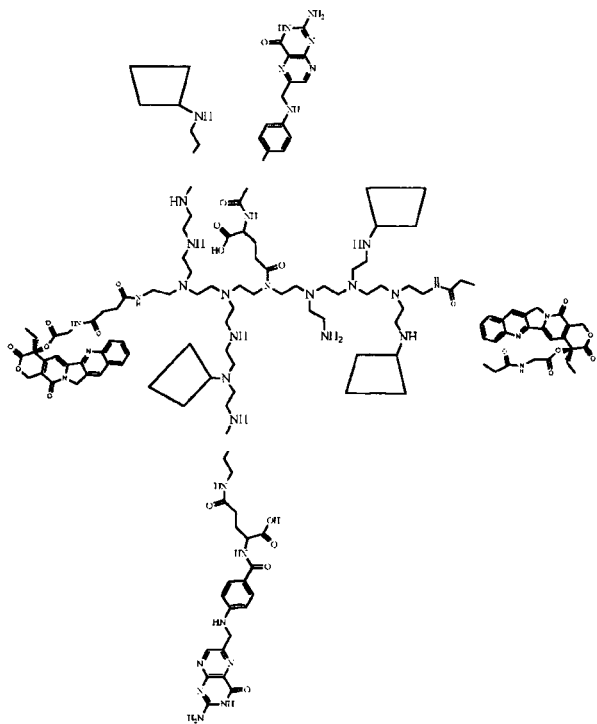
"

CERTIFICATE OF CORRECTION (continued)
U.S. Pat. No. 8,110,179 B2

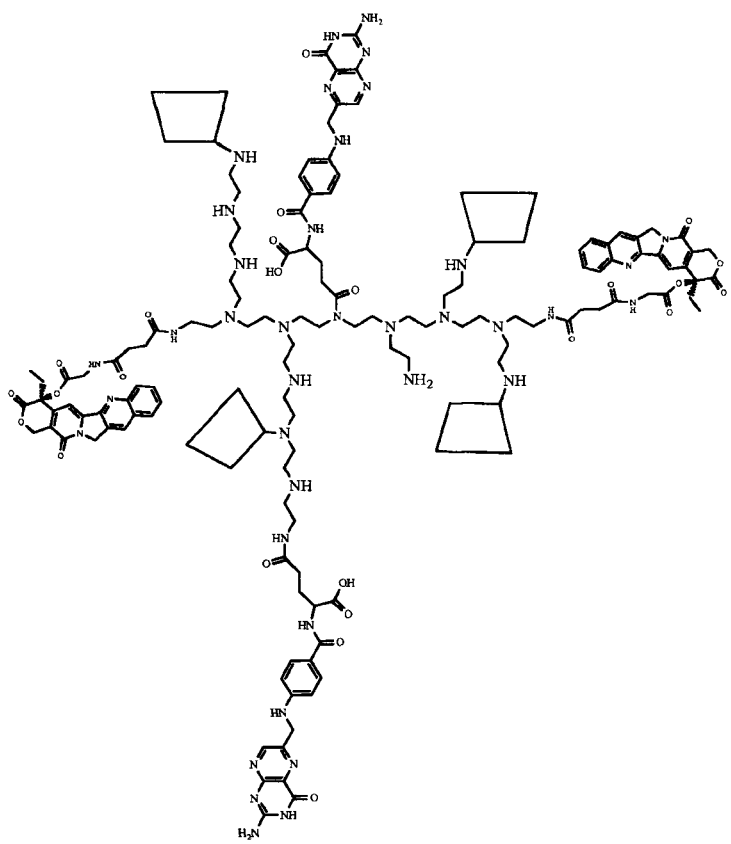

and insert -- --

In Claim 17, delete " 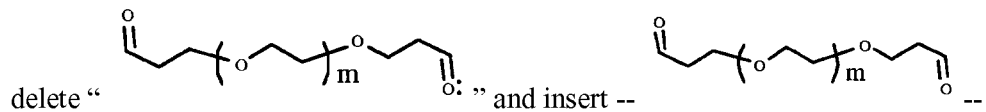 " and insert -- --

In Claim 21, at the last structure, delete " 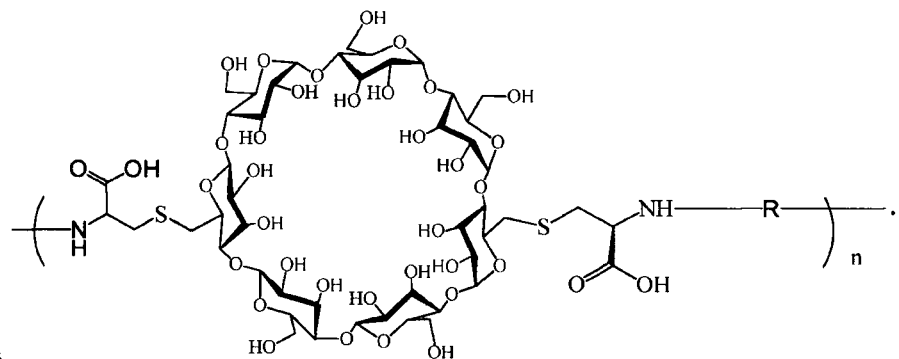 "

and insert -- 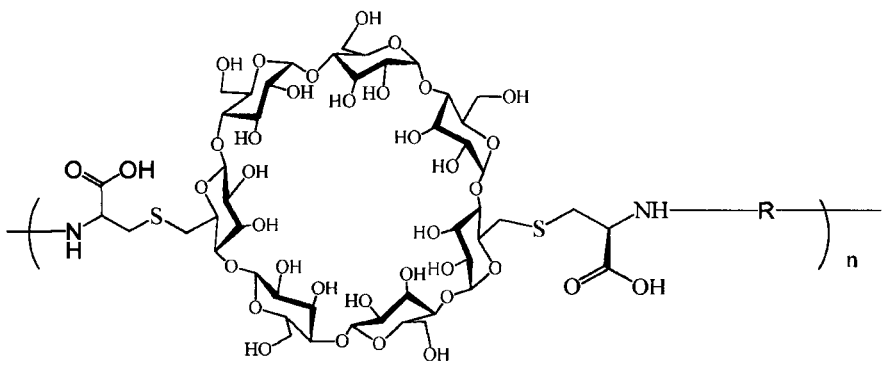 . --

In Claim 23, approx. line 15, delete "wherein the least four" and insert -- wherein the at least four --

In Claim 25, line 23, delete "the cyclodextrin monomers was achieved" and insert -- the cyclodextrin moieties was achieved --

In Claim 31, line 45, delete "wherein a therapeutic agent" and insert -- wherein the therapeutic agent --

In Claim 61, delete " 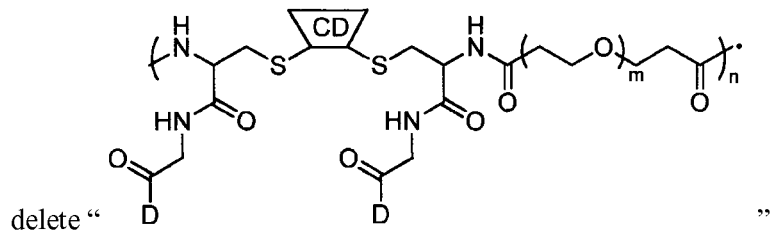 " and insert -- 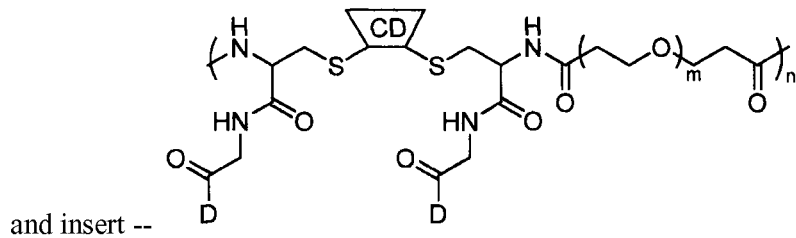 . --

In Claim 72, line 63, delete "wherein a therapeutic agent" and insert -- wherein the therapeutic agent --

In Claim 127, line 46, delete "beta cyclodextin moieties" and insert -- beta cyclodextrin moieties --